(12) United States Patent
Wood et al.

(10) Patent No.: US 7,629,338 B2
(45) Date of Patent: Dec. 8, 2009

(54) SUBSTITUTED MONOCYCLIC CGRP RECEPTOR ANTAGONISTS

(75) Inventors: Michael R. Wood, Harleysville, PA (US); Steven N. Gallicchio, Horsham, PA (US); Harold G. Selnick, Ambler, PA (US); C. Blair Zartman, Hatfield, PA (US); Ian M. Bell, Harleysville, PA (US); Craig A. Stump, Pottstown, PA (US)

(73) Assignee: Merck & Co., Inc., Rahway, NJ (US)

( * ) Notice: Subject to any disclaimer, the term of this patent is extended or adjusted under 35 U.S.C. 154(b) by 260 days.

(21) Appl. No.: 11/800,626

(22) Filed: May 7, 2007

(65) Prior Publication Data

US 2007/0265225 A1 Nov. 15, 2007

Related U.S. Application Data

(60) Provisional application No. 60/799,071, filed on May 9, 2006.

(51) Int. Cl.
| | |
|---|---|
| *C07D 401/12* | (2006.01) |
| *C07D 409/14* | (2006.01) |
| *C07D 417/12* | (2006.01) |
| *C07D 471/04* | (2006.01) |
| *C07D 519/00* | (2006.01) |
| *A61K 31/403* | (2006.01) |
| *A61K 31/407* | (2006.01) |
| *A61K 31/4184* | (2006.01) |
| *A61K 31/4188* | (2006.01) |
| *A61K 31/4439* | (2006.01) |
| *A61K 31/438* | (2006.01) |
| *A61P 25/06* | (2006.01) |

(52) U.S. Cl. .................. 514/221; 514/228.2; 514/229.8; 514/232.8; 514/249; 514/250; 514/250.06; 514/253.02; 514/278; 514/322; 540/500; 544/58.2; 544/101; 544/142; 544/238; 544/343; 544/349; 544/361; 546/17; 546/18; 546/187

(58) Field of Classification Search ................ 514/221, 514/228.2, 229.8, 232.8, 249, 250, 252.06, 514/253.02, 278, 322; 540/500; 544/58.2, 544/101, 142, 238, 343, 349, 361; 546/17, 546/18, 187
See application file for complete search history.

(56) References Cited

U.S. PATENT DOCUMENTS

| | | | |
|---|---|---|---|
| 6,953,790 | B2 | 10/2005 | Burgey et al. |
| 7,189,722 | B2 | 3/2007 | Bell et al. |
| 7,192,954 | B2 | 3/2007 | Bell et al. |
| 7,196,079 | B2 | 3/2007 | Burgey et al. |
| 7,202,251 | B2 | 4/2007 | Bell et al. |
| 7,205,292 | B2 | 4/2007 | Burgey et al. |
| 7,205,293 | B2 | 4/2007 | Bell et al. |
| 7,235,545 | B2 | 6/2007 | Burgey et al. |
| 7,390,798 | B2 | 6/2008 | Williams et al. |
| 7,452,903 | B2 | 11/2008 | Burgey et al. |
| 7,476,665 | B2 | 1/2009 | Burgey et al. |
| 7,491,713 | B2 | 2/2009 | Burgey et al. |
| 7,534,784 | B2 | 5/2009 | Burgey et al. |
| 2006/0173046 | A1 | 8/2006 | Bell et al. |
| 2007/0287697 | A1 | 12/2007 | Paone et al. |
| 2008/0004304 | A1 | 1/2008 | Bell et al. |
| 2008/0070899 | A1 | 3/2008 | Burgey et al. |
| 2008/0090806 | A1 | 4/2008 | Paone et al. |
| 2008/0096878 | A1 | 4/2008 | Bell et al. |
| 2008/0113966 | A1 | 5/2008 | Burgey et al. |
| 2008/0125413 | A1 | 5/2008 | Burgey et al. |
| 2008/0214511 | A1 | 9/2008 | Bell et al. |
| 2008/0261972 | A1 | 10/2008 | Paone et al. |
| 2008/0318927 | A1 | 12/2008 | Wood et al. |
| 2009/0054408 | A1 | 2/2009 | Bell et al. |
| 2009/0105219 | A1 | 4/2009 | Bell et al. |
| 2009/0105228 | A1 | 4/2009 | Williams |

FOREIGN PATENT DOCUMENTS

| | | |
|---|---|---|
| WO | WO 2004/082605 | 9/2004 |
| WO | WO 2004/082678 | 9/2004 |
| WO | WO 2004/083187 | 9/2004 |

(Continued)

OTHER PUBLICATIONS

PCT International Search Report and PCT Written Opinion of the International Searching Authority for PCT International Application No. PCT/US2007/010953.

(Continued)

*Primary Examiner*—Bruck Kifle
(74) *Attorney, Agent, or Firm*—William Provatin; Raynard Yuro

(57) ABSTRACT

Compounds of formula I:

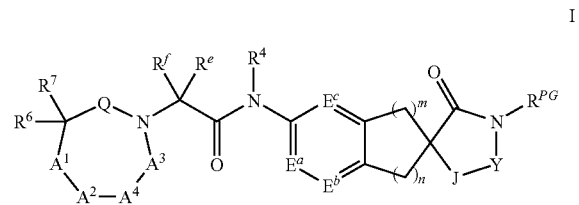

(wherein variables $A^1$, $A^2$, $A^3$, $A^4$, m, n, J, Q, $R^4$, $E^a$, $E^b$, $E^c$, $R^6$, $R^7$, $R^e$, $R^f$, $R^{PG}$ and Y are as described herein) which are antagonists of CGRP receptors and which are useful in the treatment or prevention of diseases in which the CGRP is involved, such as migraine. The invention is also directed to pharmaceutical compositions comprising these compounds and the use of these compounds and compositions in the prevention or treatment of such diseases in which CGRP is involved.

41 Claims, No Drawings

FOREIGN PATENT DOCUMENTS

| WO | WO 2006/029153 | 3/2006 |
|---|---|---|
| WO | WO 2006/031491 | 3/2006 |
| WO | WO 2006/031513 | 3/2006 |
| WO | WO 2006/031606 | 3/2006 |
| WO | WO 2006/031610 | 3/2006 |
| WO | WO 2006/031676 | 3/2006 |
| WO | WO 2006/044504 | 4/2006 |
| WO | WO 2007/016087 | 2/2007 |
| WO | WO 2007/061677 | 5/2007 |
| WO | WO 2007/061692 | 5/2007 |
| WO | WO 2007/061694 | 5/2007 |
| WO | WO 2007/061696 | 5/2007 |
| WO | WO 2007/067695 | 6/2007 |
| WO | 2008/011190 A1 | 1/2008 |
| WO | 2008/112159 A2 | 9/2008 |
| WO | 2008/127584 A1 | 10/2008 |
| WO | 2008/130512 A1 | 10/2008 |

OTHER PUBLICATIONS

PCT International Search Report and PCT Written Opinion of the International Searching Authority for PCT International Application No. PCT/US2007/010952.

Copending U.S. Appl. No. 12/085,057, U.S. National Stage Entry of PCT/US2006/044088, filed Nov. 14, publshed as WO 2007/061677.

Copending U.S. Appl. No. 12/085,005, U.S. National Stage Entry of PCT/US2006/044194, filed Nov. 14, 2006, published as WO 2007/061695.

Copending U.S. Appl. No. 12/085,008, U.S. National Stage Entry of PCT/US2006/044190, filed Nov. 14, 2006, published as WO 2007/061694.

Copending U.S. Appl. No. 12/084,917, U.S. National Stage Entry of PCT/US2006/044086, filed Nov. 14, 2006, published as WO 2007/061676.

Copending U.S. Appl. No. 11/662,702, U.S. National Stage Entry of PCT/US2005/032288, filed Sep. 9, 2005, published as WO 2006/031676.

Copending U.S. Appl. No. 12/085,131, U.S. National Stage Entry of PCT/US2006/044212, filed Nov. 14, 2006, published as WO 2007/061696.

Copending U.S. Appl. No. 12/517,674, U.S. National Stage Entry of PCT/US2007/024913, filed Dec. 5, 2007, published as WO 2008/073251.

Copending U.S. Appl. No. 12/520,132, U.S. National Stage Entry of PCT/US2007/025690, filed Dec. 14, 2007, published as WO 2008/085317.

Copending U.S. Appl. No. 12/417,911, filed Apr. 3, 2009.

Bell, et al., Bioorganic & Medicinal Chemistry Letters (2006), 16(24), 6165-6169.

SUBSTITUTED MONOCYCLIC CGRP RECEPTOR ANTAGONISTS

RELATED APPLICATION DATA

This is a filing which claims priority from U.S. Ser. No. 60/799,071, filed May 9, 2006.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human α-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent neuromodulator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187), salivary levels of CGRP are elevated in migraine subjects between attacks (Bellamy et al., Headache, 2006, 46, 24-33), and CGRP itself has been shown to trigger migrainous headache (Lassen et al., Cephalalgia, 2002, 22, 54-61). In clinical trials, the CGRP antagonist BIBN4096BS has been shown to be effective in treating acute attacks of migraine (Olesen et al., New Engl. J. Med., 2004, 350, 1104-1110) and was able to prevent headache induced by CGRP infusion in a control group (Petersen et al., Clin. Pharmacol. Ther., 2005, 77, 202-213).

CGRP-mediated activation of the trigeminovascular system may play a key role in migraine pathogenesis. Additionally, CGRP activates receptors on the smooth muscle of intracranial vessels, leading to increased vasodilation, which is thought to contribute to headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358); morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache.

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds of the formula I:

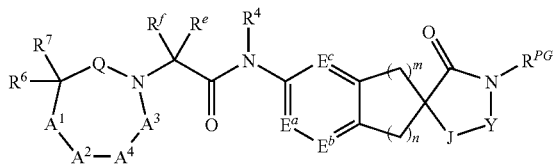

(wherein variables $A^1$, $A^2$, $A^3$, $A^4$, m, n, J, Q, $R^4$, $E^a$, $E^b$, $E^c$, $R^6$, $R^7$, $R^e$, $R^f$, $R^{PG}$ and Y are as described herein) which are antagonists of CGRP receptors and which are useful in the treatment or prevention of diseases in which CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of the formula I:

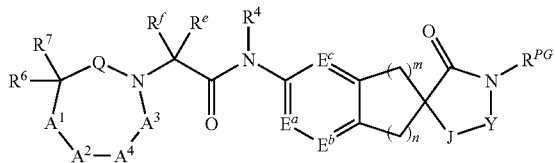

wherein:

$A^1$ is selected from:
(1) —O—,
(2) —S(O)$_v$—,
(3) —Si(OR$^a$)—C$_{1-4}$alkyl-, where alkyl is unsubstituted or substituted with 1-5 halo,
(4) —Si(C$_{1-4}$alkyl)$_2$, where each alkyl is independently unsubstituted or substituted with 1-5 halo-,
(5) —CR$^6$R$^7$—,
(6) —N(R$^8$)—,
(7) —(C═O)—,
(8) —C(R$^8$)(R$^a$)—,
(9) —C(N(R$^b$)—SO$_2$R$^d$)(R$^a$)—,
(10) —C(N(R$^b$)(C═O)R$^a$)(R$^a$)—,
(11) —C(R$^b$)(C═O)OR$^a$)(R$^a$)—,
(12) —CR$^{10}$R$^{11}$—, and
(13) —N(R$^{11}$)—;

$A^2$ is selected from:
(1) —CR$^6$R$^7$—,
(2) —CR$^{10}$R$^{11}$—, and
(3) —(C═O)—;

$A^3$ is selected from:
(1) —CR$^6$R$^7$—,
(2) —N(R$^8$)—,
(3) —CR$^{10}$R$^{11}$—, and
(4) —N(R$^{11}$)—;

$A^4$ is selected from:
(1) —CR$^6$R$^7$—,
(2) —(C═O)—,
(3) —N(R$^8$)—,
(4) —CR$^{10}$R$^{11}$—,
(5) —N(R$^{11}$)—, and
(6) a bond between $A^2$ and $A^3$;

$E^a$ is selected from:
(1) —C(R$^{5a}$)═,
(2) —N═, and
(3) —(N$^+$—O$^-$)═;

$E^b$ is selected from:
(1) —C(R$^{5b}$)═,
(2) —N═, and
(3) —(N$^+$—O$^-$)═;

$E^c$ is selected from:
(1) —C(R$^{5c}$)═,
(2) —N═, and
(3) —(N$^+$—O$^-$)═;

Q is selected from:
(1) —(C═O)—,
(2) —SO$_2$—,
(3) —SO—, and
(4) —C(R$^a$)$_2$—;

$R^4$ is selected from:
(1) hydrogen,
(2) —C$_{1-6}$alkyl, which is unsubstituted or substituted with 1-5 substituents each independently selected from:
 (a) halo,
 (b) —C$_{3-6}$cycloalkyl,
 (c) —CF$_3$, and
 (d) —O—R$^a$,
(3) —C$_{3-6}$cycloalkyl,
(4) benzyl, and
(5) phenyl;

$R^{5a}$, $R^{5b}$ and $R^{5c}$ are each independently selected from:
(1) hydrogen,
(2) —C$_{1-6}$alkyl, which is unsubstituted or substituted with 1-6 halo,
(3) halo,
(4) —OR$^a$, and
(5) —CN;

$R^6$ and $R^7$ are each independently selected from:
(1) hydrogen,
(2) —C$_{1-6}$alkyl, which is unsubstituted or substituted with 1-5 substituents each independently selected from:
 (a) halo,
 (b) —OR$^a$,
 (c) —C$_{3-6}$cycloalkyl,
 (d) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl, indolyl, indazolyl, benzimidazolyl, and oxazolyl, which phenyl or heterocycle is unsubstituted or substituted with 1-5 substituents each independently selected from:
(i) halo,
(ii) —$C_{1-6}$alkyl, which is unsubstituted or substituted with 1-5 halo,
(iii) —OR$^a$,
(iv) —NR$^b$R$^c$,
(v) —CN, and
(vi) oxo;
(e) —CO$_2$R$^a$,
(f) —C(=O)NR$^b$R$^c$,
(g) —S(O)$_v$R$^d$,
(h) —CN,
(i) —NR$^b$R$^c$,
(j) —N(R$^b$)C(=O)R$^a$,
(k) —N(R$^b$)SO$_2$R$^d$,
(l) —CF$_3$,
(m) —O—CO$_2$R$^d$,
(n) —O—(C=O)—NR$^b$R$^c$,
(o) —NR$^b$—(C=O)—NR$^b$R$^c$, and
(p) —C(=O)R$^a$,
(3) —$C_{3-8}$cycloalkyl, which is unsubstituted or substituted with 1-5 substituents each independently selected from:
(a) halo,
(b) —CN,
(c) —$C_{1-4}$alkyl, which is unsubstituted or substituted with 1-3 halo, and
(d) —OR$^a$,
(4) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
(a) halo,
(b) —OR$^a$,
(c) —$C_{3-6}$cycloalkyl,
(d) phenyl, which is unsubstituted or substituted with 1-5 substituents each independently selected from:
(i) halo,
(ii) —$C_{1-6}$alkyl, which is unsubstituted or substituted with 1-6 halo, and
(iii) —OR$^a$,
(e) —CO$_2$R$^a$,
(f) —C(=O)NR$^b$R$^c$,
(g) —S(O)$_v$R$^d$,
(h) —CN,
(i) —NR$^b$R$^c$,
(j) —N(R$^b$)C(=O)R$^a$,
(k) —N(R$^b$)SO$_2$R$^d$,
(l) —O—CO$_2$R$^d$,
(m) —O—(C=O)—NR$^b$R$^c$,
(n) —NR$^b$—(C=O)—NR$^b$R$^c$,
(o) —C(=O)R$^a$,
(p) —$C_{1-6}$alkyl, which is unsubstituted or substituted with 1-6 halo, and
(q) oxo;
(5) halo,
(6) —OR$^a$,
(7) —CN,
(8) —CO$_2$R$^a$,
(9) —N(R$^b$)C(=O)R$^a$,
(10) —NR$^b$R$^c$,
(11) —C(=O)NR$^b$R$^c$, and
(12) —O(C=O)R$^a$;
or R$^6$ and R$^7$ and the carbon atom or atoms to which they are attached join to form a ring selected from cyclopropyl, cyclobutyl, cyclopentyl, cyclohexyl, cycloheptyl, cyclooctyl, cyclononyl, cyclobutenyl, cyclopentenyl, cyclohexenyl, cycloheptenyl, cyclooctenyl, dioxolanyl, dioxanyl, aziridinyl, azetidinyl, pyrrolidinyl, piperidinyl, piperazinyl, morpholinyl, tetrahydrofuranyl, tetrahydropyranyl, tetrahydrothiopyranyl, oxetanyl, thietanyl and tetrahydrothienyl, wherein the sulfur is optionally oxidized to the sulfone or sulfoxide, which ring is unsubstituted or substituted with 1-5 substituents each independently selected from:
(a) —$C_{1-6}$alkyl, which is unsubstituted or substituted with 1-3 substituents each independently selected from:
(i) halo,
(ii) —OR$^a$,
(iii) —$C_{3-6}$cycloalkyl,
(iv) —CO$_2$R$^a$,
(v) —NR$^b$R$^c$,
(vi) —S(O)$_v$R$^d$,
(vii) —C(=O)NR$^b$R$^c$, and
(viii) phenyl,
(b) —$C_{3-6}$cycloalkyl, wherein the $C_{3-6}$cycloalkyl group is optionally fused to the ring, and which $C_{3-6}$cycloalkyl group is unsubstituted or substituted with 1-3 substituents each independently selected from:
(i) halo,
(ii) —OR$^a$,
(iii) —$C_{3-6}$cycloalkyl,
(iv) —CO$_2$R$^a$,
(v) —NR$^b$R$^c$,
(vi) —S(O)$_v$R$^d$,
(vii) —C(=O)NR$^b$R$^c$, and
(viii) phenyl,
(c) phenyl or heterocycle, wherein heterocycle is selected from: pyridyl, pyrimidinyl, pyrazinyl, pyridazinyl, piperidinyl, piperazinyl, pyrrolidinyl, thienyl, morpholinyl, imidazolyl, furanyl, tetrahydrofuranyl, thiazolyl and oxazolyl, wherein the phenyl or heterocycle is optionally fused to the ring, and which phenyl or heterocycle is unsubstituted or substituted with 1-5 substituents each independently selected from:
(i) halo,
(ii) —$C_{1-6}$alkyl, which is unsubstituted or substituted with 1-5 halo,
(iii) —OR$^a$,
(iv) —CO$_2$R$^a$,
(v) —O(C=O)R$^a$,
(vi) —CN,
(vii) —NR$^b$R$^c$,
(viii) oxo,
(ix) —C(=O)NR$^b$R$^c$,
(x) —N(R$^b$)C(=O)R$^a$,
(xi) —N(R$^b$)CO$_2$R$^a$,
(xii) —O(C=O)NR$^b$R$^c$, and
(xiii) —S(O)$_v$R$^d$,
(d) —OR$^a$,
(e) —CO$_2$R$^a$,
(f) —C(=O)NR$^b$R$^c$,
(g) —S(O)$_v$R$^d$,
(h) —CN,
(i) halo,
(j) —NR$^b$R$^c$,
(k) —N(R$^b$)C(=O)R$^a$,
(l) —N(R$^b$)SO$_2$R$^d$,
(m) —O—CO$_2$R$^d$,
(n) —O—(C=O)—NR$^b$R$^c$, (o) —NR$^b$—(C=O)—NR$^b$R$^c$,
(p) —C(=O)R$^a$, and
(q) oxo;

R$^8$ is independently selected from:
(1) hydrogen,
(2) —C(=O)R$^a$,
(3) —CO$_2$R$^a$,
(4) —S(=O)R$^d$,
(5) —SO$_2$R$^d$,
(6) —C(=O)NR$^b$R$^c$,
(7) —C$_{1-6}$alkyl, which is unsubstituted or substituted with 1-5 substituents each independently selected from:
  (a) halo,
  (b) —OR$^a$,
  (c) —C$_{3-6}$cycloalkyl,
  (d) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
    (i) halo,
    (ii) —C$_{1-6}$alkyl, which is unsubstituted or substituted with 1-5 halo, and
    (iii) —OR$^a$,
    (iv) —NR$^b$R$^c$,
    (v) —C(=O)R$^a$,
    (vi) —CO$_2$R$^a$, and
    (vii) oxo,
  (e) —CO$_2$R$^a$,
  (f) —C(=O)NR$^b$R$^c$,
  (g) —S(O)$_v$R$^d$,
  (h) —CN,
  (i) —NR$^b$R$^c$,
  (j) —N(R$^b$)C(=O)R$^a$,
  (k) —N(R$^b$)SO$_2$R$^d$,
  (l) —CF$_3$,
  (m) —O—CO$_2$R$^d$,
  (n) —O—(C=O)—NR$^b$R$^c$,
  (o) —NR$^b$—(C=O)—NR$^b$R$^c$, and
  (p) —C(=O)R$^a$,
(8) —C$_{3-6}$cycloalkyl, which is unsubstituted or substituted with 1-6 substituents each independently selected from:
  (a) halo,
  (b) —CN,
  (c) —OR$^a$, and
  (d) C$_{1-6}$alkyl, which is unsubstituted or substituted with 1-6 halo;
or R$^7$ and R$^8$ and the atoms to which they are attached join to form a 4-, 5-, 6- or 7-membered alkyl- or heteroalkyl-ring optionally containing an additional heteroatom selected from N, O, and S, wherein the sulfur is optionally oxidized to the sulfone or sulfoxide, which ring is unsubstituted or substituted with 1-4 substituents each independently selected from:
  (a) halo,
  (b) phenyl, which is unsubstituted or substituted with 1-3 substituents each independently selected from: halo, OR$^a$, CN, and —C(=O)OR$^a$,
  (c) —OR$^a$, and
  (d) —C$_{1-6}$alkyl, which is unsubstituted or substituted with 1-6 halo;

R$^{10}$ is independently selected from:
(1) hydrogen,
(2) —C$_{1-6}$alkyl, which is unsubstituted or substituted with 1-5 substituents each independently selected from:
  (a) halo,
  (b) —OR$^a$,
  (c) —CN,
  (d) phenyl, and
  (e) —C$_{3-6}$cycloalkyl, which is unsubstituted or substituted with 1-6 halo,
(3) —C$_{3-6}$cycloalkyl, which is unsubstituted or substituted with 1-6 halo;

R$^{11}$ is independently selected from the group consisting of:
phenyl, naphthyl, tetrahydronaphthyl, indanyl, biphenyl, phenanthryl, anthryl, azepinyl, azepanyl, azetidinyl, benzimidazolyl, benzisoxazolyl, benzofuranyl, benzofurazanyl, benzopyranyl, benzothiopyranyl, benzofuryl, 1,3-benzodioxolyl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiamorpholinyl sulfone, thiazolyl, thiazolinyl, thienofuryl, thienothienyl, thienyl, triazolyl, isoxazolyl, tetrahydrothienyl, tetrahydropyranyl, oxetanyl, tetrahydrothiopyranyl, and thietanyl, where R$^{11}$ is unsubstituted or substituted with 1-5 substituents each independently selected from R$^{12}$, R$^{13}$, R$^{14}$, R$^{15a}$ and R$^{15b}$;

R$^{12}$, R$^{13}$, R$^{14}$, R$^{15a}$ and R$^{15b}$ are each independently selected from:
(1) —C$_{1-6}$alkyl, which is unsubstituted or substituted with 1-5 substituents each independently selected from:
  (a) halo,
  (b) —OR$^a$,
  (c) —C$_{3-6}$cycloalkyl,
  (d) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
    (i) halo,
    (ii) —C$_{1-6}$alkyl, which is unsubstituted or substituted with 1-5 halo, and
    (iii) —OR$^a$,
  (e) —CO$_2$R$^a$,
  (f) —C(=O)NR$^b$R$^c$,
  (g) —S(O)$_v$R$^d$,
  (h) —CN,
  (i) —NR$^b$R$^c$,
  (j) —N(R$^b$)C(=O)R$^a$,
  (k) —N(R$^b$)SO$_2$R$^d$,
  (l) —CF$_3$,
  (m) —O—CO$_2$R$^d$, (n) —O—(C=O)—NR$^b$R$^c$,
(o) —NR$^b$—(C=O)—NR$^b$R$^c$, and
(p) —C(=O)R$^a$, (2) —C$_{1-6}$cycloalkyl, which is unsubstituted or substituted with 1-5 substituents each independently selected from:
(a) halo,
(b) —CN,
(c) —C$_{1-6}$alkyl, which is unsubstituted or substituted with 1-5 halo,
(d) —OR$^a$, and
(e) phenyl, which is unsubstituted or substituted with 1-5 substituents where the substituents are each independently selected from:
  (i) —OR$^a$,
  (ii) halo,
  (iii) —CN, and
  (iv) —C$_{1-6}$alkyl, which is unsubstituted or substituted with 1-5 halo, (3) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
(a) halo,
(b) —OR$^a$,
(c) —C$_{3-6}$cycloalkyl,
(d) phenyl, which is unsubstituted or substituted with 1-5 substituents each independently selected from:
  (i) halo,
  (ii) —C$_{1-6}$alkyl, which is unsubstituted or substituted with 1-6 halo, and
  (iii) —OR$^a$,
(e) —CO$_2$R$^a$,
(f) —C(=O)NR$^b$R$^c$,
(g) —S(O)$_v$R$^d$,
(h) —CN,
(i) —NR$^b$R$^c$,
(j) —N(R$^b$)C(=O)R$^a$,
(k) —N(R$^b$)SO$_2$R$^d$,
(l) —O—CO$_2$R$^d$,
(m) —O—(C=O)—NR$^b$R$^c$,
(n) —NR$^b$—(C=O)—NR$^b$R$^c$,
(o) —C(=O)R$^a$, and
(p) —C$_{1-6}$alkyl, which is unsubstituted or substituted with 1-6 halo, (4) halo,
(5) oxo,
(6) —OR$^a$,
(7) —CN,
(8) —CO$_2$R$^a$,
(9) —C(=O)R$^a$,
(10) —NR$^b$R$^c$,
(11) —S(O)$_v$R$^d$,
(12) —C(=O)NR$^b$R$^c$,
(13) —O—CO$_2$R$^d$,
(14) —N(R$^b$)CO$_2$R$^d$,
(15) —O—(C=O)—NR$^b$R$^c$,
(16) —NR$^b$(C=O)—NR$^b$R$^c$,
(17) —SO$_2$NR$^b$R$^c$,
(18) —N(R$^b$)SO$_2$R$^d$, or R$^{15a}$ and R$^{15b}$ and the atom(s) to which they are attached join to form a ring selected from cyclopropyl, cyclobutyl, cyclopentyl, cyclohexyl, cycloheptyl, aziridinyl, azetidinyl, pyrrolidinyl, piperidinyl, piperazinyl, morpholinyl, thietanyl and tetrahydrothienyl, wherein the sulfur is optionally oxidized to the sulfone or sulfoxide, which ring is unsubstituted or substituted with 1-5 substituents each independently selected from:
(a) —C$_{1-6}$alkyl, which is unsubstituted or substituted with 1-3 substituents each independently selected from:
  (i) halo,
  (ii) —OR$^a$,
  (iii) —C$_{3-6}$cycloalkyl,
  (iv) —CO$_2$R$^a$,
  (v) —NR$^b$R$^c$,
  (vi) —S(O)$_v$R$^d$,
  (vii) —C(=O)NR$^b$R$^c$, and
  (viii) phenyl,
(b) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
  (i) halo,
  (ii) —C$_{1-6}$alkyl, which is unsubstituted or substituted with 1-5 halo, and
  (iii) —OR$^a$,
(c) —OR$^a$,
(d) halo,
(e) —CO$_2$R$^a$,
(f) —C(=O)NR$^b$R$^c$,
(g) —S(O)$_v$R$^d$,
(h) —CN,
(i) —NR$^b$R$^c$,
(j) —N(R$^b$)C(=O)R$^a$,
(k) —N(R$^b$)SO$_2$R$^d$,
(l) —O—CO$_2$R$^d$,
(m) —O—(C=O)—NR$^b$R$^c$,
(n) —NR$^b$—(C=O)—NR$^b$R$^c$, and
(o) —C(=O)R$^a$;

R$^{PG}$ is independently selected from:
(1) hydrogen,
(2) —C$_{1-6}$alkyl which is unsubstituted or substituted with 1-5 halo,
(3) —CH$_2$OR$^a$,
(4) —CH$_2$—O—CH$_2$CH$_2$Si(CH$_3$)$_3$,
(5) —CH$_2$OP(=O)(OR$^c$)$_2$,
(6) —(CH$_2$)$_k$-phenyl, which is unsubstituted or substituted with 1-3 substituents each independently selected from:
(a) halo,
(b) —OR$^a$,
(c) —CN, and
(d) —C$_{1-6}$alkyl, which is unsubstituted or substituted with 1-6 halo;

J is independently selected from:
(1) =C(R$^{16a}$)—,
(2) —CR$^{17}$R$^{18}$—,
(3) —C(=O)—, and
(4) —N(R$^b$)—;

Y is independently selected from:
(1) =C(R$^{16b}$)—,
(2) —CR$^{17}$R$^{18}$,
(3) —C(=O)—,
(4) =N—, and
(5) —N(R$^{16b}$)—;

R$^{17}$ and R$^{18}$ are each independently selected from:
(1) hydrogen,
(2) halo, (3) —OR$^a$,
(4) —C$_{1-6}$alkyl, which is unsubstituted or substituted with 1-4 substituents each independently selected from:
  (a) halo,
  (b) —OR$^a$,
  (c) —CN,
  (d) phenyl or heterocycle, wherein said heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from:
    (i) —OR$^a$,
    (ii) halo,
    (iii) —CN,
    (iv) —C$_{1-6}$alkyl which is unsubstituted or substituted with 1-6 halo,
(5) phenyl or heterocycle wherein heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from:
  (a) halo,
  (b) —CN,
  (c) —OR$^a$,
  (d) nitro,
  (e) —C$_{1-6}$alkyl which is unsubstituted or substituted with 1-6 halo;
or R$^{17}$ and R$^{18}$ and the atom to which they are attached join to form a 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
  (a) halo,
  (b) —OR$^a$,
  (c) —C$_{1-6}$alkyl, which is unsubstituted or substituted with 1-6 halo, and
  (d) phenyl;

R$^{16a}$ and R$^{16b}$ are each independently selected from:
(1) hydrogen,
(2) —C$_{1-4}$alkyl, which is unsubstituted or substituted with 1-5 substituents each independently selected from:
  (a) halo,
  (b) —OR$^a$,
  (c) —C$_{3-6}$cycloalkyl,
  (d) phenyl or heterocycle, wherein said heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl, isoxazolyl and morpholinyl, which phenyl or heterocycle is unsubstituted or substituted with 1-3 substituents each independently selected from:
    (i) halo,
    (ii) —OR$^a$,
    (iii) —CN, and
    (iv) C$_{1-6}$alkyl, which is unsubstituted or substituted with 1-6 halo,
(3) phenyl or heterocycle, wherein heterocycle is selected from: imidazolyl, oxazolyl, pyridyl, pyrimidinyl, pyrazinyl, pyridazinyl, tetrahydrofuryl, piperidinyl, piperazinyl, pyrrolidinyl, azetidinyl, thiazolyl, thienyl, triazolyl, isoxazolyl and morpholinyl, which phenyl or heterocycle is unsubstituted or substituted with 1-3 substituents each independently selected from:
  (a) halo,
  (b) —OR$^a$,
  (c) —C$_{3-6}$cycloalkyl,
  (d) —C$_{1-4}$alkyl which is unsubstituted or substituted with 1-6 halo, and
  (e) phenyl, which is unsubstituted or substituted with 1-5 substituents each independently selected from:
    (i) halo,
    (ii) —C$_{1-6}$alkyl, which is unsubstituted or substituted with 1-6 halo, and
    (iii) —OR$^a$,
(4) halo,
(5) —OR$^a$,
(6) —CN,
(7) —CO$_2$R$^a$,
(8) NR$^b$R$^c$, and
(9) —C(=O)NR$^b$R$^c$;
or R$^{16a}$ and R$^{16b}$ and the atom(s) to which they are attached join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
  (a) —C$_{1-6}$alkyl, which is unsubstituted or substituted with 1-3 substituents each independently selected from:
    (i) halo,
    (ii) —OR$^a$,
    (iii) —C$_{3-6}$cycloalkyl,
    (iv) phenyl or heterocycle, wherein heterocycle is selected from pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from:
      (I) —OR$^a$,
      (II) halo,
      (III) —CN, and
      (IV) —C$_{1-6}$alkyl which is unsubstituted or substituted with 1-6 halo,
    (v) —CO$_2$R$^a$,
    (vi) —NR$^b$R$^c$,
    (vii) —S(O)$_v$R$^d$,
    (viii) —C(=O)NR$^b$R$^c$,
    (ix) —N(R$^b$)CO$_2$R$^a$, and
    (x) —N(R$^b$)SO$_2$R$^d$,
  (b) phenyl or heterocycle, wherein said heterocycle is selected from pyridyl, pyrimidinyl, pyrazinyl, pyridazinyl, piperidinyl, azetidinyl, piperazinyl, pyrrolidinyl, thienyl and morpholinyl, which phenyl or heterocycle is unsubstituted or substituted with 1-5 substituents each independently selected from:
    (i) halo,
    (ii) —OR$^a$,
    (iii) —CN, and
    (iv) —C$_{1-6}$alkyl which is unsubstituted or substituted with 1-6 halo,
  (c) halo,
  (d) —S(O)$_v$R$^d$,
  (e) —OR$^a$,
  (f) —CN,
  (g) —C(=O)R$^a$,
  (h) —NR$^b$R$^c$, (i) —C(=O)NR$^b$R$^c$,
(j) —CO$_2$R$^a$,
(k) —(NR$^b$)CO$_2$R$^a$,
(l) —O—(C=O)—NR$^b$R$^c$,
(m) —(NR$^b$)—(C=O)—NR$^b$R$^c$,
(n) oxido,
(o) oxo, and
(p) —(R$^b$)SO$_2$R$^d$;

R$^a$ is independently selected from:
  (1) hydrogen,
  (2) C$_{1-6}$alkyl, which is unsubstituted or substituted with 1-7 substituents each independently selected from:
    (a) halo,
    (b) —O—C$_{1-6}$alkyl, which is unsubstituted or substituted with 1-6 halo,
    (c) hydroxyl,
    (d) —CN, and
    (e) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
      (i) halo,
      (ii) —O—C$_{1-6}$alkyl, which is unsubstituted or substituted with 1-6 halo,
      (iii) —CN,
      (iv) nitro,
      (v) hydroxyl, and
      (vi) —C$_{1-6}$alkyl, which is unsubstituted or substituted with 1-6 halo,
  (3) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (a) halo,
    (b) —CN,
    (c) —O—C$_{1-6}$alkyl, which is unsubstituted or substituted with 1-6 halo,
    (d) nitro,
    (e) hydroxyl, and
    (f) —C$_{1-6}$alkyl, which is unsubstituted or substituted with 1-6 halo, and
  (4) —C$_{3-6}$cycloalkyl, which is unsubstituted or substituted with 1-6 halo;

R$^b$ and R$^c$ are independently selected from:
  (1) hydrogen,
  (2) C$_{1-6}$alkyl, which is unsubstituted or substituted with 1-7 substituents each independently selected from:
    (a) halo,
    (b) —OR$^a$,
    (c) —CN,
    (d) —CO$_2$R$^a$,
    (e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
      (i) halo,
      (ii) —OR$^a$,
      (iii) —C$_{1-6}$alkyl, which is unsubstituted or substituted with 1-6 halo, and
      (iv) nitro,
  (3) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (a) halo,
    (b) —OR$^a$,
    (c) —C$_{1-6}$alkyl, which is unsubstituted or substituted with 1-6 halo,
    (d) —C$_{3-6}$cycloalkyl, which is unsubstituted or substituted with 1-6 halo,
    (e) —CN, and
    (f) —CO$_2$R$^a$,
  (4) —C$_{3-6}$cycloalkyl, which is unsubstituted or substituted with 1-6 halo;
  or R$^b$ and R$^c$ and the nitrogen to which they are attached join to form a 4-, 5-, or 6-membered ring optionally containing an additional heteroatom selected from N, O, and S, wherein the sulfur is optionally oxidized to the sulfone or sulfoxide, which ring is unsubstituted or substituted with 1-4 substituents each independently selected from:
    (a) halo,
    (b) —OR$^a$, and
    (c) —C$_{1-6}$alkyl, which is unsubstituted or substituted with 1-6 halo, and
    (d) phenyl;

R$^d$ is independently selected from:
  (1) C$_{1-6}$alkyl, which is unsubstituted or substituted with 1-4 substituents each independently selected from:
    (a) halo,
    (b) —OR$^a$,
    (c) —CO$_2$R$^a$,
    (d) —CN, and
    (e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
      (i) halo,
      (ii) —OR$^a$,
      (iii) —C$_{1-6}$alkyl, which is unsubstituted or substituted with 1-6 halo, and
      (iv) nitro,
  (2) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (a) halo,
    (b) —OR$^a$,
    (c) —C$_{1-6}$alkyl, which is unsubstituted or substituted with 1-6 halo,
    (d) —C$_{3-6}$cycloalkyl, which is unsubstituted or substituted with 1-6 halo
    (e) —CN, and
    (f) —CO$_2$R$^a$, and (3) —$C_{3-6}$cycloalkyl, which is unsubstituted or substituted with 1-6 halo;

$R^e$ and $R^f$ are independently selected from:
(1) hydrogen,
(2) —$C_{1-4}$alkyl, which is unsubstituted or substituted with 1-6 halo,
(3) phenyl, and
(4) benzyl;
or where $R^e$ and $R^f$ and the atom to which they are attached join to form a 3-, 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
(a) halo,
(b) —$OR^a$,
(c) —$C_{1-6}$alkyl, which is unsubstituted or substituted with 1-6 halo, and
(d) phenyl;

m is 1, 2, or 3;

n is 1, 2, or 3;

v is 0, 1, or 2;

k is 0, 1, or 2;

and pharmaceutically acceptable salts thereof and individual enantiomers and diastereomers thereof.

An embodiment of the invention includes compounds of formula Ia:

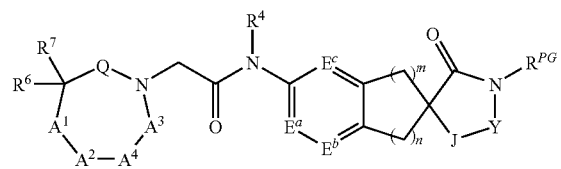

Ia wherein $A^1$, $A^2$, $A^3$, $A^4$, m, n, J, Q, $R^4$, $E^a$, $E^b$, $E^c$, $R^6$, $R^7$, $R^{PG}$ and Y are defined herein;

and pharmaceutically acceptable salts thereof and individual enantiomers and diastereomers thereof.

Another embodiment of the invention includes compounds of formula Ib:

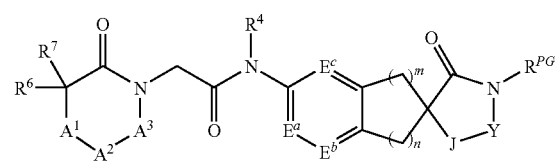

Ib wherein $A^1$, $A^2$, $A^3$, J, Y, $R^4$, $E^a$, $E^b$, $E^c$, $R^6$, $R^7$, $R^{PG}$ m and n are defined herein;

and pharmaceutically acceptable salts thereof and individual enantiomers and diastereomers thereof.

Another embodiment of the invention includes compounds of formula Ic:

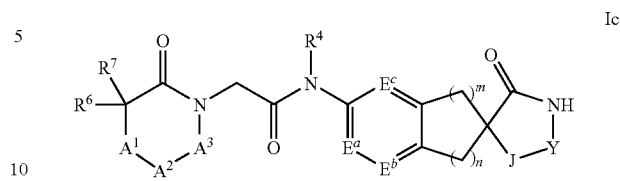

Ic wherein $A^1$, $A^2$, $A^3$, J, Y, $R^4$, $E^a$, $E^b$, $E^c$, $R^6$, $R^7$, m and n are defined herein;

and pharmaceutically acceptable salts thereof and individual enantiomers and diastereomers thereof.

Another embodiment of the invention includes compounds of formula Id:

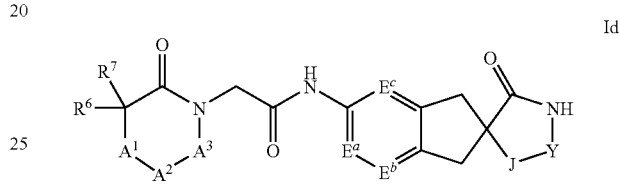

Id wherein $A^1$, $A^2$, $A^3$, J, Y, $E^a$, $E^b$, $E^c$, $R^6$, and $R^7$ are defined herein;

and pharmaceutically acceptable salts thereof and individual enantiomers and diastereomers thereof.

Another embodiment of the invention includes compounds of formula Ie:

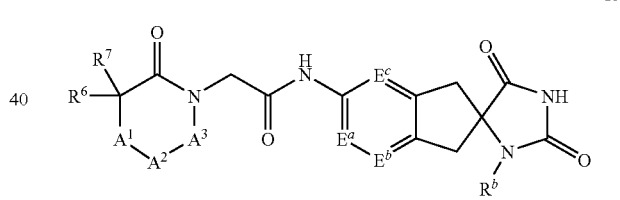

Ie wherein $A^1$, $A^2$, $A^3$, $E^a$, $E^b$, $E^c$, $R^b$, $R^6$, and $R^7$ are defined herein;

and pharmaceutically acceptable salts thereof and individual enantiomers and diastereomers thereof.

Another embodiment of the invention includes compounds of formula If:

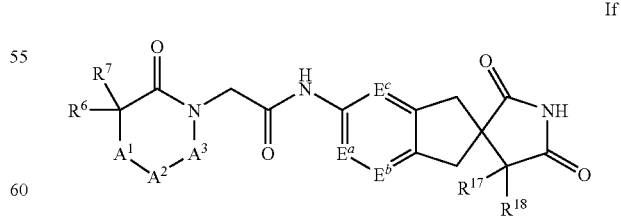

If wherein $A^1$, $A^2$, $A^3$, $E^a$, $E^b$, $E^c$, $R^6$, $R^7$, $R^{17}$ and $R^{18}$ are defined herein;

and pharmaceutically acceptable salts thereof and individual enantiomers and diastereomers thereof.

Another embodiment of the invention includes compounds of formula Ig:

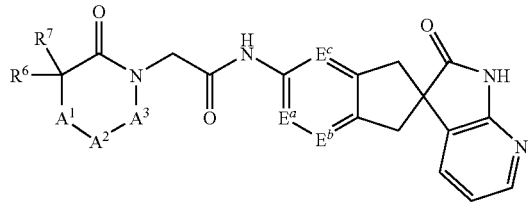

wherein $A^1, A^2, A^3, E^a, E^b, E^c, R^6$ and $R^7$ are defined herein;

and pharmaceutically acceptable salts thereof and individual enantiomers and diastereomers thereof.

Another embodiment of the invention includes compounds of formula Ih:

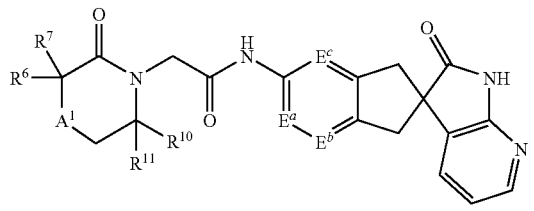

wherein $A^1, E^a, E^b, E^c, R^7, R^{10}$ and $R^{11}$ are defined herein;

and pharmaceutically acceptable salts thereof and individual enantiomers and diastereomers thereof.

In an embodiment of the present invention $A^1$ is independently selected from:
(1) —O—,
(2) —S(O)$_v$—,
(3) —Si(OR$^a$)(—C$_{1-4}$alkyl, which is unsubstituted or substituted with 1-5 halo)-,
(4) —Si(—C$_{1-4}$alkyl, which is unsubstituted or substituted with 1-5 halo)$_2$-,
(5) —CR$^6$R$^7$—,
(6) —N(R$^8$)—,
(7) —(C=O)—,
(8) —C(R$^8$)(R$^a$)—,
(9) —C(N(R$^b$)—SO$_2$R$^d$)(R$^a$)—,
(10) —C(N(R$^b$)(C=O)R$^a$)(R$^a$)—,
(11) —C(N(R$^b$)(C=O)OR$^a$)(R$^a$)—,
(12) —CR$^{10}$R$^{11}$—, and
(13) —N(R$^{11}$)—, wherein v, R$^6$, R$^7$, R$^8$, R$^a$, R$^b$, R$^c$, R$^d$, R$^{10}$ and R$^{11}$ are defined herein.

In an embodiment of the present invention $A^1$ is independently selected from:
(1) —O—,
(2) —S(O)$_v$—,
(3) —CR$^6$R$^7$—,
(4) —N(R$^8$)—,
(5) —C(N(R$^b$)(C=O)OR$^a$)(R$^a$)—,
(6) —(C=O)—, and
(7) —N(R$^{11}$)—, wherein v, R$^6$, R$^7$, R$^8$, R$^a$, R$^b$, R$^c$ and R$^{11}$ are defined herein.

In an embodiment of the present invention $A^1$ is —O—.
In an embodiment of the present invention $A^1$ is —S(O)$_v$—, wherein v is defined herein.

In an embodiment of the present invention $A^1$ is —CR$^6$R$^7$—, wherein R$^6$ and R$^7$ are defined herein.
In an embodiment of the present invention $A^1$ is CH$_2$.
In an embodiment of the present invention $A^1$ is —N(R$^8$)—, wherein R$^8$ is defined herein.
In an embodiment of the present invention $A^1$ is —NH—.
In an embodiment of the present invention $A^1$ is —C(OR$^a$)H—, wherein R$^a$ is defined herein.
In an embodiment of the present invention $A^1$ is —C(=O)—.
In an embodiment of the present invention $A^1$ is —C(NR$^b$R$^c$)H—, wherein R$^b$ and R$^c$ are defined herein.
In an embodiment of the present invention $A^1$ is —C(N(R$^b$)(C=O)OR$^a$)H—, wherein R$^a$ and R$^b$ are defined herein.

In an embodiment of the present invention $A^2$ is independently selected from:
(1) —CR$^6$R$^7$—,
(2) —CR$^{10}$R$^{11}$—, and
(3) —(C=O)—, wherein R$^6$, R$^7$, R$^{10}$ and R$^{11}$ are defined herein.

In an embodiment of the present invention $A^2$ is —CR$^6$R$^7$—, wherein R$^6$ and R$^7$ are defined herein.
In an embodiment of the present invention $A^2$ is —CH$_2$—.
In an embodiment of the present invention $A^2$ is —(C=O)—.

In an embodiment of the present invention $A^3$ is independently selected from:
(1) —CR$^6$R$^7$—,
(2) —CR$^{10}$R$^{11}$—, and
(3) —N(R$^{11}$)—, wherein R$^6$, R$^7$, R$^{10}$ and R$^{11}$ are defined herein.

In an embodiment of the present invention $A^3$ is —CR$^6$R$^7$—, wherein R$^6$ and R$^7$ are defined herein.
In an embodiment of the present invention $A^3$ is —CR$^{10}$R$^{11}$—, wherein R$^{10}$ and R$^{11}$ are defined herein.

In an embodiment of the present invention $A^4$ is independently selected from:
(1) —CR$^6$R$^7$—,
(2) —CR$^{10}$R$^{11}$—,
(3) —N(R$^{11}$)—,
(4) —N(R$^8$)—, and
(4) a bond between $A^2$ and $A^3$, wherein R$^6$, R$^7$, R$^8$, R$^{10}$ and R$^{11}$ are defined herein.

In an embodiment of the present invention $A^4$ is CH$_2$.
In an embodiment of the present invention $A^4$ is a bond between $A^2$ and $A^3$.

In an embodiment of the present invention $E^a$ is independently selected from:
(1) —C(R$^{5a}$)=,
(2) —N=, and
(3) —(N$^+$—O$^-$)=, wherein R$^{5a}$ is defined herein.

In an embodiment of the present invention $E^a$ is —C(R$^{5a}$)=, wherein R$^{5a}$ is defined herein.
In an embodiment of the present invention $E^a$ is —C(H)=.
In an embodiment of the present invention $E^a$ is —N=.

In an embodiment of the present invention $E^b$ is independently selected from:
(1) —C(R$^{5b}$)=,
(2) —N=, and
(3) —(N$^+$—O$^-$)=, wherein R$^{5b}$ is defined herein.

In an embodiment of the present invention $E^b$ is —C(R$^{5b}$)=, wherein R$^{5b}$ is defined herein.
In an embodiment of the present invention $E^b$ is —C(H)=.
In an embodiment of the present invention $E^b$ is —N=.

In an embodiment of the present invention $E^c$ is independently selected from:
(1) —C($R^{5c}$)=,
(2) —N=, and
(3) —($N^+$—$O^-$)=, wherein $R^{5c}$ is defined herein.

In an embodiment of the present invention $E^c$ is —C($R^{5c}$)=, wherein $R^{5c}$ is defined herein.

In an embodiment of the present invention $E^c$ is —C(H)=.

In an embodiment of the present invention $E^c$ is —N=.

In an embodiment of the present invention Q is —(C=O)—.

In an embodiment of the present invention $R^4$ is selected from: hydrogen and —$C_{1-6}$alkyl, which is unsubstituted or substituted with 1-5 fluoro.

In an embodiment of the present invention $R^4$ is hydrogen.

In an embodiment of the present invention $R^{5a}$, $R^{5b}$ and $R^{5c}$ are independently selected from hydrogen, halo, and —$C_{1-6}$alkyl, which is unsubstituted or substituted with 1-5 fluoro.

In an embodiment of the present invention $R^{5a}$, $R^{5b}$ and $R^{5c}$ are independently selected from hydrogen and halo.

In an embodiment of the present invention $R^{5a}$, $R^{5b}$ and $R^{5c}$ are hydrogen.

In an embodiment of the present invention $R^6$ and $R^7$ are independently selected from:
(1) hydrogen,
(2) —$C_{1-6}$alkyl, which is unsubstituted or substituted with 1-5 substituents where the substitutents are each independently selected from: halo, phenyl, and —$OR^a$,
(3) —$C_{3-6}$cycloalkyl, which is unsubstituted or substituted with 1-5 fluoro,
(4) phenyl or heterocycle, which is unsubstituted or substituted with 1-5 halo, wherein heterocycle is defined herein,
(5) halo,
(6) —$OR^a$,
(7) —$NR^bR^c$, and
(8) —O(C=O)$R^a$, wherein $R^a$, $R^b$ and $R^c$ are defined herein.

In an embodiment of the present invention $R^6$ and $R^7$ are independently selected from:
(1) hydrogen,
(2) —$C_{1-6}$alkyl, which is unsubstituted or substituted with 1-5 fluoro,
(3) phenyl, which is unsubstituted or substituted with 1-5 halo, and
(4) halo,
(5) —$OR^a$, and
(6) —$NR^bR^c$, wherein $R^a$, $R^b$ and $R^c$ are defined herein.

In an embodiment of the present invention $R^6$ and $R^7$ are independently selected from hydrogen, OH and —$C_{1-6}$alkyl, which is unsubstituted or substituted with 1-5 fluoro.

In an embodiment of the present invention $R^6$ and $R^7$ are independently selected from hydrogen, —$NR^bR^c$ and —$C_{1-6}$alkyl, which is unsubstituted or substituted with 1-5 fluoro, wherein $R^b$ and $R^c$ are defined herein.

In an embodiment of the present invention $R^6$ and $R^7$ are independently selected from hydrogen, —$NH_2$ and —$C_{1-6}$alkyl, which is unsubstituted or substituted with 1-5 fluoro.

In an embodiment of the present invention $R^6$ and $R^7$ are independently selected from hydrogen and —$C_{1-6}$alkyl, which is unsubstituted or substituted with 1-5 fluoro.

In an embodiment of the present invention $R^6$ and $R^7$ are ethyl, which are unsubstituted or substituted with 1-5 fluoro.

In an embodiment of the present invention $R^6$ and $R^7$ are methyl, which are unsubstituted or substituted with 1-3 fluoro.

In an embodiment of the present invention $R^6$ and $R^7$ and the carbon atom or atoms to which they are attached join to form a ring selected from cyclopropyl, cyclobutyl, cyclopentyl, cyclohexyl, cycloheptyl, cyclooctyl, cyclopentenyl, cyclohexenyl, cycloheptenyl, dioxolanyl, dioxanyl, tetrahydrofuranyl, tetrahydropyranyl, pyrrolidinyl, and piperidinyl, which ring is unsubstituted or substituted with 1-6 substituents each independently selected from:
(1) —$C_{1-6}$alkyl, which is unsubstituted or substituted with 1-3 substituents where the substitutents are each independently selected from: halo, —$OR^a$, and phenyl,
(2) —$C_{3-6}$cycloalkyl, wherein the $C_{3-6}$cycloalkyl group is optionally fused to the ring, and which $C_{3-6}$cycloalkyl group is unsubstituted or substituted with 1-3 substituents each independently selected from: halo, —$OR^a$, and phenyl,
(3) phenyl or heterocycle, wherein heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, wherein the phenyl or heterocycle is optionally fused to the ring, and which phenyl or heterocycle is unsubstituted or substituted with 1-3 substituents each independently selected from: halo, —$OR^a$, and —$C_{1-4}$alkyl, which is unsubstituted or substituted with 1-5 fluoro,
(4) halo,
(5) oxo,
(6) —$CO_2R^a$, and
(7) —C(=O)$R^a$,
wherein $R^a$ is defined herein.

In an embodiment of the present invention $R^6$ and $R^7$ and the carbon atom or atoms to which they are attached join to form a ring selected from cyclopropyl, cyclobutyl, cyclopentyl, dioxolanyl, cyclohexyl, cycloheptyl, cyclopentenyl, cyclohexenyl, tetrahydropyranyl, pyrrolidinyl, and piperidinyl, which ring is unsubstituted or substituted with 1-6 substituents each independently selected from:
(1) —$C_{1-6}$alkyl, which is unsubstituted or substituted with 1-3 substituents where the substitutents are each independently selected from: halo, and —$OR^a$,
(2) phenyl or pyridyl, wherein the phenyl or pyridyl is optionally fused to the ring, and which phenyl or pyridyl is unsubstituted or substituted with 1-3 substituents each independently selected from: halo, —$OR^a$, and —$C_{1-4}$ alkyl, which is unsubstituted or substituted with 1-5 fluoro,
(3) halo, and
(4) —$CO_2R^a$,
wherein $R^a$ is defined herein.

In an embodiment of the present invention $R^6$ and $R^7$ and the carbon atom or atoms to which they are attached join to form a ring selected from cyclopropyl, cyclobutyl, cyclopentyl, cyclohexyl, cycloheptyl, tetrahydropyranyl, pyrrolidinyl, and piperidinyl, which ring is unsubstituted or substituted with 1-6 substituents each independently selected from:
(1) —$C_{1-6}$alkyl, which is unsubstituted or substituted with 1-3 halo,
(2) phenyl, wherein the phenyl is optionally fused to the ring, and which phenyl is unsubstituted or substituted with 1-3 substituents each independently selected from: halo, —$OR^a$, and —$C_{1-4}$alkyl, which is unsubstituted or substituted with 1-3 fluoro, and
(3) halo, wherein $R^a$ is defined herein.

In an embodiment of the present invention $R^8$ is selected from: hydrogen, —C(=O)$R^a$, —CO$_2$$R^a$, —SO$_2$$R^d$, and —C$_{1-6}$alkyl, which is unsubstituted or substituted with 1-5 fluoro, wherein $R^a$ and $R^d$ are defined herein.

In an embodiment of the present invention $R^8$ is selected from: hydrogen, and —C$_{1-6}$alkyl, which is unsubstituted or substituted with 1-5 fluoro.

In an embodiment of the present invention $R^8$ is hydrogen.

In an embodiment of the present invention $R^8$ is methyl

In an embodiment of the present invention $R^8$ and $R^7$ and the atoms to which they are attached join to form a 4-, 5-, 6- or 7-membered alkyl- or heteroalkyl-ring optionally containing an additional heteroatom selected from N, O, and S, wherein the sulfur is optionally oxidized to the sulfone or sulfoxide, which ring is unsubstituted or substituted with 1-4 substituents each independently selected from:

(1) halo,
(2) phenyl, which is unsubstituted or substituted with 1-3 substituents each independently selected from: halo, O$R^a$, CN, and —C(=O)O$R^a$,
(3) —O$R^a$, and
(4) —C$_{1-6}$alkyl, which is unsubstituted or substituted with 1-6 halo, wherein $R^a$ is defined herein.

In an embodiment of the present invention $R^{10}$ is selected from: hydrogen, and —C$_{1-6}$alkyl, which is unsubstituted or substituted with fluoro.

In an embodiment of the present invention $R^{10}$ is hydrogen.

In an embodiment of the present invention $R^{11}$ is independently selected from the group consisting of:

phenyl, naphthyl, tetrahydronaphthyl, indanyl, biphenyl, phenanthryl, anthryl, azepinyl, azepanyl, azetidinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiamorpholinyl sulfone, thiazolyl, thiazolinyl, thienofuryl, thienothienyl, thienyl, triazolyl, isoxazolyl, tetrahydrothienyl, tetrahydropyranyl, oxetanyl, tetrahydrothiopyranyl, and thietanyl, where $R^{11}$ is unsubstituted or substituted with 1-5 substituents each independently selected from $R^{12}$, $R^{13}$, $R^{14}$, $R^{15a}$ and $R^{15b}$, wherein $R^{12}$, $R^{13}$, $R^{14}$, $R^{15a}$ and $R^{15b}$ are defined herein.

In an embodiment of the present invention $R^{11}$ is independently selected from the group consisting of:

phenyl, furanyl, pyrazinyl, pyridinyl, pyridyl, pyrimidinyl, pyrimidyl, tetrazolyl, thienyl, triazolyl, and isoxazolyl, where $R^{11}$ is unsubstituted or substituted with 1-5 substituents each independently selected from $R^{12}$, $R^{13}$, $R^{14}$, $R^{15a}$ and $R^{15b}$, wherein $R^{12}$, $R^{13}$, $R^{14}$, $R^{15a}$ and $R^{15b}$ are defined herein.

In an embodiment of the present invention $R^{11}$ is independently selected from the group consisting of:

phenyl, pyridyl, and thienyl, where $R^{11}$ is unsubstituted or substituted with 1-5 substituents each independently selected from $R^{12}$, $R^{13}$, $R^{14}$, $R^{15a}$ and $R^{15b}$, wherein $R^{12}$, $R^{13}$, $R^{14}$, $R^{15a}$ and $R^{15b}$ are defined herein.

In an embodiment of the present invention $R^{11}$ is phenyl, which is unsubstituted or substituted with 1-5 substituents each independently selected from $R^{12}$, $R^{13}$, $R^{14}$, $R^{15a}$ and $R^{15b}$, wherein $R^{12}$, $R^{13}$, $R^{14}$, $R^{15a}$ and $R^{15b}$ are defined herein.

In an embodiment of the present invention $R^{PG}$ is selected from:

(1) hydrogen,
(2) —C$_{1-6}$alkyl, which is unsubstituted or substituted with 1-3 halo,
(3) —CH$_2$O$R^a$, and
(4) —CH$_2$—O—CH$_2$CH$_2$Si(CH$_3$)$_3$,
(5) —CH$_2$OP(=O)(O$R^c$)$_2$,
wherein $R^a$ and $R^c$ are defined herein.

In an embodiment of the present invention $R^{PG}$ is selected from: hydrogen and —C$_{1-6}$alkyl, which is unsubstituted or substituted with 1-3 halo.

In an embodiment of the present invention $R^{PG}$ is methyl.

In an embodiment of the present invention $R^{PG}$ is hydrogen.

In an embodiment of the present invention J is =C($R^{16a}$)—, —C$R^{17}R^{18}$— or —N($R^b$)—, wherein $R^{16a}$, $R^{17}$, $R^{18}$ and $R^b$ are defined herein.

In an embodiment of the present invention J is =C($R^{16a}$)—, wherein $R^{16a}$ is defined herein.

In an embodiment of the present invention J is —C$R^{17}R^{18}$—, wherein $R^{17}$ and $R^{18}$ are defined herein.

In an embodiment of the present invention J is —CH$_2$—.

In an embodiment of the present invention J is —N($R^b$)—, wherein $R^b$ is defined herein.

In an embodiment of the present invention J is —N(CH$_3$)—.

In an embodiment of the present invention Y is =C($R^{16b}$)—, —C$R^{17}R^{18}$— or —C(=O)—, wherein $R^{16b}$, $R^{17}$ and $R^{18}$ are defined herein.

In an embodiment of the present invention Y is =C($R^{16b}$)—, wherein $R^{16b}$ is defined herein.

In an embodiment of the present invention Y is —C(=O)—.

In an embodiment of the present invention $R^{16a}$ and $R^{16b}$ are independently selected from:

(1) hydrogen,
(2) —C$_{1-4}$alkyl, which is unsubstituted or substituted with 1-3 substituents each independently selected from: halo, —O$R^a$, —C$_{3-6}$cycloalkyl, and phenyl,
(3) phenyl or heterocycle, wherein heterocycle is selected from: pyridyl, pyrimidinyl, pyrazinyl, thiazolyl, thienyl, triazolyl, isoxazolyl and morpholinyl, which phenyl or heterocycle is unsubstituted or substituted with 1-3 substituents each independently selected from: —C$_{1-4}$alkyl which is unsubstituted or substituted with 1-3 halo, —O$R^a$, and halo,
(4) halo,
(5) O$R^a$, and
(6) —N$R^bR^c$, wherein $R^a$, $R^b$ and $R^c$ are defined herein.

In an embodiment of the present invention $R^{16a}$ and $R^{16b}$ are independently selected from:

(1) hydrogen,
(2) —C$_{1-4}$alkyl, which is unsubstituted or substituted with 1-3 fluoro, and (3) phenyl or heterocycle, wherein heterocycle is selected from: pyridyl, pyrimidinyl, pyrazinyl, thiazolyl, thienyl, triazolyl, isoxazolyl and morpholinyl.

In an embodiment of the present invention $R^{16a}$ and $R^{16b}$ and the atom(s) to which they are attached join to form a ring selected from cyclohexenyl, phenyl, pyridyl, pyrimidinyl, pyrazinyl, pyridazinyl, furanyl, oxazolyl, isoxazolyl, imidazolyl, and thienyl, which ring is unsubstituted or substituted with 1-3 substituents each independently selected from:
(1) —$C_{1-6}$alkyl, which is unsubstituted or substituted with 1-3 substituents each independently selected from: halo, $OR^a$, —$CO_2R^a$, —$NR^bR^c$, and $CONR^bR^c$,
(2) phenyl or heterocycle, wherein heterocycle is selected from pyridyl, pyrimidinyl, pyrazinyl, pyridazinyl, piperidinyl, azetidinyl, piperazinyl, pyrrolidinyl, thienyl and morpholinyl, which phenyl or heterocycle is unsubstituted or substituted with 1-3 substituents each independently selected from: halo, $OR^a$ and —$C_{1-4}$alkyl, which is unsubstituted or substituted with 1-3 fluoro,
(3) halo,
(4) $OR^a$,
(5) —CN,
(6) —$NR^bR^c$,
(7) $CONR^bR^c$, and
(8) oxo, wherein $R^a$, $R^b$ and $R^c$ are defined herein.

In an embodiment of the present invention $R^{16a}$ and $R^{16b}$ and the atom(s) to which they are attached join to form a ring selected from phenyl, pyridyl, and pyrimidinyl, which ring is unsubstituted or substituted with 1-3 substituents each independently selected from: halo, $OR^a$ and —$C_{1-4}$alkyl, which is unsubstituted or substituted with 1-3 fluoro, wherein $R^a$ is defined herein.

In an embodiment of the present invention $R^{16a}$ and $R^{16b}$ and the atom(s) to which they are attached join to form a ring selected from pyridyl, and pyrimidinyl.

In an embodiment of the present invention m is 1.
In an embodiment of the present invention n is 1.
In an embodiment of the present invention n is 2.

It is to be understood that where one or more of the above recited structures or substructures recite multiple substituents having the same designation each such variable may be the same or different from each similarly designated variable. For example, if $R^8$ is recited multiple times in an embodiment of formula I, each instance of $R^8$ in formula I may independently be any of the substructures defined under $R^8$. The invention is not limited to structures and substructures wherein each $R^8$ must be the same for a given structure. The same is true with respect to any variable appearing multiple times in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The present invention includes compounds of formula I wherein one or more hydrogen atoms are replaced by deuterium.

Tautomers of compounds defined in Formula I are also included within the scope of the present invention. For example, compounds including carbonyl —$CH_2C(=O)$— groups (keto forms) may undergo tautomerism to form hydroxyl —CH=C(OH)— groups (enol forms). Both keto and enol forms are included within the scope of the present invention.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, not all of the $R^6$ and $R^7$ substituents are capable of forming a ring structure. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear, branched and cyclic structures having no carbon-to-carbon double or triple bonds. Thus $C_{1-6}$alkyl is defined to identify the group as having 1, 2, 3, 4, 5 or 6 carbons in a linear or branched arrangement, such that $C_{1-6}$alkyl specifically includes, but is not limited to, methyl, ethyl, n-propyl, iso-propyl, n-butyl, iso-butyl, tert-butyl, pentyl and hexyl. "Cycloalkyl" is an alkyl, part or all of which forms a ring of three or more atoms. $C_0$ or $C_0$alkyl is defined to identify the presence of a direct covalent bond.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. Thus $C_{2-6}$alkynyl is defined to identify the group as having 2, 3, 4, 5 or 6 carbons in a linear or branched arrangement, such that $C_{2-6}$alkynyl specifically includes 2-hexynyl and 2-pentynyl.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronaphthyl, indanyl, or biphenyl.

The term "heterocycle" or "heterocyclic", as used herein except where noted, represents a stable 4- to 8-membered monocyclic- or stable 8- to 12-membered bicyclic heterocyclic ring system which is either saturated or unsaturated, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which is selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J Pharmacol.* 415, 39-44). Briefly, membranes (25 µg) were incubated in 1 mL of binding buffer [10 mM HEPES, pH 7.4, 5 mM MgCl$_2$ and 0.2% bovine serum albumin (BSA)] containing 10 pM $^{125}$I-CGRP and antagonist. After incubation at room temperature for 3 h, the assay was terminated by filtration through GFB glass fibre filter plates (PerkinElmer) that had been blocked with 0.5% polyethyleneimine for 3 h. The filters were washed three times with ice-cold assay buffer (10 mM HEPES, pH 7.4 and 5 mM MgCl$_2$), then the plates were air dried. Scintillation fluid (50 µL) was added and the radioactivity was counted on a Topcount (Packard Instrument). Data analysis was carried out by using Prism and the K$_i$ was determined by using the Cheng-Prusoff equation (Cheng & Prusoff (1973) *Biochem. Pharmacol.* 22, 3099-3108).

RECOMBINANT RECEPTOR: Human CL receptor (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. HEK 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 µg/mL streptomycin, and maintained at 37° C. and 95% humidity. Cells were subcultured by treatment with 0.25% trypsin with 0.1% EDTA in HBSS. Stable cell line generation was accomplished by co-transfecting 10 µg of DNA with 30 µg Lipofectamine 2000 (Invitrogen) in 75 cm$^2$ flasks. CL receptor and RAMP1 expression constructs were co-transfected in equal amounts. Twenty-four hours after transfection the cells were diluted and selective medium (growth medium+300 µg/mL hygromycin and 1 µg/mL puromycin) was added the following day. A clonal cell line was generated by single cell deposition utilizing a FACS Vantage SE (Becton Dickinson). Growth medium was adjusted to 150 µg/mL hygromycin and 0.5 µg/mL puromycin for cell propagation.

RECOMBINANT RECEPTOR BINDING ASSAY: Cells expressing recombinant human CL receptor/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 20 µg of membranes were incubated in 1 ml binding buffer (10 mM HEPES, pH 7.4, 5 mM MgCl$_2$, and 0.2% BSA) for 3 hours at room temperature containing 10 pM $^{125}$I-hCGRP (GE Healthcare) and antagonist. The assay was terminated by filtration through 96-well GFB glass fiber filter plates (PerkinElmer) that had been blocked with 0.05% polyethyleneimine. The filters were washed 3 times with ice-cold assay buffer (10 mM HEPES, pH 7.4 and 5 mM MgCl$_2$). Scintillation fluid was added and the plates were counted on a Topcount (Packard). Non-specific binding was determined and the data analysis was carried out with the apparent dissociation constant (K$_i$) determined by using a non-linear least squares fitting the bound CPM data to the equation below:

$$Y_{obsd} = \frac{Y_{min} + (Y_{max} - Y_{min})(100 - \% I_{max}/100)}{1 + ([Drug]/K_i(1 + [Radioladel]/K_d)^{nH})} + \frac{(Y_{max} - Y_{min})(\% I_{max} - \% I_{min}/100) +}{}$$

Where Y is observed CPM bound, Y$_{max}$ is total bound counts, Y$_{min}$ is non specific bound counts, (Y$_{max}$-Y$_{min}$) is specific bound counts, % I$_{max}$ is the maximum percent inhibition, % I min is the minimum percent inhibition, radiolabel is the probe, and the K$_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 µM and incubated for 30 min at 37° C. Human α-CGRP was added to the cells at a concentration of 0.3 nM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; GE Healthcare). Dose response curves were plotted and IC$_{50}$ values determined from a 4-parameter logistic fit as defined by the equation $y=((a-d)/(1+(x/c)^b)+d$, where y=response, x=dose, a=max response, d=min response, c=inflection point and b=slope.

In particular, the compounds of the following examples had activity as antagonists of the CGRP receptor in the aforementioned assays, generally with a $K_i$ or $IC_{50}$ value of less than about 50 μM. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-migraine agent, such as ergotamine and dihydroergotamine, or other serotonin agonists, especially a $5\text{-HT}_{1B/1D}$ agonist, for example sumatriptan, naratriptan, zolmitriptan, eletriptan, almotriptan, frovatriptan, donitriptan, and rizatriptan, a $5\text{-HT}_{1D}$ agonist such as PNU-142633 and a $5\text{-HT}_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sulfentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin $5\text{HT}_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocomine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-$HT_1$ agonist, especially a 5-$HT_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

SCHEME 1

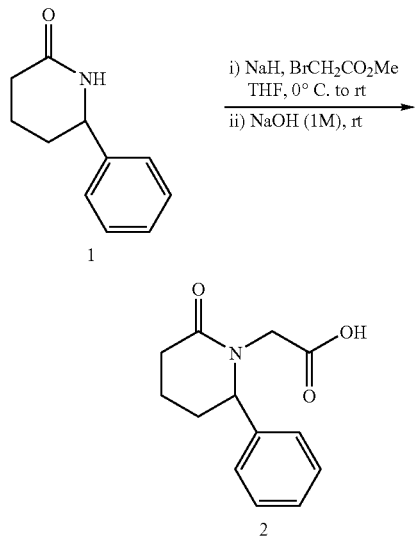

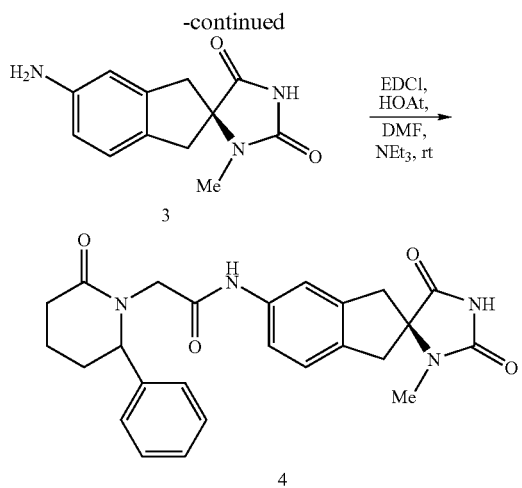

Lactam 1 can be deprotonated with the strong base sodium hydride, in THF, to provide the amide anion which smoothly reacts with the electrophilic methyl bromoacetate. Subsequent treatment of this ester product, still in THF, with aqueous sodium hydroxide gives the acid 2. Acid 2 can be coupled to the known aniline 3 (Bell, I. M., et al., PCT Int. Appl., WO 2004082605 A2 20040930) employing the standard peptide coupling reagent combination of EDCI, HOAt and triethylamine, in DMF, to provided the claimed compound 4. Analogs of lactam 1, if not commercially available, can be prepared by a variety of common methods, one of which is illustrated in Scheme 2, for the preparation of Intermediate 1.

SCHEME 2

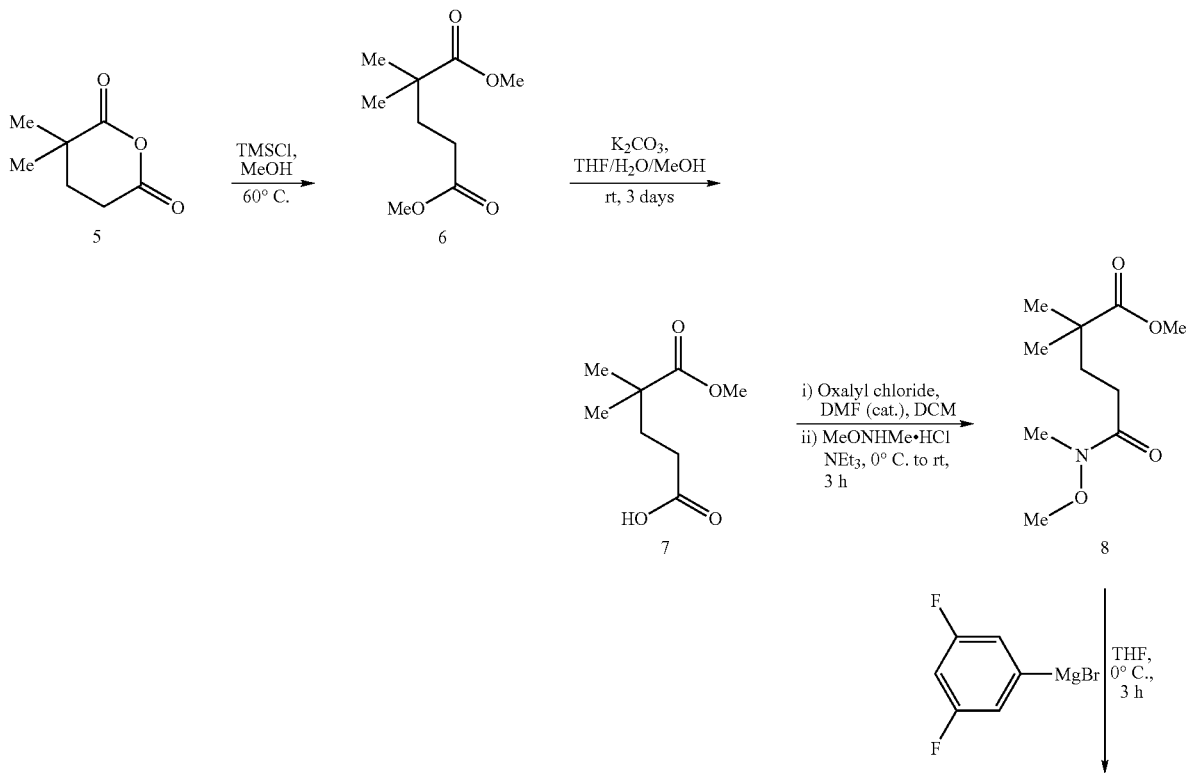

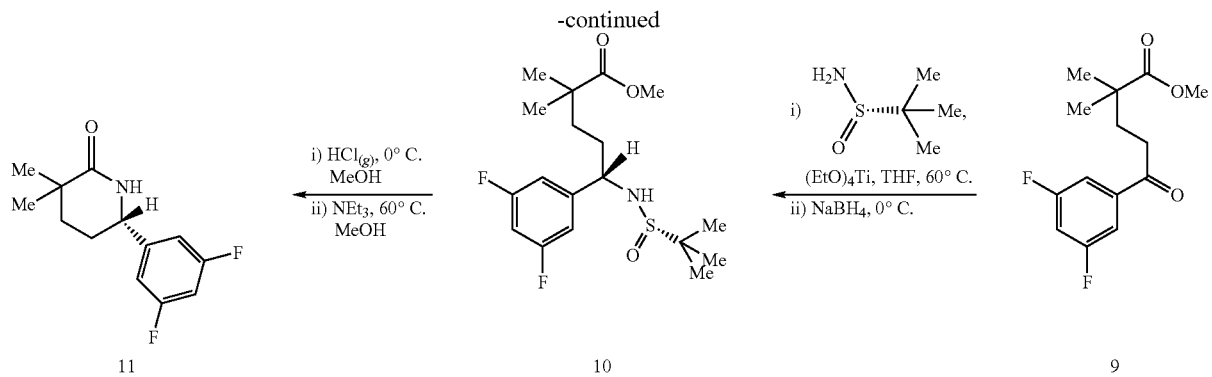

Anhydride 5 can be converted to the bis-ester 6, though heating in methanol, in the presence of HCl (generated from the reaction of TMSCl with MeOH). The less hindered ester of 6 can be selectively hydrolyzed with potassium carbonate, in a mixture of THF, water and MeOH over the course of a few days. This acid can be converted in situ to the corresponding acid chloride utilizing oxalyl chloride and a catalytic amount of DMF, in DCM, at ambient temperature. In the same reaction vessel, excess amine (or an amine hydrochloride-triethylamine mixture) can be introduced to give the amide 8. The amide 8 yields the ketone 9 upon treatment with a Grignard reagent, or alternative organometallics, in THF at reduced temperatures. Alternatively, the pyrrolidinyl amide analog of 8 can be of similar utility. Aryl ketone 9, can then be transformed into the sulfinamide 10 according to the one-pot procedure of Ellman and coworkers, *Tetrahedron Lett.,* 1999, 40, 6709-6712. Treatment of 10 with anhydrous HCl in MeOH removes the t-butyl sulfinyl group, and upon addition of sufficient triethylamine, produces Intermediate 1 (compound 11), where heating is employed as necessary.

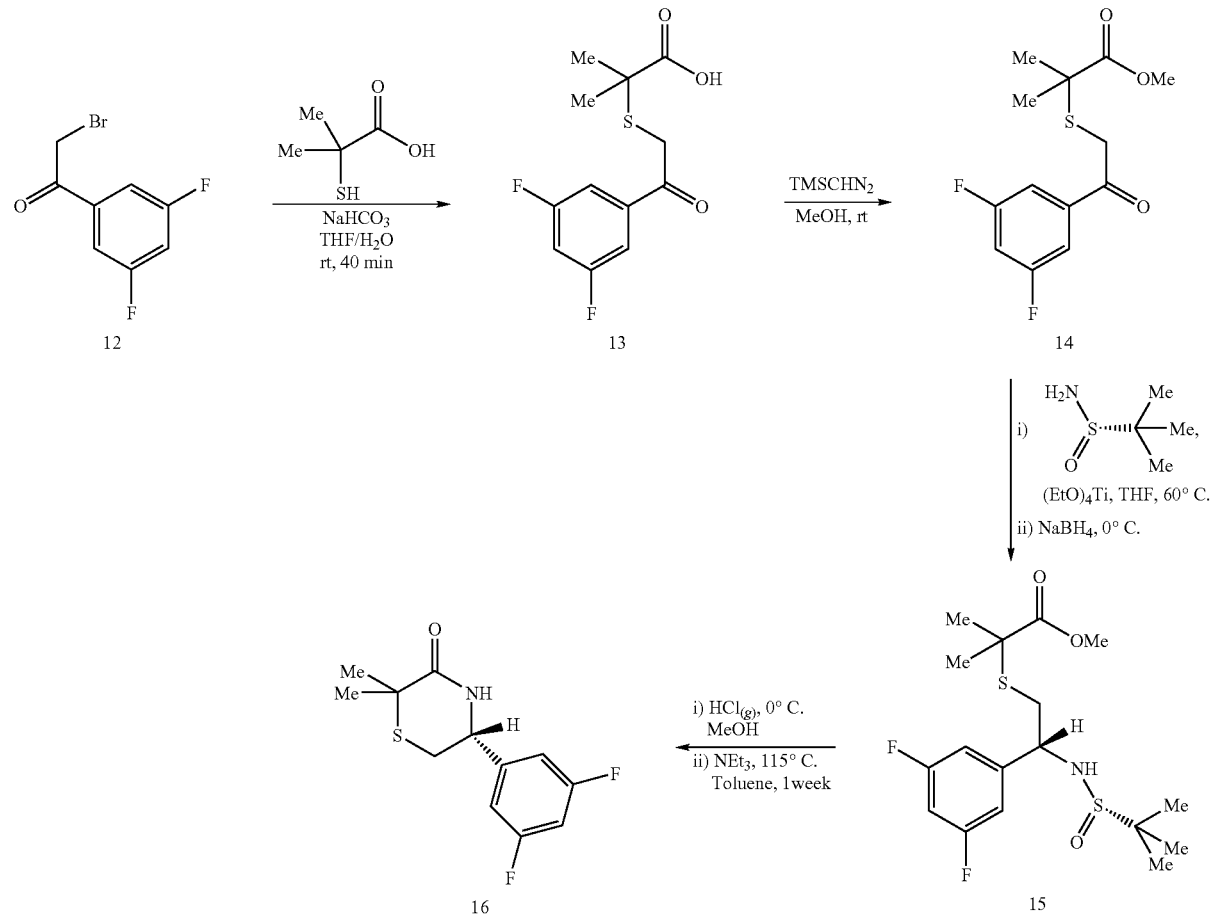

Bromide 12 can react with the thiol carboxylic acid in the presence of NaHCO$_3$ in a mixture of THF and water to produce the aryl ketone 13 at ambient temperature. The carboxylic acid 13 can be converted to the methyl ester 14 through treatment with TMS diazomethane. Compound 14, can then be transformed into the sulfinamide 15 according to the one-pot procedure of Ellman and coworkers, *Tetrahedron Lett.*, 1999, 40, 6709-6712. Treatment of 15 with anhydrous HCl in MeOH removes the t-butyl sulfinyl group, and upon addition of sufficient triethylamine, produces Intermediate 2 (compound 16), under refluxing conditions.

SCHEME 4

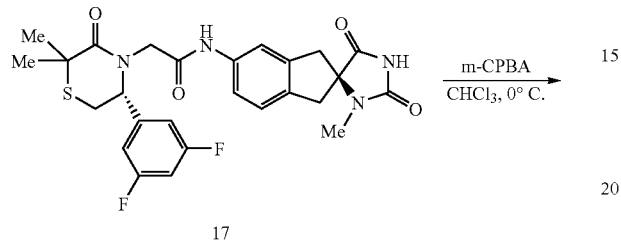

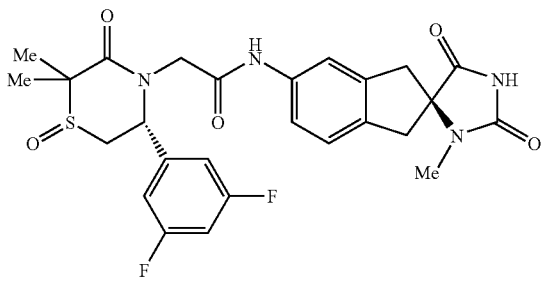

Compound 17, prepared from 16 according to Scheme 1, can be oxidized with m-CPBA in chloroform at 0° C. to generate 18 as a mixture of sulfoxides.

SCHEME 5

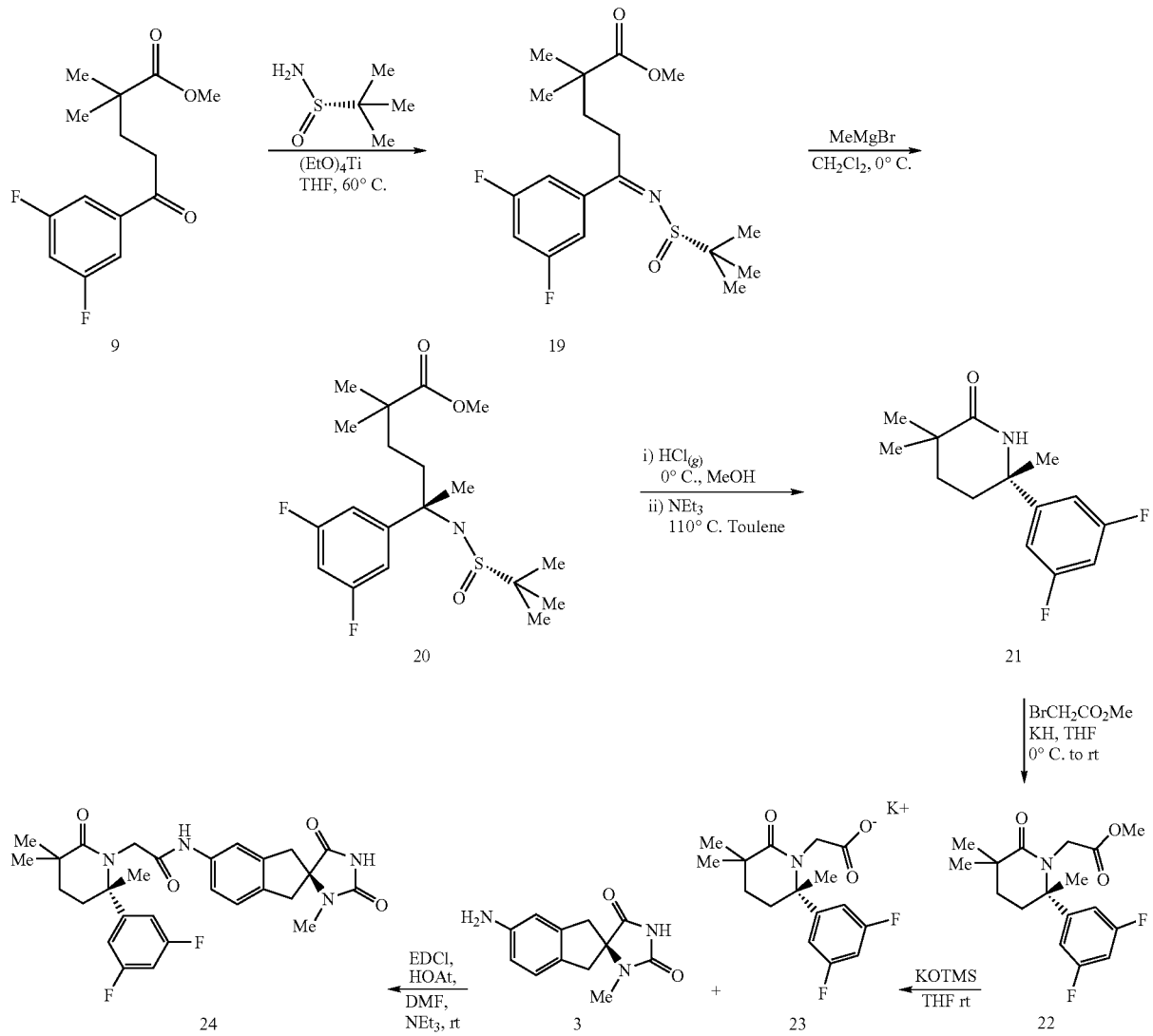

The aryl ketone 9 (from Scheme 2) can be transformed into the sulfinimine 19 utilizing Ti(OEt)$_4$ in THF at elevated temperatures. The sulfinimine can then be treated with a Grignard reagent, or alternative organometallics, in THF at reduced temperatures to produce the sulfinamide 20. Treatment of 20 with anhydrous HCl in MeOH removes the t-butyl sulfinyl group, and upon addition of sufficient triethylamine, produces the lactam 21, under refluxing conditions in toluene. Lactam 21 can be deprotonated with the strong base potassium hydride, in THF, to provide the amide anion which smoothly reacts with methyl bromoacetate. Treatment of this ester product 22, in THF with potassium trimethylsilanolate gives the potassium carboxylate 23. Compound 23 can be coupled to aniline 3 (Scheme 1), employing the standard peptide coupling reagent combination of EDCI, HOAt and triethylamine, in DMF, to provide the claimed compound 24.

pared by employing appropriately substituted starting materials or by derivatization of any intermediates and/or final products as desired by methods known in the art.

Scheme 7 illustrates a route to the 3-aminopyridine 41. 7-Azaindole (33) may be protected with a variety of protecting groups, such as the 2-(trimethylsilyl)ethoxymethyl group shown in Scheme 7. Following the method of Marfat and Carter [(1987) *Tetrahedron Lett.* 28, 4027], treatment of 34 with pyridine hydrobromide perbromide provides the dibromoazaoxindole 35, which may be reduced to the corresponding azaoxindole 36 by reaction with zinc. Bis-alkylation of the azaoxindole 36 with 1,4-dibromobutan-2-one [de Meijere et al. (2001) *Eur. J Org. Chem.* 3789] provides the cyclopentanone 37. Condensation of ketone 37 with ammonia and 1-methyl-3,5-dinitropyridin-2(1H)-one [Tohda et al. (1990) *Bull. Chem. Soc. Japan* 63, 2820] in refluxing methanol leads

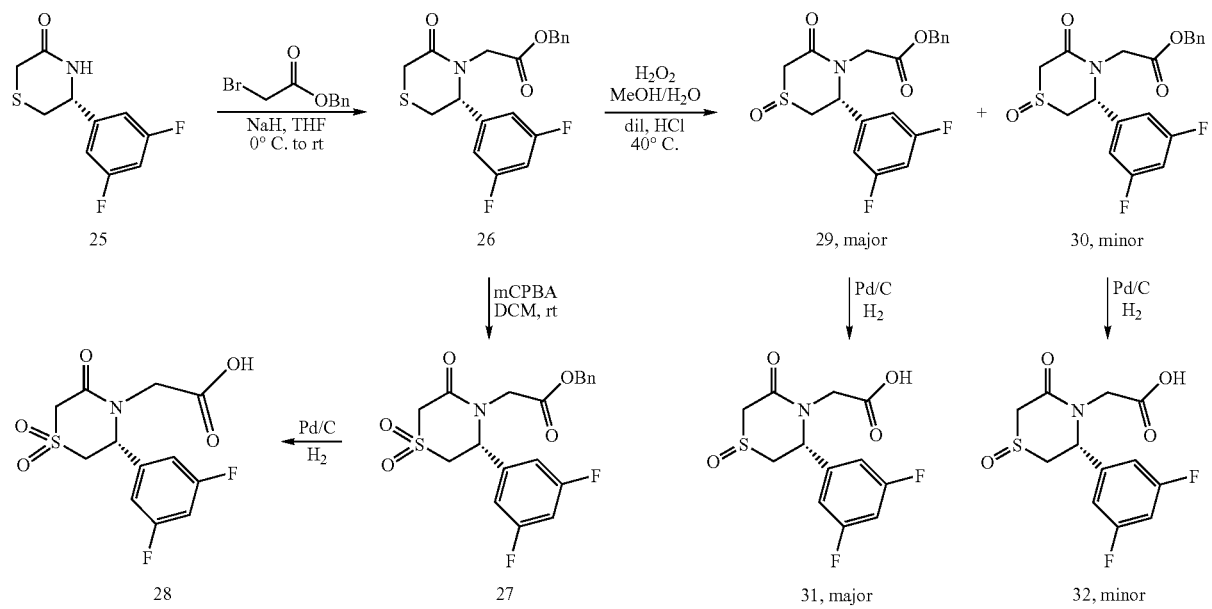

Individual sulfoxides and sulfones can be accessed as shown in Scheme 6, where these carboxylic acids (28, 31 and 32) can be utilized in a manner similar to compound 2, Scheme 1. Compound 25 (prepared according to Scheme 3) can be alkylated with benzyl bromoacetate in THF, subsequent to deprotonation with sodium hydride, to yield benzyl ester 26. The sulfur of 26 can be oxidized to the sulfone 27 using mCPBA in DCM, at ambient temperature. The benzyl ester of 27 can then be removed using palladium on carbon under an atmosphere of hydrogen to yield the carboxylic acid 28. The sulfur of 26 can be oxidized to a mixture of major and minor sulfoxides (29 and 30) using hydrogen peroxide, in an acidic mixture of water and methanol, at 40° C. This mixture of sulfoxides can be separated into the individual epimers prior to removal of the benzyl ester using palladium on carbon under an atmosphere of hydrogen to individually produce the carboxylic acids 31 and 32.

The synthesis of some heterocyclic amine intermediates may be conducted as described in Schemes 7-9. The methodology shown in these schemes is not limited to the azaoxindoles shown but may be applied to a variety of heterocyclic systems to give the corresponding spiro compounds. Related intermediates bearing a variety of substituents may be preto the 3-nitropyridine derivative 39. Catalytic hydrogenation may be used to provide the corresponding amine 40. Standard deprotection of 40 using sequential acid and base treatments affords the 3-aminopyridine intermediate 41.

SCHEME 7

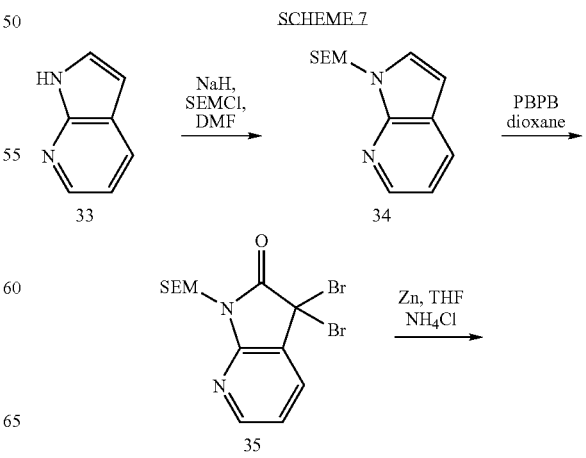

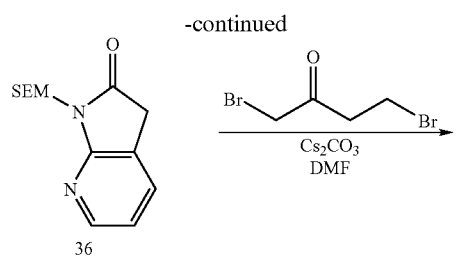
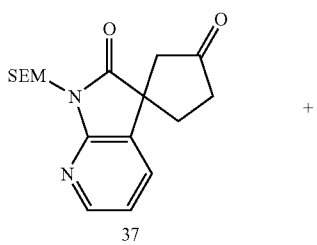
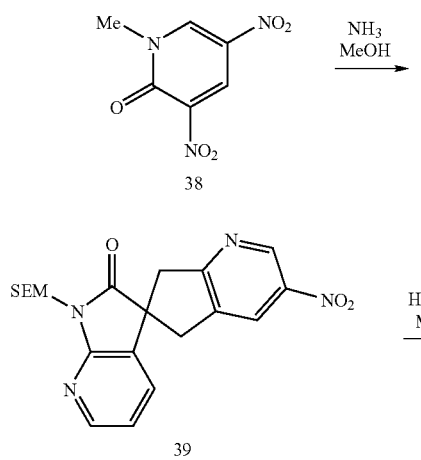
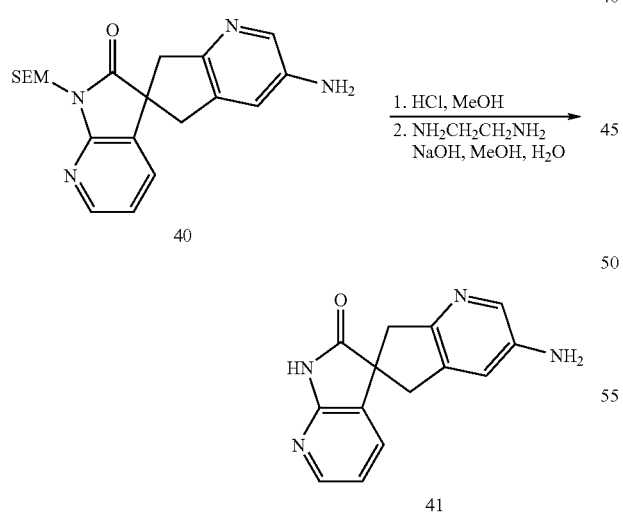

A representative synthesis of an isomer of compound 41, the 2-aminopyridine 47, is shown in Scheme 8. The known pyridine diester 42 [Hashimoto et al. (1997) *Heterocycles* 46, 581] may be reduced to the corresponding diol 43 with lithium borohydride. This diol can be converted to the dibromide 44 by reaction with phosphorus tribromide in THF. The previously described azaoxindole [Marfat & Carter (1987) *Tetrahedron Lett.* 28, 4027] may be reacted with dibromide 44 using lithium hydroxide in aqueous THF to afford the spiroazaoxindole 45. A variety of other bases and solvents may be employed in this alkylation reaction, and use of a different alkylating agent than the dibromide shown here can lead to other products. Treatment of compound 45 with aqueous NaOH at reflux effects hydrolysis of the nitrile, affording the carboxylate salt 46. This carboxylic acid salt may be subjected to known Curtius rearrangement conditions to provide, after deprotection, aminopyridine 47.

SCHEME 8

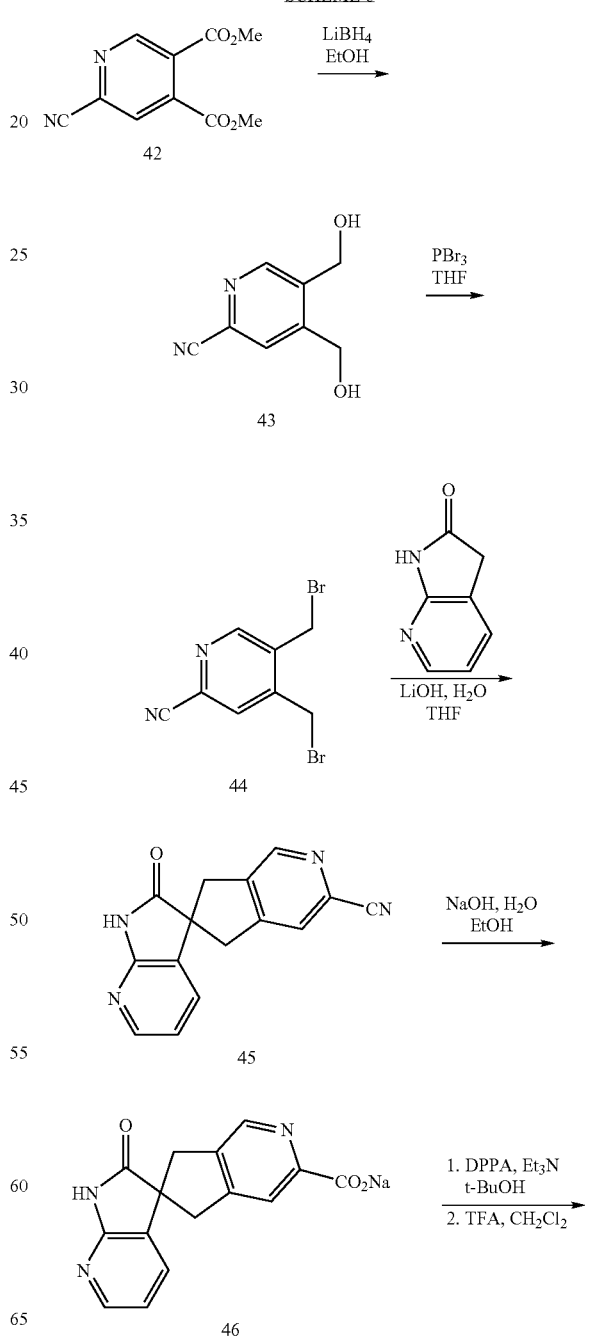

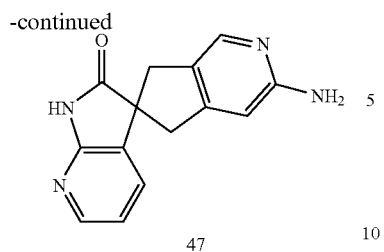

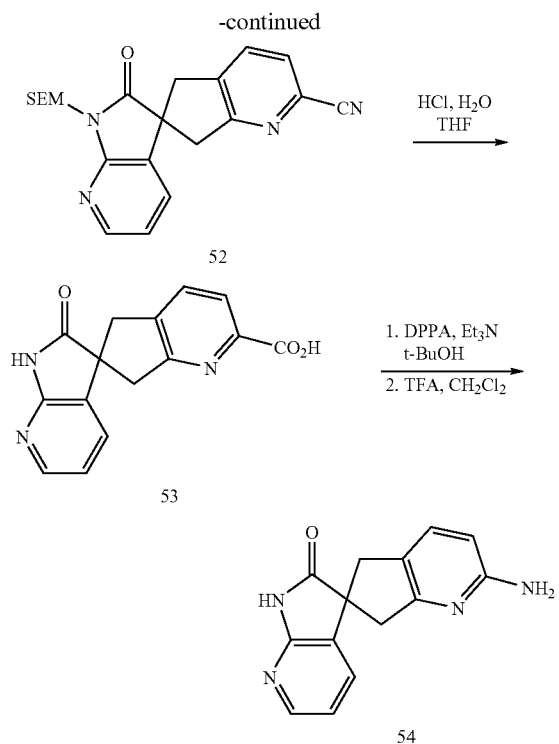

A synthetic route to another isomer of compound 41, the 2-aminopyridine 54, is shown in Scheme 9. The known pyridine N-oxide 48 [Niiyami et al. (2002) *Bioorg. Med. Chem. Lett.* 12, 3041] is reacted with trimethylsilyl cyanide and dimethylcarbamoyl chloride in DME to give nitrile 49. This diester may be reduced to the corresponding diol 50 with lithium borohydride, and the diol can be converted to the dibromide 51 in analogy with the chemistry described in Scheme 8. The protected azaoxindole 36 may be reacted with dibromide 51 in DMF using cesium carbonate as base to afford the spiroazaoxindole 52. A variety of other bases and solvents may be employed in this alkylation reaction, and use of a different alkylating agent than the dibromide shown here can lead to other products. Treatment of compound 52 with aqueous HCl at reflux effects simultaneous hydrolysis of the nitrile and deprotection of the azaoxindole, affording the key acid intermediate 53. This carboxylic acid may be subjected to a similar Curtius rearrangement and subsequent deprotection to that shown in Scheme 8 to afford the desired aminopyridine 54.

Spiroazaoxindole intermediates, such as those illustrated in these schemes (vide supra), may be resolved to give pure enantiomers using techniques familiar to those skilled in the art. For example, chromatography of the suitable intermediates on a chiral column can be used to provide the individual stereoisomers. Resolution may also be effected by other methodologies, such as fractional crystallization of diastereomeric salts, and it may be carried out on other synthetic intermediates or on the final products. Alternatively, an asymmetric synthesis of a key intermediate could be used to provide an enantiomerically enriched final product.

The synthesis of a number of piperidinone intermediates may be conducted as described in Schemes 10-12.

SCHEME 9

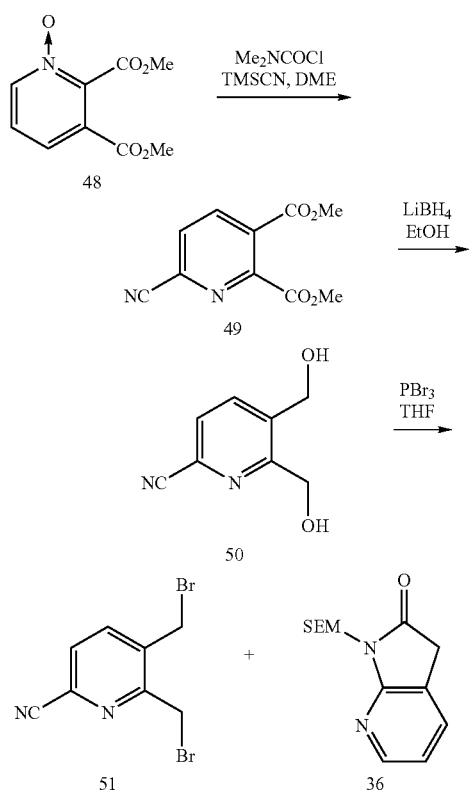

SCHEME 10

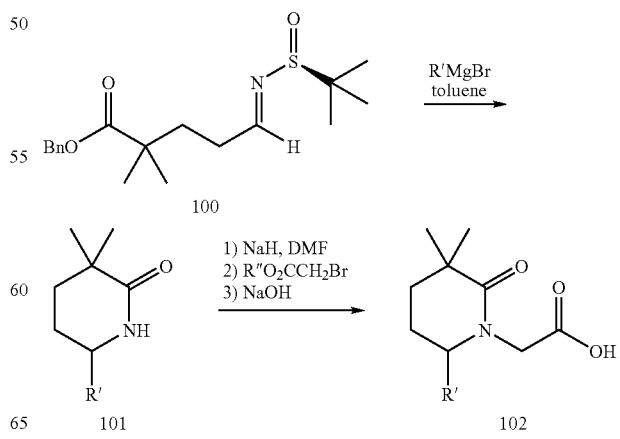

Scheme 10 illustrates a route to 6-substituted piperidin-2-ones, based upon addition of a Grignard reagent (R'MgBr) to the tert-butylsulfinyl imine 100, in analogy with methodology developed by Ellman and coworkers (Ellman et al., *Acc. Chem. Res.*, 2002, 35, 984-995). After addition of the Grignard reagent, which usually proceeds with high diastereoselectivity, the mixture may be heated to reflux to effect deprotection of the resulting sulfinamide and cyclization to provide predominantly one enantiomer of the piperidinone 101. One modification of these procedures involves use of an alternative organometallic reagent, such as an organolithium (R'Li), which may also be used to provide lactam product 101 under similar conditions. The lactam 101 may be alkylated with, for example, methyl bromoacetate (R"=Me) using sodium hydride as base and the intermediate ester can be saponified in situ using sodium hydroxide to provide the desired carboxylic acid derivative 102. In some cases, it is desirable to chromatograph intermediates such as 102 using a chiral column in order to improve their enantiomeric purity.

SCHEME 11

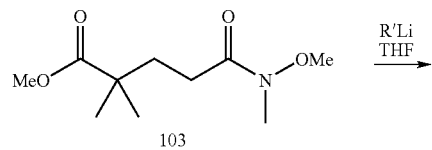

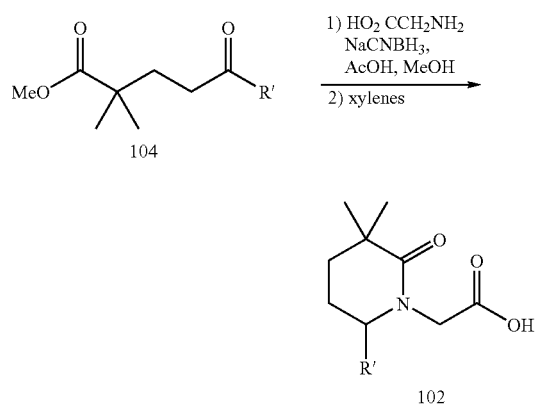

An alternative route to piperidinones of general structure 102 is shown in Scheme 11. In this case, the organometallic reagent, such as an organolithium (R'Li) is reacted with the Weinreb amide 103 to afford the corresponding ketone 104. Reductive amination of 104 with glycine under standard conditions, followed by addition of xylenes and heating at reflux to effect cyclization of the intermediate amine, provides lactam 102 as a racemate.

SCHEME 12

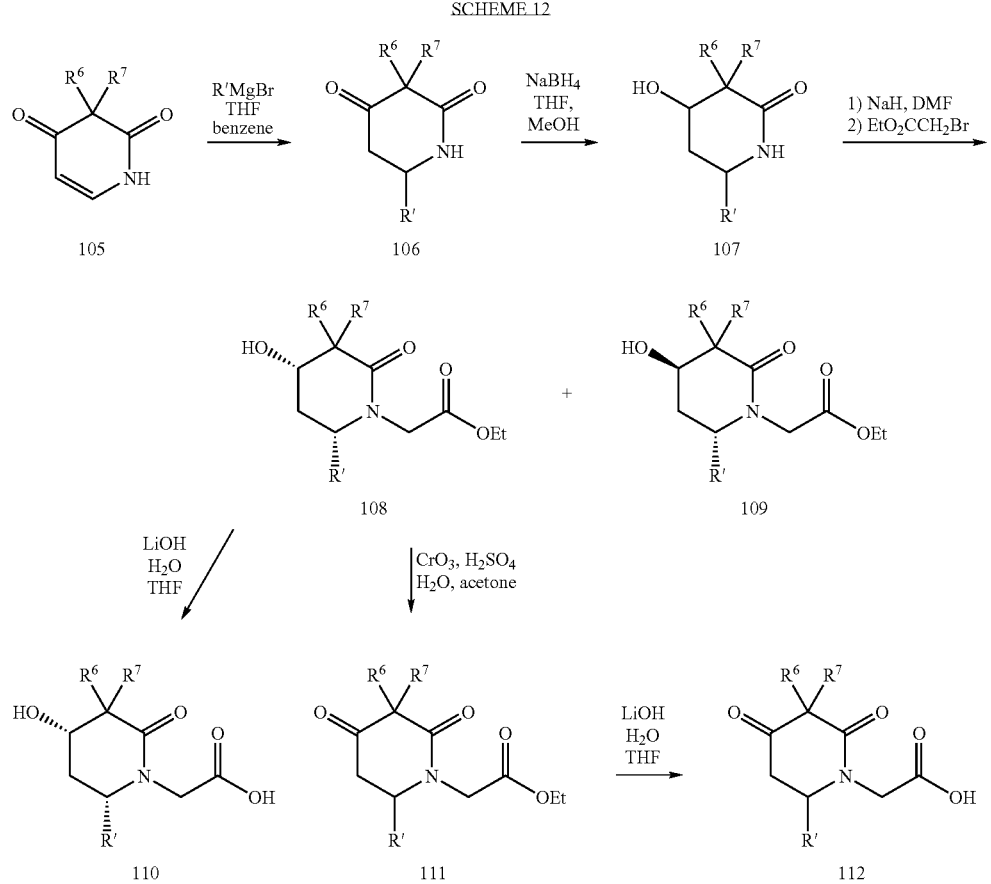

Scheme 12 shows a route to analogues of the piperidin-2-one 102 bearing hydroxy- or oxo-substituents at the 4-position. Starting from a 3,3-disubstituted pyridine-2,4-dione (105), a substituent at the 6-position may be introduced by addition of a Grignard reagent (R'MgBr) using published procedures (U.S. Pat. No. 2,525,231). The resulting ketolactam 106 is subjected to borohydride reduction to afford the corresponding alcohol 107 as a mixture of four stereoisomers. Standard alkylation methodology can then be applied to derivatize 107 with, for example, ethyl bromoacetate and the resulting mixture may be separated to afford the cis-isomer 108 and trans-isomer 109. These diastereomers may also be resolved to provide the individual enantiomers of 108 and 109 via chiral chromatography. Saponification of the ester 108 leads to the key acid intermediate 110, and similar conditions may be used to saponify 109. Alternatively, alcohol 108 may be subjected to oxidation with Jones reagent to give ketone 111, which may be deprotected to the acid intermediate 112.

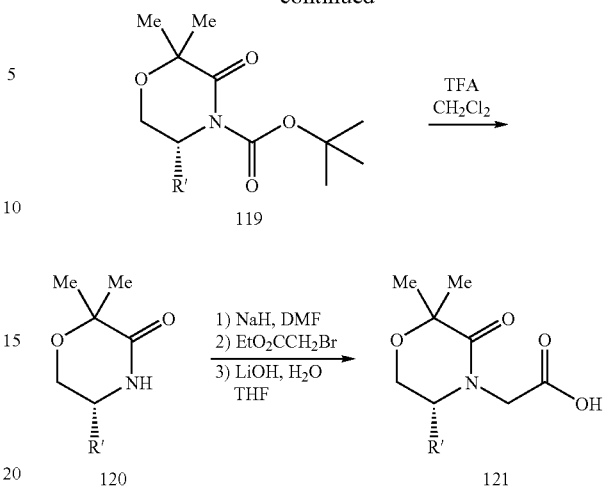

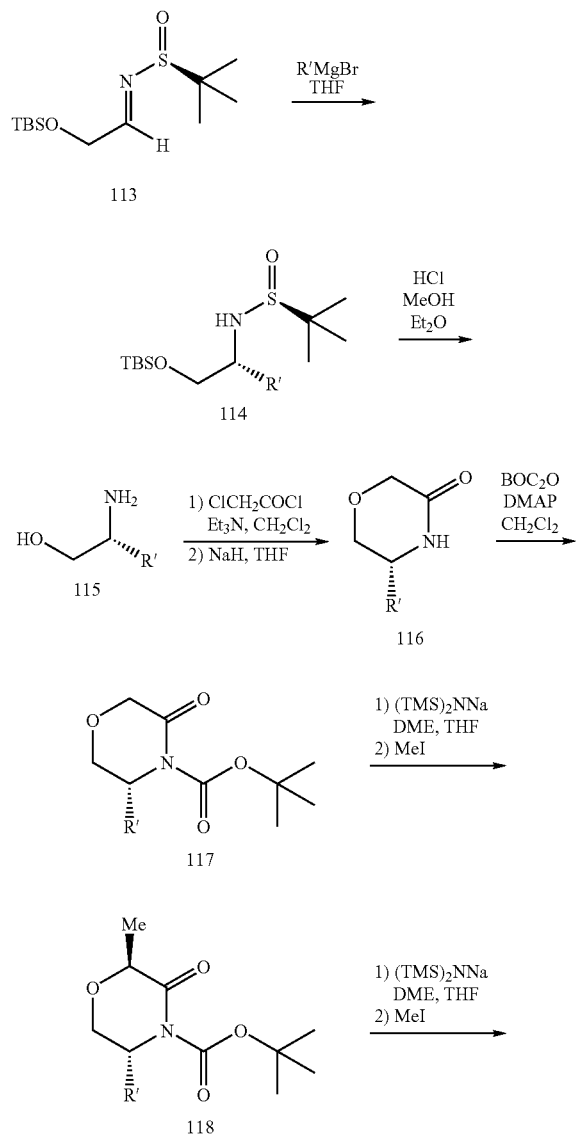

Scheme 13 shows a route to morpholinone intermediates. Addition of a Grignard reagent (R'MgBr) to sulfinimine 113 in THF proceeds with reasonable diastereoselectivity to provide sulfinamide 114 as described in the literature (Barrow et al., *Tetrahedron Lett.*, 2001, 42, 2051-2054). After purification and deprotection, the (R)-glycinol derivative 115 may be obtained. There are numerous other synthetic routes for the synthesis of 115, as described in the literature, and these may be employed as alternatives to the route illustrated herein. Elaboration of 115 to give the protected morpholinone 119 may be carried out in analogy with published methodology (Anthony et al., *Tetrahedron Lett.*, 1995, 36, 3821-3824). Essentially, treatment of 115 with chloroacetyl chloride, followed by sodium hydride, provides morpholinone 116, which may be protected to give 117. Treatment of 117 with sodium bis(trimethylsilyl)amide followed by iodomethane provides the trans-substituted morpholinone 118, and retreatment with base followed by iodomethane leads to the dimethyl analogue 119. Standard removal of the Boc group is effected using trifluoroacetic acid to give 120, which may be converted to the acetate derivative 121 in analogy with previous schemes. It is understood by those skilled in the art of organic synthesis that simple modifications of this route may give rise to other compounds of interest. For example, the monomethyl derivative 118 may be deprotected and alkylated using similar conditions as those used to elaborate 119, to provide the corresponding (2S,5R)-2-methylmorpholinone analogue. Alternatively, other alkylating agents may be used in place of iodomethane, such as iodoethane or benzyl bromide, to provide a variety of morpholinone derivatives.

SCHEME 14

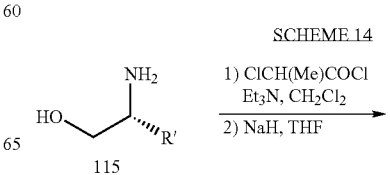

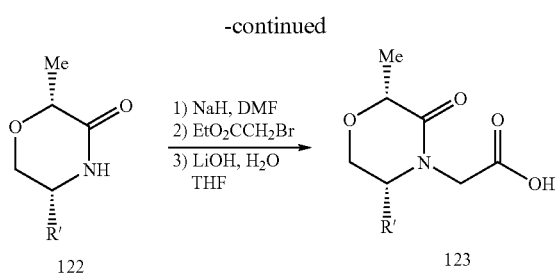

Following the initial procedures in Scheme 14, but using 2-chlorobutyryl chloride for the acylation, leads to the 3-ethylmorpholinone derivative 124. This morpholinone intermediate may be elaborated in analogy with morpholinone 116 in Scheme 13. Instead of sequential dialkylation with iodomethane, a monoalkylation procedure is performed using iodoethane as the electrophile to afford the diethylmorpholinone 126, which may be converted to the key acid intermediate 128 as shown.

In Scheme 14, the synthesis of the cis-substituted morpholinone intermediate 123 is outlined. In this case, reaction of glycinol 115 with 2-chloropropionyl chloride, followed by treatment with sodium hydride, leads selectively to the (2R, 5R)-2-methylmorpholinone 122, which may be elaborated to the acid intermediate 123 using standard procedures. A combination of the methodology illustrated in the two previous schemes may also be employed to provide intermediates of interest, as shown in Scheme 15.

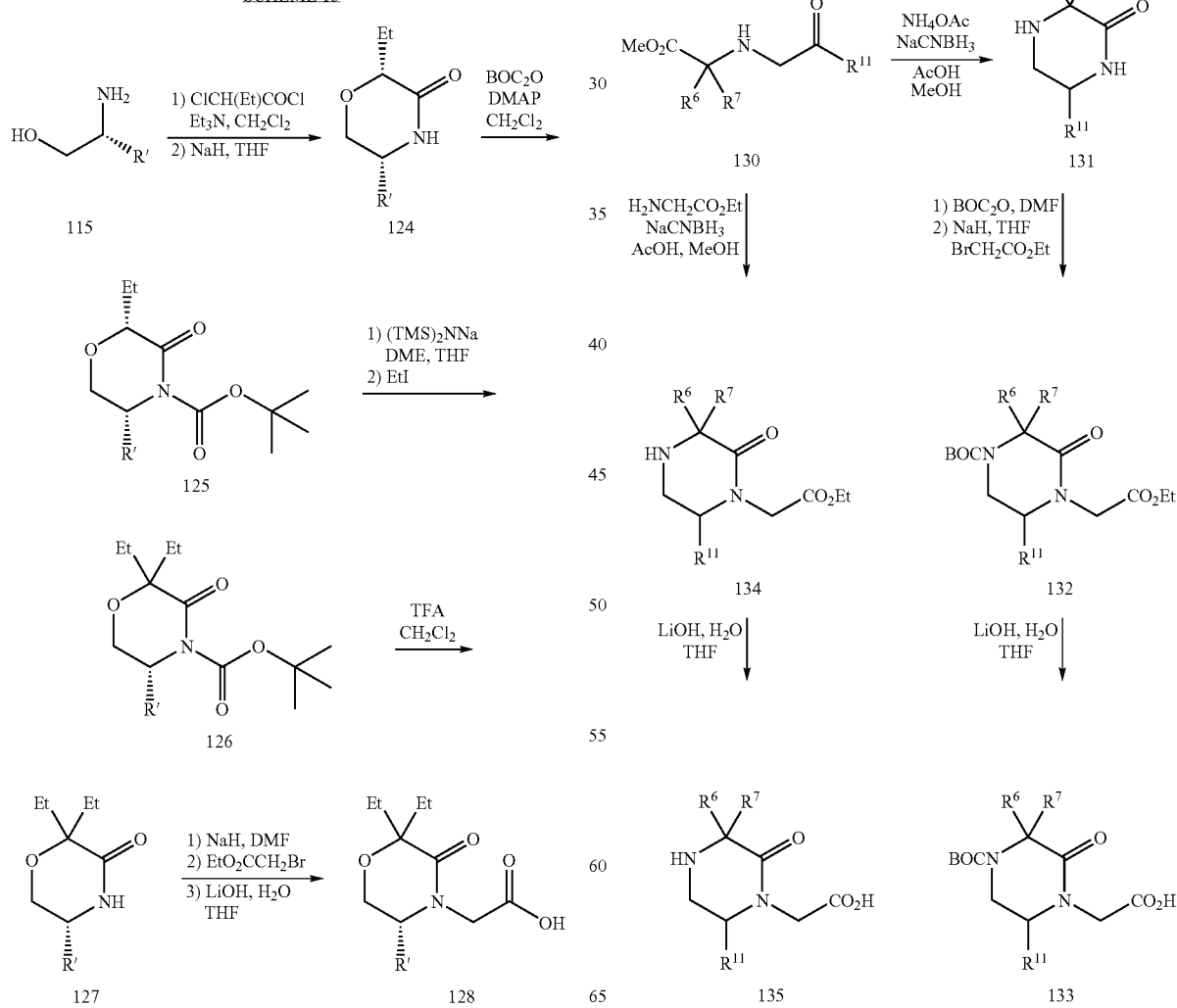

Scheme 16 illustrates methodology for synthesis of piperazinone intermediates, such as 133 and 135. Alkylation of an α-aminoester with bromide 129 may be used to provide the aminoketone 130. A variety of bases, including NaHCO$_3$, K$_2$CO$_3$, and Na$_3$PO$_4$ may be utilized in this alkylation reaction. The aminoketone product may be subjected to reductive amination with ammonium acetate to give the corresponding diamine, which usually undergoes cyclization in situ to provide piperazinone 131. Protection of 131 as the tert-butyl carbamate, followed by alkylation with ethyl bromoacetate, leads to the ester 132 as shown and saponification provides the corresponding acid 133. An alternative strategy is reductive amination of aminoketone 130 with, for example, glycine ethyl ester as shown in Scheme 16. Under the acidic conditions of the reaction, the initial diester intermediate cyclizes to give piperazinone 134, which may be saponified to give acid 135. Simple modifications of the routes illustrated in Scheme 16 may be used to provide other piperazinone intermediates of interest. For example, addition of formaldehyde to the reductive amination reaction once piperazinone 134 is produced can lead to a rapid methylation reaction, affording the N-Me analogue of compound 134. Other standard derivatizations of the piperazinone ring, including alkylation, acylation, or sulfonylation, may be applied to intermediates like 134 or to the final amide products to provide analogues of interest. In some cases, use of known protecting group strategies may be usefully applied. For example, protection of piperazinone 134 with a tert-butyl carbamate group would provide compound 132 and this may facilitate subsequent purification and synthesis. In Scheme 16, the intermediates 131-135 are obtained as mixtures of stereoisomers, but straightforward techniques, such as chiral chromatography, may be applied to such intermediates to effect separation of these isomers.

Simple modifications of these routes, including different protecting group strategies, application of well-precedented methodology, and the use of starting materials and reagents other than those described in the foregoing schemes, may be used to provide other acids of interest Intermediates, such as those described above, may be converted to a variety of other key intermediates that are useful in the synthesis of the compounds of the present invention. While the methodology shown in Scheme 1 is exemplified using lactam 1, it is understood that it may be applied to a variety of lactam substrates, such as those described herein, in order to provide various compounds of the present invention. For example, Scheme 17 illustrates the synthesis of claimed compounds that are analogous to those in Scheme 1 but of a more general structure. A lactam of general structure 136, may be alkylated with an electrophile of general formula BrR$^e$R$^f$CCO$_2$Me after deprotonation with a suitable base, such as sodium hydride, in an appropriate solvent, such as THF. The ester, although not limited to methyl ester, may then be hydrolyzed by an appropriate base, such as NaOH, to provide acid 137. Acid 137 may then be coupled to aniline 138 using a variety of peptide coupling reagent combinations, such as EDCI and HOAt, in the presence of an appropriate base, such as triethylamine, in an appropriate solvent, such as DMF, to yield compound 139.

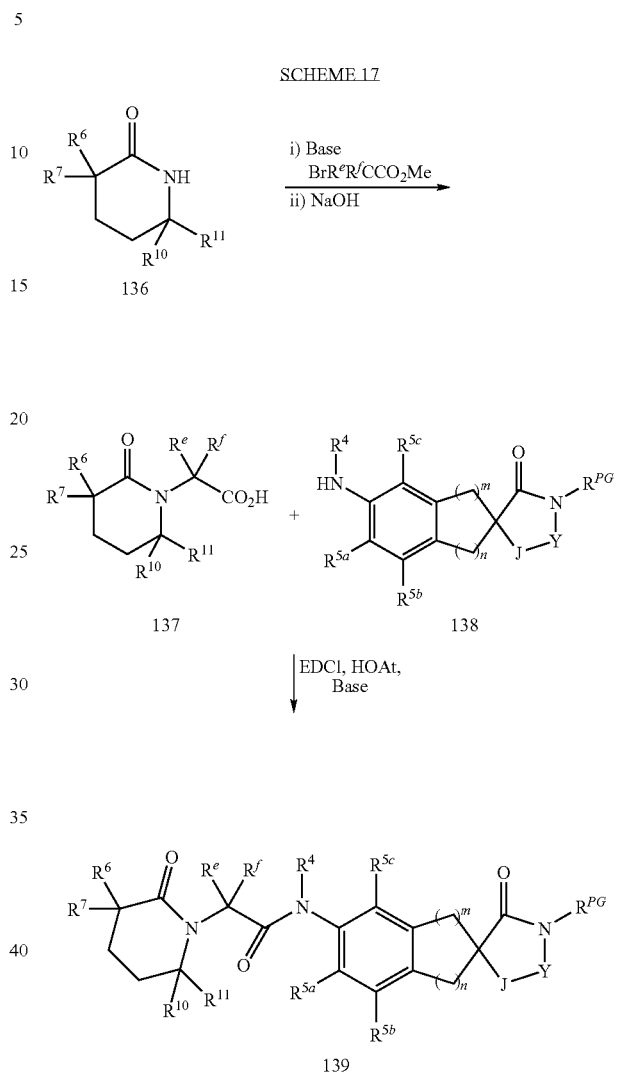

It is understood by those skilled in the art that in some cases alternative reagents or conditions may be used to effect the transformations in Scheme 17. The exact choice of reagents, solvents, temperatures, and other reaction conditions, depends upon the nature of the intended product. In some cases, additional chemical steps may be required to obtain the compounds of interest, or various protecting group strategies may be employed.

The lactam intermediates, such as 1, may be obtained from commercial sources or prepared according to Scheme 2, such as 11. While the methodology shown in Scheme 2 is exemplified using anhydride 5, it is understood that it may be applied to a variety of substrates, such as those described herein, in order to provide various lactam intermediates. For example, Scheme 18 illustrates the synthesis of key intermediates that are analogous to those in Scheme 2 but of a more general structure.

SCHEME 18

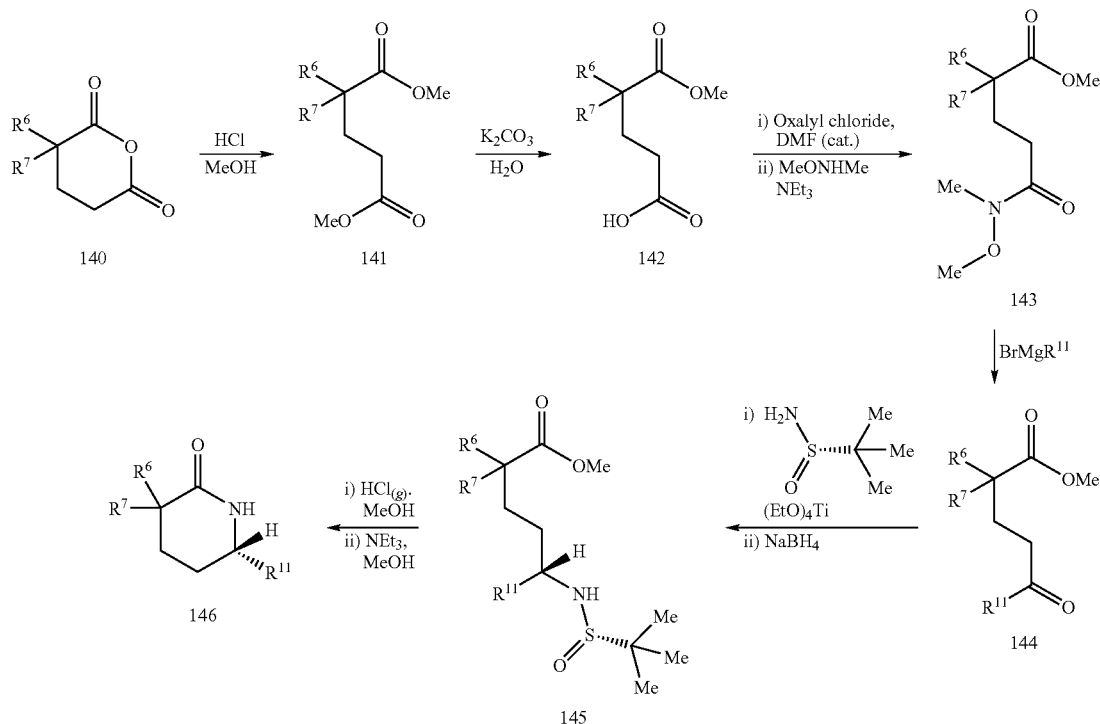

Anhydrides of general structure 140 can be converted to a number of bis-esters analogous to 141, using an appropriate alcohol, such as MeOH, and an acid catalyst, such as HCl. Selective deprotection of one ester may be accomplished using a mild base, such as $K_2CO_3$, in an appropriate solvent mixture, to provide acid 142. Acid 142, may then be coupled with an appropriate amine, such as methylmethoxyamine or pyrrolidine, using an appropriate amide-forming reagent combination, such as oxalyl chloride and catalytic DMF, to provide an amide, such as 143, in preparation for ketone formation. A variety of organometallic reagents, such as BrMgR[11], may then be allowed to react with 143, to provide ketone 144. Conversion of ketone 144 to sulfinamide 145 may be achieved using a variety of known methodology, [see, for example Ellman et al. (1987) *Tetrahedron Lett.* 40, 6709-6712]. Conversion of compound 145 into key lactam intermediate 146 may be achieved using an appropriate acid, such as HCl, followed by an appropriate base, such as triethylamine to allow spontaneous lactamization in an appropriate solvent, such as MeOH, at a temperature ranging from 0-150° C. It is understood that alternative methodologies may also be employed in the synthesis of these key intermediates. For instance, racemic reaction sequences may be utilized, followed by chiral separations at appropriate steps to provide compounds of the present invention. The exact choice of reagents, solvents, temperatures, and other reaction conditions, depends upon the nature of the intended product. In some cases, appropriate protecting group strategies may be used.

SCHEME 19

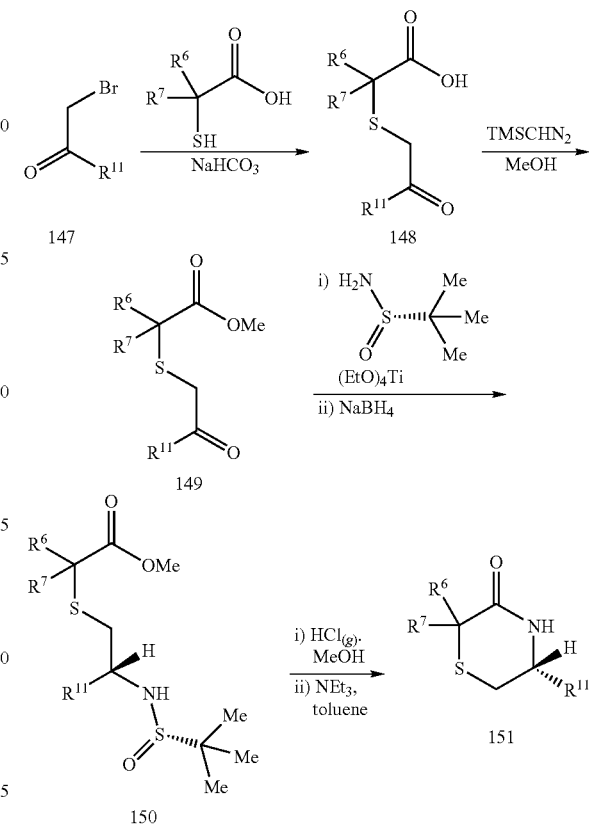

Alpha-halo ketones 147, can react with various alpha-thio carboxylic acids (HS(R⁶)(R⁷)CCO₂H), in the presence of an appropriate base, such as NaHCO₃, in a mixture of solvents, such as THF/water to give the carboxylic acid 148. This carboxylic acid may be converted to the ester 149 under a variety of conditions, such as TMS diazomethane in an appropriate solvent, such as methanol. Alternatively, alpha-halo ketones 147, may react with various alpha-thio carboxylic acid esters (HS(R⁶)(R⁷)CCO₂Me), to provide 149 directly. Conversion of ketone 149 to sulfinamide 150 may be achieved using a variety of known methodology, such as Ellman et al. (1987) *Tetrahedron Lett.* 40, 6709-6712. Conversion of compound 150 into key lactam intermediate 151 may be achieved using an appropriate acid, such as HCl, followed by an appropriate base, such as triethylamine to allow spontaneous lactamization in an appropriate solvent, such as toluene, at a temperature ranging from 0-150° C. Compound 151 may be elaborated in an analogous manner as compound 1 to provide claimed compounds.

Thioether of general formula 152, may be oxidized with an appropriate oxidant, such as mCPBA or hydrogen peroxide, in an appropriate solvent, such as DCM or a mixture of an alcohol and water, at a temperature ranging from 0-150° C., to give sulfur-oxidized compounds 153.

SCHEME 21

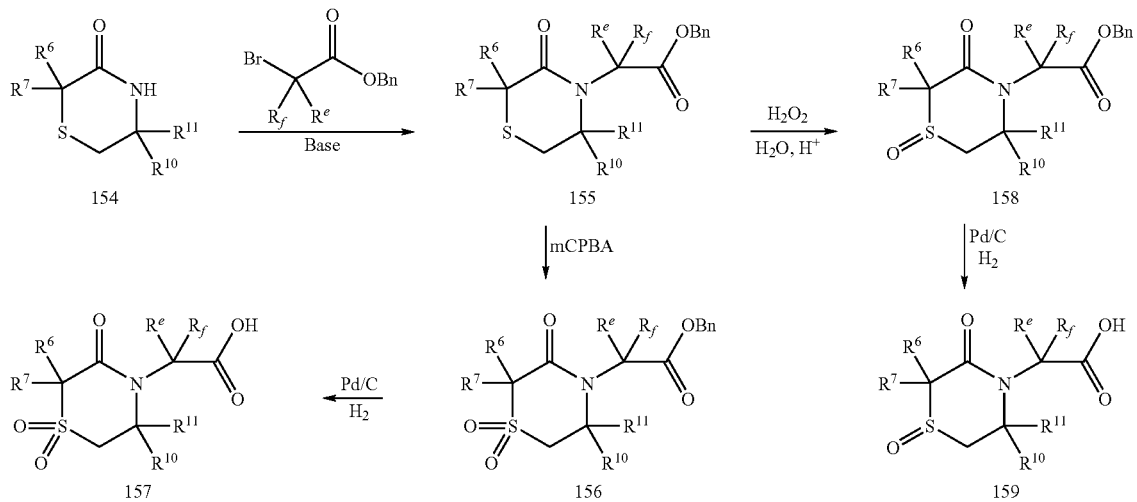

Alternatively, amide of general structure 154, may be alkylated with an electrophile of general formula BrRᵉRᶠCCO₂Me after deprotonation with a suitable base, such as potassium hydride, in an appropriate solvent, such as THF to provide 155. Oxidation of 155 with an oxidant, such as mCPBA, in an appropriate solvent, such as DCM, provides the sulfone 156. The benzyl ester of 156 can then be cleaved using a metal catalyst, such as palladium on carbon, under an atmosphere of hydrogen, or other reducing conditions, to yield the carboxylic acid 157. Sulfoxide 158, may be obtained from compound 155, by employing alternative oxidation conditions, such as aqueous hydrogen peroxide, in an appropriate co-solvent, such as MeOH, under acidic conditions, and over a temperature range of 0-150° C. The benzyl ester of 158 can then be cleaved using a metal catalyst, such as palladium on carbon, under an atmosphere of hydrogen, or other reducing conditions, to yield the carboxylic acid 159. Compounds 157 and 159 may be elaborated in an analogous manner as compound 2 to provide claimed compounds.

SCHEME 20

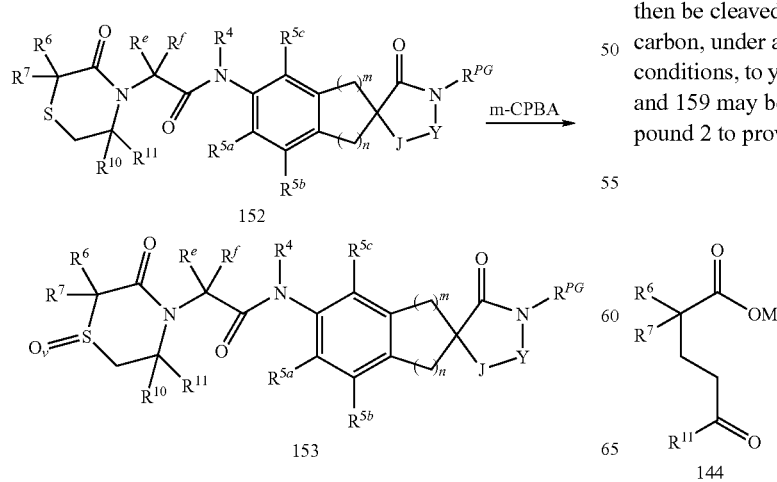

SCHEME 22

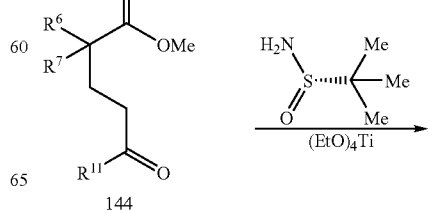

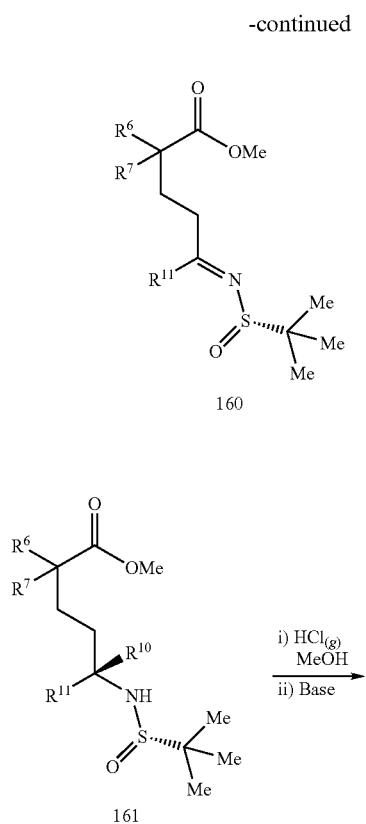

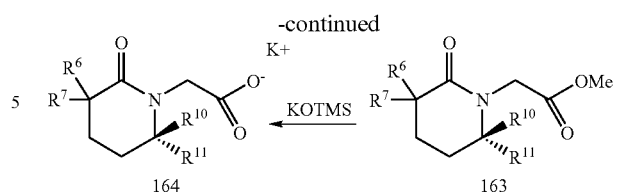

Ketone 144 (Scheme 18) may be converted to the sulfinimine 160 utilizing an appropriate dehydration reagent, such as titanium tetraethoxide, in a solvent, such at THF, in a temperature range of 20-150° C. Treating 160 with an appropriate organometallic reagent, such as $R^{10}MgBr$, in an aprotic solvent, such as DCM, at a temperature between −78 and 25° C. yields compound 161. Conversion of compound 161 into key lactam intermediate 162 may be achieved using an appropriate acid, such as HCl, followed by an appropriate base, such as triethylamine to allow lactamization in an appropriate solvent, such as MeOH or toluene, at a temperature ranging from 0-150° C. Lactam of general structure 162, may be alkylated with an electrophile of general formula $BrH_2CCO_2Me$ after deprotonation with a suitable base, such as potassium hydride, in an appropriate solvent, such as THF to provide 163. Dealkylation of the methyl ester in 163, may be effected using KOTMS in an appropriate solvent, such as THF, in a temperature range of 0 to 40° C., to provide the potassium carboxylate 164. Alternatively, hydrolysis may be achieved under a variety of basic or acidic conditions. Compound 164 may be elaborated in an analogous manner as compound 2 to provide claimed compounds.

SCHEME 23

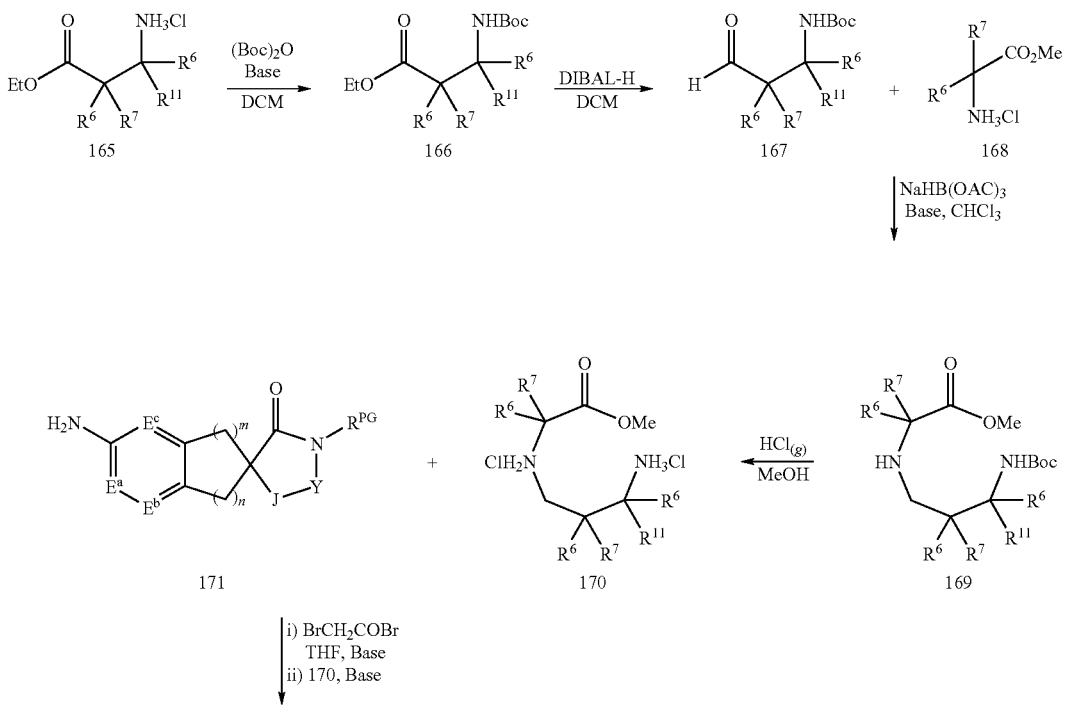

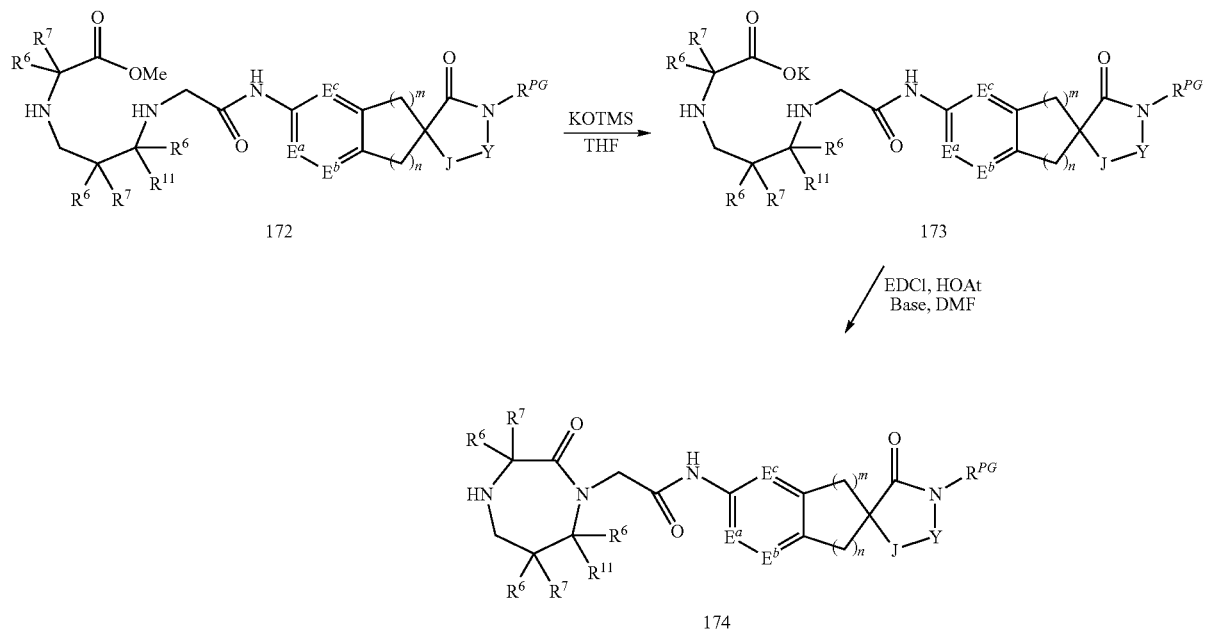

The amine of beta-amino acid esters of general formula 165, although not limited to ethyl esters, may be protected as their N-Boc derivatives using standard conditions such as Boc-anhydride, a base, such as triethylamine, in an appropriate solvent, such as DCM, to provide ester 166. This ester may be reduced to the corresponding aldehyde 167 using a reductant, such as diisobutylaluminum hydride, in an appropriate solvent, such as DCM, at a temperature between −78° C. and rt. Ester-protected amino acids of general formula 168, although not limited to methyl esters, may then be reductively alkylated with aldehyde 167 using a reducing reagent, such as NaHB(OAc)$_3$, a base as needed, such as Hunig's base, in a solvent, such as chloroform, at a temperature ranging from −30 to 100° C., to provide 169. The amine protecting group of 169 may then be removed under standard conditions using a strong acid such as hydrogen chloride, in an appropriate solvent, such as MeOH, to provide 170. The coupling of fragments 170 and 171 may be affected by first allowing the aryl amine of 171 to react with an appropriate acylating reagent, such as bromoacetyl bromide, in the presence of excess base, such as triethylamine, in an aprotic solvent, such as THF, at a temperature between 0° C. and rt, for an appropriate length of time, after which 170 and additional base may be added prior to an increase in the reaction temperature to the range of 30-70° C., ultimately providing 172. The ester of 172, although not limited to methyl ester, may then be deported to the corresponding acid or carboxylate salt 173 using an appropriate reagent, such as KOTMS, in a solvent such as THF over a temperature range of −20 to 60° C. The potassium carboxylate salt 173, or the corresponding carboxylic acid, may then be cyclized using a variety of peptide-coupling reagent combinations, such as EDCI and HOAt, in the presence of an appropriate base (as needed), such as triethylamine, in an appropriate solvent, such as DMF, to yield compound 174.

SCHEME 24

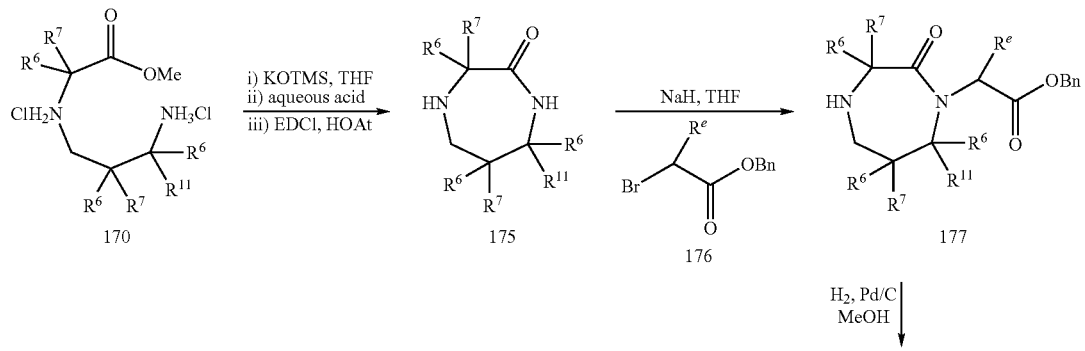

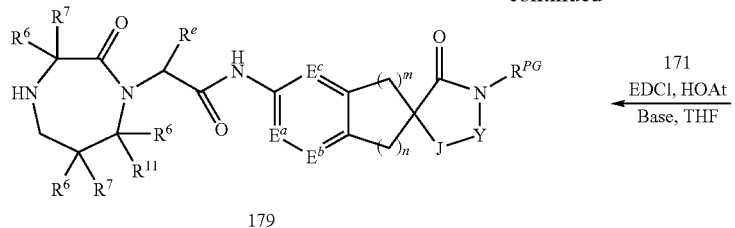

Alternatively, as shown in Scheme 24, compound 170 from Scheme 23 may be cyclized to 175 by first deprotection of the ester with a suitable reagent, such as KOTMS, in an appropriate solvent, such as THF. Subsequent to the cleavage of the ester, the pH of the solution may be adjusted to approximately pH=8, by the addition of an aqueous acid, such as 1 M HCl, followed by addition of an appropriate peptide coupling reagent combination, such as EDCI and HOAt, to provide 175. The amide nitrogen of 175 may then be alkylated by the addition of a strong base, such as NaH, in an appropriate solvent, such as THF, followed by the addition of an appropriate alkylating reagent 176, such as benzyl bromoacetate, to provide 177. The ester of 177 may be converted to the acid under reducing conditions, such as Pd/C in the presence of hydrogen, or alternatively aqueous hydrolysis methods, to provide acid 178. Acid 178 may then be coupled to aryl amine 171 using a variety of peptide coupling reagent combinations, such as EDCI and HOAt, in the presence of an appropriate base, such as triethylamine, in an appropriate solvent, such as THF, to yield compound 179.

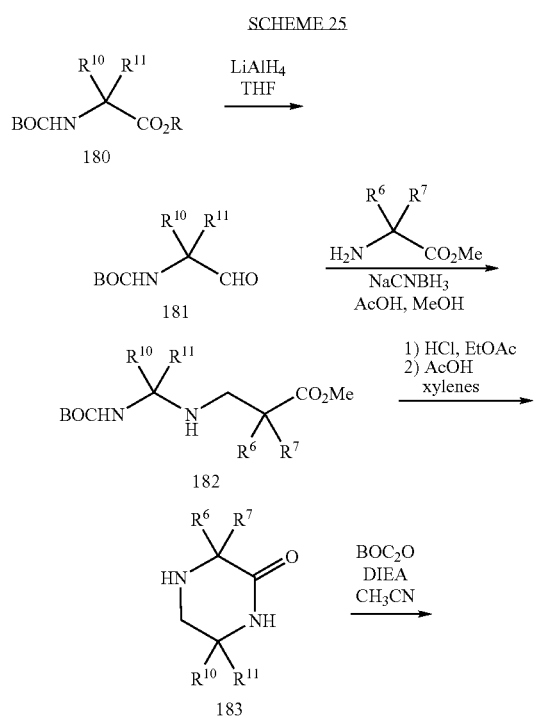

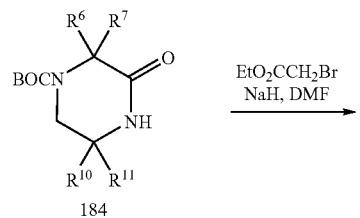

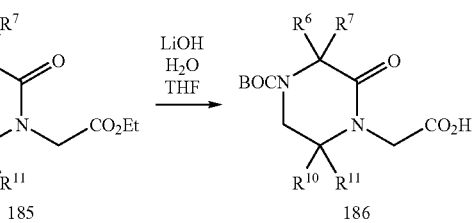

In Scheme 25, an alternative strategy for the synthesis of piperazinone intermediates is illustrated. This methodology is useful for the synthesis of examples for which $R^{10}$ is not hydrogen. This route begins with the protected amino ester 180, which may be synthesized via a number of routes that are known in the chemical literature. In this illustrative case, a tert-butyl carbamate protecting group is shown on 180, but other protecting group strategies may be equally effective. Reduction of the ester group in 180, using LiAlH$_4$ or an alternative reducing agent, may provide the corresponding aldehyde 181 directly, depending upon the nature of R, $R^{10}$, and $R^{11}$. In some cases, it may be advantageous or necessary to access aldehyde 181 via a two-step procedure in which the ester is reduced to the corresponding alcohol and the alcohol is oxidized to afford aldehyde 181 using, for example, Swern conditions. Reductive amination of 181 with a suitable amino ester under standard conditions can be used to provide the amine 182, and this may be deprotected and cyclized under acidic conditions to give piperazinone 183. Piperazinone 183 may be further elaborated in analogy with Scheme 16 to give key acid intermediates like 186. In Scheme 25, the intermediates 183-186 are obtained as mixtures of stereoisomers, but straightforward techniques, such as chiral chromatography, may be applied to such intermediates to effect separation of these isomers.

SCHEME 26

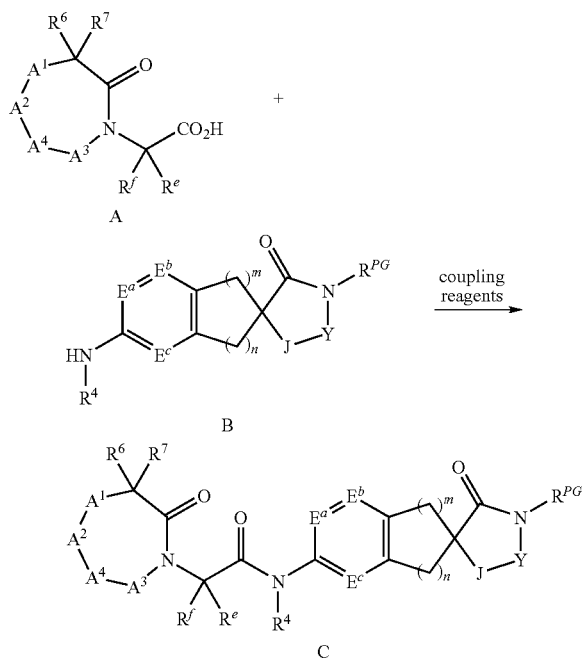

The various carboxylic acid intermediates described in these schemes (vide supra) may be coupled to a variety of amines to give the compounds of the present invention. A general reaction is illustrated in Scheme 26, in which carboxylic acid A is coupled to amine B to give the desired product amide C. There are many known strategies for effecting such coupling chemistry, including use of coupling reagents, such as EDC with HOBT, PyBOP, HATU, CDI and the like. Alternatively, the carboxylic acid A may be activated as an acid chloride or anhydride, for example, to facilitate reaction with the amine of interest. Activation of the amine B, for example as the corresponding aluminum amide which may be reacted with an ester derivative of carboxylic acid A, may also be a useful strategy in cases where the amine is relatively unreactive. In some cases, various protecting group strategies familiar to one skilled in the art of organic synthesis may be employed to allow preparation of a particular compound of the present invention.

It is understood that alternative methodologies may also be employed in the synthesis of these key intermediates. For instance, racemic reaction sequences may be utilized, followed by chiral separations at appropriate steps to provide compounds of the present invention. The exact choice of reagents, solvents, temperatures, and other reaction conditions, depends upon the nature of the intended product. In some cases, appropriate protecting group strategies may be used.

In some cases the final product may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. Additionally, various protecting group strategies may be employed to facilitate the reaction or to avoid unwanted reaction products. The following examples are provided so that the invention might be more fully understood. These examples are illustrative only and should not be construed as limiting the invention in any way.

INTERMEDIATE 1

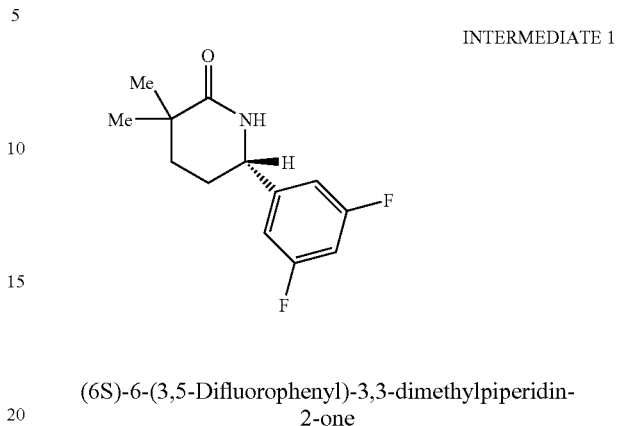

(6S)-6-(3,5-Difluorophenyl)-3,3-dimethylpiperidin-2-one

Step A. Dimethyl 2,2-dimethylpentanedioate

To a solution of 3,3-dimethyldihydro-2H-pyran-2,6(3H)-dione (20.0 g, 141 mmol) in MeOH (140 mL), at ambient temperature and under a constant stream of nitrogen, was added TMSCl (7.64 g, 70.3 mmol). The reaction mixture was then heated to 60° C. for 3.25 h, before being cooled to ambient temperature. The reaction mixture was then concentrated in vacuo before being diluted with diethyl ether (200 mL) and water (100 mL). The organics were then washed with 100 mL, individually, of each of the following aqueous solutions: 1 M NaOH, 1 M HCl, water, half-saturated brine and saturated brine. The organics were then dried over sodium sulfate, filtered and concentrated in vacuo to give the title compound, which was used without further purification. MS: m/z=189 (M+1).

Step B. 5-Methoxy-4,4-dimethyl-5-oxopentanoic acid

To a solution of dimethyl 2,2-dimethylpentanedioate from Step A (25.4 g, 135 mol) in MeOH (150 mL), THF (100 mL) and water (100 mL), was added potassium carbonate (36.2 g, 262 mmol). This biphasic solution was allowed to stir for 68 h, at ambient temperature, after which time the reaction was about 50% complete. Solvents were carefully removed in vacuo such that the starting materials did not vaporize. The aqueous layer was diluted with water (266 mL) and then extracted with diethyl ether until no additional SM was detected in the aqueous layer. The aqueous layer was made acidic by the addition of 6 M HCl (95 mL), and was then saturated with NaCl. This aqueous layer was extracted once with diethyl ether (250 mL). This ethereal layer was washed with brine, then dried over sodium sulfate, filtered and concentrated in vacuo to give the title compound. MS: m/z=175 (M+1).

Step C. Methyl 5-[methoxy(methyl)amino]-2,2-dimethyl-5-oxopentanoate

To a solution of 5-methoxy-4,4-dimethyl-5-oxopentanoic acid from Step B (7.00 g, 40.2 mmol), in DCM, was added DMF (0.1 mL), followed by the slow addition of oxalyl chloride (5.00 g, 39.4 mmol) over 33 minutes, during which time the reaction flask was maintained under a constant stream of dry nitrogen. Stirring was continued under a light stream of dry nitrogen for an additional hour, during which time the rate of carbon dioxide evolution diminished. This freshly formed acid chloride was then transferred via canula into a 500 mL round bottom flask, cooled to 0° C., which already contained N-methoxymethanamine hydrochloride (5.76 g, 59.1 mmol) and triethylamine (15.9 g, 158 mmol). Fifteen minutes after complete addition of the acid chloride, the ice bath was removed and the reaction was allowed to warm to ambient temperature. After 1 h at ambient temperature, diethyl ether (100 mL) was added to precipitate some of the triethylamine hydrochloride, which was filtered and washed with more diethyl ether. The combined organics were then washed with 1M HCl (100 mL×2), 1M NaOH (100 mL), water (100 mL), half-saturated brine (100 mL) and saturated brine (100 mL). The organics were then dried over sodium sulfate, filtered and concentrated in vacuo to provide the title compound which was used without further purification. MS: m/z=218 (M+1).

Step D. Methyl 5-(3,5-difluorophenyl)-2,2-dimethyl-5-oxopentanoate

To a solution of methyl 5-[methoxy(methyl)amino]-2,2-dimethyl-5-oxopentanoate from Step C (4.68 g, 21.6 mmol) in THF (46.8 mL), cooled to 0° C., was added 3,5-difluorophenyl magnesium bromide (65 mL, 0.5 M in THF, 32.3 mmol) over 30 minutes. The reaction was allowed to stir at ambient temperature for 2 h, after which time no additional reaction progress was observed. Additional 3,5-difluorophenyl magnesium bromide (50 mL, 0.5 M in THF, 25.0 mmol) was added over 30 minutes. After 3 h at 0° C., the reaction was quenched by the rapid addition of a cold (0° C.) solution of EtOH (71 mL) and conc. HCl (5.0 mL). The reaction was then diluted with water (200 mL) and diethyl ether (400 mL). The organics were washed with water (200 mL×3) and brine (100 mL), then dried over sodium sulfate, filtered, and concentrated in vacuo to give a residue. This residue was purified by silica gel chromatography, eluting with a gradient of $CH_2Cl_2$: hexanes—50:50 to 100:0, to give the title compound. MS: m/z=239 (M−31(MeO⁻)).

Step E. Methyl (5S)-5-{[(S)-tert-butylsulfinyl] amino}-5-(3,5-difluorophenyl)-2,2-dimethylpentanoate To a solution of methyl 5-(3,5-difluorophenyl)-2,2-dimethyl-5-oxopentanoate from Step D (500. mg, 1.85 mmol) and (S)-2-methylpropane-2-sulfinamide (336 mg, 2.78 mmol) in THF (6.5 mL), was added titanium tetraethoxide (616 mg, 2.52 mmol). The reaction vessel was quickly sealed and placed into a 60° C. bath for 3 hours. After cooling to ambient temperature a septum and nitrogen inlet were attached prior to cooling to 0° C. Sodium borohydride (191 mg, 5.05 mmol) was then added, and a complete reaction was observed after 15 minutes. Methyl alcohol was then slowly added until gas evolution had stopped. The reaction mixture was then diluted with saturated brine (6.5 mL) while experiencing rapid stirring. The resultant slurry was filtered through celite, washing with EtOAc as needed. The combined organics were then washed with brine, dried over sodium sulfate, filtered and concentrated in vacuo to give an oil. This oil was purified by silica gel chromatography, eluting with a gradient of EtOAc:Hexanes—10:90 to 70:30, to give the title compound containing about 12% of the corresponding ethyl ester. MS: m/z=376 (M+1).

Step F. (6S)-6-(3,5-Difluorophenyl)-3,3-dimethylpiperidin-2-one

A solution of methyl (5S)-5-{[(S)-tert-butylsulfinyl] amino}-5-(3,5-difluorophenyl)-2,2-dimethylpentanoate from Step E (300. mg, 0.800 mmol) in MeOH (16 mL) was cooled to 0° C. Hydrogen chloride gas (anhydrous) was bubbled through this cold solution for about 30 seconds, after which time the reaction vessel was sealed and allowed to sit in the ice bath for 15 minutes. Dry nitrogen was then bubbled through the solution for 30 minutes, prior to removal of solvent in vacuo. More MeOH (~50 mL) was added, and then removed in vacuo. After dissolving in a third volume of MeOH (16 mL), triethylamine (323 mg, 3.2 mmol) was introduced and the mixture was heated to 65° C. for 16 hours. After cooling to ambient temperature, the solvent was removed in vacuo and the residue was partitioned between diethyl ether (50 mL) and 1 M HCl (50 mL). The organics were washed with additional 1 M HCl (50 mL), water (50 mL) and saturated brine (50 mL). The ethereal solution was dried over sodium sulfate, filtered and then concentrated in vacuo to provide the title compound, which could be used without further purification. MS: m/z=240 (M+1).

INTERMEDIATE 2

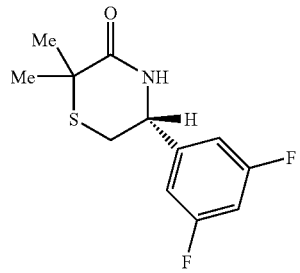

(5R)-5-(3,5-Difluorophenyl)-2,2-dimethylthiomorpholin-3-one

Step A. 2-{[2-(3,5-Difluorophenyl)-2-oxoethyl] thio}-2-methylpropanoic acid

To a solution of 3,5-difluorophenacyl bromide (845 mg, 3.60 mmol) in THF (12 mL) and water (12 mL) was added sodium bicarbonate (317 mg, 3.78 mmol) and 2-mercaptoisobutyric acid (432 mg, 3.60 mmol). The reaction mixture was allowed to stir at ambient temperature for 1.0 h under a stream of nitrogen. The reaction mixture was diluted with diethyl ether (50 mL) and 1 M HCl (15 mL). The organic layer was then washed with 20 mL saturated brine. The organics were then dried over sodium sulfate, filtered and concentrated in vacuo to give the title compound, which was used without further purification. MS: m/z=229 (M−CO₂H).

Step B. Methyl 2-{[2-(3,5-difluorophenyl)-2-oxoethyl]thio}-2-methylpropanoate

To a solution of 2-{[2-(3,5-difluorophenyl)-2-oxoethyl] thio}-2-methylpropanoic acid from Step A (400. mg, 1.46 mmol) in MeOH (3 mL), was added trimethylsilyldiazomethane (2 M in hexanes) until yellow color persists. The reaction mixture was stirred for an additional twenty minutes. The reaction mixture was diluted with ether (30 mL) and water (10 mL). The organics were washed with 5% sodium bicarbonate and then with saturated brine. The organics were dried over sodium sulfate, filtered, and concentrated in vacuo to give a residue. This residue was purified by silica gel chromatography, eluting with a gradient of CH$_2$Cl$_2$:Hexanes—40:60 to 90:10, to give the title compound. MS: m/z=229 (M−CO$_2$Me).

Step C. Ethyl 2-{[(2R)-2-[(tert-butylsulfinyl)amino]-2-(3,5-difluorophenyl)ethyl]thio}-2-methylpropanoate To methyl 2-{[2-(3,5-difluorophenyl)-2-oxoethyl]thio}-2-methylpropanoate from Step B (500. mg, 1.74 mmol) was added (R)-(+)-2-methyl-2-propanesulfinamide (254 mg, 2.09 mmol) under a constant stream of nitrogen. The reagents were dissolved in THF (17 mL), and to the above mixture was added titanium ethoxide (796 mg, 3.49 mmol). The reaction was sealed and stirred at 60° C. for 15 hours. The reaction was complete as determined by LCMS analysis and transesterification was observed. The reaction was cooled gradually to 0° C. under nitrogen. To the reaction mixture was added sodium borohydride (132 mg, 3.49 mmol). The reaction was complete after fifteen minutes as indicated by LCMS analysis. The reaction was quenched after an additional twenty minutes of stirring with methanol until gas evolution ceased. Saturated brine (30 mL) was added with heavy stirring and the resulting slurry was filtered through celite and washed with aliquots of ethyl acetate. The organic layer was then washed with brine and dried over sodium sulfate. The solution was filtered and concentrated in vacuo to provide a residue that was purified by silica gel chromatography, eluting with a gradient of EtOAc:Hexanes—20:80 to 75:25, to give the title compound (containing 10% of the undesired diastereomer). MS: m/z=408 (M+1).

Step D. (5R)-5-(3,5-Difluorophenyl)-2,2-dimethylthiomorpholin-3-one

To a solution of methyl 2-{[(2R)-2-[(tert-butylsulfinyl)amino]-2-(3,5-difluorophenyl)ethyl]thio}-2-methylpropanoate from Step C (428 mg, 1.09 mmol) in MeOH (20 mL), cooled to 0° C., was added anhydrous HCl gas for 1 minute. The reaction was sealed and allowed to sit at 0° C. for fifteen minutes, after which nitrogen was bubbled through the reaction for twenty minutes. The reaction was concentrated in vacuo. Additional MeOH (30 mL) was added and it was again concentrated in vacuo. This was repeated with another addition of MeOH and triethylamine (440. mg, 4.35 mmol). To the resulting residue was added toluene (10 mL) and triethylamine (440. mg, 4.35 mmol). A reflux condenser was attached and the mixture stirred at 115° C. After one week of stirring, the reaction was judged to be 90% complete by LCMS. The mixture was cooled to ambient temperature and concentrated in vacuo. The residue was diluted with diethyl ether (50 mL) and washed individually with 20 mL of each of the following aqueous solutions: 1 M HCl (twice), water, and saturated brine. The organic layer was then dried over sodium sulfate, filtered, and concentrated in vacuo to give a residue that was purified by silica gel chromatography, eluting with a gradient of MeOH:CH$_2$Cl$_2$—1:99 to 5:95, to give the title compound. MS: m/z=258 (M+1).

INTERMEDIATE 3

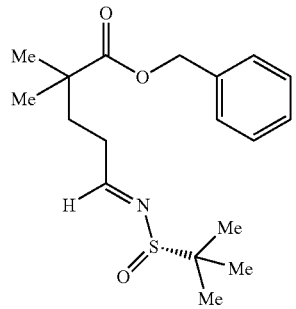

Benzyl 5-{[(S)-tert-butylsulfinyl]imino}-2,2-dimethylpentanoate

Step A. Benzyl 2,2-dimethylpent-4-enoate

To a mixture of K$_2$CO$_3$ (1.58 g, 11.5 mmol), 2,2-dimethylpent-4-enoic acid (1.30 g, 10.1 mmol) and DMF (8.1 mL) was added benzyl bromide (1.40 g, 8.19 mmol) slowly over 15 minutes. After 4 hours the mixture was diluted with a mixture of water (80 mL) and diethylether (80 mL). The organic layer was separated and sequentially washed with 80 mL of 5% aqueous sodium bicarbonate, saturated copper sulfate, slightly acidic water, half-saturated brine, and then saturated brine. The organics were then dried over sodium sulfate, filtered and concentrated in vacuo to give the title compound which was used without further purification. MS: m/z=219 (M+1).

Step B. Benzyl 5-hydroxy-2,2-dimethylpentanoate

To a solution of benzyl 2,2-dimethylpent-4-enoate (5.74 g, 26.3 mmol, prepared according to Step A) in THF (100 mL) was added a solution of 9-BBN (63.1 mL, 31.6 mmol, 0.5 M in THF) over 20 minutes, while under nitrogen. The reaction was allowed to stir at ambient temperature for 17 hours. An aqueous solution of sodium acetate (7.3 g, 89 mmol, in 18 mL of water) was then added, followed by the slow addition of aqueous hydrogen peroxide (18 mL, 30% by weight solution) with occasional chilling in a 0° C. bath. This mixture was allowed to stir at ambient temperature for 1.5 hours, before being extracted with ethyl acetate. The combined organics were washed with saturated brine. The organics were then dried over sodium sulfate, filtered, and concentrated in vacuo to give a residue that was purified by silica gel chromatography, eluting with a gradient of MeOH:DCM—1:99 to 10:90, to give the title compound. MS: m/z=237 (M+1).

Step C. Benzyl 2,2-dimethyl-5-oxopentanoate

To a −78° C. solution of oxalyl chloride (4.80 g, 37.8 mmol) in DCM (200 mL) was add DMSO (5.91 g, 75.6 mmol) dropwise over 10 minutes. After 25 minutes of additional stirring, a −78° C. solution of benzyl 5-hydroxy-2,2-dimethylpentanoate (4.06 g, 17.2 mmol, Step B) in DCM (200 mL) was added via cannula over 75 minutes. After stirring for an additional 30 minutes, triethylamine (13.9 g, 137 mmol) was added slowly over 25 minutes. The cooling bath was allowed to warm, while the reaction stirred for an additional 18 hours. Reaction solvent was then removed in vacuo, and the residue was dissolved in a mixture of diethyl ether and water (containing enough HCl to remain acidic). The organics were then dried over sodium sulfated, filtered and concentrated in vacuo to give the title compound (3.67 g), which was used without further purification.

Step D. Benzyl 5-{[(S)-tert-butylsulfinyl]imino}-2,2-dimethylpentanoate

To a mixture of benzyl 2,2-dimethyl-5-oxopentanoate (1.06 g, 4.54 mmol, Step C) and anhydrous CuSO$_4$ (1.59 g, 9.98 mmol) in DCM (10 mL) was added (S)-2-methylpropane-2-sulfinamide (0.550 g, 4.54 mmol). This mixture was stirred for 22 hours, before being filtered through a pad of celite. Additional DCM was used to wash the celite. The combined organics were concentrated in vacuo to give a residue that was purified by silica gel chromatography, eluting with a gradient of MeOH:DCM—0.5:99.5 to 1.5:98.5, to give the title compound. MS: m/z=338 (M+1).

INTERMEDIATE 4

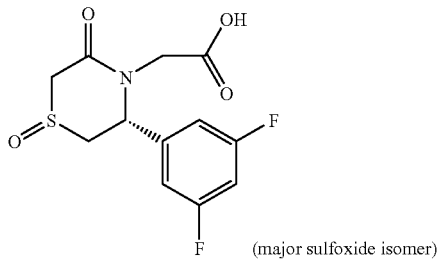

[(3R)-3-(3,5-Difluorophenyl)-1-oxido-5-oxothiomorpholin-4-yl]acetic acid (major sulfoxide isomer)

Step A. Benzyl [(3R)-3-(3,5-difluorophenyl)-5-oxothiomorpholin-4-yl]acetate

To a 0° C. solution of (5R)-5-(3,5-difluorophenyl)thiomorpholin-3-one (247 mg, 1.08 mmol, prepared by analogy to Intermediate 2) in THF (8.0 mL) was added sodium hydride (38 mg, 1.5 mmol, 95% by weight). After 5 minutes, the ice bath was removed and the reaction was allowed to warm to ambient temperature. Once hydrogen gas evolution had ceased, as judged by an oil bubbler, the reaction mixture was cooled to 0° C., prior to the introduction of benzyl acetate (272 mg, 1.19 mmol). After 5 minutes, the ice bath was removed and the reaction was stirred for 15 hours. The bulk of the THF was removed under reduced pressure. The residue was then diluted with water and ether. The aqueous layer was extracted once with ether and the combined organics were washed with saturated brine. The organics were then dried over sodium sulfate, filtered, and concentrated in vacuo to give a residue that was purified by silica gel chromatography, eluting with a gradient of MeOH:DCM—0.5:99.5 to 5:95, to give the title compound. MS: m/z=378 (M+1).

Step B. Benzyl [(3R)-3-(3,5-difluorophenyl)-1-oxido-5-oxothiomorpholin-4-yl]acetate To a solution of benzyl [(3R)-3-(3,5-difluorophenyl)-5-oxothiomorpholin-4-yl]acetate (151 mg, 0.399 mmol, from Step A.) in MeOH (10 mL) was added aqueous hydrogen peroxide (30 drops, ~0.8 mL, 30% by weight), and aqueous HCl (5 drops, 3 M HCl). This mixture was then heated to 40° C. for 2.5 hours. After cooling to ambient temperature, the bulk of the MeOH was removed in vacuo, and the residue was partitioned between 50 mL of water and 100 mL of diethyl ether. The organics were washed with saturated brine, then dried over sodium sulfate, filtered, and concentrated in vacuo to give a residue that was purified by silica gel chromatography eluting with a gradient of Hexanes:EtOAc—1:1 to 100% EtOAc, to yield 24.5 mg of the minor sulfoxide isomer and 93.6 mg of the major sulfoxide isomer. MS: m/z=394 (M+1).

Step C. [(3R)-3-(3,5-Difluorophenyl)-1-oxido-5-oxothiomorpholin-4-yl]acetic acid (major sulfoxide isomer)

A solution of benzyl [(3R)-3-(3,5-difluorophenyl)-1-oxido-5-oxothiomorpholin-4-yl]acetate (93.6 mg, 0.238 mmol, major isomer, from Step B) in MeOH (5 mL) was purged with nitrogen. The septum sealing the reaction vessel was briefly removed to allow introduction of Pd/C (~18 mg, 10% Pd/C). The vessel was then purged with hydrogen from a balloon, before a fresh balloon of hydrogen was attached. After LCMS analysis indicated that the reaction had stalled at 60% conversion, the hydrogen atmosphere was replaced with nitrogen. The mixture was then filtered through a pad of celite, washing with MeOH as needed. The filtrate was concentrated in vacuo to provide a residue which was diluted with aqueous sodium bicarbonate (2%) and ether. The aqueous layer was extracted with ether (4 times) to remove un-reacted starting material. The aqueous layer was then made acidic by the addition of 3M HCl, and was then saturated with NaCl. This acidic aqueous layer was then extracted three times with DCM and three times with EtOAc. Both organics were dried over sodium sulfate, filtered and concentrated in vacuo to give the title compound. MS: m/z=304 (M+1).

INTERMEDIATE 5

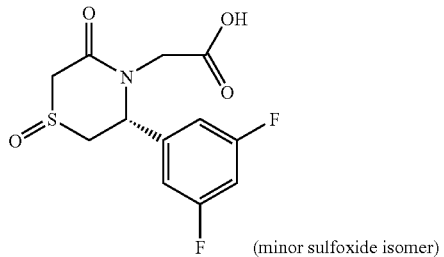

[(3R)-3-(3,5-Difluorophenyl)-1-oxido-5-oxothiomorpholin-4-yl]acetic acid (minor sulfoxide isomer)

A solution of benzyl [(3R)-3-(3,5-difluorophenyl)-1-oxido-5-oxothiomorpholin-4-yl]acetate (24.5 mg, 0.062 mmol, minor isomer, from the preparation of Intermediate 4, Step B) in MeOH (2 mL) was purged with nitrogen. The septum sealing the reaction vessel was briefly removed to allow introduction of Pd/C (~6 mg, 10% Pd/C). The vessel was then purged with hydrogen from a balloon, before a fresh balloon of hydrogen was attached. After LCMS analysis indicated that the reaction was progressing slowly, a suspension of 10% Pd/C was introduced via syringe. After 2.25 hours the hydrogen atmosphere was replaced with nitrogen. The mixture was then filtered through a pad of celite, washing with MeOH as needed. The filtrate was concentrated in vacuo to provide the title compound, which was used without further purification. MS: m/z=304 (M+1).

INTERMEDIATE 6

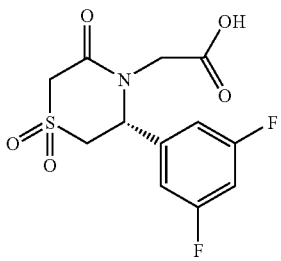

[(3R)-3-(3,5-Difluorophenyl)-1,1-dioxido-5-oxothiomorpholin-4-yl]acetic acid

Step A. Benzyl [(3R)-3-(3,5-difluorophenyl)-1,1-dioxido-5-oxothiomorpholin-4-yl]acetate To a solution of benzyl [(3R)-3-(3,5-difluorophenyl)-5-oxothiomorpholin-4-yl]acetate (65.9 mg, 0.175 mmol, from the preparation of Intermediate 4, Step A) in DCM (3 mL) was added m-CPBA (86.0 mg, 0.350 mmol, 70% by weight). After stirring for 17 hours at ambient temperature, the reaction mixture was applied to a silica gel column for purification, eluting with a gradient of Hexanes:EtOAc—95:5 to 50:50, to give the title compound, which is 83% pure (balance being m-CPBA), and was used without further purification.

Step B. [(3R)-3-(3,5-Difluorophenyl)-1,1-dioxido-5-oxothiomorpholin-4-yl]acetic acid A solution of benzyl [(3R)-3-(3,5-difluorophenyl)-1,1-dioxido-5-oxothiomorpholin-4-yl]acetate (71.7 mg, 0.145 mmol, 83%, from Step A) in MeOH (3 mL) was purged with nitrogen. The septum sealing the reaction vessel was briefly removed to allow introduction of Pd/C (~14 mg, 10% Pd/C). The vessel was then purged with hydrogen from a balloon, before a fresh balloon of hydrogen was attached. After 30 minutes the hydrogen atmosphere was replaced with nitrogen. The mixture was then filtered through a pad of celite, washing with MeOH as needed. The filtrate was concentrated in vacuo to provide the title compound. MS: m/z=320 (M+1).

INTERMEDIATE 7

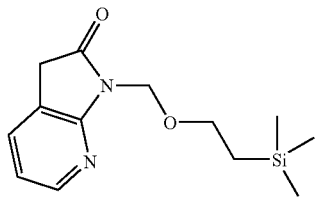

1-{[2-(Trimethylsilyl)ethoxy]methyl}-1,3-dihydro-2H-pyrrolo[2,3-b]pyridin-2-one

Step A. 1-{[2-(Trimethylsilyl)ethoxy]methyl}-1H-pyrrolo[2,3-b]pyridine

Sodium hydride (60% dispersion in mineral oil; 16.2 g, 0.404 mol) was added in portions over 25 min to a solution of 7-azaindole (39.8 g, 0.337 mol) in DMF (200 mL) at 0° C. and the mixture was stirred for 1 h. 2-(Trimethylsilyl)ethoxymethyl chloride (71.8 mL, 0.404 mol) was then added slowly over 15 min, keeping the temperature of the reaction mixture below 10° C. After 1 h, the reaction was quenched with water (500 mL) and the mixture was extracted with $CH_2Cl_2$ (5×300 mL). The combined organic layers were washed with saturated brine, dried over $MgSO_4$, filtered, concentrated and dried under high vacuum to give the title compound. MS: m/z=249 (M+1).

Step B. 3,3-Dibromo-1-{[2-(trimethylsilyl)ethoxy]methyl}-1,3-dihydro-2H-pyrrolo[2,3-b]pyridin-2-one A solution of 1-{[2-(trimethylsilyl)ethoxy]methyl}-1H-pyrrolo[2,3-b]pyridine from Step A (43.1 g, 0.1735 mol) in dioxane (300 mL) was added dropwise over 30 min to a suspension of pyridine hydrobromide perbromide (277 g, 0.8677 mol) in dioxane (300 mL). The reaction was stirred at ambient temperature using an overhead mechanical stirrer to produce two layers. After 60 min, the reaction was quenched with water (300 mL) and extracted with EtOAc (500 mL). The aqueous layer was extracted further with EtOAc (2×300 mL) and the combined organic layers were washed with $H_2O$ (4×300 mL; the final wash was pH 5-6), then brine (300 mL), dried over $MgSO_4$, filtered and concentrated in vacuo. The crude product was immediately dissolved in $CH_2Cl_2$ and the solution filtered through a plug of silica, eluting with $CH_2Cl_2$ until the dark red color had completely eluted from the plug. The filtrate was washed with saturated aqueous $NaHCO_3$ (400 mL), then brine (400 mL), dried over $MgSO_4$ filtered, and concentrated in vacuo to give the title compound. MS: m/z=423 (M+1).

Step C. 1-{[2-(Trimethylsilyl)ethoxy]methyl}-1,3-dihydro-2H-pyrrolo[2,3-b]pyridin-2-one Zinc (100 g, 1.54 mol) was added to a solution of 3,3-dibromo-1-{[2-(trimethylsilyl)ethoxy]methyl}-1,3-dihydro-2H-pyrrolo[2,3-b]pyridin-2-one (65 g, 0.154 mol) in THF (880 mL) and saturated aqueous $NH_4Cl$ (220 mL). After 3 h, the reaction mixture was filtered and concentrated in vacuo. The residue was partitioned between EtOAc and $H_2O$ which resulted in the formation of a white precipitate. Both layers were filtered through a Celite pad and the layers were separated. The aqueous layer was washed with EtOAc (2×500 mL) and the combined organic layers were washed with $H_2O$, dried over $MgSO_4$, filtered, and concentrated under reduced pressure. The crude product was purified by silica gel chromatography, eluting with $CH_2Cl_2$:EtOAc—90:10, to give the title compound. MS: m/z=265 (M+1).

INTERMEDIATE 8

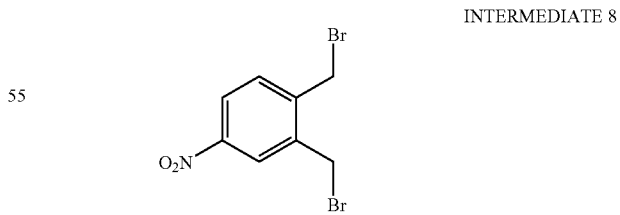

1,2-Bis(bromomethyl)-4-nitrobenzene

Step A. (4-Nitro-1,2-phenylene)dimethanol

A solution of 4-nitrophthalic acid (40 g, 189.5 mmol) in THF (500 mL) was added dropwise over 1.5 h to a solution of borane-THF complex (1 M, 490 mL, 490 mmol), keeping the reaction temperature between 0° C. and 5° C. After the addition, the reaction mixture was allowed to warm slowly to ambient temperature and stirred for 18 h. MeOH (100 mL) was added carefully and the precipitated solid dissolved. The mixture was concentrated in vacuo to about 500 mL, cooled to 0° C., and 10 N NaOH was added to adjust the pH to 10-11. This mixture was extracted with EtOAc (3×600 mL) and the combined organic layers were washed with brine, dried over $Na_2SO_4$, filtered, and concentrated in vacuo to give the title compound. MS: m/z=207 (M−OH+$CH_3CN$).

Step B. 1,2-Bis(bromomethyl)-4-nitrobenzene

Phosphorus tribromide (20.1 mL, 212 mmol) in $Et_2O$ (250 mL) was added dropwise over 1.5 h to a solution of (4-nitro-1,2-phenylene)dimethanol from Step A (35.3 g, 193 mmol) in $Et_2O$ (750 mL). After 18 h, the reaction mixture was cooled to 0° C. and quenched with $H_2O$ (100 mL). The layers were separated and the organic layer was washed with $H_2O$ (2×200 mL), then saturated aqueous $NaHCO_3$, dried over $Na_2SO_4$, filtered, and concentrated in vacuo to give the title compound. MS: m/z=309 (M+1).

INTERMEDIATE 9

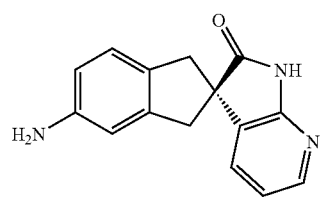

(R)-5-Amino-1,3-dihydrospiro[indene-2,3'-pyrrolo[2,3-b]pyridin]-2'(1'H)-one

Step A. (±)-5-Nitro-1'-{[2-(trimethylsilyl)ethoxy]methyl}-1,3-dihydrospiro[indene-2,3'-pyrrolo[2,3-b]pyridin]-2'(1'H)-one To a solution of 1,2-bis(bromomethyl)-4-nitrobenzene (40.9 g, 132 mmol, described in Intermediate 8) and 1-{[2-(trimethylsilyl)ethoxy]methyl}-1,3-dihydro-2H-pyrrolo[2,3-b]pyridin-2-one (31.5 g, 119 mmol, described in Intermediate 7) in DMF (2 L) was added cesium carbonate (129 g, 397 mmol), portionwise, over 5 min. After 18 h, acetic acid (7.6 mL) was added and the mixture was concentrated to a volume of about 500 mL, then partitioned between EtOAc (1.5 L) and $H_2O$ (1 L). The organic layer was washed with $H_2O$ (1 L), then brine (500 mL), then dried over $Na_2SO_4$, filtered, and concentrated in vacuo. The crude product was purified by silica gel chromatography, eluting with a gradient of hexane:EtOAc—100:0 to 0:100, to give the title compound. MS: m/z=412 (M+1).

Step B. (±)-5-Amino-1'-{[2-(trimethylsilyl)ethoxy]methyl}-1,3-dihydrospiro[indene-2,3'-pyrrolo[2,3-b]pyridin]-2'(1'H)-one A mixture of 10% Pd/C (3 g) and (±)-5-nitro-1'-{[2-(trimethylsilyl)ethoxy]methyl}-1,3-dihydrospiro[indene-2,3'-pyrrolo[2,3-b]pyridin]-2'(1'H)-one from Step A (19.1 g, 46.4 mmol) was stirred vigorously in EtOH (400 mL) under an atmosphere of hydrogen (ca. 1 atm). After 18 h, the mixture was filtered through a pad of Celite, washing extensively with MeOH, and the filtrate was concentrated in vacuo to give the title compound. MS: m/z=382 (M+1).

Step C. tert-Butyl (R)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate A solution of (±)-5-amino-1'-{[2-(trimethylsilyl)ethoxy]methyl}-1,3-dihydrospiro[indene-2,3'-pyrrolo[2,3-b]pyridin]-2'(1'H)-one from Step B (104 g, 273 mmol) and di-tert-butyl dicarbonate (71.5 g, 328 mmol) in $CHCl_3$ (1 L) was heated to reflux for 17 h. The cooled mixture was concentrated in vacuo and the residue was purified by silica gel chromatography, eluting with hexane:EtOAc—100:0 to 50:50, to give the racemic product. The enantiomers were resolved by HPLC, utilizing a ChiralPak AD column and eluting with EtOH. The first major peak to elute was tert-butyl (S)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate, and the second major peak to elute was tert-butyl (R)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate, the title compound. MS: m/z=482 (M+1).

Step D. (R)-5-Amino-1,3-dihydrospiro[indene-2,3'-pyrrolo[2,3-b]pyridin]-2'(1'H)-one A solution of tert-butyl (R)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate from Step C (13.4 g 27.8 mmol) in MeOH (300 mL) was saturated with HCl (g). The mixture was resaturated with HCl (g) every 30 min until the starting material was consumed, and then concentrated in vacuo. The residue was dissolved in MeOH (150 mL) and treated with ethylenediamine (1.9 mL, 27.8 mmol) and 10 N sodium hydroxide (6 mL, 60 mmol) to adjust the mixture to pH 10. After 30 min, the mixture was diluted with $H_2O$ (400 mL) and extracted with $CHCl_3$ (1 L). The organic layer was dried over $Na_2SO_4$, filtered, and concentrated in vacuo. The crude material was triturated with MeOH (35 mL) to give the title compound. MS: m/z=252 (M+1).

INTERMEDIATE 10

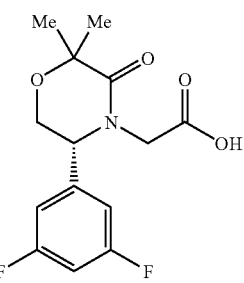

[(5R)-5-(3,5-Difluorophenyl)-2,2-dimethyl-3-oxo-morpholin-4-yl]acetic acid

Step A. N—[($S_S$,1R)-2-{[tert-Butyl(dimethyl)silyl]oxy}-1-(3,5-difluorophenyl)ethyl]-2-methylpropane-2-sulfinamide To a stirred solution of ($S_S$)—N-((1E)-2-{[tert-butyl(dimethyl)silyl]oxy}ethylidene)-2-methylpropane-2-sulfinamide (5.00 g, 17.9 mmol) [Tang et al. (2001) *J. Org. Chem.*, 66, 8772-8778] in THF (75 mL) at −78° C. was added 3,5-difluorophenylmagnesium bromide (71.6 mL of a 0.5 M solution in THF, 35.8 mmol) dropwise. The reaction mixture was stirred at −78° C. for 5 h, and then allowed to warm slowly to ambient temperature and stirring was continued for 18 h. The mixture was quenched with saturated aqueous NH$_4$Cl (25 mL) and extracted with EtOAc (3×75 mL). The combined organic layers were dried over Na$_2$SO$_4$, filtered, and concentrated in vacuo. The crude product was purified by silica gel chromatography, eluting with a gradient of CH$_2$Cl$_2$:EtOAc—100:0 to 80:20, to give the title compound. MS: m/z=392 (M+1).

Step B. (2R)-2-Amino-2-(3,5-difluorophenyl)ethanol

To a solution of N—[(S$_S$,1R)-2-{[tert-butyl(dimethyl)silyl]oxy}-1-(3,5-difluorophenyl)ethyl]-2-methylpropane-2-sulfinamide from Step A (1.50 g, 3.81 mmol) in MeOH (40 mL) at 0° C. was added HCl (9.5 mL of a 2 M solution in Et$_2$O, 19 mmol). After 20 min, the reaction mixture was concentrated to dryness in vacuo. The residue was dissolved in H$_2$O (25 mL) and the mixture was extracted with EtOAc (2×50 mL) and these organic extracts were discarded. The aqueous phase was adjusted to pH 10 by addition of 1 N NaOH and extracted with EtOAc (2×50 mL). These organic layers were dried over Na$_2$SO$_4$, filtered, and concentrated in vacuo to give the title compound. MS: m/z=174 (M+1).

Step C. 2-Chloro-N-[(1R)-1-(3,5-difluorophenyl)-2-hydroxyethyl]acetamide

To a solution of (2R)-2-amino-2-(3,5-difluorophenyl)ethanol from Step B (630 mg, 3.64 mmol) and triethylamine (0.51 mL, 3.64 mmol) in CH$_2$Cl$_2$ (40 mL) at 0° C. was added chloroacetyl chloride (0.29 mL, 3.64 mmol). After 20 min, the reaction mixture was quenched with saturated aqueous NaHCO$_3$ (15 mL) and extracted with CH$_2$Cl$_2$ (2×25 mL). The combined organic extracts were washed with 10% citric acid, then brine, then dried over Na$_2$SO$_4$, filtered, and concentrated in vacuo to give the title compound. MS: m/z=250 (M+1).

Step D. (5R)-5-(3,5-Difluorophenyl)morpholin-3-one

To a solution of 2-chloro-N-[(1R)-1-(3,5-difluorophenyl)-2-hydroxyethyl]acetamide from Step C (840 mg, 3.37 mmol) in THF (75 mL) at 0° C. was added NaH (291 mg of a 60% dispersion in oil, 7.28 mmol) and the mixture was stirred at ambient temperature for 1 h. Saturated aqueous NH$_4$Cl (10 mL) was added and the mixture was extracted with EtOAc (2×20 mL). The combined organic layers were dried over Na$_2$SO$_4$, filtered, and concentrated in vacuo. The crude product was purified by silica gel chromatography, eluting with a gradient of hexane:EtOAc—75:25 to 25:75, to give the title compound. MS: m/z=214 (M+1).

Step E. tert-Butyl (3R)-3-(3,5-difluorophenyl)-5-oxomorpholine-4-carboxylate

A solution of (5R)-5-(3,5-difluorophenyl)morpholin-3-one from Step D (570 mg, 2.67 mmol), di-tert-butyl dicarbonate (584 mg, 2.67 mmol), and 4-dimethylaminopyridine (327 mg, 2.67 mmol) in CH$_2$Cl$_2$ (30 mL) was stirred at ambient temperature for 1 h. The solvent was removed under reduced pressure and the residue was purified by silica gel chromatography, eluting with a gradient of hexane:EtOAc—90:10 to 50:50, to give the title compound. MS: m/z=377 (M+Na+CH$_3$CN).

Step F. tert-Butyl (5R)-5-(3,5-difluorophenyl)-2,2-dimethyl-3-oxomorpholine-4-carboxylate To a 1 M solution of sodium bis(trimethylsilyl)amide in THF (1.60 mL, 1.60 mmol) at −78° C. was added dropwise a solution of tert-butyl (3R)-3-(3,5-difluorophenyl)-5-oxomorpholine-4-carboxylate from Step E (500 mg, 1.60 mmol) in DME (15 mL) at −78° C. The resulting mixture was stirred at −78° C. for 10 min then iodomethane (0.099 mL, 1.60 mmol) was added. After stirring at −78° C. for a further 1 h, the reaction mixture was slowly transferred via cannula into a 1 M solution of sodium bis(trimethylsilyl)amide in THF (1.60 mL, 1.60 mmol) at −78° C. The resulting mixture was stirred at −78° C. for 10 min then a second equivalent of iodomethane (0.099 mL, 1.60 mmol) was added. After stirring at −78° C. for a further 1 h, the reaction mixture was quenched with saturated aqueous NH$_4$Cl (10 mL) and extracted with EtOAc (2×25 mL). The combined organic layers were dried over Na$_2$SO$_4$, filtered, and concentrated in vacuo. The crude product was purified by silica gel chromatography, eluting with a gradient of hexane:EtOAc—90:10 to 60:40, to give the title compound. MS: m/z=286 (M−C$_4$H$_7$).

Step G. (5R)-5-(3,5-Difluorophenyl)-2,2-dimethyl-morpholin-3-one

To a solution of tert-butyl (5R)-5-(3,5-difluorophenyl)-2,2-dimethyl-3-oxomorpholine-4-carboxylate from Step F (225 mg, 0.66 mmol) in CH$_2$Cl$_2$ (3 mL) at ambient temperature was added TFA (0.49 mL, 6.6 mmol). After stirring for 1 h, the reaction mixture was concentrated in vacuo to give the title compound. MS: m/z=242 (M+1).

Step H. Ethyl [(5R)-5-(3,5-difluorophenyl)-2,2-dimethyl-3-oxomorpholin-4-yl]acetate To a stirred solution of (5R)-5-(3,5-difluorophenyl)-2,2-dimethylmorpholin-3-one from Step G (150 mg, 0.62 mmol) in DMF (2 mL) at 0° C. was added NaH (27 mg of a 60% dispersion in oil, 0.68 mmol). After 10 min, ethyl bromoacetate (104 mg, 0.62 mmol) was added and the mixture was stirred at 0° C. for 30 min. Saturated aqueous NaHCO$_3$ (5 mL) was added and the mixture was extracted with EtOAc (2×10 mL). The combined organic layers were dried over Na$_2$SO$_4$, filtered, and concentrated in vacuo. The crude product was purified by silica gel chromatography, eluting with a gradient of hexane:EtOAc—95:5 to 70:30, to give the title compound. MS: m/z=328 (M+1).

Step I. [(5R)-5-(3,5-Difluorophenyl)-2,2-dimethyl-3-oxomorpholin-4-yl]acetic acid To a solution of ethyl [(5R)-5-(3,5-difluorophenyl)-2,2-dimethyl-3-oxomorpholin-4-yl]acetate from Step H (150 mg, 0.46 mmol) in THF (3 mL) and H$_2$O (3 mL) was added 1 N aqueous LiOH (0.55 mL, 0.55 mmol) and the resulting mixture was stirred at ambient temperature for 18 h. The reaction mixture was purified directly by HPLC using a reversed phase C18 column and eluting with a gradient of H$_2$O:CH$_3$CN:CF$_3$CO$_2$H—90:10:0.1 to 5:95:0.1. Lyophilization provided the title compound. MS: m/z=300 (M+1).

INTERMEDIATE 11

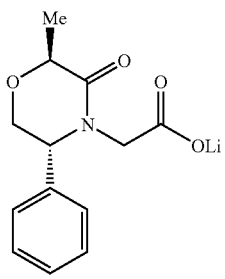

Lithium [(2S,5R)-2-methyl-3-oxo-5-phenylmorpholin-4-yl]acetate

Step A.
2-Chloro-N-[(1R)-2-hydroxy-1-phenylethyl]acetamide

To a solution of (R)-2-phenylglycinol (10 g, 73 mmol) and triethylamine (10.2 mL, 73 mmol) in CH$_2$Cl$_2$ (500 mL) at 0° C. was slowly added chloroacetyl chloride (5.8 mL, 73 mmol). After 20 min, the reaction mixture was quenched with saturated aqueous NaHCO$_3$ (150 mL) and extracted with CH$_2$Cl$_2$ (2×250 mL). The combined organic extracts were washed with 10% citric acid, then brine, then dried over Na$_2$SO$_4$, filtered, and concentrated in vacuo to give the title compound. MS: m/z=214 (M+1).

Step B. (5R)-5-Phenylmorpholin-3-one

To a solution of 2-chloro-N-[(1R)-2-hydroxy-1-phenylethyl]acetamide from Step A (12.0 g, 56 mmol) in THF (750 mL) at 0° C. was added NaH (4.48 g of a 60% dispersion in oil, 112 mmol) in portions over 1 h and the mixture was stirred at ambient temperature for 1 h. Saturated aqueous NH$_4$Cl (100 mL) was added and the mixture was extracted with EtOAc (2×200 mL). The combined organic layers were dried over Na$_2$SO$_4$, filtered, and concentrated in vacuo to give the title compound. MS: m/z=178 (M+1).

Step C. tert-Butyl (5R)-3-oxo-5-phenylmorpholine-4-carboxylate

A solution of (5R)-5-phenylmorpholin-3-one from Step B (9.00 g, 50.8 mmol), di-tert-butyl dicarbonate (11.1 g, 50.8 mmol), and 4-dimethylaminopyridine (6.21 mg, 50.8 mmol) in CH$_2$Cl$_2$ (750 mL) was stirred at ambient temperature for 18 h. The solvent was removed under reduced pressure and the residue was purified by silica gel chromatography, eluting with a gradient of hexane:EtOAc—50:50 to 0:100, to give the title compound. MS: m/z=222 (M−C$_4$H$_7$).

Step D. tert-Butyl (2S,5R)-2-methyl-3-oxo-5-phenylmorpholine-4-carboxylate

To a 1 M solution of sodium bis(trimethylsilyl)amide in THF (0.79 mL, 0.79 mmol) at −78° C. was added dropwise a solution of tert-butyl (5R)-3-oxo-5-phenylmorpholine-4-carboxylate from Step C (200 mg, 0.72 mmol) in DME (5 mL) at −78° C. The resulting mixture was stirred at −78° C. for 10 min then iodomethane (0.049 mL, 0.79 mmol) was added. After stirring at −78° C. for a further 1 h, the reaction mixture was quenched with saturated aqueous NH$_4$Cl (5 mL) and extracted with EtOAc (2×10 mL). The combined organic layers were dried over Na$_2$SO$_4$, filtered, and concentrated in vacuo. The crude product was partially purified by silica gel chromatography, eluting with a gradient of hexane:EtOAc—90:10 to 60:40. Further purification was achieved by HPLC, using a ChiralPak AS column and eluting with hexane:i-PrOH—90:10, to give the title compound. MS: m/z=236 (M−C$_4$H$_7$).

Step E. (2S,5R)-2-Methyl-5-phenylmorpholin-3-one

To a solution of tert-butyl (2S,5R)-2-methyl-3-oxo-5-phenylmorpholine-4-carboxylate from Step D (160 mg, 0.55 mmol) in CH$_2$Cl$_2$ (2 mL) at ambient temperature was added TFA (0.41 mL, 5.5 mmol). After stirring for 1 h, the reaction mixture was concentrated in vacuo to give the title compound. MS: m/z=192 (M+1).

Step F. Ethyl [(2S,5R)-2-methyl-3-oxo-5-phenylmorpholin-4-yl]acetate

To a stirred solution of (2S,5R)-2-methyl-5-phenylmorpholin-3-one from Step E (90 mg, 0.47 mmol) in DMF (2 mL) at 0° C. was added NaH (20 mg of a 60% dispersion in oil, 0.50 mmol). After 10 min, ethyl bromoacetate (79 mg, 0.47 mmol) was added and the mixture was stirred at 0° C. for 2 h. Saturated aqueous NaHCO$_3$ (3 mL) was added and the mixture was extracted with EtOAc (2×30 mL). The combined organic layers were dried over Na$_2$SO$_4$, filtered, and concentrated in vacuo. The crude product was purified by silica gel chromatography, eluting with a gradient of hexane:EtOAc—90:10 to 60:40, to give the title compound. MS: m/z=278 (M+1).

Step G. Lithium [(2S,5R)-2-methyl-3-oxo-5-phenylmorpholin-4-yl]acetate

To a solution of ethyl [(2S,5R)-2-methyl-3-oxo-5-phenylmorpholin-4-yl]acetate from Step F (125 mg, 0.45 mmol) in THF (4 mL) and H$_2$O (4 mL) was added 1 N aqueous LiOH (0.54 mL, 0.54 mmol) and the resulting mixture was stirred at ambient temperature for 18 h. The mixture was adjusted to pH 6 by addition of 1 N HCl and concentrated to dryness in vacuo to give the title compound. MS: m/z=250 (M+1).

INTERMEDIATE 12

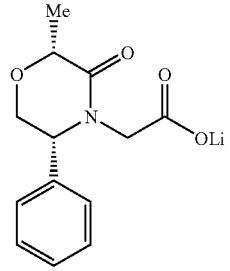

Lithium [(2R,5R)-2-methyl-3-oxo-5-phenylmorpholin-4-yl]acetate

Step A. 2-Chloro-N-[(1R)-2-hydroxy-1-phenylethyl] propanamide

To a solution of (R)-2-phenylglycinol (1.00 g, 7.3 mmol) and triethylamine (1.02 mL, 7.3 mmol) in CH$_2$Cl$_2$ (50 mL) at 0° C. was slowly added 2-chloropropionyl chloride (0.72 mL, 7.3 mmol). After 20 min, the reaction mixture was quenched with saturated aqueous NaHCO$_3$ (20 mL) and extracted with $CH_2Cl_2$ (2×50 mL). The combined organic extracts were washed with 10% citric acid, then brine, then dried over $Na_2SO_4$, filtered, and concentrated in vacuo to give the title compound. MS: m/z=228 (M+1).

Step B. (2R,5R)-2-Methyl-5-phenylmorpholin-3-one

To a solution of 2-chloro-N-[(1R)-2-hydroxy-1-phenylethyl]propanamide from Step A (1.30 g, 5.71 mmol) in THF (100 mL) at 0° C. was added NaH (493 mg of a 60% dispersion in oil, 12.3 mmol) and the mixture was stirred at ambient temperature for 18 h. Saturated aqueous $NaHCO_3$ (10 mL) was added and the mixture was extracted with EtOAc (3×20 mL). The combined organic layers were dried over $Na_2SO_4$, filtered, and concentrated in vacuo. The crude product was purified by silica gel chromatography, eluting with a gradient of hexane:EtOAc—75:25 to 0:100, to give the title compound. MS: m/z=192 (M+1).

Step C. Ethyl [(2R,5R)-2-methyl-3-oxo-5-phenylmorpholin-4-yl]acetate

To a stirred solution of (2R,5R)-2-methyl-5-phenylmorpholin-3-one from Step B (500 mg, 2.62 mmol) in DMF (15 mL) at 0° C. was added NaH (113 mg of a 60% dispersion in oil, 2.83 mmol). After 10 min, ethyl bromoacetate (437 mg, 2.62 mmol) was added and the mixture was stirred at 0° C. for 2 h. Saturated aqueous $NaHCO_3$ (3 mL) was added and the mixture was extracted with EtOAc (2×30 mL). The combined organic layers were dried over $Na_2SO_4$, filtered, and concentrated in vacuo. The crude product was purified by silica gel chromatography, eluting with a gradient of hexane:EtOAc—90:10 to 60:40, to give the title compound. MS: m/z=278 (M+1).

Step D. Lithium [(2S,5R)-2-methyl-3-oxo-5-phenylmorpholin-4-yl]acetate

To a solution of ethyl [(2R,5R)-2-methyl-3-oxo-5-phenylmorpholin-4-yl]acetate from Step C (590 mg, 2.13 mmol) in THF (5 mL) and $H_2O$ (5 mL) was added 1 N aqueous LiOH (2.55 mL, 2.55 mmol) and the resulting mixture was stirred at ambient temperature for 18 h. The mixture was adjusted to pH 6 by addition of 1 N HCl and concentrated to dryness in vacuo to give the title compound. MS: m/z=250 (M+1).

INTERMEDIATE 13

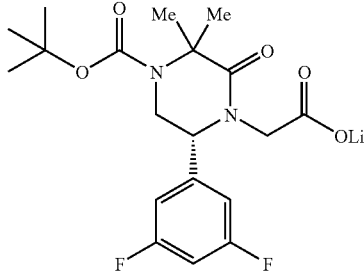

Lithium [(6R)-4-(tert-butoxycarbonyl)-6-(3,5-difluorophenyl)-3,3-dimethyl-2-oxopiperazin-1-yl]acetate Step A. Methyl 2-{[2-(3,5-difluorophenyl)-2-oxoethyl]amino}-2-methylpropanoate A mixture of methyl α-aminoisobutyrate hydrochloride (10.3 g, 67.0 mmol), 3,5-difluorophenacyl bromide (15.0 g, 63.8 mmol), and $K_2CO_3$ (17.6 g, 128 mmol) in DMF (100 mL) was stirred at ambient temperature for 3 h. Saturated aqueous $NaHCO_3$ (400 mL) was added and the mixture was extracted with EtOAc (1 L). The organic layer was washed with brine, dried over $Na_2SO_4$, filtered, and concentrated in vacuo. The crude product was purified by silica gel chromatography, eluting with a gradient of hexane:EtOAc—100:0 to 0:100, to give the title compound. MS: m/z=272 (M+1).

Step B. (±)-Ethyl [6-(3,5-difluorophenyl)-3,3-dimethyl-2-oxopiperazin-1-yl]acetate A mixture of methyl 2-{[2-(3,5-difluorophenyl)-2-oxoethyl]amino}-2-methylpropanoate from Step A (8.60 g, 31.7 mmol), glycine ethyl ester hydrochloride (44.3 g, 317 mmol), and AcOH (5.71 mL, 95 mmol) in MeOH (300 mL) was stirred at ambient temperature for 10 min. $NaCNBH_3$ (2.39 g, 38.0 mmol) was added and the pH of the mixture was checked and adjusted to pH ~5 as necessary. The reaction mixture was heated to 50° C. for 18 h. Additional AcOH (4 mL) was added and the reaction mixture was heated to 60° C. for 6 h then allowed to cool and concentrated in vacuo to a volume of ca. 150 mL. The resulting mixture was carefully quenched with saturated aqueous $NaHCO_3$ (300 mL) and then extracted with $CH_2Cl_2$ (1 L). The organic extract was washed with brine, dried over $Na_2SO_4$, filtered, and concentrated in vacuo. The crude product was purified by silica gel chromatography, eluting with hexane:EtOAc—100:0 to 0:100, to give the title compound. MS: m/z=327 (M+1).

Step C. tert-Butyl (5R)-5-(3,5-difluorophenyl)-4-(2-ethoxy-2-oxoethyl)-2,2-dimethyl-3-oxopiperazine-1-carboxylate A solution of ethyl [8-(3,5-difluorophenyl)-10-oxo-6,9-diazaspiro[4.5]dec-9-yl]acetate from Step B (2.27 g, 6.96 mmol), N,N-diisopropylethylamine (0.607 mL, 3.48 mmol), and di-tert-butyl dicarbonate (15.2 g, 69.6 mmol) in acetonitrile (30 mL) was stirred at 60° C. for 18 h, then cooled and concentrated under reduced pressure. The crude product was purified by silica gel chromatography, eluting with a gradient of hexane:EtOAc—100:0 to 0:100, to give the racemic product. The enantiomers were separated by SFC, using a Chiralcel OD column and eluting with $CO_2$:MeOH—80:20. The first major peak to elute was tert-butyl (5S)-5-(3,5-difluorophenyl)-4-(2-ethoxy-2-oxoethyl)-2,2-dimethyl-3-oxopiperazine-1-carboxylate and the second major peak to elute was tert-butyl (5R)-5-(3,5-difluorophenyl)-4-(2-ethoxy-2-oxoethyl)-2,2-dimethyl-3-oxopiperazine-1-carboxylate, the title compound. MS: m/z=371 (M–$C_4H_7$).

Step D. Lithium [(6R)-4-(tert-butoxycarbonyl)-6-(3,5-difluorophenyl)-3,3-dimethyl-2-oxopiperazin-1-yl]acetate To a solution of tert-butyl (5R)-5-(3,5-difluorophenyl)-4-(2-ethoxy-2-oxoethyl)-2,2-dimethyl-3-oxopiperazine-1-car boxylate from Step C (1.18 g, 2.77 mmol) in THF (18 mL) and H₂O (2 mL) was added 1 N aqueous LiOH (3.04 mL, 3.04 mmol) and the resulting mixture was stirred at ambient temperature for 5 h. The mixture was adjusted to pH 6 by addition of 1 N HCl and concentrated to dryness in vacuo to give the title compound. MS: m/z=343 (M−C₄H₇).

eluting with a gradient of H₂O:CH₃CN:CF₃CO₂H—90:10: 0.1 to 5:95:0.1. The compound was further purified by SFC, utilizing a ChiralPak AD column and eluting with CO₂: MeOH—91:9, to give the title compound. MS: m/z=294 (M+1).

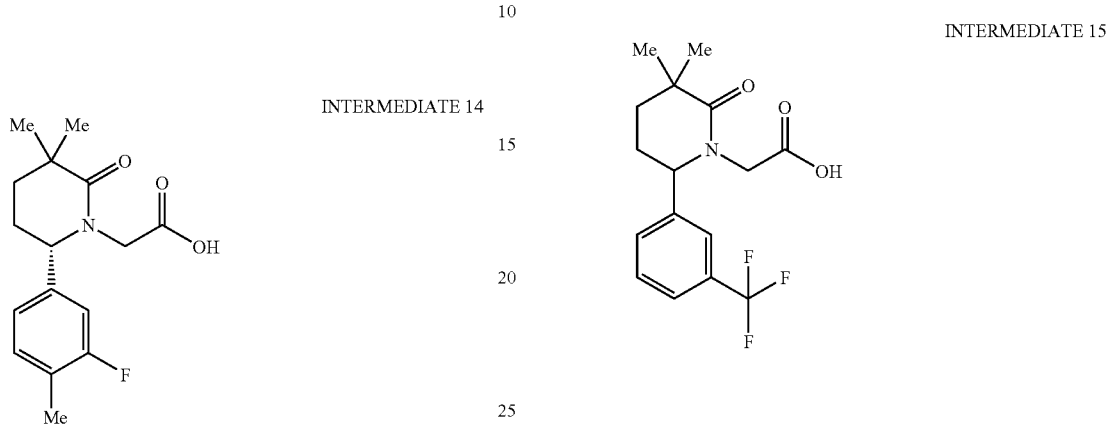

INTERMEDIATE 14

(S)-[6-(3-Fluoro-4-methylphenyl)-3,3-dimethyl-2-oxopiperidin-1-yl]acetic acid

Step A. (S)-6-(3-Fluoro-4-methylphenyl)-3,3-dimethylpiperidin-2-one

To a stirred solution of benzyl (S_S)-5-[(tert-butylsulfinyl)imino]-2,2-dimethylpentanoate (1.00 g, 2.96 mmol, described in Intermediate 3) in toluene (28 mL) at −78° C. was added 3-fluoro-4-methylphenylmagnesium bromide (11.9 mL of a 0.5 M solution in THF, 5.93 mmol). The reaction mixture was warmed to ambient temperature for 2 h, and then heated at reflux for 2 h. The solvent was removed in vacuo and the crude solid dissolved in DMSO (5 mL). The crude product was purified by HPLC using a reversed phase C18 column and eluting with a gradient of H₂O:CH₃CN: CF₃CO₂H—90:10:0.1 to 5:95:0.1. Lyophilization provided the title compound. MS: m/z=236 (M+1).

Step B. (S)-[6-(3-Fluoro-4-methylphenyl)-3,3-dimethyl-2-oxopiperidin-1-yl]acetic acid To a stirred solution of (S)-6-(3-fluoro-4-methylphenyl)-3,3-dimethylpiperidin-2-one from Step A (80 mg, 0.340 mmol) in DMF (3 mL) at ambient temperature was added NaH (19 mg of a 60% dispersion in oil, 0.476 mmol). After 15 min, methyl bromoacetate (0.051 mL, 0.544 mmol) was added and the mixture was stirred for 16 h. Sodium hydroxide (0.061 mL of a 10 M solution, 0.612 mmol) was added and the mixture stirred for 2 h. The crude product was purified directly by HPLC using a reversed phase C18 column and

INTERMEDIATE 15

{(±)-3,3-Dimethyl-2-oxo-6-[3-(trifluoromethyl)phenyl]piperidin-1-yl}acetic acid

Step A. Methyl 2,2-dimethyl-5-oxo-5-[3-(trifluoromethyl)phenyl]pentanoate

To a stirred solution of 3-bromobenzenetrifluoride (337 mg, 1.50 mmol) in THF (3 mL) at −78° C. was added tert-butyllithium (1.76 mL of a 1.7 M solution in pentane, 2.99 mmol) dropwise. The reaction mixture was stirred for 1 h at −78° C., and then a solution of methyl 5-[methoxy(methyl)amino]-2,2-dimethyl-5-oxopentanoate (325 mg, 1.50 mmol, described in Intermediate 1) in THF (5 mL) was added. The reaction mixture was stirred for 1 h at −78° C. The solvent was removed in vacuo and the crude solid dissolved in DMSO (5 mL). The crude product was purified by HPLC using a reversed phase C18 column and eluting with a gradient of H₂O:CH₃CN:CF₃CO₂H—90:10:0.1 to 5:95:0.1. Lyophilization provided the title compound. MS: m/z=303 (M+1).

Step B. {(±)-3,3-Dimethyl-2-oxo-6-[3-(trifluoromethyl)phenyl]piperidin-1-yl}acetic acid To a stirred solution of methyl 2,2-dimethyl-5-oxo-5-[3-(trifluoromethyl)phenyl]pentanoate from Step A (45.0 mg, 0.149 mmol) and glycine (99.0 mg, 1.32 mmol) in MeOH (2 mL) and acetic acid (0.045 mL) was added sodium cyanoborohydride (50.0 mg, 0.794 mmol). The reaction mixture was heated to reflux for 18 h. To the resulting mixture was added xylenes (3 mL) and heated to 140° C. for 4 h. The solvent was removed in vacuo and the crude solid dissolved in DMSO (1 mL). The crude product was purified by HPLC using a reversed phase C18 column and eluting with a gradient of H₂O:CH₃CN:CF₃CO₂H—90:10:0.1 to 5:95:0.1. Lyophilization provided the title compound. MS: m/z=330 (M+1).

INTERMEDIATE 16

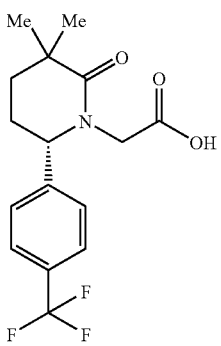

3,3-Dimethyl-2-oxo-6-[4-(trifluoromethyl)phenyl]piperidin-1-yl}acetic acid

Step A. 3,3-Dimethyl-6-[4-(trifluoromethyl)phenyl]piperidin-2-one

To a stirred solution of 4-bromobenzenetrifluoride (333 mg, 1.48 mmol) in THF (3 mL) at −78° C. was added tert-butyllithium (1.74 mL of a 1.7 M solution in pentane, 2.96 mmol) dropwise. The reaction mixture was stirred for 1 h at −78° C., and then a solution of benzyl (S$_S$)-5-[(tert-butylsulfinyl)imino]-2,2-dimethylpentanoate (250 mg, 0.741 mmol, described in Intermediate 3) in toluene (5 mL) was added. The reaction mixture was stirred for 20 min at −78° C., 1 h at ambient temperature, and 1 h at reflux. The solvent was removed in vacuo and the crude solid dissolved in DMSO (5 mL). The crude product was purified by HPLC using a reversed phase C18 column and eluting with a gradient of H$_2$O:CH$_3$CN:CF$_3$CO$_2$H—90:10:0.1 to 5:95:0.1. Lyophilization provided the title compound. MS: m/z=272 (M+1).

3,3-Dimethyl-2-oxo-6-[4-(trifluoromethyl)phenyl]piperidin-1-yl}acetic acid

Essentially following the procedures described for Intermediate 14, but using 3,3-dimethyl-6-[4-(trifluoromethyl)phenyl]piperidin-2-one in place of (S)-6-(3-fluoro-4-methylphenyl)-3,3-dimethylpiperidin-2-one, the title compound was prepared. MS: m/z=330 (M+1).

INTERMEDIATE 17

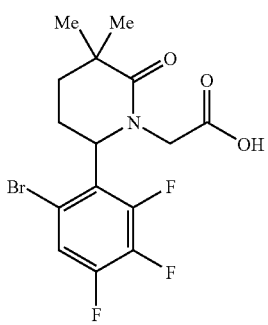

[6-(6-Bromo-2,3,4-trifluorophenyl)-3,3-dimethyl-2-oxopiperidin-1-yl]acetic acid

Step A. 6-(6-Bromo-2,3,4-trifluorophenyl)-3,3-dimethylpiperidin-2-one

To a stirred solution of 1-bromo-3,4,5-trifluorobenzene (313 mg, 1.48 mmol) in THF (3 mL) at −78° C. was added tert-butyllithium (1.74 mL of a 1.7 M solution in pentane, 2.96 mmol) dropwise. The reaction mixture was stirred for 1 h at −78° C., 3 h at 0° C., and then cooled back down to −78° C. A solution of benzyl (S$_S$)-5-[(tert-butylsulfinyl)imino]-2,2-dimethylpentanoate (250 mg, 0.741 mmol, described in Intermediate 3) in toluene (5 mL) was added. The reaction mixture was stirred for 20 min at −78° C., 16 h at ambient temperature, and 1 h at reflux. The solvent was removed in vacuo and the crude solid dissolved in DMSO (5 mL). The crude product was purified by HPLC using a reversed phase C18 column and eluting with a gradient of H$_2$O:CH$_3$CN:CF$_3$CO$_2$H—90:10:0.1 to 5:95:0.1. Lyophilization provided the title compound. MS: m/z=337 (M+1).

[6-(6-Bromo-2,3,4-trifluorophenyl)-3,3-dimethyl-2-oxopiperidin-1-yl]acetic acid

Essentially following the procedures described for Intermediate 14, but using 6-(6-bromo-2,3,4-trifluorophenyl)-3,3-dimethylpiperidin-2-one in place of (S)-6-(3-fluoro-4-methylphenyl)-3,3-dimethylpiperidin-2-one, the title compound was prepared. MS: m/z=395 (M+1).

INTERMEDIATE 18

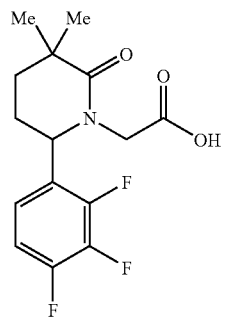

[3,3-Dimethyl-2-oxo-6-(2,3,4-trifluorophenyl)piperidin-1-yl]acetic acid

Step A. 3,3-Dimethyl-6-(2,3,4-trifluorophenyl)piperidin-2-one

A solution of 6-(6-bromo-2,3,4-trifluorophenyl)-3,3-dimethylpiperidin-2-one (27.0 mg, 0.080 mmol, described in Intermediate 17) and 10% palladium on carbon in degassed EtOH (2 mL) was stirred under a hydrogen balloon for 3 h. The reaction mixture was filtered through a Celite pad and concentrated in vacuo to provide the title compound. MS: m/z=258 (M+1).

[3,3-Dimethyl-2-oxo-6-(2,3,4-trifluorophenyl)piperidin-1-yl]acetic acid

Essentially following the procedures described for Intermediate 14, but using 3,3-dimethyl-6-(2,3,4-trifluorophenyl)piperidin-2-one in place of (S)-6-(3-fluoro-4-methylphenyl)-3,3-dimethylpiperidin-2-one, the title compound was prepared. MS: m/z=316 (M+1).

INTERMEDIATE 19

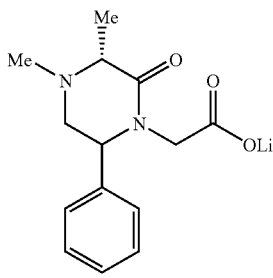

Lithium [(3R)-3,4-dimethyl-2-oxo-6-phenylpiperazin-1-yl]acetate

Step A. Methyl (2R)-2-[(2-oxo-2-phenylethyl)amino]propanoate, TFA salt

A mixture of (R)-alanine methyl ester hydrochloride (1.00 g, 7.16 mmol), 2-bromoacetophenone (2.85 g, 14.3 mmol), and NaHCO₃ (1.20 g, 14.3 mmol) in DMF (20 mL) was stirred at ambient temperature for 6 h. The reaction mixture was quenched with 1 N aqueous HCl (25 mL) and the mixture was extracted with EtOAc (2×35 mL) and the organic phase was discarded. The aqueous phase was adjusted to pH 10 with saturated aqueous Na₂CO₃ and then extracted with EtOAc (3×75 mL). The combined organic extracts were dried over Na₂SO₄, filtered, and concentrated in vacuo. The crude product was purified by HPLC using a reversed phase C18 column and eluting with a gradient of H₂O:CH₃CN:CF₃CO₂H—90:10:0.1 to 5:95:0.1. Concentration of product-containing fractions in vacuo provided the title compound. MS: m/z=222 (M+1).

Step B. Methyl [(3R)-3,4-dimethyl-2-oxo-6-phenylpiperazin-1-yl]acetate

To a stirred mixture of methyl (2R)-2-[(2-oxo-2-phenylethyl)amino]propanoate, TFA salt, from Step A (152 mg, 0.452 mmol) and glycine methyl ester hydrochloride (85 mg, 0.678 mmol) in MeOH (1 mL) was added N,N-diisopropylethylamine (0.197 mL, 1.13 mmol), followed by AcOH (0.155 mL, 2.71 mmol). The resulting mixture was stirred at ambient temperature for 10 min, then NaCNBH₃ (34 mg, 0.54 mmol) was added. The reaction mixture was heated to 50° C. for 18 h then allowed to cool. Formaldehyde (0.067 mL of a 37% aqueous solution, 0.90 mmol) was added and the mixture was stirred at ambient temperature for 30 min. The reaction mixture was quenched with 1 N aqueous HCl (5 mL) and the mixture was extracted with EtOAc (2×10 mL) and the organic phase was discarded. The aqueous phase was adjusted to pH 10 with saturated aqueous Na₂CO₃ and then extracted with EtOAc (3×15 mL). The combined organic extracts were dried over Na₂SO₄, filtered, and concentrated in vacuo. The crude product was purified by HPLC using a reversed phase C18 column and eluting with a gradient of H₂O:CH₃CN:CF₃CO₂H—90:10:0.1 to 5:95:0.1. The product-containing fractions were combined, basified with saturated aqueous NaHCO3, and extracted with EtOAc. The organic extracts were dried over Na₂SO₄, filtered, and concentrated in vacuo to provide the title compound. MS: m/z=277 (M+1).

Step C. Lithium [(3R)-3,4-dimethyl-2-oxo-6-phenylpiperazin-1-yl]acetate

A solution of methyl [(3R)-3,4-dimethyl-2-oxo-6-phenylpiperazin-1-yl]acetate from Step B (50 mg, 0.18 mmol) in THF (1 mL) was added 1 N aqueous LiOH (0.20 mL, 0.20 mmol) and the resulting mixture was stirred at ambient temperature for 4 h. The mixture was adjusted to pH 6 by addition of 1 N HCl and concentrated to dryness in vacuo to give the title compound. MS: m/z=263 (M+1).

INTERMEDIATE 20

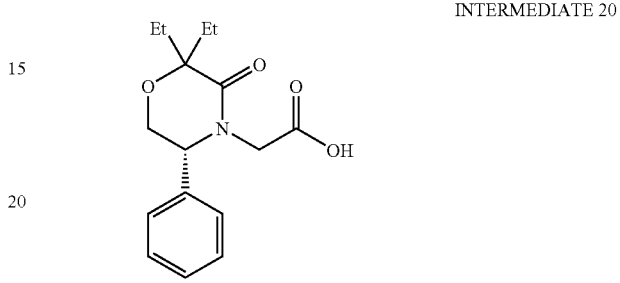

[(5R)-2,2-Diethyl-3-oxo-5-phenylmorpholin-4-yl]acetic acid

Step A. 2-Chloro-N-[(1R)-2-hydroxy-1-phenylethyl]butanamide

To a solution of (R)-2-phenylglycinol (2.00 g, 14.6 mmol) and triethylamine (2.03 mL, 14.6 mmol) in CH₂Cl₂ (100 mL) at 0° C. was slowly added 2-chlorobutyryl chloride (1.66 mL, 14.6 mmol). After 30 min, the reaction mixture was quenched with saturated aqueous NaHCO₃ (30 mL) and extracted with CH₂Cl₂ (2×75 mL). The combined organic extracts were washed with 10% citric acid, then brine, then dried over Na₂SO₄, filtered, and concentrated in vacuo. The crude product was purified by silica gel chromatography, eluting with a gradient of hexane:EtOAc—70:30 to 0:100, to give the title compound. MS: m/z=242 (M+1).

Step B. (2R,5R)-2-Ethyl-5-phenylmorpholin-3-one

To a solution of 2-chloro-N-[(1R)-2-hydroxy-1-phenylethyl]butanamide from Step A (2.75 g, 11.4 mmol) in THF (200 mL) at 0° C. was added NaH (983 mg of a 60% dispersion in oil, 24.6 mmol) and the mixture was stirred at ambient temperature for 18 h. Saturated aqueous NaHCO₃ (20 mL) was added and the mixture was extracted with EtOAc (3×40 mL). The combined organic layers were dried over Na₂SO₄, filtered, and concentrated in vacuo. The crude product was purified by silica gel chromatography, eluting with a gradient of hexane:EtOAc—75:25 to 0:100, to give the title compound. MS: m/z=206 (M+1).

Step C. tert-Butyl (2R,5R)-2-ethyl-3-oxo-5-phenylmorpholine-4-carboxylate

A solution of (2R,5R)-2-ethyl-5-phenylmorpholin-3-one from Step B (900 mg, 4.41 mmol), di-tert-butyl dicarbonate (962 mg, 4.41 mmol), and 4-dimethylaminopyridine (538 mg, 4.41 mmol) in CH₂Cl₂ (50 mL) was stirred at ambient temperature for 4 h. The mixture was washed with 10% citric acid (35 mL), then dried over Na₂SO₄, filtered, and concentrated in vacuo. The crude product was purified by silica gel chromatography, eluting with a gradient of hexane:EtOAc—95:5 to 60:40, to give the title compound. MS: m/z=250 (M−C$_4$H$_7$).

Step D. tert-Butyl (5R)-2,2-diethyl-3-oxo-5-phenyl-morpholine-4-carboxylate

To a 1 M solution of sodium bis(trimethylsilyl)amide in THF (1.64 mL, 1.64 mmol) at −78° C. was added dropwise a solution of tert-butyl (2R,5R)-2-ethyl-3-oxo-5-phenylmorpholine-4-carboxylate from Step C (500 mg, 1.64 mmol) in DME (25 mL) at −78° C. The resulting mixture was stirred at −78° C. for 10 min then iodoethane (0.131 mL, 1.64 mmol) was added. After stirring at −78° C. for 30 min, then at −30° C. for 30 min, the reaction mixture was cooled to −78° C. and quenched with saturated aqueous NH$_4$Cl (20 mL) then extracted with EtOAc (2×40 mL). The combined organic layers were dried over Na$_2$SO$_4$, filtered, and concentrated in vacuo. The crude product was purified by silica gel chromatography, eluting with a gradient of hexane:EtOAc—95:5 to 70:30, to give the title compound. MS: m/z=278 (M−C$_4$H$_7$).

Step E. [(5R)-2,2-Diethyl-3-oxo-5-phenylmorpholin-4-yl]acetic acid

Essentially following the procedures described for Intermediate 10, but using tert-butyl (5R)-2,2-diethyl-3-oxo-5-phenylmorpholine-4-carboxylate in place of tert-butyl (5R)-5-(3,5-difluorophenyl)-2,2-dimethyl-3-oxomorpholine-4-carboxylate, the title compound was prepared. MS: m/z=292 (M+1).

INTERMEDIATE 21

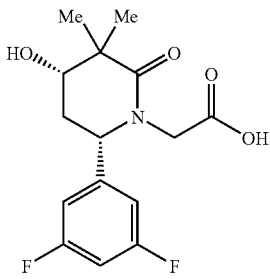

[(4S,6S)-6-(3,5-Difluorophenyl)-4-hydroxy-3,3-dimethyl-2-oxopiperidin-1-yl]acetic acid Step A. 6-(3,5-Difluorophenyl)-3,3-dimethylpiperidine-2,4-dione To a solution of 3,3-dimethylpyridine-2,4(1H,3H)-dione (978 mg, 7.03 mmol) [U.S. Pat. No. 2,525,231] in benzene (10 mL) was added 3,5-difluorophenylmagnesium bromide (50 mL of a 0.5 M solution in THF, 25 mmol) and the resulting mixture was heated to reflux for 1.5 h. The mixture was cooled, quenched with 1 N aqueous HCl (10 mL), made basic with saturated NaHCO$_3$ solution (100 mL) and extracted with EtOAc (2×150 mL). The combined organic layers were washed with H$_2$O (50 mL), then brine (50 mL), and dried over Na$_2$SO$_4$, filtered, and concentrated in vacuo. The crude product was purified by silica gel chromatography, eluting with a gradient of hexane:EtOAc—100:0 to 60:40, to give the title compound. MS: m/z=254 (M+1).

Step B. cis-6-(3,5-Difluorophenyl)-4-hydroxy-3,3-dimethylpiperidin-2-one

To a solution of 6-(3,5-difluorophenyl)-3,3-dimethylpiperidine-2,4-dione from Step A (20.18 g, 80 mmol) in THF (600 mL) and CH$_3$OH (25 mL) at 0° C. was added NaBH$_4$ (4.57 g, 121 mmol). After 2.5 h, the reaction mixture was quenched with H$_2$O (200 mL) and concentrated in vacuo. The residue was partitioned between H$_2$O (600 mL), saturated aqueous NaHCO$_3$ (200 mL) and EtOAc (1 L). The organic layer was separated and the aqueous layer was extracted with EtOAc (600 mL). The combined organic layers were dried over Na$_2$SO$_4$, filtered, and concentrated in vacuo. The crude product was purified by silica gel chromatography, eluting with a gradient of CH$_2$Cl$_2$:CH$_3$OH—100:0 to 88:12, to give the title compound, which contained approximately 20% of the corresponding trans-isomer. MS: m/z=256 (M+1).

Step C. Ethyl [(4S,6S)-6-(3,5-difluorophenyl)-4-hydroxy-3,3-dimethyl-2-oxopiperidin-1-yl]acetate To a solution of cis-6-(3,5-difluorophenyl)-4-hydroxy-3,3-dimethylpiperidin-2-one from Step B (17.1 g, 67.0 mmol) in THF (400 mL) at 0° C. was added NaH (60% dispersion in oil, 4.91 g, 73.7 mmol). After 30 min, ethyl bromoacetate (8.20 mL, 73.7 mmol) was added. After 30 min, the reaction mixture was quenched with saturated aqueous NH$_4$Cl (100 mL), diluted with H$_2$O (700 mL) and brine (100 mL) and extracted with EtOAc (700 mL). The organic extract was dried over Na$_2$SO$_4$, filtered, and concentrated in vacuo. The crude product was purified by silica gel chromatography, eluting with a gradient of hexane:EtOAc—100:0 to 0:100, to give the alcohol as a mixture of four isomers. Additional purification was achieved by HPLC, using a ChiralPak AD column and eluting with hexane:EtOH:Et$_2$NH—90:10:0.1. The first major peak to elute was a mixture of ethyl [(4S,6S)-6-(3,5-difluorophenyl)-4-hydroxy-3,3-dimethyl-2-oxopiperidin-1-yl]acetate and ethyl [(4S,6R)-6-(3,5-difluorophenyl)-4-hydroxy-3,3-dimethyl-2-oxopiperidin-1-yl]acetate (ca. 5:1). The second major peak to elute was a mixture of ethyl [(4R,6R)-6-(3,5-difluorophenyl)-4-hydroxy-3,3-dimethyl-2-oxopiperidin-1-yl]acetate and ethyl [(4R,6S)-6-(3,5-difluorophenyl)-4-hydroxy-3,3-dimethyl-2-oxopiperidin-1-yl]acetate (ca. 3:1). Further purification of the second major peak was achieved by SFC, using a ChiralPak AD column and eluting with CO$_2$:MeOH:Et$_2$NH—90:10:0.1, to give ethyl [(4R,6R)-6-(3,5-difluorophenyl)-4-hydroxy-3,3-dimethyl-2-oxopiperidin-1-yl]acetate, which eluted first, and ethyl [(4R,6S)-6-(3,5-difluorophenyl)-4-hydroxy-3,3-dimethyl-2-oxopiperidin-1-yl]acetate, which eluted second. Further purification of the first major peak was achieved by SFC, using a ChiralPak AD column and eluting with CO$_2$:MeOH:Et$_2$NH—90:10:0.1, to give ethyl [(4S,6R)-6-(3,5-difluorophenyl)-4-hydroxy-3,3-dimethyl-2-oxopiperidin-1-yl]acetate, which eluted first, and ethyl [(4S,6S)-6-(3,5-difluorophenyl)-4-hydroxy-3,3-dimethyl-2-oxopiperidin-1-yl]acetate, which eluted second, the title compound. MS: m/z=342 (M+1).

Step D. [(4S,6S)-6-(3,5-Difluorophenyl)-4-hydroxy-3,3-dimethyl-2-oxopiperidin-1-yl]acetic acid To a solution of ethyl [(4S,6S)-6-(3,5-difluorophenyl)-4-hydroxy-3,3-dimethyl-2-oxopiperidin-1-yl]acetate from Step C (64 mg, 187 mmol) in THF (1 mL) and H$_2$O (0.5 mL) was added LiOH monohydrate (14 mg, 334 mmol) and the resulting mixture was stirred at ambient temperature for 1 h. The reaction mixture was quenched with 1 N HCl (0.40 mL,

INTERMEDIATE 22

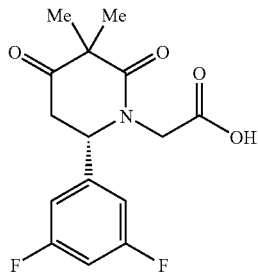

[(6S)-6-(3,5-Difluorophenyl)-3,3-dimethyl-2,4-dioxopiperidin-1-yl]acetic acid

Step A. Ethyl [(6S)-6-(3,5-difluorophenyl)-3,3-dimethyl-2,4-dioxopiperidin-1-yl]acetate To a solution of ethyl [(4S,6S)-6-(3,5-difluorophenyl)-4-hydroxy-3,3-dimethyl-2-oxopiperidin-1-yl]acetate (470 mg, 1.377 mmol, described in Intermediate 21) in acetone (24 mL) at 0° C. was added a solution of chromium (VI) trioxide (174 mg, 1.740 mmol) in $H_2O$ (0.5 mL) and $H_2SO_4$ (0.147 mL, 2.75 mmol), in three portions over 5 min and the mixture was stirred at 0° C. for 30 min. Most of the acetone was removed by concentration in vacuo, and the residue was basified with saturated aqueous $NaHCO_3$ (75 mL) and extracted with EtOAc (2×100 mL). The combined organic layers were washed with brine (40 mL) and dried over $Na_2SO_4$, filtered, and concentrated in vacuo. The crude product was purified by silica gel chromatography, eluting with a gradient of $CH_2Cl_2$:$CH_3OH$—100:0 to 92:8, to give the title compound. MS: m/z=340 (M+1).

Step B. [(6S)-6-(3,5-Difluorophenyl)-3,3-dimethyl-2,4-dioxopiperidin-1-yl]acetic acid To a solution of ethyl [(6S)-6-(3,5-difluorophenyl)-3,3-dimethyl-2,4-dioxopiperidin-1-yl]acetate from Step A (170 mg, 0.501 mmol) in THF (2 mL) and $H_2O$ (1 mL) was added LiOH monohydrate (36 mg, 0.858 mmol) and the resulting mixture was stirred at ambient temperature for 18 h. The reaction mixture was quenched with 1 N HCl (1 mL, 1 mmol), concentrated in vacuo and dried to afford the title compound. MS: m/z=312 (M+1).

INTERMEDIATE 23

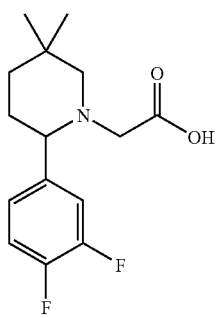

[2-(3,4-Difluorophenyl)-5,5-dimethylpiperidin-1-yl]acetic acid

Step A. 2-(3,4-Difluorophenyl)-5,5-dimethylpiperidine

To a stirred solution of 6-(3,4-difluorophenyl)-3,3-dimethylpiperidin-2-one (50.0 mg, 0.209 mmol, prepared according to Intermediate 14, Step A) in THF (1 mL) at 0° C. was added diisobutylaluminum hydride (1.05 mL of a 1 M solution in toluene, 1.05 mmol). The reaction mixture was stirred for 4 days, with additional diisobutylaluminum hydride (1.05 mL of a 1 M solution in toluene, 1.05 mmol) added on the $2^{nd}$ and $3^{rd}$ days. The reaction was quenched with saturated potassium sodium tartrate (5 mL) and extracted with EtOAc (3×10 mL). The combined organic extracts were dried over $MgSO_4$, filtered, and concentrated in vacuo. The crude product was purified by silica gel chromatography, eluting with a gradient of MeOH:$CH_2Cl_2$—0:100 to 5:95, to give the title compound. MS: m/z=226 (M+1).

Step B. [6-(3,4-Difluorophenyl)-3,3-dimethyl-2-oxopiperidin-1-yl]acetic acid To a stirred solution of 2-(3,4-difluorophenyl)-5,5-dimethylpiperidine from Step A (47.0 mg, 0.209 mmol) in THF (2 mL) at 0° C. was added NaH (12.0 mg of a 60% dispersion in oil, 0.292 mmol). After 15 min, methyl bromoacetate (0.022 mL, 0.229 mmol) was added and the mixture was stirred at ambient temperature for 4 d, with additional methyl bromoacetate (0.022 mL, 0.229 mmol) added on the $2^{nd}$ and $3^{rd}$ days. Added NaOH (0.627 mL of a 1M solution) and the mixture was stirred at 50° C. for 16 h. The reaction mixture was acidified with 1 M HCl (5 mL) and extracted with EtOAc (3×10 mL). The combined organic extracts were washed with brine (5 mL), dried over $Na_2SO_4$, filtered, and concentrated in vacuo to provide the title compound. MS: m/z=284 (M+1).

INTERMEDIATE 24

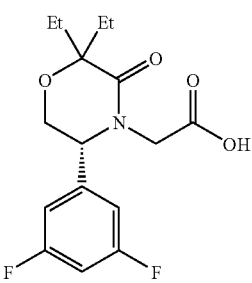

[(5R)-2,2-Diethyl-5-(3,5-difluorophenyl)-3-oxomorpholin-4-yl]acetic acid

Step A. 2-Chloro-N-[(1R)-1-(3,5-difluorophenyl)-2-hydroxyethyl]butanamide

To a solution of (2R)-2-amino-2-(3,5-difluorophenyl)ethanol (2.60 g, 15.0 mmol, described in Intermediate 10) and triethylamine (4.19 mL, 30.0 mmol) in $CH_2Cl_2$ (150 mL) at 0° C. was slowly added 2-chlorobutyryl chloride (1.71 mL, 15.0 mmol). After 60 min, the reaction mixture was quenched with saturated aqueous $NaHCO_3$ (40 mL) and extracted with $CH_2Cl_2$ (2×100 mL). The combined organic extracts were dried over $Na_2SO_4$, filtered, and concentrated in vacuo. The (400 mmol), concentrated in vacuo and dried to afford the title compound. MS: m/z=314 (M+1).

crude product was purified by silica gel chromatography, eluting with a gradient of hexane:EtOAc—70:30 to 0:100, to give the title compound. MS: m/z=278 (M+1).

[(5R)-2,2-Diethyl-5-(3,5-difluorophenyl)-3-oxomorpholin-4-yl]acetic acid

Essentially following the procedures described for Intermediate 20, but using 2-chloro-N-[(1R)-1-(3,5-difluorophenyl)-2-hydroxyethyl]butanamide in place of 2-chloro-N-[(1R)-2-hydroxy-1-phenylethyl]butanamide, the title compound was prepared. MS: m/z=328 (M+1).

INTERMEDIATE 25

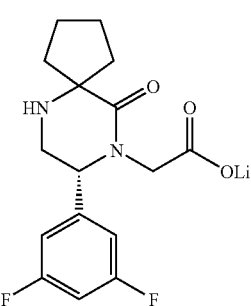

Lithium [(8R)-8-(3,5-difluorophenyl)-10-oxo-6,9-diazaspiro[4.5]dec-9-yl]acetate

Step A. Methyl 1-aminocyclopentanecarboxylate hydrochloride

A solution of 1-aminocyclopentanecarboxylic acid (2.00 g, 15.5 mmol) in MeOH (30 mL) was saturated with HCl (g). The resulting mixture was aged at ambient temperature for 2 h and concentrated in vacuo to provide the title compound. MS: m/z=144 (M+1).

Step B. Methyl 1-{[2-(3,5-difluorophenyl)-2-oxoethyl]amino}cyclopentanecarboxylate A mixture of methyl 1-aminocyclopentanecarboxylate hydrochloride from Step A (1.50 g, 10.5 mmol), 3,5-difluorophenacyl bromide (3.20 g, 13.6 mmol), and NaHCO$_3$ (1.32 g, 15.7 mmol) in DMF (30 mL) was stirred at ambient temperature for 6 h. 1 N aqueous HCl (50 mL) was added and the mixture was extracted with EtOAc (75 mL) and this organic extract was discarded. The aqueous layer was adjusted to pH 10 by addition of saturated aqueous Na$_2$CO$_3$ (150 mL) and the mixture was extracted with EtOAc (3×75 mL). The combined organic layers were washed with brine, dried over Na$_2$SO$_4$, filtered, and concentrated in vacuo. The crude product was purified by HPLC using a reversed phase C18 column and eluting with a gradient of H$_2$O:CH$_3$CN:CF$_3$CO$_2$H—90:10:0.1 to 5:95:0.1. The product-containing fractions were combined and concentrated to provide the title compound as the TFA salt. MS: m/z=298 (M+1).

Step C. Ethyl [(8R)-8-(3,5-difluorophenyl)-10-oxo-6,9-diazaspiro[4.5]dec-9-yl]acetate To a stirred mixture of methyl 1-{[2-(3,5-difluorophenyl)-2-oxoethyl]amino}cyclopentanecarboxylate, TFA salt, from Step B (1.10 g, 2.67 mmol) and glycine ethyl ester hydrochloride (560 mg, 4.01 mmol) in MeOH (7.5 mL) was added N,N-diisopropylethylamine (1.17 mL, 6.69 mmol), followed by AcOH (0.77 mL, 13.4 mmol). The resulting mixture was stirred at ambient temperature for 10 min, then NaCNBH$_3$ (252 mg, 4.01 mmol) was added. The reaction mixture was heated to 60° C. for 72 h then allowed to cool. The reaction mixture was quenched with saturated aqueous NaHCO$_3$ and then extracted with EtOAc (3×50 mL). The combined organic extracts were dried over Na$_2$SO$_4$, filtered, and concentrated in vacuo. The crude product was purified by HPLC using a reversed phase C18 column and eluting with a gradient of H$_2$O:CH$_3$CN:CF$_3$CO$_2$H—90:10:0.1 to 5:95:0.1. The product-containing fractions were combined, basified with saturated aqueous NaHCO$_3$, and extracted with EtOAc. The organic extracts were dried over Na$_2$SO$_4$, filtered, and concentrated in vacuo to give the racemic product. The enantiomers were separated by SFC, using a ChiralPak AD column and eluting with CO$_2$:MeOH—90:10. The first major peak to elute was ethyl [(8S)-8-(3,5-difluorophenyl)-10-oxo-6,9-diazaspiro[4.5]dec-9-yl]acetate, and the second major peak to elute was ethyl [(8R)-8-(3,5-difluorophenyl)-10-oxo-6,9-diazaspiro[4.5]dec-9-yl]acetate, the title compound. MS: m/z=353 (M+1).

Step D. Lithium [(8R)-8-(3,5-difluorophenyl)-10-oxo-6,9-diazaspiro[4.5]dec-9-yl]acetate To a solution of ethyl [(8R)-8-(3,5-difluorophenyl)-10-oxo-6,9-diazaspiro[4.5]dec-9-yl]acetate from Step C (90 mg, 0.26 mmol) in THF (3 mL) and H$_2$O (1 mL) was added 1 N aqueous LiOH (0.31 mL, 0.31 mmol) and the resulting mixture was stirred at ambient temperature for 1 h. The mixture was adjusted to pH 6 by addition of 1 N HCl and concentrated to dryness in vacuo to give the title compound. MS: m/z=325 (M+1).

INTERMEDIATE 26

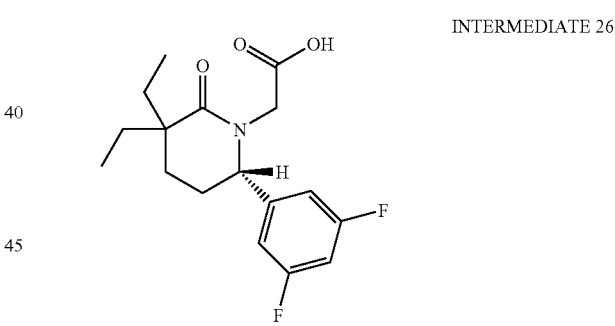

[(6S)-6-(3,5-Difluorophenyl)-3,3-diethyl-2-oxopiperidin-1-yl]acetic acid

Step A. Ethyl (5S)-5-{[(S)-tert-butylsulfinyl]amino}-5-(3,5-difluorophenyl)pentanoate To a solution of ethyl 5-(3,5-difluorophenyl)-5-oxovalerate (5.00 g, 19.5 mmol) and (S)-2-methylpropane-2-sulfinamide (2.88 g, 23.8 mmol) in THF (123 mL) was added titanium tetraethoxide (8.18 mL, 39.0 mmol). The reaction vessel was quickly sealed and placed into a 60° C. bath for 16 h. After cooling to ambient temperature a septum and nitrogen inlet were attached prior to cooling to 0° C. Sodium borohydride (1.48 g, 39.0 mmol) was then added, and a complete reaction was observed after 1 h. Methyl alcohol was then slowly added until gas evolution had stopped. The reaction mixture was then diluted with brine (60 mL) while experiencing rapid stirring. The resultant slurry was filtered through celite, washing with EtOAc as needed. The combined organics were then washed with brine, dried over sodium sulfate, filtered and concentrated in vacuo to give an oil. This oil was purified by silica gel chromatography, eluting with a gradient of EtOAc:Hexanes—10:90 to 50:50, to give the title compound. MS: m/z=362 (M+1).

Step B. (6S)-6-(3,5-Difluorophenyl)-piperidin-2-one

A solution of ethyl (5S)-5-{[(S)-tert-butylsulfinyl]amino}-5-(3,5-difluorophenyl)pentanoate from Step A (4.42 g, 12.2 mmol) in MeOH (200 mL) was cooled to 0° C. Hydrogen chloride gas (anhydrous) was bubbled through this cold solution for about 1 minute, after which time the reaction vessel was sealed and allowed to sit in the ice bath for 15 minutes. Dry nitrogen was then bubbled through the solution for 30 minutes, prior to removal of solvent in vacuo. More MeOH (~50 mL) was added, and then removed in vacuo. After dissolving in a third volume of MeOH (100 mL), triethylamine (6.78 mL, 48.9 mmol) was introduced and the mixture was heated to 65° C. for 3 hours. After cooling to ambient temperature, the solvent was removed in vacuo and the residue was partitioned between diethyl ether (100 mL) and 1 M HCl (50 mL). The organics were washed with additional 1 M HCl (50 mL), water (50 mL) and saturated brine (50 mL). The ethereal solution was dried over sodium sulfate, filtered and then concentrated in vacuo to provide the title compound, which could be used without further purification. MS: m/z=212 (M+1).

Step C. tert-Butyl (2S)-2-(3,5-difluorophenyl)-6-oxopiperidine-1-carboxylate

A solution of (6S)-6-(3,5-difluorophenyl)-piperidin-2-one from Step B (2.08 g, 9.85 mmol), di-tert-butyl dicarbonate (4.30 g, 19.7 mmol), and 4-dimethylaminopyridine (1.20 g, 9.85 mmol) in $CH_2Cl_2$ (50 mL) was stirred at ambient temperature for 20 h. An additional portion of di-tert-butyl dicarbonate (1.25 g, 5.73 mmol) was added and the solution stirred for a further 16 h. The solvent was removed under reduced pressure and the residue was purified by silica gel chromatography, eluting with a gradient of hexane:EtOAc—100:0 to 0:100, to give the title compound. MS: m/z=256 (M–$C_4H_7$).

Step D. tert-Butyl (6S)-6-(3,5-difluorophenyl)-3,3-diethylpiperidin-2-one-1-carboxylate To a solution of tert-butyl (2S)-2-(3,5-difluorophenyl)-6-oxopiperidine-1-carboxylate from Step C (1.53 g, 4.91 mmol) and iodoethane (0.993 mL, 12.3 mmol) in THF (15 mL) at −78° C. was added a 1 M solution of sodium bis(trimethylsilyl)amide in THF (10.8 mL, 10.8 mmol) dropwise over 15 min. The resulting mixture was stirred at −78° C. for 10 min and at 0° C. for 2 h, then quenched with saturated aqueous $NH_4Cl$ (50 mL) and extracted with EtOAc (3×50 mL). The combined organic layers were dried over $Na_2SO_4$, filtered, and concentrated in vacuo. The crude product was purified by silica gel chromatography, eluting with a gradient of hexane:EtOAc—100:0 to 50:50, to give the title compound. MS: m/z=312 (M–$C_4H_7$).

Step E. (6S)-6-(3,5-Difluorophenyl)-3,3-diethylpiperidin-2-one

To a solution of tert-butyl (6S)-6-(3,5-difluorophenyl)-3,3-diethylpiperidin-2-one-1-carboxylate from Step D (1.22 g, 3.32 mmol) in $CH_2Cl_2$ (7 mL) at ambient temperature was added TFA (3 mL). After stirring for 1.5 h, the reaction mixture was concentrated in vacuo. The residue was partitioned between $CH_2Cl_2$ (30 mL) and saturated $NaHCO_3$ (30 mL). The layers were separated and the aqueous layer was further extracted with $CH_2Cl_2$ (2×30 mL). The combined organics were dried over sodium sulfate, filtered and then concentrated in vacuo to provide the title compound, which could be used without further purification. MS: m/z=268 (M+1).

Step F. [(6S)-6-(3,5-Difluorophenyl)-3,3-diethyl-2-oxopiperidin-1-yl]acetic acid To a stirred solution of (6S)-6-(3,5-difluorophenyl)-3,3-diethylpiperidin-2-one from Step E (850 mg, 3.18 mmol) in THF (15 mL) at ambient temperature was added NaH (178 mg of a 60% dispersion in oil, 4.45 mmol). After 15 min, methyl bromoacetate (0.469 mL, 5.09 mmol) was added and the mixture was stirred for 1 h. Sodium hydroxide (9.54 mL of a 1 M solution, 9.54 mmol) was added and the mixture stirred for an additional 16 h at 50° C. The reaction mixture was poured onto 1 M HCl (30 mL) and extracted with EtOAc (3×30 mL). The combined organic layers were dried over $Na_2SO_4$, filtered, and concentrated in vacuo to provide the title compound, which could be used without further purification. MS: m/z=326 (M+1).

INTERMEDIATE 27

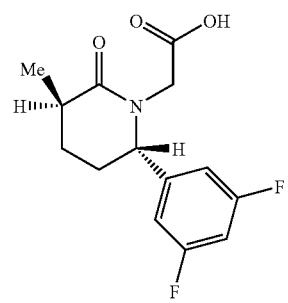

[(3R,6S)-6-(3,5-Difluorophenyl)-3-methyl-2-oxopiperidin-1-yl]acetic acid

Step A. tert-Butyl (3R,6S)-6-(3,5-difluorophenyl)-3-methylpiperidin-2-one-1-carboxylate To a 1 M solution of sodium bis(trimethylsilyl)amide in THF (0.642 mL, 0.642 mmol) at −78° C. was added dropwise a solution of tert-butyl (2S)-2-(3,5-difluorophenyl)-6-oxopiperidine-1-carboxylate (200 mg, 0.642 mmol, described in Intermediate 26) in DME (10 mL) at −78° C. The resulting mixture was stirred at −78° C. for 10 min then iodomethane (0.040 mL, 0.642 mmol) was added. After stirring at −78° C. for 30 min and at −30° C. for 30 min, the reaction mixture was cooled to −78° C. and quenched with saturated aqueous $NH_4Cl$ (10 mL) and extracted with EtOAc (2×10 mL). The combined organic layers were dried over $Na_2SO_4$, filtered, and concentrated in vacuo. The crude product was purified by silica gel chromatography, eluting with a gradient of hexane:EtOAc—100:0 to 90:10. MS: m/z=270 (M–$C_4H_7$).

[(3R,6S)-6-(3,5-Difluorophenyl)-3-methyl-2-oxopiperidin-1-yl]acetic acid

Essentially following the procedures described for Intermediate 26, but using tert-butyl (3R,6S)-6-(3,5-difluorophenyl)-3-methylpiperidin-2-one-1-carboxylate in place of tert-butyl (6S)-6-(3,5-difluorophenyl)-3,3-diethylpiperidin-2-one-1-carboxylate, the title compound was prepared. MS: m/z=284 (M+1).

INTERMEDIATE 28

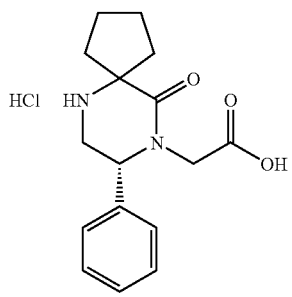

[(8R)-10-Oxo-8-phenyl-6,9-diazaspiro[4.5]dec-9-yl]acetic acid hydrochloride

Step A. Methyl 1-[(2-oxo-2-phenylethyl)amino]cyclopentanecarboxylate

A mixture of methyl 1-aminocyclopentanecarboxylate hydrochloride (2.00 g, 11.1 mmol, described in Intermediate 25), 2-bromoacetophenone (2.44 g, 12.2 mmol), and NaHCO$_3$ (2.34 g, 27.9 mmol) in DMF (20 mL) was stirred at ambient temperature for 5 h. H$_2$O (25 mL) was added and the mixture was extracted with EtOAc (2×75 mL). The combined organic layers were dried over Na$_2$SO$_4$, filtered, and concentrated in vacuo. The crude product was purified by HPLC using a reversed phase C18 column and eluting with a gradient of H$_2$O:CH$_3$CN:CF$_3$CO$_2$H—90:10:0.1 to 5:95:0.1. The product-containing fractions were combined, adjusted to pH 10 by addition of saturated aqueous Na$_2$CO$_3$ and extracted with EtOAc (2×75 mL). The combined organic layers were dried over Na$_2$SO$_4$, filtered, and concentrated in vacuo to provide the title compound. MS: m/z=262 (M+1).

Step B. Ethyl [(8R)-10-oxo-8-phenyl-6,9-diazaspiro[4.5]dec-9-yl]acetate

To a stirred mixture of methyl 1-[(2-oxo-2-phenylethyl)amino]cyclopentanecarboxylate from Step A (1.10 g, 2.67 mmol) and glycine ethyl ester hydrochloride (881 mg, 6.31 mmol) in EtOH (10 mL) was added AcOH (0.72 mL, 12.6 mmol). The resulting mixture was stirred at ambient temperature for 5 min, then NaCNBH$_3$ (397 mg, 6.31 mmol) was added. The reaction mixture was heated to 70° C. for 3 h then allowed to cool. The reaction mixture was quenched with saturated aqueous NaHCO$_3$ and then extracted with EtOAc (3×50 mL). The combined organic extracts were dried over Na$_2$SO$_4$, filtered, and concentrated in vacuo. The crude product was purified by HPLC using a reversed phase C18 column and eluting with a gradient of H$_2$O:CH$_3$CN:CF$_3$CO$_2$H—90:10:0.1 to 5:95:0.1. The product-containing fractions were combined, basified with saturated aqueous NaHCO$_3$, and extracted with EtOAc. The organic extracts were dried over Na$_2$SO$_4$, filtered, and concentrated in vacuo to give the racemic product. The enantiomers were separated by HPLC, using a Chiralcel OD column and eluting with hexane:EtOH—60:40. The first major peak to elute was ethyl [(8S)-10-oxo-8-phenyl-6,9-diazaspiro[4.5]dec-9-yl]acetate and the second major peak to elute was ethyl [(8R)-10-oxo-8-phenyl-6,9-diazaspiro[4.5]dec-9-yl]acetate, the title compound. MS: m/z=317 (M+1).

Step C. [(8R)-10-Oxo-8-phenyl-6,9-diazaspiro[4.5]dec-9-yl]acetic acid hydrochloride To a solution of ethyl [(8R)-10-oxo-8-phenyl-6,9-diazaspiro[4.5]dec-9-yl]acetate from Step B (407 mg, 1.29 mmol) in THF (8 mL) and H$_2$O (2 mL) was added 1 N aqueous LiOH (1.54 mL, 1.54 mmol) and the resulting mixture was stirred at ambient temperature for 4 h. The mixture was adjusted to pH 4 by addition of 1 N HCl and concentrated to dryness in vacuo to give the title compound. MS: m/z=289 (M+1).

INTERMEDIATE 29

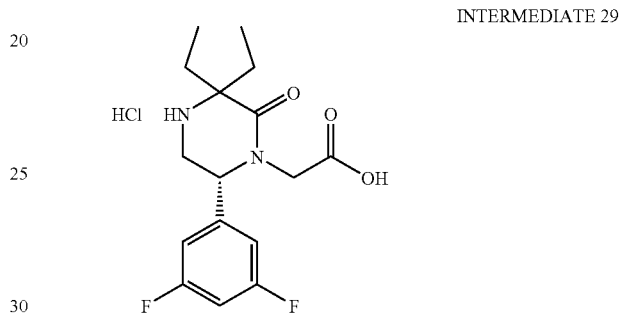

[(6R)-6-(3,5-Difluorophenyl)-3,3-diethyl-2-oxopiperazin-1-yl]acetic acid hydrochloride

Step A. Methyl 2-amino-2-ethylbutanoate hydrochloride

A solution of 2-amino-2-ethylbutanoic acid (3.00 g, 22.9 mmol) in MeOH (200 mL) was saturated with HCl (g). The resulting mixture was heated at reflux for 24 h, during which time it was allowed to cool to ambient temperature and was again saturated with HCl (g) twice. After 24 h at reflux, the cooled mixture was concentrated in vacuo to provide the title compound. MS: m/z=146 (M+1).

Step B. Methyl 2-{[2-(3,5-difluorophenyl)-2-oxoethyl]amino}-2-ethylbutanoate A mixture of methyl 2-amino-2-ethylbutanoate hydrochloride from Step A (2.10 g, 11.6 mmol), 3,5-difluorophenacyl bromide (2.99 g, 12.7 mmol), and NaHCO$_3$ (2.43 g, 28.9 mmol) in DMF (20 mL) was stirred at 45° C. for 1 h, and at ambient temperature for 2 h. 1 N aqueous HCl (50 mL) was added and the mixture was extracted with EtOAc (75 mL) and this organic extract was discarded. The aqueous layer was adjusted to pH 10 by addition of saturated aqueous Na$_2$CO$_3$ (150 mL) was added and the mixture was extracted with EtOAc (3×75 mL). The combined organic layers were treated with CF$_3$CO$_2$H (1.5 mL), dried over Na$_2$SO$_4$, filtered, and concentrated in vacuo. The crude product was purified by HPLC using a reversed phase C18 column and eluting with a gradient of H$_2$O:CH$_3$CN:CF$_3$CO$_2$H—90:10:0.1 to 5:95:0.1. The product-containing fractions were combined, basified with saturated aqueous NaHCO$_3$, and extracted with EtOAc. The organic extracts were dried over Na$_2$SO$_4$, filtered, and concentrated in vacuo to give the title compound. MS: m/z=300 (M+1).

Step C. Methyl [(6R)-6-(3,5-difluorophenyl)-3,3-diethyl-2-oxopiperazin-1-yl]acetate To a stirred mixture of methyl 2-{[2-(3,5-difluorophenyl)-2-oxoethyl]amino}-2-ethylbutanoate from Step B (475 mg, 1.59 mmol) and glycine ethyl ester hydrochloride (332 mg, 2.38 mmol) in MeOH (5 mL) were added titanium(IV) isopropoxide (1.16 mL, 3.97 mmol) and AcOH (0.273 mL, 4.76 mmol). The resulting mixture was stirred at ambient temperature for 15 min, then NaCNBH$_3$ (150 mg, 2.38 mmol) was added. The stirred reaction mixture was heated at 50° C. for 18 h, then at 70° C. for 24 h, and allowed to cool. The mixture was quenched with saturated aqueous NaHCO$_3$ and then extracted with EtOAc (2×30 mL). The combined organic extracts were dried over Na$_2$SO$_4$, filtered, and concentrated in vacuo. The crude product was purified by HPLC using a reversed phase C18 column and eluting with a gradient of H$_2$O:CH$_3$CN:CF$_3$CO$_2$H—90:10:0.1 to 5:95:0.1. The product-containing fractions were combined, basified with saturated aqueous NaHCO$_3$, and extracted with EtOAc. The organic extracts were dried over Na$_2$SO$_4$, filtered, and concentrated in vacuo to give the racemic product. The enantiomers were separated by HPLC, using a Chiralcel OD column and eluting with hexane:EtOH—60:40. The first major peak to elute was methyl [(6S)-6-(3,5-difluorophenyl)-3,3-diethyl-2-oxopiperazin-1-yl]acetate and the second major peak to elute was methyl [(6R)-6-(3,5-difluorophenyl)-3,3-diethyl-2-oxopiperazin-1-yl]acetate, the title compound. MS: m/z=341 (M+1).

Step D. [(6R)-6-(3,5-Difluorophenyl)-3,3-diethyl-2-oxopiperazin-1-yl]acetic acid hydrochloride To a solution of methyl [(6R)-6-(3,5-difluorophenyl)-3,3-diethyl-2-oxopiperazin-1-yl]acetate from Step C (43 mg, 0.126 mmol) in THF (0.75 mL) and H$_2$O (0.25 mL) was added 1 N aqueous LiOH (0.139 mL, 0.139 mmol) and the resulting mixture was stirred at ambient temperature for 1 h. The mixture was adjusted to pH 4 by addition of 1 N HCl and concentrated to dryness in vacuo to give the title compound. MS: m/z=327 (M+1).

INTERMEDIATE 30

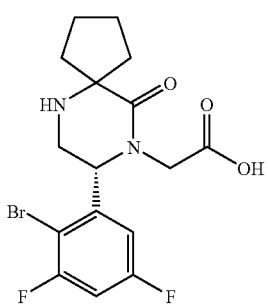

[(8R)-8-(2-Bromo-3,5-difluorophenyl)-10-oxo-6,9-diazaspiro[4.5]dec-9-yl]acetic acid

Step A. [(8R)-8-(2-Bromo-3,5-difluorophenyl)-10-oxo-6,9-diazaspiro[4.5]dec-9-yl]acetic acid To a suspension of ethyl [(8R)-8-(3,5-difluorophenyl)-10-oxo-6,9-diazaspiro[4.5]dec-9-yl]acetate (197 mg, 0.56 mmol, described in Intermediate 25) in boron trifluoride dihydrate (1.3 mL) was added N-bromosuccinimide (119 mg, 0.67 mmol) and the resulting mixture was stirred at ambient temperature for 19 h, then at 60° C. for 5 h. The mixture was diluted with H$_2$O (2 mL) and purified by HPLC using a reversed phase C18 column and eluting with a gradient of H$_2$O:CH$_3$CN:CF$_3$CO$_2$H—90:10:0.1 to 5:95:0.1. The product-containing fractions were combined and concentrated to dryness in vacuo to give the title compound as the TFA salt. MS: m/z=403 (M+1).

INTERMEDIATE 31

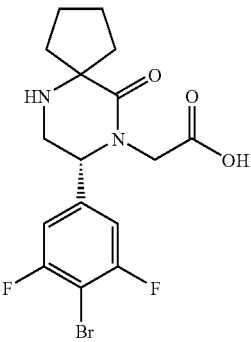

[(8R)-8-(4-Bromo-3,5-difluorophenyl)-10-oxo-6,9-diazaspiro[4.5]dec-9-yl]acetic acid This compound was generated as a byproduct in the reaction used to prepare Intermediate 30. The mixture was diluted with H$_2$O (2 mL) and purified by HPLC using a reversed phase C18 column and eluting with a gradient of H$_2$O:CH$_3$CN:CF$_3$CO$_2$H—90:10:0.1 to 5:95:0.1. The product-containing fractions were combined and concentrated to dryness in vacuo to give the title compound as the TFA salt. MS: m/z=403 (M+1).

INTERMEDIATE 32

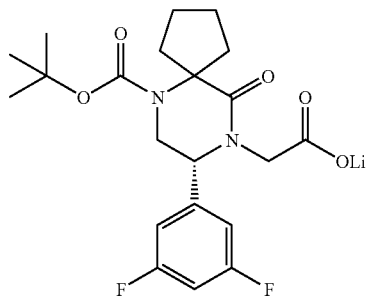

Lithium [(8R)-6-(tert-butoxycarbonyl)-8-(3,5-difluorophenyl)-10-oxo-6,9-diazaspiro[4.5]dec-9-yl]acetate

Step A. Methyl 1-{[2-(3,5-difluorophenyl)-2-oxoethyl]amino}cyclopentanecarboxylate A mixture of methyl 1-aminocyclopentanecarboxylate hydrochloride (10.0 g, 55.7 mmol, described in Intermediate 25), 3,5-difluorophenacyl bromide (14.4 g, 61.2 mmol), and Na$_3$PO$_4$ (22.8 g, 139 mmol) in DMF (100 mL) was stirred at ambient temperature for 3.5 h. The reaction mixture was acidified with 1 N aqueous HCl and the mixture was extracted with EtOAc (200 mL) and this organic extract was discarded.

The aqueous layer was adjusted to pH 8-9 by addition of saturated aqueous NaHCO$_3$ and the mixture was extracted with EtOAc (3×250 mL). The combined organic layers were washed with brine, dried over Na$_2$SO$_4$, filtered, and concentrated in vacuo. The crude product was purified by silica gel chromatography, eluting with a gradient of hexane:EtOAc—90:10 to 50:50, to give the title compound. MS: m/z=298 (M+1).

Step B. Ethyl [8-(3,5-difluorophenyl)-10-oxo-6,9-diazaspiro[4.5]dec-9-yl]acetate A mixture of methyl 1-{[2-(3,5-difluorophenyl)-2-oxoethyl]amino}cyclopentanecarboxylate from Step A (10.0 g, 33.6 mmol), glycine ethyl ester hydrochloride (46.9 g, 336 mmol), and AcOH (5.78 mL, 101 mmol) in MeOH (300 mL) was stirred at ambient temperature for 10 min. NaCNBH$_3$ (2.54 g, 40.4 mmol) was added and the pH of the mixture was checked and adjusted to pH ~5 as necessary by addition of AcOH. The reaction mixture was heated to 50° C. for 18 h then allowed to cool. The reaction mixture was carefully quenched with saturated aqueous NaHCO$_3$ (250 mL) and then extracted with CH$_2$Cl$_2$ (3×200 mL). The combined organic extracts were dried over Na$_2$SO$_4$, filtered, and concentrated in vacuo. The crude product was purified by silica gel chromatography, eluting with hexane:EtOAc—100:0 to 0:100, to give the title compound. MS: m/z=353 (M+1).

Step C. tert-Butyl (8R)-8-(3,5-difluorophenyl)-9-(2-ethoxy-2-oxoethyl)-10-oxo-6,9-diazaspiro[4.5]decane-6-carboxylate A solution of ethyl [8-(3,5-difluorophenyl)-10-oxo-6,9-diazaspiro[4.5]dec-9-yl]acetate from Step B (3.00 g, 8.51 mmol), N,N-diisopropylethylamine (0.743 mL, 4.26 mmol), and di-tert-butyl dicarbonate (9.29 g, 42.6 mmol) in acetonitrile (25 mL) was stirred at 60° C. for 6 h, then cooled and concentrated under reduced pressure. The crude product was purified by silica gel chromatography, eluting with a gradient of hexane:EtOAc—95:5 to 50:50, to give the racemic product. The enantiomers were separated by HPLC, using a Chiralcel OD column and eluting with hexane:i-PrOH: Et$_2$NH—60:40:0.1. The first major peak to elute was tert-butyl (8S)-8-(3,5-difluorophenyl)-9-(2-ethoxy-2-oxoethyl)-10-oxo-6,9-diazaspiro[4.5]decane-6-carboxylate and the second major peak to elute was tert-butyl (8R)-8-(3,5-difluorophenyl)-9-(2-ethoxy-2-oxoethyl)-10-oxo-6,9-diazaspiro[4.5]decane-6-carboxylate, the title compound. MS: m/z=397 (M−C$_4$H$_7$).

Step D. Lithium [(8R)-6-(tert-butoxycarbonyl)-8-(3,5-difluorophenyl)-10-oxo-6,9-diazaspiro[4.5]dec-9-yl]acetate To a solution of tert-butyl (8R)-8-(3,5-difluorophenyl)-9-(2-ethoxy-2-oxoethyl)-10-oxo-6,9-diazaspiro[4.5]decane-6-carboxylate from Step C (50 mg, 0.11 mmol) in THF (0.75 mL) and H$_2$O (0.25 mL) was added 1 N aqueous LiOH (0.12 mL, 0.12 mmol) and the resulting mixture was stirred at ambient temperature for 6 h. The mixture was adjusted to pH 7 by addition of 1 N HCl and concentrated to dryness in vacuo to give the title compound. MS: m/z=369 (M−C$_4$H$_7$).

INTERMEDIATE 33

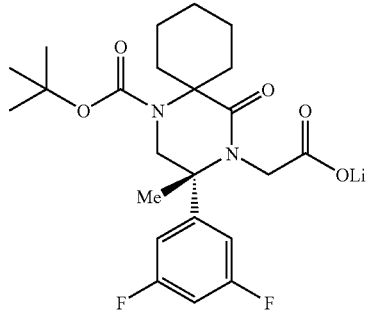

Lithium [(3R)-1-(tert-butoxycarbonyl)-3-(3,5-difluorophenyl)-3-methyl-5-oxo-1,4-diazaspiro[5.5]undec-4-yl]acetate Step A. Di-tert-butyl [1-(3,5-difluorophenyl)ethyl]imidodicarbonate To a solution of [1-(3,5-difluorophenyl)ethyl]amine (10.0 g, 63.6 mmol) in CH$_2$Cl$_2$ (200 mL) at 0° C. was added di-tert-butyl dicarbonate (13.9 g, 63.6 mmol) and the resulting mixture was stirred at ambient temperature for 18 h. The solvent was removed under reduced pressure. To the residue was added di-tert-butyl dicarbonate (20.8 g, 95.4 mmol) and DMAP (7.78 g, 63.6 mmol) and the reaction mixture was heated at 80° C. for 2 h. The mixture was allowed to cool and additional di-tert-butyl dicarbonate (69.4 g, 318 mmol) was added. The reaction mixture was heated at 80° C. for 2 h, allowed to cool, and concentrated in vacuo. The crude product was purified by silica gel chromatography, eluting with a gradient of hexane:EtOAc—98:2 to 90:10, to give the title compound. MS: m/z=421 (M+Na+CH$_3$CN).

Step B. tert-Butyl 2-[(tert-butoxycarbonyl)amino]-2-(3,5-difluorophenyl)propanoate To a stirred suspension of potassium tert-butoxide in THF (300 mL) at −78° C. was added a solution of di-tert-butyl [1-(3,5-difluorophenyl)ethyl]imidodicarbonate from Step A (22.0 g, 61.6 mmol) in THF (200 mL), dropwise, over 45 min. The reaction mixture was allowed to warm to ambient temperature and stirring was continued for 3 h. The reaction mixture was cooled to −78° C. and quenched with 1 N aqueous HCl (300 mL), warmed to 0° C., and poured into Et$_2$O (300 mL). The organic layer was extracted and the aqueous layer was extracted further with Et$_2$O (300 mL). The combined organic extracts were dried over Na$_2$SO$_4$, filtered, and concentrated in vacuo. The crude product was purified by silica gel chromatography, eluting with hexane:EtOAc—95:5 to 80:20, to give the title compound. MS: m/z=421 (M+Na+CH$_3$CN).

Step C. tert-Butyl [1-(3,5-difluorophenyl)-1-methyl-2-oxoethyl]carbamate

To a stirred solution of tert-butyl 2-[(tert-butoxycarbonyl)amino]-2-(3,5-difluorophenyl)propanoate from Step B (2.00 g, 5.60 mmol) in THF (20 mL) at −78° C. was added LiAlH$_4$ (5.60 mL of a 1 M solution in THF, 5.60 mmol), dropwise. The reaction mixture was stirred at −78° C. for 6 h, then quenched with EtOAc (5.6 mL), then H$_2$O (15.6 mL), then 1 N aqueous NaOH (5.6 mL), then EtOAc (17 mL). The reaction mixture was warmed to ambient temperature, stirred for 1 h, filtered, and extracted with EtOAc (2×40 mL). The organic extracts were dried over Na$_2$SO$_4$, filtered, and concentrated in vacuo to afford the title compound in sufficient purity for use in the next step. MS: m/z=186 (M–CO$_2$C$_4$H$_7$).

Step D. Methyl 1-aminocyclohexanecarboxylate hydrochloride

Essentially following the procedures described in Intermediate 25 for methyl 1-aminocyclopentanecarboxylate hydrochloride, but using 1-aminocyclohexanecarboxylic acid in place of 1-aminocyclopentanecarboxylic acid, the title compound was obtained. MS: m/z=158 (M+1).

Step E. Methyl 1-{[2-[(tert-butoxycarbonyl)amino]-2-(3,5-difluorophenyl)propyl]amino}cyclohexanecarboxylate A mixture of tert-butyl [1-(3,5-difluorophenyl)-1-methyl-2-oxoethyl]carbamate from Step C (500 mg, 1.75 mmol), methyl 1-aminocyclohexanecarboxylate hydrochloride from Step D (1.38 g, 8.76 mmol), and AcOH (0.301 mL, 5.26 mmol) in MeOH (15 mL) was stirred at ambient temperature for 30 min. NaCNBH$_3$ (165 mg, 2.63 mmol) was added and the pH of the mixture was checked and adjusted to pH ~5 as necessary by addition of AcOH. The reaction mixture was stirred at ambient temperature for 1 h, then quenched with saturated aqueous NaHCO$_3$ (10 mL) and extracted with CH$_2$Cl$_2$ (2×50 mL). The combined organic extracts were dried over Na$_2$SO$_4$, filtered, and concentrated in vacuo. The crude product was purified by silica gel chromatography, eluting with hexane:EtOAc—100:0 to 80:20, to give the title compound. MS: m/z=427 (M+1).

Step F. Methyl 1-{[2-amino-2-(3,5-difluorophenyl)propyl]amino}cyclohexanecarboxylate A solution of methyl 1-{[2-[(tert-butoxycarbonyl)amino]-2-(3,5-difluorophenyl)propyl]amino}cyclohexanecarboxylate from Step E (280 mg, 0.657 mmol) in EtOAc (5 mL) at 0° C. was saturated with HCl (g). The reaction mixture was aged at 0° C. for 30 min, then poured carefully into saturated aqueous NaHCO$_3$ (10 mL). The resulting mixture was extracted with EtOAc (2×15 mL). The combined organic extracts were dried over Na$_2$SO$_4$, filtered, and concentrated in vacuo to give the title compound. MS: m/z=327 (M+1).

Step G. (3R)-3-(3,5-Difluorophenyl)-3-methyl-1,4-diazaspiro[5.5]undecan-5-one

A solution of methyl 1-{[2-amino-2-(3,5-difluorophenyl)propyl]amino}cyclohexanecarboxylate from Step F (205 mg, 0.628 mmol), and AcOH (0.36 mL, 6.28 mmol) in xylenes (5 mL) was heated at 80° C. for 3 h, allowed to cool, then poured into saturated aqueous NaHCO$_3$ (5 mL). The resulting mixture was extracted with EtOAc (2×10 mL). The combined organic extracts were dried over Na$_2$SO$_4$, filtered, and concentrated under reduced pressure. The crude product was purified by silica gel chromatography, eluting with a gradient of EtOAc:MeOH—100:0 to 92:8, to give the racemic product. The enantiomers were separated by HPLC, using a ChiralPak AD column and eluting with hexane:EtOH:Et$_2$NH—40:60:0.1. The first major peak to elute was (3R)-3-(3,5-difluorophenyl)-3-methyl-1,4-diazaspiro[5.5]undecan-5-one, the title compound, and the second major peak to elute was (3S)-3-(3,5-difluorophenyl)-3-methyl-1,4-diazaspiro[5.5]undecan-5-one. MS: m/z=295 (M+1).

Step H. tert-Butyl (3R)-3-(3,5-difluorophenyl)-3-methyl-5-oxo-1,4-diazaspiro[5.5]undecane-1-carboxylate A solution of (3R)-3-(3,5-difluorophenyl)-3-methyl-1,4-diazaspiro[5.5]undecan-5-one from Step G (90 mg, 0.306 mmol), N,N-diisopropylethylamine (0.027 mL, 0.153 mmol), and di-tert-butyl dicarbonate (667 mg, 3.06 mmol) in acetonitrile (2 mL) was stirred at 60° C. for 8 h, then cooled and concentrated under reduced pressure. The crude product was purified by silica gel chromatography, eluting with a gradient of hexane:EtOAc—95:5 to 50:50, to give the title compound. MS: m/z=339 (M–C$_4$H$_7$).

Step I. tert-Butyl (3R)-3-(3,5-difluorophenyl)-4-(2-ethoxy-2-oxoethyl)-3-methyl-5-oxo-1,4-diazaspiro[5.5]undecane-1-carboxylate To a stirred solution of tert-butyl (3R)-3-(3,5-difluorophenyl)-3-methyl-5-oxo-1,4-diazaspiro[5.5]undecane-1-carboxylate from Step H (60 mg, 0.152 mmol) in THF (0.5 mL) at 0° C. was added NaH (12 mg of a 60% dispersion in oil, 0.30 mmol). After 5 min, ethyl bromoacetate (437 mg, 2.62 mmol) was added and the mixture was allowed to warm to ambient temperature and stirring was continued for 1 h. Saturated aqueous NaHCO$_3$ (2 mL) was added and the mixture was extracted with EtOAc (2×5 mL). The combined organic layers were dried over Na$_2$SO$_4$, filtered, and concentrated in vacuo. The crude product was purified by silica gel chromatography, eluting with a gradient of hexane:EtOAc—95:5 to 60:40, to give the title compound. MS: m/z=425 (M–C$_4$H$_7$).

Step J. Lithium [(3R)-1-(tert-butoxycarbonyl)-3-(3,5-difluorophenyl)-3-methyl-5-oxo-1,4-diazaspiro[5.5]undec-4-yl]acetate To a solution of tert-butyl (3R)-3-(3,5-difluorophenyl)-4-(2-ethoxy-2-oxoethyl)-3-methyl-5-oxo-1,4-diazaspiro[5.5]undecane-1-carboxylate from Step I (65 mg, 0.135 mmol) in THF (1.5 mL) and H$_2$O (0.5 mL) was added 1 N aqueous LiOH (0.14 mL, 0.14 mmol) and the resulting mixture was stirred at ambient temperature for 1 h. The mixture was adjusted to pH 7 by addition of 1 N HCl and concentrated to dryness in vacuo to give the title compound. MS: m/z=397 (M–C$_4$H$_7$).

INTERMEDIATE 34

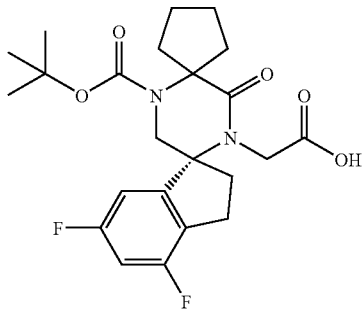

[(5"R)-1'-(tert-Butoxycarbonyl)-4",6"-difluoro-3'-oxo-2",3"-dihydro-4'H-dispiro[cyclopentane-1,2'-piperazine-5',1"-inden]-4'-yl]acetic acid Step A. 4',6'-Difluoro-2',3'-dihydro-2H,5H-spiro[imidazolidine-4,1'-indene]-2,5-dione A mixture of 4,6-difluoroindan-1-one [Musso et al. (2003) J. Med. Chem., 46, 399-408] (14.5 g, 86 mmol), NaCN (12.9 g, 262 mmol), and (NH$_4$)$_2$CO$_3$ (16.8 g, 175 mmol) in H$_2$O (150 mL) and EtOH (150 mL) was heated at 70° C. for 3 h. Additional (NH$_4$)$_2$CO$_3$ (16.8 g, 175 mmol) was added and heating at 70° C. was continued for 4 h. The mixture was concentrated to dryness under reduced pressure. To the residue was added H$_2$O (200 mL) and the precipitate was isolated by filtration, washed with H$_2$O, and dried to give the title compound. MS: m/z=280 (M+1+CH$_3$CN).

Step B. 1-Amino-4,6-difluoroindane-1-carboxylic acid hydrochloride

A mixture of 4',6'-difluoro-2',3'-dihydro-2H,5H-spiro [imidazolidine-4,1'-indene]-2,5-dione from Step A (16.7 g, 70.1 mmol) and conc. HCl (90 mL) in a high pressure reactor was heated at 180° C. for 5 h. The mixture was cooled to 0° C., vented carefully, and concentrated to dryness in vacuo to afford the title compound. MS: m/z=214 (M+1).

Step C. Methyl 1-amino-4,6-difluoroindane-1-carboxylate hydrochloride

A solution of 1-amino-4,6-difluoroindane-1-carboxylic acid hydrochloride (2.00 g, 15.5 mmol) in MeOH (100 mL) was saturated with HCl (g). The resulting mixture was heated at reflux for 20 h and concentrated in vacuo to provide the title compound. MS: m/z=228 (M+1).

Step D. Methyl 1-[(tert-butoxycarbonyl)amino]-4,6-difluoroindane-1-carboxylate A solution of methyl 1-amino-4,6-difluoroindane-1-carboxylate hydrochloride from Step C (3.82 g, 14.5 mmol), N,N-diisopropylethylamine (5.62 g, 43.5 mmol), and di-tert-butyl dicarbonate (15.8 g, 72.5 mmol) in acetonitrile (40 mL) was stirred at 60° C. for 3 h, then cooled and concentrated under reduced pressure. The crude product was purified by silica gel chromatography, eluting with a gradient of hexane:EtOAc—100:0 to 40:60, to give the title compound. MS: m/z=228 (M−CO$_2$C$_4$H$_7$).

Step E. tert-Butyl [4,6-difluoro-1-(hydroxymethyl)-2,3-dihydro-1H-inden-1-yl]carbamate To a stirred solution of methyl 1-[(tert-butoxycarbonyl) amino]-4,6-difluoroindane-1-carboxylate from Step D (2.80 g, 8.55 mmol) in THF (30 mL) at −78° C. was added LiAlH$_4$ (18.0 mL of a 1 M solution in THF, 18.0 mmol), dropwise, over 30 min. The reaction mixture was stirred at −78° C. for 2 h, then quenched with H$_2$O (1 mL), then 1 N aqueous NaOH (2 mL), then H$_2$O (2 mL), then EtOAc (2 mL). The reaction mixture was warmed to ambient temperature, saturated aqueous NaHCO$_3$ (150 mL) was added, and the mixture was extracted with EtOAc (200 mL). The organic extract was dried over Na$_2$SO$_4$, filtered, and concentrated in vacuo. The crude product was purified by silica gel chromatography, eluting with a gradient of hexane:EtOAc—100:0 to 50:50, to give the title compound. MS: m/z=244 (M−C$_4$H$_7$).

Step F. tert-Butyl (4,6-difluoro-1-formyl-2,3-dihydro-1H-inden-1-yl)carbamate To a stirred solution of oxalyl chloride (0.91 mL, 10.4 mmol) in CH$_2$Cl$_2$ (40 mL) at −78° C. was added DMSO (1.48 mL, 20.9 mmol), dropwise, over 5 min. The reaction mixture was stirred for 30 min, during which time it warmed to −60° C., then a solution of tert-butyl [4,6-difluoro-1-(hydroxymethyl)-2,3-dihydro-1H-inden-1-yl]carbamate from Step E (2.08 g, 6.95 mmol) in CH$_2$Cl$_2$ (22 mL) was added, dropwise, over 30 min. During the addition, the reaction temperature rose to −45° C. and it was stirred at this temperature for an additional 15 min. To the resulting mixture was added N,N-diisopropylethylamine (7.28 mL, 41.7 mmol), dropwise, over 2 min. The mixture was allowed to warm to 0° C., stirred for 15 min then poured into ice (60 mL) and 1 N aqueous HCl (30 mL). The resulting mixture was extracted with CH$_2$Cl$_2$ (2×100 mL). The combined organic extracts were washed with H$_2$O (30 mL), then brine (50 mL), then dried over Na$_2$SO$_4$, filtered, and concentrated in vacuo to give the title compound. MS: m/z=224 (M−OC$_4$H$_9$).

Step G. Methyl 1-[({1-[(tert-butoxycarbonyl)amino]-4,6-difluoro-2,3-dihydro-1H-inden-1-yl}methyl) amino]cyclopentanecarboxylate A mixture of tert-butyl (4,6-difluoro-1-formyl-2,3-dihydro-1H-inden-1-yl)carbamate from Step F (890 mg, 2.99 mmol), methyl 1-aminocyclopentanecarboxylate (4.25 g, 29.7 mmol, described in Intermediate 25), and AcOH (2.10 mL, 36.7 mmol) in MeOH (32 mL) was stirred at ambient temperature for 20 min. NaCNBH$_3$ (405 mg, 6.44 mmol) was added and the pH of the mixture was checked and adjusted to pH ~5 as necessary by addition of AcOH. The reaction mixture was stirred at ambient temperature for 23 h, then quenched with saturated aqueous NaHCO$_3$ (80 mL) and extracted with EtOAc (200 mL). The organic extract was washed with H$_2$O (50 mL), dried over Na$_2$SO$_4$, filtered, and concentrated in vacuo. The crude product was purified by silica gel chromatography, eluting with hexane:EtOAc—100:0 to 30:70, to give the title compound. MS: m/z=425 (M+1).

Step H. Methyl 1-{[(1-amino-4,6-difluoro-2,3-dihydro-1H-inden-1-yl)methyl] amino}cyclopentanecarboxylate hydrochloride A solution of methyl 1-[({1-[(tert-butoxycarbonyl) amino]-4,6-difluoro-2,3-dihydro-1H-inden-1-yl}methyl) amino]cyclopentanecarboxylate from Step G (753 mg, 1.77 mmol) in EtOAc (40 mL) at 0° C. was saturated with HCl (g). The reaction mixture was aged at 0° C. for 45 min then concentrated in vacuo to give the title compound. MS: m/z=325 (M+1).

Step I. 4",6"-Difluoro-2",3"-dihydro-3'H-dispiro [cyclopentane-1,2'-piperazine-5',1"-inden]-3'-one A solution of methyl 1-{[(1-amino-4,6-difluoro-2,3-dihydro-1H-inden-1-yl)methyl]amino}cyclopentanecarboxylate hydrochloride from Step H (741 mg, 2.05 mmol), and AcOH (5.0 mL, 6.28 mmol) in xylenes (50 mL) was heated at 150° C. for 24 h, allowed to cool, and concentrated to dryness under reduced pressure. The residue was partitioned between saturated aqueous NaHCO$_3$ (80 mL) and EtOAc (100 mL). The organic extract was washed with H$_2$O (60 mL), dried over Na$_2$SO$_4$, filtered, and concentrated under reduced pressure to give the title compound. MS: m/z=293 (M+1).

Step J. tert-Butyl (5"R)-4",6"-difluoro-3'-oxo-2",3"-dihydro-1'H-dispiro[cyclopentane-1,2'-piperazine-5',1"-indene]-1'-carboxylate A solution of 4",6"-difluoro-2",3"-dihydro-3'H-dispiro[cyclopentane-1,2'-piperazine-5',1"-inden]-3'-one from Step 1 (453 mg, 1.55 mmol), N,N-diisopropylethylamine (0.135 mL, 0.78 mmol), and di-tert-butyl dicarbonate (3.45 g, 15.8 mmol) in acetonitrile (6 mL) was stirred at 50° C. for 18 h. The reaction mixture was partitioned between saturated aqueous NaHCO₃ (40 mL) and EtOAc (60 mL). The organic extract was dried over Na₂SO₄, filtered, and concentrated under reduced pressure The crude product was purified by silica gel chromatography, eluting with a gradient of hexane:EtOAc—100:0 to 50:50, to give the racemic product. The enantiomers were separated by HPLC, using a ChiralPak AD column and eluting with hexane:EtOH:Et₂NH—40:60:0.1. The first major peak to elute was tert-butyl (5"R)-4",6"-difluoro-3'-oxo-2",3"-dihydro-1'H-dispiro[cyclopentane-1,2'-piperazine-5',1"-indene]-1'-carboxylate, the title compound, and the second major peak to elute was tert-butyl (5"S)-4",6"-difluoro-3'-oxo-2",3"-dihydro-1'H-dispiro[cyclopentane-1,2'-piperazine-5',1"-indene]-1'-carboxylate. MS: m/z=337 (M–C₄H₇).

Step K. tert-Butyl (5"R)-4'-(2-ethoxy-2-oxoethyl)-4",6"-difluoro-3'-oxo-2",3"-dihydro-1'H-dispiro[cyclopentane-1,2'-piperazine-5',1"-indene]-1'-carboxylate To a stirred solution of tert-butyl (5"R)-4",6"-difluoro-3'-oxo-2",3"-dihydro-1'H-dispiro[cyclopentane-1,2'-piperazine-5',1"-indene]-1'-carboxylate from Step J (217 mg, 0.553 mmol) in THF (4 mL) at ambient temperature was added NaH (44 mg of a 60% dispersion in oil, 1.11 mmol). After 15 min, ethyl bromoacetate (185 mg, 1.11 mmol) was added and the mixture was allowed to warm to ambient temperature and stirring was continued for 3 h. Saturated aqueous NaHCO₃ (25 mL) was added and the mixture was extracted with EtOAc (2×30 mL). The combined organic layers were washed with brine, dried over Na₂SO₄, filtered, and concentrated in vacuo. The crude product was purified by silica gel chromatography, eluting with a gradient of hexane:EtOAc—100:0 to 50:50, to give the title compound. MS: m/z=479 (M+1).

Step L. [(5"R)-1'-(tert-Butoxycarbonyl)-4",6"-difluoro-3'-oxo-2",3"-dihydro-4'H-dispiro[cyclopentane-1,2'-piperazine-5',1"-inden]-4'-yl]acetic acid To a solution of tert-butyl (5"R)-4'-(2-ethoxy-2-oxoethyl)-4",6"-difluoro-3'-oxo-2",3"-dihydro-1'H-dispiro[cyclopentane-1,2'-piperazine-5',1"-indene]-1'-carboxylate from Step K (258 mg, 0.539 mmol) in THF (3 mL) was added 1 N aqueous LiOH (0.65 mL, 0.65 mmol) and the resulting mixture was stirred at ambient temperature for 20 h. To the reaction mixture was added THF (3 mL), EtOH (0.2 mL), and 1 N aqueous LiOH (0.20 mL, 0.20 mmol) and the resulting mixture was stirred at ambient temperature for 16 h. The mixture was acidified by addition of 1 N aqueous HCl (0.9 mL, 0.9 mmol) and concentrated to dryness in vacuo to give the title compound. MS: m/z=451 (M+1).

INTERMEDIATE 35

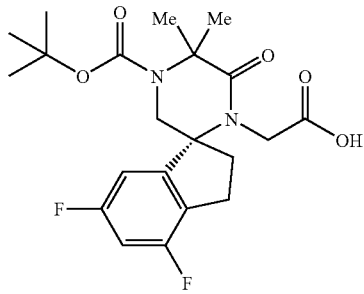

(±)-[4'-(tert-Butoxycarbonyl)-4,6-difluoro-5',5'-dimethyl-6'-oxo-2,3-dihydro-1'H-spiro[indene-1,2'-piperazin]-1'-yl]acetic acid Essentially following the procedures described in Intermediate 34, but using methyl α-aminoisobutyrate in place of methyl 1-aminocyclopentanecarboxylate, the title compound was obtained. MS: m/z=425 (M+1).

INTERMEDIATE 36

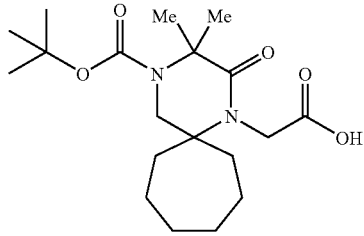

[4-(tert-Butoxycarbonyl)-3,3-dimethyl-2-oxo-1,4-diazaspiro[5.6]dodec-1-yl]acetic acid Essentially following the procedures described in Intermediate 34, but using methyl α-aminoisobutyrate in place of methyl 1-aminocyclopentanecarboxylate, and using methyl 1-aminocycloheptanecarboxylate hydrochloride in place of methyl 1-amino-4,6-difluoroindane-1-carboxylate hydrochloride, the title compound was obtained. MS: m/z=369 (M+1).

INTERMEDIATE 37

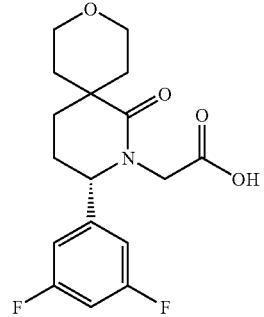

[(3S)-3-(3,5-Difluorophenyl)-1-oxo-9-oxa-2-azaspiro[5.5]undec-2-yl]acetic acid

Essentially following the procedures described in Intermediate 26, but using 2-iodoethyl ether in place of iodoethane, the title compound was obtained. MS: m/z=340 (M+1).

INTERMEDIATE 38

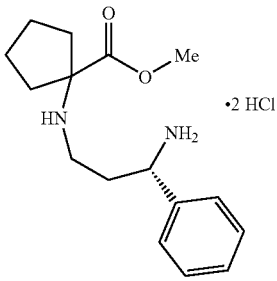

Methyl 1-{[(3S)-3-amino-3-phenylpropyl]
amino}cyclopentanecarboxylate bis-hydrochloride

Step A. Ethyl (3S)-3-[(tert-butoxycarbonyl)amino]-3-phenylpropanoate

To a solution of (S)-3-amino-3-phenylpropanoic acid ethyl ester hydrochloride (2.50 g, 10.9 mmol) and Boc-anhydride (2.38 g, 10.9 mmol) in CH$_2$Cl$_2$ (16.3 mL) was slowly added triethylamine (3.03 mL, 21.8 mmol). After 4.5 hours, the reaction mixture was applied to the top of a silica gel column, and following elution with a gradient of EtOAc:hexanes—5:95 to 40:60 the title compound was obtained. MS: m/z=294 (M+1).

Step B. tert-Butyl [(1S)-3-oxo-1-phenylpropyl]carbamate

To a dry, cooled (−78° C.) solution of ethyl (3S)-3-[(tert-butoxycarbonyl)amino]-3-phenylpropanoate from Step A (1.00 g, 3.41 mmol) was added a solution of DiBAl—H (6.82 mL, 6.82 mmol, 1 M in CH$_2$Cl$_2$) slowly over 30 min. After an additional 30 min of stirring at −78° C., the reaction was quenched by the rapid addition of saturated aqueous Rochelle's salt (32 mL). The cooling bath was then removed and the reaction was allowed to rapidly stir until a noticeable decrease in the amount of emulsion was observed. The layers were separated and the aqueous layer was extracted with CH$_2$Cl$_2$ (2×30 mL). Combined organics were dried over sodium sulfate, filtered and concentrated in vacuo to give an oil. This oil was purified by silica gel chromatography, eluting with a gradient of EtOAc:hexanes 5:95 to 40:60, to give the title compound. MS: m/z=150 (M−CO$_2$C$_4$H$_7$).

Step C. Methyl 1-({(3S)-3-[(tert-butoxycarbonyl)amino]-3-phenylpropyl}amino)cyclopentanecarboxylate To a solution of tert-butyl [(1S)-3-oxo-1-phenylpropyl]carbamate from Step B (0.820 g, 3.29 mmol) and methyl 1-aminocyclopentanecarboxylate hydrochloride (0.591 g, 3.29 mmol) in chloroform (33 mL) was added Hunig's base (0.574 mL, 3.29 mmol). After stirring at ambient temperature for 20 min, NaHB(OAc)$_3$ (1.74 g, 8.22 mmol) was added as a solid. Upon completion of the reaction, saturated aqueous NaHCO$_3$ (3 mL) was added and the mixture was allowed to stir for at least 2 h. Water (5 mL) and additional saturated NaHCO$_3$ (3 mL) was then added to form two layers. The aqueous layer was extracted once with chloroform (50 mL). The combined organic layers were dried over sodium sulfate, filtered and concentrated in vacuo to give an oil. This oil was purified by silica gel chromatography, eluting with a gradient of MeOH:DCM 1:99 to 6:94, to give the title compound. MS: m/z=377 (M+1).

Step D. Methyl 1-{[(3S)-3-amino-3-phenylpropyl]amino}cyclopentanecarboxylate bis-hydrochloride To a cooled (0° C.) solution of methyl 1-({(3S)-3-[(tert-butoxycarbonyl)amino]-3-phenylpropyl}amino)cyclopentanecarboxylate from Step C (0.920 g, 2.44 mmol) in MeOH (49 mL) was added excess anhydrous hydrogen chloride gas. After 30 min the solution was purged with dry nitrogen for about 40 min. The solvent was then removed in vacuo to provide a solid/oil mix. Additional MeOH (50 mL) was then added and subsequently removed in vacuo to provide the title compound. MS: m/z=277 (M+1).

INTERMEDIATE 39

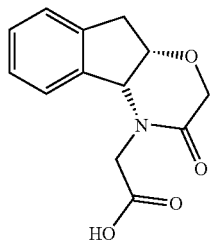

[(4aR,9aS)-3-Oxo-2,3,9,9a-tetrahydroindeno[2,1-b][1,4]oxazin-4(4aH)-yl]acetic acid

Step A. 2-Chloro-N-[(1R,2S)-2-hydroxy-2,3-dihydro-1H-inden-1-yl]acetamide

To a mixture of (1R,2S)-1-amino-2-indanol (500 mg, 3.35 mmol) and triethylamine (0.51 mL, 3.69 mmol) in anhydrous CH$_2$Cl$_2$ at 0° C. was added chloroacetyl chloride (0.295 mL, 3.69 mmol) dropwise. The resulting mixture was stirred for 30 min, quenched with saturated aqueous NaHCO$_3$ (15 mL) and then extracted with EtOAc (2×75 mL). The combined organic extracts were dried over Na$_2$SO$_4$, filtered, and concentrated in vacuo. The crude product was purified by silica gel chromatography, eluting with a gradient of hexane:EtOAc 70:30 to 0:100, to give the title compound. MS: m/z=226 (M+1).

Step B. (4aR,9aS)-4,4a,9,9a-Tetrahydroindeno[2,1-b][1,4]oxazin-3(2H)-one

To a stirred mixture of 2-chloro-N-[(1R,2S)-2-hydroxy-2,3-dihydro-1H-inden-1-yl]acetamide from Step A (780 mg, 3.46 mmol) in anhydrous THF (75 mL) at 0° C. was added NaH (498 mg of a 60% dispersion in oil, 12.4 mmol). The resulting mixture was stirred for 3 h, quenched with saturated aqueous NaHCO$_3$ (20 mL) and then extracted with EtOAc (3×50 mL). The combined organic layers were dried over Na$_2$SO$_4$, filtered, and concentrated in vacuo to give the title compound. MS: m/z=190 (M+1).

Step C. Ethyl [(4aR,9aS)-3-oxo-2,3,9,9a-tetrahydroindeno[2,1-b][1,4]oxazin-4(4aH)-yl]acetate To a solution of (4aR,9aS)-4,4a,9,9a-tetrahydroindeno[2,1-b][1,4]oxazin-3(2H)-one from Step B (600 mg, 3.17 mmol) in DMF (15 mL) at 0° C. was added NaH (228 mg of a 60% dispersion in oil, 5.71 mmol) and the resulting mixture was stirred for 10 min. Ethyl bromoacetate (0.288 mL, 3.5 mmol) was added and the reaction mixture was stirred for 18 h. The reaction mixture was quenched with saturated aqueous NaHCO$_3$ (10 mL) and then extracted with EtOAc (2×40 mL). The combined organic layers were dried over Na$_2$SO$_4$, filtered, and concentrated in vacuo. The crude product was purified by silica gel chromatography, eluting with a gradient of hexane:EtOAc 80:20 to 0:100, to give the title compound. MS: m/z=276 (M+1)

Step D. [(4aR,9aS)-3-Oxo-2,3,9,9a-tetrahydroindeno[2,1-b][1,4]oxazin-4(4aH)-yl]acetic acid To a solution of ethyl [(4aR,9aS)-3-oxo-2,3,9,9a-tetrahydroindeno[2,1-b][1,4]oxazin-4(4aH)-yl]acetate from Step C (480 mg, 1.74 mmol) in THF (7.5 mL) and H$_2$O (2.5 mL) was added 1 N aqueous LiOH (2.1 mL, 2.09 mmol) and the resulting mixture was stirred at ambient temperature for 4 h. The mixture was adjusted to pH 4 by addition of 1 N HCl and concentrated to dryness in vacuo to give the title compound. MS: m/z=248 (M+1).

INTERMEDIATE 40

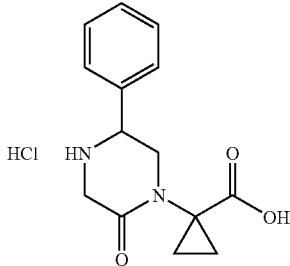

1-(2-Oxo-5-phenylpiperazin-1-yl)cyclopropanecarboxylic acid

Step A. Ethyl 1-[(2-oxo-2-phenylethyl)amino]cyclopropanecarboxylate

A mixture of ethyl 1-aminocyclopropanecarboxylate hydrochloride (1.0 g, 7.74 mmol), 2-bromoacetophenone (3.08 g, 15.5 mmol), and NaHCO$_3$ (1.30 g, 15.5 mmol) in DMF (20 mL) was stirred at ambient temperature for 18 h. H$_2$O (20 mL) was added and the mixture was extracted with EtOAc (2×75 mL). The combined organic layers were dried over Na$_2$SO$_4$, filtered, and concentrated in vacuo. The crude product was purified by HPLC using a reversed phase C18 column and eluting with a gradient of H$_2$O:CH$_3$CN:CF$_3$CO$_2$H—90:10:0.1 to 5:95:0.1. The product-containing fractions were combined, adjusted to pH 10 by addition of saturated aqueous Na$_2$CO$_3$ and extracted with EtOAc (2×75 mL). The combined organic layers were dried over Na$_2$SO$_4$, filtered, and concentrated in vacuo to provide the title compound. MS: m/z=248 (M+1).

Step B. Ethyl 1-(2-oxo-5-phenylcyclohexyl)cyclopropanecarboxylate

To a stirred mixture of ethyl 1-[(2-oxo-2-phenylethyl)amino]cyclopropanecarboxylate from Step A (500 mg, 2.02 mmol) and glycine ethyl ester hydrochloride (339 mg, 2.43 mmol) in MeOH (5 mL) was added AcOH (0.58 mL, 10.1 mmol). The resulting mixture was stirred at ambient temperature for 10 min, then NaCNBH$_3$ (152 mg, 2.43 mmol) was added. The reaction mixture was heated to 50° C. for 6 h then allowed to cool. The reaction mixture was quenched with saturated aqueous NaHCO$_3$ and then extracted with EtOAc (3×40 mL). The combined organic extracts were dried over Na$_2$SO$_4$, filtered, and concentrated in vacuo. The crude product was purified by HPLC using a reversed phase C18 column and eluting with a gradient of H$_2$O:CH$_3$CN:CF$_3$CO$_2$H—90:10:0.1 to 5:95:0.1. The product-containing fractions were combined and concentrated in vacuo to give the titled compound as a colorless oil. MS: m/z=289 (M+1).

Step C. 1-(2-Oxo-5-phenylpiperazin-1-yl)cyclopropanecarboxylic acid

To a solution of ethyl 1-(2-oxo-5-phenylcyclohexyl)cyclopropanecarboxylate from Step B (35 mg, 0.121 mmol) in THF (0.75 mL) and H$_2$O (0.25 mL) was added 1 N aqueous LiOH (0.146 mL, 0.146 mmol) and the resulting mixture was stirred for 18 h. The mixture was adjusted to pH 4 by addition of 1 N HCl and concentrated to dryness in vacuo to give the title compound. MS: m/z=261 (M+1).

INTERMEDIATE 41

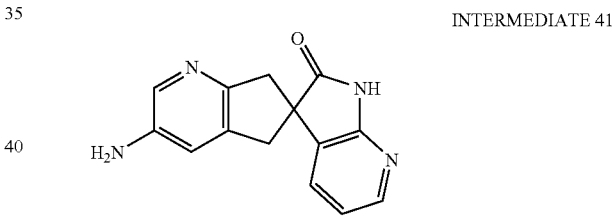

3-Amino-5,7-dihydrospiro[cyclopenta[b]pyridine-6,3'-pyrrolo[2,3-b]pyridin]-2'(1'H)-one, isomer A

Step A. (±)-1'-{[2-(Trimethylsilyl)ethoxy]methyl}-3H-spiro[cyclopentane-1,3'-pyrrolo[2,3-b]pyridine]-2',3(1'H)-dione To a solution of 1-{[2-(trimethylsilyl)ethoxy]methyl}-1,3-dihydro-2H-pyrrolo[2,3-b]pyridin-2-one (2.50 g, 9.46 mmol, described in Intermediate 7) and cesium carbonate (6.78 g, 20.8 mmol) in DMF (45 mL) was added dropwise a solution of 1,4-dibromobutan-2-one [Meijere et al. (2001) *Eur. J. Org. Chem.* 20, 3789-3795] (1.59 g, 12.3 mmol) in DMF (45 mL). After 68 h, the mixture was partitioned between Et$_2$O (200 mL) and H$_2$O (200 mL). The organic layer was separated and the aqueous layer was further extracted with Et$_2$O (2×100 mL). The combined organic layers were dried over Na$_2$SO$_4$, filtered, and concentrated in vacuo. The crude product was purified by silica gel chromatography, eluting with a gradient of hexane:EtOAc—100:0 to 75:25, to give the title compound. MS: m/z=333 (M+1).

Step B. (±)-3-Nitro-1'-{[2-(trimethylsilyl)ethoxy]methyl}-5,7-dihydrospiro[cyclopenta[b]pyridine-6,3'-pyrrolo[2,3-b]pyridin]-2'(1'H)-one A mixture of (±)-1'-{[2-(trimethylsilyl)ethoxy]methyl}-3H-spiro[cyclopentane-1,3'-pyrrolo[2,3-b]pyridine]-2',3(1'H)-dione from Step A (230 mg, 0.692 mmol) and 1-methyl-3,5-dinitropyridin-2(1H)-one [Tohda et al. (1990) *Bull. Chem. Soc. Japan* 63, 2820-2827] (173 mg, 0.869 mmol) in 2 M ammonia in MeOH (3.5 mL) was heated to reflux for 18 h. The mixture was concentrated in vacuo and purified by silica gel chromatography, eluting with a gradient of hexane:EtOAc—100:0 to 50:50, to give the title compound. MS: m/z=413 (M+1).

Step C. (±)-3-Amino-1'-{[2-(trimethylsilyl)ethoxy]methyl}-5,7-dihydrospiro[cyclopenta[b]pyridine-6,3'-pyrrolo[2,3-b]pyridin]-2'(1'H)-one A mixture of 10% Pd/C (20 mg) and (±)-3-nitro-1'-{[2-(trimethylsilyl)ethoxy]methyl}-5,7-dihydrospiro[cyclopenta[b]pyridine-6,3'-pyrrolo[2,3-b]pyridin]-2'(1'H)-one from Step B (117 mg, 0.284 mmol) was stirred vigorously in MeOH (5 mL) under an atmosphere of hydrogen (ca. 1 atm). After 4.5 h, the mixture was filtered through a pad of Celite, washing extensively with MeOH, and the filtrate was concentrated in vacuo to give the title compound. MS: m/z=383 (M+1).

Step D. 3-Amino-5,7-dihydrospiro[cyclopenta[b]pyridine-6,3'-pyrrolo[2,3-b]pyridin]-2'(1'H)-one, isomer A A solution of (±)-3-amino-1'-{[2-(trimethylsilyl)ethoxy]methyl}-5,7-dihydrospiro[cyclopenta[b]pyridine-6,3'-pyrrolo[2,3-b]pyridin]-2'(1'H)-one from Step C (117 mg, 0.306 mmol) in MeOH (5 mL) was saturated with HCl (g). The mixture was stirred for 30 min and then concentrated in vacuo. The residue was dissolved in MeOH (3 mL) and treated with ethylenediamine (0.020 mL, 0.306 mmol) and 10 N sodium hydroxide to adjust the mixture to pH 10. After 1 h, the reaction mixture was purified directly by HPLC using a reversed phase C18 column and eluting with a gradient of $H_2O:CH_3CN:CF_3CO_2H$—90:10:0.1 to 5:95:0.1. Lyophilization provided the racemic title compound as the TFA salt. The enantiomers were resolved by HPLC, utilizing a ChiralPak AD column and eluting with EtOH. The first major peak to elute was 3-amino-5,7-dihydrospiro[cyclopenta[b]pyridine-6,3'-pyrrolo[2,3-b]pyridin]-2'(1'H)-one, isomer A, the title compound, and the second major peak to elute was 3-amino-5,7-dihydrospiro[cyclopenta[b]pyridine-6,3'-pyrrolo[2,3-b]pyridin]-2'(1'H)-one, isomer B. MS: m/z=253(M+1).

INTERMEDIATE 42

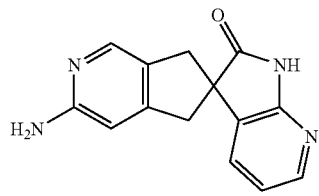

3-Amino-5,7-dihydrospiro[cyclopenta[c]pyridine-6,3'-pyrrolo[2,3-b]pyridin]-2'(1'H)-one, isomer A

Step A. 4,5-Bis(hydroxymethyl)pyridine-2-carbonitrile

To a solution of dimethyl 6-cyanopyridine-3,4-dicarboxylate [Hashimoto et al. (1997) *Heterocycles* 46, 581] (2.00 g, 9.08 mmol) in EtOH (50 mL) was added lithium borohydride (4.54 mL of a 2 M solution in THF, 9.08 mmol) dropwise. The reaction mixture was stirred at ambient temperature for 3 h, and then cooled to 0° C. Saturated aqueous $NaHCO_3$ (20 mL) was added slowly and the quenched mixture was extracted with EtOAc (9×100 mL). The combined organic extracts were dried over $Na_2SO_4$, filtered, and concentrated in vacuo. The crude product was purified by silica gel chromatography, eluting with a gradient of $CH_2Cl_2$:MeOH—100:0 to 85:15, to give the title compound. MS: m/z=165 (M+1).

Step B. 4,5-Bis(bromomethyl)pyridine-2-carbonitrile

To a solution of 4,5-bis(hydroxymethyl)pyridine-2-carbonitrile from Step A (750 mg, 4.57 mmol) in THF (15 mL) was added phosphorus tribromide (1.61 g, 5.94 mmol) in THF (5 mL) dropwise. The reaction mixture was stirred at ambient temperature for 2 h, and then cooled to 0° C. Saturated aqueous $NaHCO_3$ (5 mL) was added slowly and the quenched mixture was extracted with $CHCl_3$ (2×30 mL). The combined organic extracts were dried over $Na_2SO_4$, filtered, and concentrated in vacuo. The crude product was purified by silica gel chromatography, eluting with a gradient of hexane:EtOAc—100:0 to 25:75, to give the title compound. MS: m/z=291 (M+1).

Step C. (±)-2'-Oxo-1',2',5,7-tetrahydrospiro[cyclopenta[c]pyridine-6,3'-pyrrolo[2,3-b]pyridine]-3-carbonitrile To a solution of 4,5-bis(bromomethyl)pyridine-2-carbonitrile from Step B (2.56 g, 8.83 mmol) and 1,3-dihydro-2H-pyrrolo[2,3-b]pyridin-2-one [Marfat & Carta (1987) *Tetrahedron Lett.* 28, 4027] (1.18 g, 8.83 mmol) in THF (120 mL) and $H_2O$ (60 mL) was added lithium hydroxide monohydrate (1.11 g, 26.5 mmol). After 20 min, the reaction mixture was poured onto water (100 mL) and extracted with EtOAc (3×100 mL). The combined organic extracts were dried over $Na_2SO_4$, filtered, and concentrated in vacuo. The crude product was purified by silica gel chromatography, eluting with a gradient of $CH_2Cl_2$:MeOH:$NH_4OH$—100:0:0 to 95:5:1, to give the title compound. MS: m/z=263 (M+1).

Step D. (±)-Sodium 2'-oxo-1',2',5,7-tetrahydrospiro[cyclopenta[c]pyridine-6,3'-pyrrolo[2,3-b]pyridine]-3-carboxylate To a solution of (±)-2'-oxo-1',2',5,7-tetrahydrospiro[cyclopenta[c]pyridine-6,3'-pyrrolo[2,3-b]pyridine]-3-carbonitrile from Step C (1.53 g, 5.83 mmol) in EtOH (20 mL) was added 5 M aqueous NaOH (3.50 mL). The mixture was heated at reflux for 72 h, with additional 5 M aqueous NaOH (2.00 mL) added at 6 h. The reaction mixture was allowed to cool and was concentrated to dryness in vacuo to afford the title compound in sufficient purity for use in subsequent steps. MS: m/z=282 (M+1).

Step E. (±)-tert-Butyl (2'-oxo-1',2',5,7-tetrahydrospiro[cyclopenta[c]pyridine-6,3'-pyrrolo[2,3-b]pyridin]-3-yl)carbamate To a suspension of (±)-sodium 2'-oxo-1',2',5,7-tetrahydrospiro[cyclopenta[c]pyridine-6,3'-pyrrolo[2,3-b]pyridine]-3-carboxylate from Step D (1.64 g, 5.83 mmol) and triethylamine (1.62 mL, 11.7 mmol) in tert-butanol (50 mL) was added diphenylphosphoryl azide (1.89 mL, 8.75 mmol) and the mixture was heated at reflux for 72 h. Additional diphenylphosphoryl azide (1.89 mL, 8.75 mmol) was added after 24 h and 56 h. The reaction mixture was concentrated in vacuo and then partitioned between $CH_2Cl_2$ (75 mL) and saturated $NaHCO_3$ (100 mL). The organic layer was separated and the aqueous layer was further extracted with $CH_2Cl_2$ (2×50 mL). The combined organic layers were dried over $Na_2SO_4$, filtered, and concentrated in vacuo. The crude product was purified by silica gel chromatography, eluting with a gradient of $CH_2Cl_2$:MeOH:$NH_4OH$—100:0:0 to 95:5:1, to give the title compound. MS: m/z=353 (M+1).

Step F. 3-Amino-5,7-dihydrospiro[cyclopenta[c]pyridine-6,3'-pyrrolo[2,3-b]pyridin]-2'(1'H)-one, isomer A A solution of (±)-tert-butyl (2'-oxo-1',2',5,7-tetrahydrospiro[cyclopenta[c]pyridine-6,3'-pyrrolo[2,3-b]pyridin]-3-yl)carbamate from Step E (1.39 g, 3.94 mmol) was stirred in $CH_2Cl_2$ (10 mL) and TFA (3 mL) for 18 h and then concentrated in vacuo to provide the racemic title compound as the TFA salt. The enantiomers were resolved by HPLC, utilizing a ChiralPak AD column and eluting with MeOH. The first major peak to elute was 3-amino-5,7-dihydrospiro[cyclopenta[c]pyridine-6,3'-pyrrolo[2,3-b]pyridin]-2'(1'H)-one, isomer A, the title compound, and the second major peak to elute was 3-amino-5,7-dihydrospiro[cyclopenta[c]pyridine-6,3'-pyrrolo[2,3-b]pyridin]-2'(1'H)-one, isomer B. MS: m/z=253 (M+1).

INTERMEDIATE 43

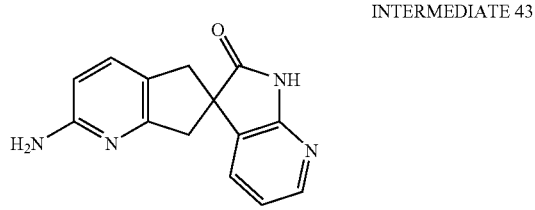

(±)-2-Amino-5,7-dihydrospiro[cyclopenta[b]pyridine-6,3'-pyrrolo[2,3-b]pyridin]-2'(1'H)-one

Step A. Dimethyl 6-cyanopyridine-2,3-dicarboxylate

To a solution of dimethyl pyridine-2,3-dicarboxylate 1-oxide [Niiyami et al. (2002) *Bioorg. Med. Chem. Lett.* 12, 3041] (15.3 g, 72.5 mmol) and trimethylsilyl cyanide (15.7 mL, 117 mmol) in DME (161 mL) was added dimethylcarbamoyl chloride (10.5 mL, 114 mmol). The reaction mixture was heated at reflux for 72 h, and then cooled to 0° C. Saturated aqueous $NaHCO_3$ (800 mL) was added slowly and the quenched mixture was extracted with EtOAc (2×1 L). The combined organic extracts were washed with brine (200 mL), dried over $Na_2SO_4$, filtered, and concentrated in vacuo. The crude product was purified by silica gel chromatography, eluting with a gradient of hexane:EtOAc—100:0 to 50:50, to give the title compound. MS: m/z=221 (M+1).

Step B. 5,6-Bis(hydroxymethyl)pyridine-2-carbonitrile

To a solution of dimethyl 6-cyanopyridine-2,3-dicarboxylate from Step A (13.0 g, 59.0 mmol) in EtOH (295 mL) was added lithium borohydride (29.5 mL of a 2 M solution in THF, 59.0 mmol) dropwise. The reaction mixture was stirred at ambient temperature for 4 h, and then cooled to 0° C. Saturated aqueous $NaHCO_3$ (200 mL) was added slowly and the quenched mixture was extracted with EtOAc (9×100 mL). The combined organic extracts were dried over $Na_2SO_4$, filtered, and concentrated in vacuo. The crude product was purified by silica gel chromatography, eluting with a gradient of $CH_2Cl_2$:MeOH—100:0 to 85:15, to give the title compound. MS: m/z=165 (M+1).

Step C. 5,6-Bis(bromomethyl)pyridine-2-carbonitrile

To a solution of 5,6-bis(hydroxymethyl)pyridine-2-carbonitrile from Step B (2.50 g, 15.2 mmol) in THF (76 mL) was added phosphorus tribromide (5.36 g, 19.8 mmol) in THF (20 mL) dropwise. The reaction mixture was stirred at ambient temperature for 2 h, and then cooled to 0° C. Saturated aqueous $NaHCO_3$ (20 mL) was added slowly and the quenched mixture was extracted with $CH_2Cl_2$ (2×200 mL). The combined organic extracts were dried over $Na_2SO_4$, filtered, and concentrated in vacuo. The crude product was purified by silica gel chromatography, eluting with a gradient of hexane:EtOAc—100:0 to 30:70, to give the title compound. MS: m/z=291 (M+1).

Step D. (±)-2'-Oxo-1'-{[2-(trimethylsilyl)ethoxy]methyl}-1',2',5,7-tetrahydrospiro[cyclopenta[b]pyridine-6,3'-pyrrolo[2,3-b]pyridine]-2-carbonitrile To a solution of 5,6-bis(bromomethyl)pyridine-2-carbonitrile from Step C (1.80 g, 6.21 mmol) and 1-{[2-(trimethylsilyl)ethoxy]methyl}-1,3-dihydro-2H-pyrrolo[2,3-b]pyridin-2-one (1.64 g, 6.21 mmol, described in Intermediate 7) in DMF (207 mL) was added cesium carbonate (6.07 g, 18.6 mmol), portionwise, over 5 min. After 18 h, the mixture was partitioned between $CH_2Cl_2$ (100 mL), saturated aqueous $NaHCO_3$ (100 mL) and brine (200 mL). The organic layer was removed and the aqueous layer was extracted further with $CH_2Cl_2$ (2×100 mL). The combined organic extracts were dried over $Na_2SO_4$, filtered, and concentrated in vacuo. The crude product was purified by silica gel chromatography, eluting with a gradient of hexane:EtOAc—100:0 to 10:90, to give the title compound. MS: m/z=393 (M+1).

Step E. (±)-2'-Oxo-1',2',5,7-tetrahydrospiro[cyclopenta[b]pyridine-6,3'-pyrrolo[2,3-b]pyridine]-2-carboxylic acid To a solution of (±)-2'-oxo-1'-{[2-(trimethylsilyl)ethoxy]methyl}-1',2',5,7-tetrahydrospiro[cyclopenta[b]pyridine-6,3'-pyrrolo[2,3-b]pyridine]-2-carbonitrile from Step D (690 mg, 1.76 mmol) in THF (5 mL) was added 3 N aqueous HCl (36 mL). The mixture was heated at reflux for 18 h, allowed to cool and concentrated to dryness in vacuo. The reaction mixture was dissolved in water (12 mL) and purified directly by HPLC using a reversed phase C18 column and eluting with a gradient of $H_2O$:$CH_3CN$:$CF_3CO_2H$—95:5:0.1 to 5:95:0.1.

Lyophilization of the product-containing fractions provided the title compound. MS: m/z=282 (M+1).

Step F. (±)-tert-Butyl (2'-oxo-1',2',5,7-tetrahydrospiro[cyclopenta[b]pyridine-6,3'-pyrrolo[2,3-b]pyridin]-2-yl)carbamate To a suspension of (±)-2'-oxo-1',2',5,7-tetrahydrospiro[cyclopenta[b]pyridine-6,3'-pyrrolo[2,3-b]pyridine]-2-carboxylic acid from Step E (224 mg, 0.796 mmol) and triethylamine (0.333 mL, 2.39 mmol) in tert-butanol (5 mL) was added diphenylphosphoryl azide (0.258 mL, 1.20 mmol) and the mixture was heated at reflux for 1 h. The reaction mixture was concentrated in vacuo and then partitioned between $CH_2Cl_2$ (20 mL) and saturated $NaHCO_3$ (20 mL). The organic layer was separated and the aqueous layer was further extracted with $CH_2Cl_2$ (2×20 mL). The combined organic layers were dried over $Na_2SO_4$, filtered, and concentrated in vacuo. The crude product was purified by silica gel chromatography, eluting with a gradient of $CH_2Cl_2$:MeOH: $NH_4OH$—100:0:0 to 95:5:1, to give the title compound. MS: m/z=353 (M+1).

Step G. (±)-2-Amino-5,7-dihydrospiro[cyclopenta[b]pyridine-6,3'-pyrrolo[2,3-b]pyridin]-2'(1'H)-one A solution of (±)-tert-butyl (2'-oxo-1',2',5,7-tetrahydrospiro[cyclopenta[b]pyridine-6,3'-pyrrolo[2,3-b]pyridin]-2-yl)carbamate from Step F (147 mg, 0.417 mmol) was stirred in $CH_2Cl_2$ (6 mL) and TFA (1 mL) for 3 h and then concentrated in vacuo to provide the title compound as the TFA salt. MS: m/z=253 (M+1).

INTERMEDIATE 44

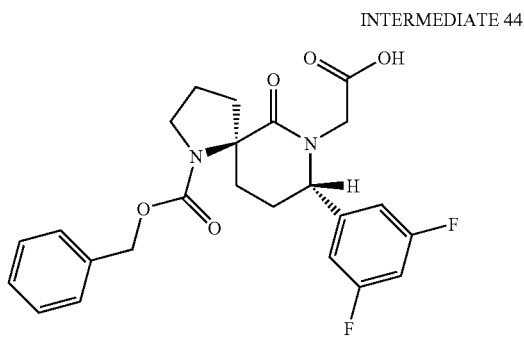

[(5R,8S)-1-[(Benzyloxy)carbonyl]-8-(3,5-difluorophenyl)-6-oxo-1,7-diazaspiro[4.5]dec-7-yl]acetic acid Step A. 1-Benzyl 2-methyl (2R)-2-(3-oxopropyl)pyrrolidine-1,2-dicarboxylate To a solution of DMSO (5.11 mL, 72.1 mmol) in $CH_2Cl_2$ (25 mL) at −78° C. was added a solution of oxalyl chloride (3.15 mL, 36.0 mmol) in $CH_2Cl_2$ (25 mL) dropwise. After 10 min of additional stirring, a solution of 1-benzyl 2-methyl (2R)-2-(3-hydroxypropyl)pyrrolidine-1,2-dicarboxylate [Cox and Lectka (1998) *J. Am. Chem. Soc.* 120, 10660-10668] (7.72 g, 24.0 mmol) in $CH_2Cl_2$ (50 mL) at −78° C. was added dropwise. After stirring for an additional 1 h, triethylamine (16.7 mL, 120 mmol) was added slowly. The reaction mixture was stirred for 1 h at −78° C. and 2.5 h at ambient temperature. Water (100 mL) was added slowly and the quenched mixture was extracted with EtOAc (3×100 mL). The combined organic extracts were washed with 10% HCl (50 mL) and brine (50 mL), dried over $Na_2SO_4$, filtered, and concentrated in vacuo. The crude product was purified by silica gel chromatography, eluting with a gradient of hexane: EtOAc—90:10 to 0:100, to give the title compound. MS: m/z=320 (M+1).

Step B. 1-Benzyl 2-methyl (2R)-2-((3E)-3-{[(S)-tert-butylsulfinyl]imino}propyl)pyrrolidine-1,2-dicarboxylate To a mixture of 1-benzyl 2-methyl (2R)-2-(3-oxopropyl)pyrrolidine-1,2-dicarboxylate from Step A (1.69 g, 5.29 mmol) and anhydrous $CuSO_4$ (2.36 g, 10.6 mmol) in $CH_2Cl_2$ (10 mL) was added (S)-2-methylpropane-2-sulfinamide (0.641 g, 5.29 mmol). This mixture was stirred for 25 h before being filtered through a pad of celite. Additional $CH_2Cl_2$ was used to wash the celite. The combined organics were concentrated in vacuo to give a residue that was purified by silica gel chromatography, eluting with a gradient of hexane:EtOAc—95:5 to 0:100, to give the title compound. MS: m/z=423 (M+1).

Step C. 1-Benzyl 2-methyl (2R)-2-[(3S)-3-{[(S)-tert-butylsulfinyl]amino}-3-(3,5-difluorophenyl)propyl]pyrrolidine-1,2-dicarboxylate To a stirred solution of 1-benzyl 2-methyl(2R)-2-((3E)-3-{[(S)-tert-butylsulfinyl]imino}propyl)pyrrolidine-1,2-dicarboxylate from Step B (1.56 g, 3.70 mmol) in toluene (30 mL) at −78° C. was added 3,5-difluorophenylmagnesium bromide (14.8 mL of a 0.5 M solution in THF, 7.41 mmol) dropwise. The reaction mixture was stirred for 30 min at −78° C., 3.5 h at −10° C., and then at ambient temperature for 1.5 h. The mixture was quenched with saturated aqueous $NH_4Cl$ (50 mL) and extracted with EtOAc (3×30 mL). The combined organic layers were washed with brine (30 mL), dried over $Na_2SO_4$, filtered, and concentrated in vacuo. The crude product was purified by silica gel chromatography, eluting with a gradient of hexane:EtOAc—95:5 to 0:100, to give the title compound. MS: m/z=537 (M+1).

Step D. Benzyl (5R,8S)-8-(3,5-difluorophenyl)-6-oxo-1,7-diazaspiro[4.5]decane-1-carboxylate HCl (g) was bubbled through a solution of 1-benzyl 2-methyl (2R)-2-[(3S)-3-{[(S)-tert-butylsulfinyl]amino}-3-(3,5-difluorophenyl)propyl]pyrrolidine-1,2-dicarboxylate from Step C (1.02 g, 1.90 mmol) in MeOH (25 mL) at 0° C. for 1 min. After stirring for 1 h, the reaction mixture was concentrated to dryness in vacuo. To the crude product suspended in toluene (25 mL) was added triethylamine (2.12 mL, 15.2 mmol), and the reaction mixture was heated to reflux for 66 h. The reaction mixture was concentrated in vacuo and the crude product was purified by silica gel chromatography, eluting with a gradient of $CH_2Cl_2$:MeOH:$NH_4OH$—100:0:0 to 95:5: 1, to give the title compound. MS: m/z=401 (M+1).

Step E. [(5R,8S)-1-[(Benzyloxy)carbonyl]-8-(3,5-difluorophenyl)-6-oxo-1,7-diazaspiro[4.5]dec-7-yl]acetic acid To a stirred solution of benzyl (5R,8S)-8-(3,5-difluorophenyl)-6-oxo-1,7-diazaspiro[4.5]decane-1-carboxylate from Step D (541 mg, 1.35 mmol) in THF (3 mL) at ambient temperature was added NaH (81 mg of a 60% dispersion in oil, 2.03 mmol). After 30 min, ethyl bromoacetate (0.196 mL, 1.76 mmol) was added and the mixture was stirred for 30 min. Sodium hydroxide (8.11 mL of a 1 M solution, 8.11 mmol) was added and the mixture stirred for 16 h. The reaction mixture was poured onto 1 M HCl (20 mL) and extracted with $CH_2Cl_2$ (3×20 mL). The combined organic layers were dried over $Na_2SO_4$, filtered, and concentrated in vacuo. The crude product was purified by HPLC using a reversed phase C18 column and eluting with a gradient of $H_2O:CH_3CN:CF_3CO_2H$—90:10:0.1 to 5:95:0.1 to give the title compound. MS: m/z=459 (M+1).

INTERMEDIATE 45

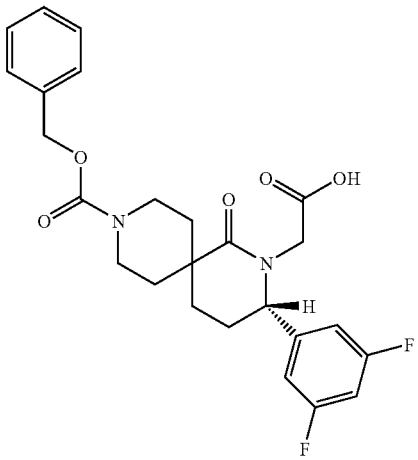

[(3S)-9-[(Benzyloxy)carbonyl]-3-(3,5-difluorophenyl)-1-oxo-2,9-diazaspiro[5.5]undec-2-yl]acetic acid Step A. Methyl 4-allylpiperidine-4-carboxylate HCl (g) was bubbled through a solution of 4-allyl-1-(tert-butoxycarbonyl)piperidine-4-carboxylic acid [Jiang et al. (2004) Bioorg. Med. Chem. Lett. 14, 3675-3678] (6.50 g, 24.1 mmol) in MeOH (200 mL). The solution was heated at reflux for 16 h and then concentrated in vacuo to give the title compound as the hydrochloride salt. MS: m/z=184(M+1).

Step B. 1-Benzyl 4-methyl 4-allylpiperidine-1,4-dicarboxylate

A mixture of methyl 4-allylpiperidine-4-carboxylate from Step A (5.30 g, 24.2 mmol), N-(benzyloxycarbonyloxy)succinimide (7.25 g, 29.1 mmol), and N,N-diisopropylethylamine (12.7 mL, 72.7 mmol) in $CH_3CN$ (61 mL) was stirred for 16 h. The solvent was removed in vacuo and the residue was partitioned between EtOAc (100 mL) and saturated $NaHCO_3$ (100 mL). The organic layer was separated and the aqueous layer was further extracted with EtOAc (2×100 mL). The combined organic extracts were concentrated in vacuo to give a residue that was purified by silica gel chromatography, eluting with a gradient of hexane:EtOAc—100:0 to 40:60, to give the title compound. MS: m/z=318 (M+1).

Step C. 1-Benzyl 4-methyl 4-(2-oxoethyl)piperidine-1,4-dicarboxylate

To a solution of 1-benzyl 4-methyl 4-allylpiperidine-1,4-dicarboxylate from Step B (4.45 g, 14.0 mmol) in THF (70 mL) at 0° C. was added borane-methyl sulfide complex (28.0 mL of a 2M solution in THF, 56.1 mmol). The reaction mixture was slowly warmed to ambient temperature and stirred for 16 h, then quenched with water and concentrated in vacuo. The residue was dissolved in $CH_2Cl_2$ (140 mL) and added drop wise to a solution of PCC (6.65 g, 30.8 mmol) and 4 Å molecular sieves (6.65 g) in $CH_2Cl_2$ (50 mL) at 0° C. The reaction mixture was warmed to ambient temperature and stirred for 16 h, then diluted with ether (200 mL) and filtered through a pad of celite. Additional ether was used to wash the celite. The combined organics were concentrated in vacuo to give a residue that was purified by silica gel chromatography, eluting with a gradient of $CH_2Cl_2$:MeOH—100:0 to 95:5, to give the title compound. MS: m/z=356 (M+Na).

[(3S)-9-[(Benzyloxy)carbonyl]-3-(3,5-difluorophenyl)-1-oxo-2,9-diazaspiro[5.5]undec-2-yl]acetic acid Essentially following the procedures described for Intermediate 44, but using 1-benzyl 4-methyl 4-(2-oxoethyl)piperidine-1,4-dicarboxylate in place of 1-benzyl 2-methyl (2R)-2-(3-oxopropyl)pyrrolidine-1,2-dicarboxylate, the title compound was prepared. MS: m/z=473 (M+1).

INTERMEDIATE 46

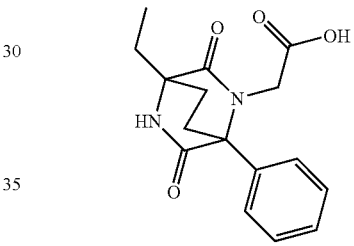

(4-Ethyl-3,6-dioxo-1-phenyl-2,5-diazabicyclo[2.2.2]oct-2-yl)acetic acid

Step A. Benzyl(5-chloro-3-ethyl-2-oxo-6-phenylpyrazin-1(2H)-yl)acetate

A solution of benzyl (3,5-dichloro-2-oxo-6-phenylpyrazin-1(2H)-yl)acetate [Parlow et al. (2003) J. Med. Chem. 46, 4050-4062] (1.05 g, 2.70 mmol), tetraethyltin (0.641 mL, 3.24 mmol), and tetrakis(triphenylphosphine)palladium (31.0 mg, 0.027 mmol) in toluene (15 mL) was heated at reflux for 5.5 h. The solution was concentrated in vacuo and the crude product purified by silica gel chromatography, eluting with a gradient of $CH_2Cl_2$:EtOAc—100:0 to 90:10 to give the title compound. MS: m/z=383 (M+1).

Step B. Benzyl(4-ethyl-3,6-dioxo-1-phenyl-2,5-diazabicyclo[2.2.2]oct-2-yl)acetate A mixture of benzyl(5-chloro-3-ethyl-2-oxo-6-phenylpyrazin-1(2H)-yl)acetate from Step A (975 mg, 2.55 mmol) in toluene (75 mL) was placed in a steel bomb. The bomb was charged to 500 psi with ethylene, sealed, and heated at 145° C. for 66 h. The reaction mixture was concentrated in vacuo and purified by silica gel chromatography, eluting with a gradient of $CH_2Cl_2$:EtOAc—100:0 to 0:100, to give the title compound. MS: m/z=393 (M+1).

Step C. (4-Ethyl-3,6-dioxo-1-phenyl-2,5-diazabicyclo[2.2.2]oct-2-yl)acetic acid To a solution of benzyl (4-ethyl-3,6-dioxo-1-phenyl-2,5-diazabicyclo[2.2.2]oct-2-yl)acetate from Step B (30 mg, 0.076 mmol) in EtOH (1 mL) at ambient temperature was added NaOH (0.229 mL of a 1M solution, 0.229 mmol). The reaction mixture was stirred at ambient temperature for 2 h, and at 50° C. for 2 h. The solvent was removed in vacuo and the crude product dissolved in DMSO and purified by HPLC using a reversed phase C18 column and eluting with a gradient of $H_2O:CH_3CN:CF_3CO_2H$—90:10:0.1 to 5:95:0.1 to give the title compound as the TFA salt. MS: m/z=303 (M+1).

INTERMEDIATE 47

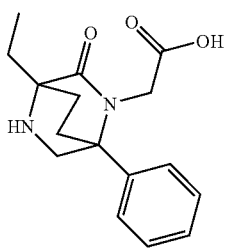

(4-Ethyl-3-oxo-1-phenyl-2,5-diazabicyclo[2.2.2]oct-2-yl)acetic acid

Step A. Benzyl (4-ethyl-3-oxo-1-phenyl-2,5-diazabicyclo[2.2.2]oct-2-yl)acetate To a solution of benzyl(4-ethyl-3,6-dioxo-1-phenyl-2,5-diazabicyclo[2.2.2]oct-2-yl)acetate (200 mg, 0.510 mmol, described in Intermediate 46) in THF (5 mL) at ambient temperature was added borane-methyl sulfide complex (0.535 mL of a 2M solution in THF, 1.07 mmol). The reaction mixture was heated at 65° C. for 2 h, then cooled and quenched with 1M HCl (5 mL). The reaction mixture was poured onto saturated $NaHCO_3$ (10 mL) and extracted with EtOAc (3×20 mL). The combined organic layers were dried over $Na_2SO_4$, filtered, and concentrated in vacuo. The crude product was dissolved in DMSO and purified by HPLC using a reversed phase C18 column and eluting with a gradient of $H_2O:CH_3CN:CF_3CO_2H$—90:10:0.1 to 5:95:0.1 to give the title compound as the TFA salt. MS: m/z=379 (M+1).

Step B. (4-Ethyl-3-oxo-1-phenyl-2,5-diazabicyclo[2.2.2]oct-2-yl)acetic acid

A mixture of benzyl (4-ethyl-3-oxo-1-phenyl-2,5-diazabicyclo[2.2.2]oct-2-yl)acetate from Step A (127 mg, 0.336 mmol) and 10% Pd/C (20 mg) in MeOH (5 mL) was stirred under a balloon of hydrogen. The reaction mixture was filtered and concentrated in vacuo to give the title compound. MS: m/z=289 (M+1).

The intermediates appearing in the following tables were prepared by analogy to the above intermediates, as described or prepared as a result of similar transformations with modifications known to those skilled in the art. The requisite starting materials were described herein (vide supra), commercially available, known in the literature, or readily synthesized by one skilled in the art. Straightforward protecting group strategies were applied in some routes. In some cases, relevant experimental procedures are indicated in the tables.

TABLE 1

| Intermediate | $R^6$ | $R^7$ | $R^{10}$ | $R^{11}$ | * | LCMS (M + 1) | Relevant experimental procedures |
|---|---|---|---|---|---|---|---|
| 48 | Me | Me | H | 3,4-difluorophenyl | ± | 298 | |
| 49 | Me | Me | H | 3,5-difluorophenyl | S | 298 | Int. 1 |
| 50 | Me | Me | H | 3-chloro-4-fluorophenyl | S | 314 | Int. 14 |
| 51 | Me | Me | H | 5-fluoro-2-methylphenyl | S | 294 | Int. 14 |
| 52 | Me | Me | H | 4-fluoro-2-methylphenyl | S | 294 | Int. 14 |
| 53 | Me | Me | H | 4-fluoro-3-methylphenyl | S | 294 | Int. 14 |
| 54 | Me | Me | H | 5-fluoro-2-methoxyphenyl | S | 310 | Int. 14 |
| 55 | Me | Me | H | 3-fluorophenyl | S | 280 | Int. 14 |
| 56 | Me | Me | H | 4-chloro-3-fluorophenyl | S | 314 | Int. 14 |
| 57 | Me | Me | H | 3-fluoro-2-methylphenyl | S | 294 | Int. 14 |
| 58 | Me | Me | H | 2-methoxyphenyl | S | 292 | Int. 14 |
| 59 | Me | Me | H | 4-methoxyphenyl | S | 292 | Int. 14 |
| 60 | Me | Me | H | 3-methoxyphenyl | S | 292 | Int. 14 |
| 61 | Me | Me | Me | 3,5-difluorophenyl | S | 312 | Ex. 4 |
| 62 | Me | Me | H | 3,5-dichlorophenyl | S | 330 | Int. 14 |
| 63 | Me | Me | H | 3-thienyl | S | 268 | Int. 14 |
| 64 | Me | Me | H | 2-thienyl | S | 268 | Int. 14 |
| 65 | Me | Me | H | 3-chloro-2-thienyl | S | 302 | Int. 14 |
| 66 | Me | Me | H | 1,3-benzodioxol-5-yl | S | 306 | Int. 14 |
| 67 | Me | Me | H | 3-fluoro-4-methoxyphenyl | S | 310 | Int. 14 |
| 68 | Me | Me | H | 3-chloro-5-fluorophenyl | S | 314 | Int. 14 |
| 69 | Me | Me | H | phenyl | S | 262 | Int. 14 |
| 70 | Me | Me | H | 2-trifluoromethylphenyl | S | 330 | Int. 14 |

TABLE 1-continued

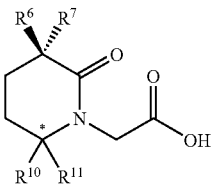

| Intermediate | $R^6$ | $R^7$ | $R^{10}$ | $R^{11}$ | * | LCMS (M + 1) | Relevant experimental procedures |
|---|---|---|---|---|---|---|---|
| 71 | Me | Me | H | 4-fluorophenyl | S | 280 | Int. 14 |
| 72 | Me | Me | H | 2-(methylthio)phenyl | S | 308 | Int. 14 |
| 73 | Me | Me | H | cyclohexyl | S | 268 | Int. 14 |
| 74 | Me | Me | H | cyclopropyl | S | 226 | Int. 14 |
| 75 | Me | Me | H | 3-chlorophenyl | S | 296 | Int. 14 |
| 76 | Me | Me | H | 3,4-dichlorophenyl | S | 330 | Int. 14 |
| 77 | Me | Me | H | 3-methylphenyl | S | 276 | Int. 14 |
| 78 | Me | Me | H | 4-methylphenyl | S | 276 | Int. 14 |
| 79 | Me | Me | H | 4-(methylthio)phenyl | S | 308 | Int. 14 |
| 80 | Me | Me | H | 4-chloro-2-methylphenyl | S | 310 | Int. 14 |
| 81 | Me | Me | H | benzyl | S | 276 | Int. 14 |
| 82 | Me | Me | H | 4-chlorophenyl | S | 296 | Int. 14 |
| 83 | Me | Me | H | isopropyl | S | 228 | Int. 14 |
| 84 | Me | Me | H | 2-methylphenyl | S | 276 | Int. 14 |
| 85 | Me | Me | H | 3-chloro-2,4-difluorophenyl | | 332 | Int. 18 |

TABLE 2

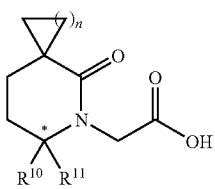

| Intermediate | n | $R^{10}$ | $R^{11}$ | * | LCMS (M + 1) | Relevant experimental procedures |
|---|---|---|---|---|---|---|
| 86 | 3 | H | 3,5-difluorophenyl | S | 324 | Int. 26 |
| 87 | 4 | H | 3,5-difluorophenyl | S | 338 | Int. 26 |
| 88 | 1 | H | phenyl | ± | 260 | Int. 26 |

TABLE 3

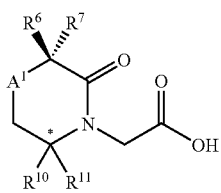

| Intermediate | $R^6$ | $R^7$ | $A^1$ | $R^{10}$ | $R^{11}$ | * | LCMS (M + 1) | Relevant experimental procedures |
|---|---|---|---|---|---|---|---|---|
| 89 | Me | Me | O | H | phenyl | R | 264 | Int. 10 |
| 90 | Me | Me | O | H | 3,5-difluorophenyl | S | 300 | Int. 10 |
| 91 | H | Et | O | H | phenyl | R | 264 | Int. 12 |
| 92 | Me | Me | $CF_2$ | H | 3,5-difluorophenyl | S | 334 | Int. 22 |
| 93 | Me | Me | 1,3-dioxolan-2-yl | H | 3-5-difluorophenyl | S | 356 | Int. 22 |

TABLE 4

| Intermediate | $R^6$ | $R^7$ | $R^{11}$ | * | LCMS (M + 1) | Relevant experimental procedures |
|---|---|---|---|---|---|---|
| 94 | Me | Me | 3,5-difluorophenyl | R | 312 | Int. 22 |
| 95 | Et | Et | 3,5-difluorophenyl | S | 340 | Int. 22 |
| 96 | Et | Et | 3,5-difluorophenyl | R | 340 | Int. 22 |

TABLE 5

| Intermediate | $R^6$ | $R^7$ | R | * | $R^{11}$ | % | LCMS (M + 1) | Relevant experimental procedures |
|---|---|---|---|---|---|---|---|---|
| 97 | Me | Me | H | R | 3,5-difluorophenyl | R | 314 | Int. 21 |
| 98 | Me | Me | H | R | 3,5-difluorophenyl | S | 314 | Int. 21 |
| 99 | Me | Me | H | S | 3,5-difluorophenyl | R | 314 | Int. 21 |
| 100 | Me | Me | Me | S | 3,5-difluorophenyl | S | 328 | Int. 21 |
| 101 | Et | Et | H | S | 3,5-difluorophenyl | S | 342 | Int. 21 |
| 102 | Et | Et | H | R | 3,5-difluorophenyl | R | 342 | Int. 21 |
| 103 | Me | Me | Me | R | 3,5-difluorophenyl | R | 328 | Int. 21 |

TABLE 6

| Intermediate | $R^6$ | $R^7$ | $R^1$ | $R^{11}$ | * | LCMS (M + 1) | Relevant experimental procedures |
|---|---|---|---|---|---|---|---|
| 104 | Me | Me | tert-butoxycarbonyl | phenyl | ± | 307 (M − $C_4H_7$) | Int. 13 |
| 105 | Me | Me | tert-butoxycarbonyl | phenyl | S | 307 (M − $C_4H_7$) | Int. 13 |
| 106 | Me | Me | tert-butoxycarbonyl | phenyl | R | 307 (M − $C_4H_7$) | Int. 13 |
| 107 | Me | Me | tert-butoxycarbonyl | 3,5-difluorophenyl | S | 343 (M − $C_4H_7$) | Int. 13 |
| 108 | Me | H | Me | phenyl | ± | 263 | Int. 19 |
| 109 | H | Bn | Me | phenyl | S | 339 | Int. 19 |
| 110 | H | Bn | Me | phenyl | R | 339 | Int. 19 |
| 111 | Et | Et | Me | phenyl | ± | 305 | Int. 19 |
| 112 | Et | Et | H | phenyl | ± | 291 | Int. 25 |
| 113 | Et | Et | H | 3,5-difluorophenyl | S | 327 | Int. 29 |
| 114 | H | Ph | Me | phenyl | S | 325 | Int. 19 |
| 115 | H | Ph | Me | phenyl | R | 325 | Int. 19 |
| 116 | H | i-Pr | Me | phenyl | S | 291 | Int. 19 |
| 117 | H | i-Pr | Me | phenyl | R | 291 | Int. 19 |
| 118 | H | i-Bu | Me | phenyl | S | 305 | Int. 19 |

TABLE 6-continued

| Intermediate | R6 | R7 | R1 | R11 | * | LCMS (M + 1) | Relevant experimental procedures |
|---|---|---|---|---|---|---|---|
| 119 | H | i-Bu | Me | phenyl | R | 305 | Int. 19 |
| 120 | i-Bu | H | Me | phenyl | S | 305 | Int. 19 |
| 121 | i-Bu | H | Me | phenyl | R | 305 | Int. 19 |
| 122 | CH2CF3 | H | tert-butoxycarbonyl | 3,5-difluorophenyl | R | 397 (M − C4H7) | Int. 25 |
| 123 | CH2CF3 | H | H | 3,5-difluorophenyl | S | 353 | Int. 25 |
| 124 | H | CH2CF3 | H | 3,5-difluorophenyl | R | 353 | Int. 25 |
| 125 | Me | Me | PhCH2 | 3,5-difluorophenyl | R | 389 | Int. 13 |
| 126 | Me | Me | CF3CH2 | 3,5-difluorophenyl | R | 381 | Int. 13 |

TABLE 7

| Intermediate | R1 | n | R10 | R11 | * | LCMS (M + 1) | Relevant experimental procedures |
|---|---|---|---|---|---|---|---|
| 127 | H | 3 | H | phenyl | S | 289 | Int. 28 |
| 128 | Me | 1 | H | phenyl | ± | 275 | Int. 19 |
| 129 | Me | 2 | H | phenyl | ± | 289 | Int. 19 |
| 130 | H | 3 | H | 3,5-difluorophenyl | S | 325 | Int. 25 |
| 131 | H | 4 | H | 3,5-difluorophenyl | R | 339 | Int. 29 |
| 132 | H | 4 | H | 3,5-difluorophenyl | S | 339 | Int. 29 |
| 133 | tert-butoxycarbonyl | 4 | Me | 3,5-difluorophenyl | S | 397 (M − C4H7) | Int. 33 |
| 134 | tert-butoxycarbonyl | 5 | Me | 3,5-difluorophenyl | R | 411 (M − C4H7) | Int. 33 |
| 135 | tert-butoxycarbonyl | 5 | Me | 3,5-difluorophenyl | S | 411 (M − C4H7) | Int. 33 |
| 136 | tert-butoxycarbonyl | 3 | Me | 3,5-difluorophenyl | R | 383 (M − C4H7) | Int. 33 |
| 137 | tert-butoxycarbonyl | 3 | Me | 3,5-difluorophenyl | S | 383 (M − C4H7) | Int. 33 |

TABLE 8

| Intermediate | R6 | # | R11 | * | LCMS (M + 1) | Relevant experimental procedures |
|---|---|---|---|---|---|---|
| 138 | H | S | phenyl | R | 275 | Int. 28 |
| 139 | H | S | phenyl | S | 275 | Int. 28 |
| 140 | H | R | phenyl | R | 275 | Int. 28 |
| 141 | H | R | phenyl | S | 275 | Int. 28 |
| 142 | Me | S | phenyl | ± | 289 | Int. 28 |
| 143 | Me | S | 3,5-difluorophenyl | ± | 325 | Int. 28 |

TABLE 9

| Intermediate | R⁶ | R⁷ | R¹ | R² | # | R¹¹ | * | LCMS (M + 1) | Relevant experimental procedures |
|---|---|---|---|---|---|---|---|---|---|
| 144 | Me | Me | H | Me | R | phenyl | R | 277 | Int. 25 |
| 145 | Me | Me | H | Me | S | phenyl | S | 277 | Int. 25 |
| 146 | Me | Me | H | Me | R | 3,5-difluorophenyl | R | 313 | Int. 25 |
| 147 | Me | Me | H | Me | S | 3,5-difluorophenyl | S | 313 | Int. 25 |

TABLE 10

| Intermediate | R¹ | X | R¹⁰ | R¹¹ | * | LCMS (M + 1) | Relevant experimental procedures |
|---|---|---|---|---|---|---|---|
| 148 | H | O | H | 3,5-difluorophenyl | R | 341 | Int. 25 |
| 149 | H | O | H | 3,5-difluorophenyl | S | 341 | Int. 25 |

TABLE 11

| Intermediate | R¹ | n | X | * | LCMS (M + 1) | Relevant experimental procedures |
|---|---|---|---|---|---|---|
| 150 | tert-butoxycarbonyl | 3 | F | S | 451 | Int. 34 |
| 151 | tert-butoxycarbonyl | 3 | H | ± | 437 (M + Na) | Int. 34 |

Example 1

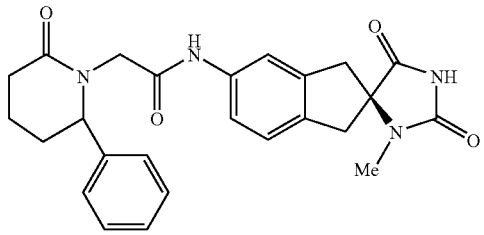

N-[(4S)-3-Methyl-2,5-dioxo-1',3'-dihydrospiro[imidazolidine-4,2'-inden]-5'-yl]-2-((6±)-2-oxo-6-phenylpiperidin-1-yl)acetamide

Step A. (±)-(2-Oxo-6-phenylpiperidin-1-yl)acetic acid

To a stirred solution of (±)-6-phenylpiperidin-2-one (155 mg, 0.885 mmol) in THF (10 mL), cooled to 0° C., was added NaH (30.0 mg, 1.24 mmol). The ice bath was removed and the reaction was allowed to warm to ambient temperature. After 1 h at ambient temperature, the reaction was cooled to 0° C. prior to the introduction of methyl bromoacetate (149 mg, 0.973 mmol). After 40 minutes, the ice bath was removed and the reaction was stirred under nitrogen for 12 h. Additional quantities of NaH and methyl bromoacetate were then added in parts to nearly consume the lactam, as judged by LCMS analysis. After sufficient lactam was consumed, 1 M aqueous sodium hydroxide was added (1 mL, 1 mmol). After a majority of the methyl ester was saponified (~3 h), the reaction was quenched with 1 M hydrochloric acid (5 mL), and EtOAc (50 mL). The organics were washed with saturated brine (twice), dried over sodium sulfate, filtered and concentrated in vacuo, to yield a residue which was used without further purification. MS: m/z=234 (M+1).

Step B. N-[(4S)-3-Methyl-2,5-dioxo-1',3'-dihydrospiro[imidazolidine-4,2'-inden]-5'-yl]-2-((6±)-2-oxo-6-phenylpiperidin-1-yl)acetamide To a solution of (±)-(2-oxo-6-phenylpiperidin-1-yl)acetic acid from Step A (100. mg, 0.429 mmol), HOAt (29.0 mg, 0.214 mmol) and (4S)-5'-amino-3-methyl-1',3'-dihydro-2H,5H-spiro[imidazolidine-4,2'-indene]-2,5-dione (109 mg, 0.472 mmol, prepared according to Bell, I. M., et al., PCT Int. Appl., WO 2004082605 A2) in DMF (5.0 mL) was added EDCI (115 mg, 0.600 mmol). This solution was stirred at ambient temperature for 15 h. The reaction was then quenched by the addition of 1 M HCl (10 mL) and EtOAc (50 mL). The organics were further washed with an additional aliquot of 1M HCl (10 mL), then saturated brine (20 mL×2), followed by drying over sodium sulfate. The organics were then filtered, concentrated in vacuo, and applied to a silica gel column for purification, eluting with a gradient of $CH_2Cl_2$:MeOH—99.5:0.5 to 95:5. Clean product-containing fractions were pooled and concentrated in vacuo to give the title compound. MS: m/z=447 (M+1). HRMS: m/z=447.2013; calculated m/z=447.2027 for $C_{25}H_{27}N_4O_4$.

Example 2

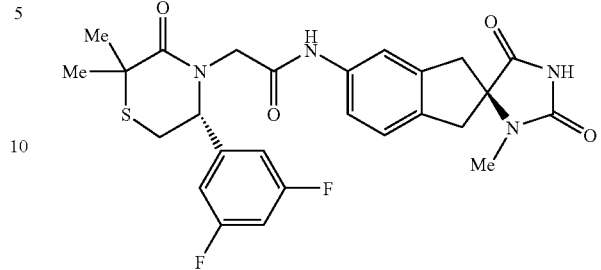

2-[(5R)-5-(3,5-Difluorophenyl)-2,2-dimethyl-3-oxo-4-thiomorpholinyl]-N-[(4S)-3-methyl-2,5-dioxo-1',3'-dihydrospiro[imidazolidine-4,2'-inden]-5'-yl]acetamide Starting from (5R)-5-(3,5-difluorophenyl)-2,2-dimethylthiomorpholin-3-one (Intermediate 2), the compound in Example 2 was prepared following analogous procedures for the preparation of Example 1, to provide the title compound. MS: m/z=551 (M+Na). HRMS: m/z=529.1734; calculated m/z=529.1716 for $C_{26}H_{26}F_2N_4O_4S$.

Example 3

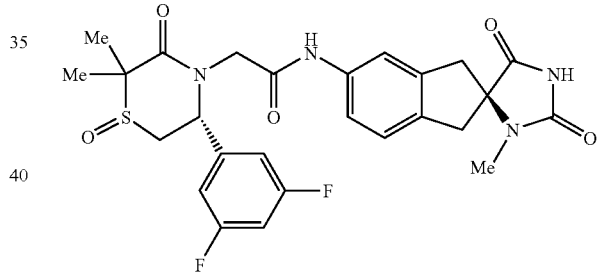

2-[(5R)-5-(3,5-Difluorophenyl)-2,2-dimethyl-1-oxido-3-oxo-4-thiomorpholinyl]-N-[(4S)-3-methyl-2,5-dioxo-1',3'-dihydrospiro[imidazolidine-4,2'-inden]-5'-yl]acetamide

Step A. (5R)-5-(3,5-Difluorophenyl)-2,2-dimethylthiomorpholin-3-one

To a solution of 2-[(5R)-5-(3,5-difluorophenyl)-2,2-dimethyl-3-oxo-4-thiomorpholinyl]-N-[(4S)-3-methyl-2,5-dioxo-1',3'-dihydrospiro[imidazolidine-4,2'-inden]-5'-yl]acetamide (Example 2) in 1.5 mL chloroform at 0° C., was added 3-chloroperoxybenzoic acid (21 mg with a purity of 77%, 0.121 mmol). An LCMS of the reaction mixture after two hours showed that all starting material was consumed. Calcium hydroxide (14 mg, 0.185 mmol) was added to the reaction and stirred for forty minutes. The mixture was then vacuum filtered through filter paper and the solid was washed with chloroform (3×10 mL). The filtrate was concentrated in vacuo to give a residue that was purified by silica gel chromatography, eluting with a gradient of MeOH:$CH_2Cl_2$—1:99 to 5:95, to give the title compound. MS: m/z=545 (M+H). HRMS: m/z 545.1653; calculated m/z=545.1665 for $C_{26}H_{26}F_2N_4O_5S$.

Example 4

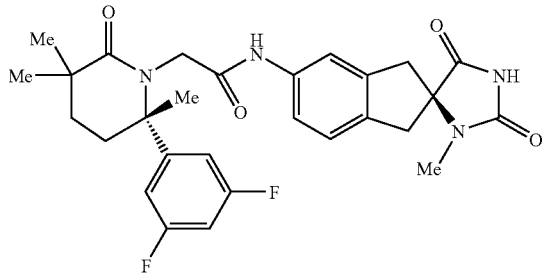

2-[(2S)-2-(3,5-Difluorophenyl)-2,5,5-trimethyl-6-oxo-1-piperidinyl]-N-[(4S)-3-methyl-2,5-dioxo-1',3'-dihydrospiro[imidazolidine-4,2'-inden]-5'-yl]acetamide Step A. Methyl (5E)-5-[(tert-butylsulfinyl)imino]-5-(3,5-difluorophenyl)-2,2-dimethylpentanoate To a solution of methyl 5-(3,5-difluorophenyl)-2,2-dimethyl-5-oxopentanoate from Intermediate 1, Step D (500 mg of 85% purity, 1.85 mmol) and (S)-2-methylpropane-2-sulfinamide (336 mg, 2.78 mmol) in THF (9.5 mL), was added titanium tetraethoxide (904 mg, 3.70 mmol). The reaction vessel was quickly sealed and placed into a 60° C. bath for 2 hours. After cooling to ambient temperature the reaction mixture was then diluted with saturated brine (9.5 mL) while experiencing rapid stirring. The resultant slurry was filtered through celite, washing with EtOAc, as needed. The combined organics were then washed with brine, dried over sodium sulfate, filtered and concentrated in vacuo to give an oil. This oil was purified by silica gel chromatography, eluting with a gradient of MeOH:CH$_2$Cl$_2$—0.5:99.5 to 3:97, to give the title compound. MS: m/z=374 (M+1).

Step B. Methyl (5S)-5-[(tert-butylsulfinyl)amino]-5-(3,5-difluorophenyl)-2,2-dimethylhexanoate To a solution of methyl (5E)-5-[(tert-butylsulfinyl)imino]-5-(3,5-difluorophenyl)-2,2-dimethylpentanoate (342 mg, 0.920 mmol) in CH$_2$Cl$_2$ (6 mL) at 0° C., was added dropwise over five minutes methyl magnesium bromide as a 3M solution in diethyl ether (0.61 mL, 1.83 mmol). After 15 minutes the reaction was determined to be complete by LCMS analysis. The reaction was quenched by the dropwise addition of 1M HCl (5 mL), followed by 5 mL of water. The aqueous layer was extracted once with CH$_2$Cl$_2$ (10 mL) and the organics were combined and washed once with brine (15 mL). The organics were dried over sodium sulfate, filtered and concentrated in vacuo to give a residue that was purified by silica gel chromatography, eluting with a gradient of EtOAc:Hexanes—10:90 to 55:45, to give the title compound. MS: m/z=390 (M+1).

Step C. (6S)-6-(3,5-Difluorophenyl)-3,3,6-trimethylpiperidin-2-one

To a solution of methyl (5S)-5-[(tert-butylsulfinyl)amino]-5-(3,5-difluorophenyl)-2,2-dimethylhexanoate (1.14 g, 2.93 mmol) in MeOH (60 mL), cooled to 0° C., was added anhydrous HCl gas for 1 minute. The reaction was sealed and allowed to sit at 0° C. for fifteen minutes at which point the reaction was complete by LCMS analysis. Nitrogen was bubbled through the reaction for twenty minutes. The reaction was concentrated in vacuo. Additional MeOH (50 mL) was added and it was again concentrated in vacuo. This was repeated with another addition of MeOH and triethylamine (1.18 g, 11.7 mmol). To the resulting residue was added toluene (50 mL) and triethylamine (1.18 g, 11.7 mmol). A reflux condenser was attached and the mixture stirred at 110° C. After five days of stirring at reflux, the reaction was judged to be complete by LCMS. The mixture was cooled to ambient temperature and concentrated in vacuo. The residue was diluted with diethyl ether (75 mL) and washed individually with 30 mL of each of the following aqueous solutions: 1 M HCl (twice), water, saturated brine. The organic layer was then dried over sodium sulfate, filtered, and concentrated in vacuo to give a residue that was purified by silica gel chromatography, eluting with a gradient of MeOH:CH$_2$Cl$_2$-1:99 to 5.5:94.5, to give the title compound. MS: m/z=254 (M+1).

Step D. Methyl [(2S)-2-(3,5-difluorophenyl)-2,5,5-trimethyl-6-oxopiperidin-1-yl]acetate To a solution of (6S)-6-(3,5-difluorophenyl)-3,3,6-trimethylpiperidin-2-one (540. mg, 2.13 mmol) in THF (20 mL), chilled to 0° C. was added potassium hydride (approximately 86 mg, 2.13 mmol, as a 30% suspension in oil) under a constant stream of nitrogen. The reaction was allowed to stir for 30 minutes at which time methyl bromoacetate (391 mg, 2.56 mmol) was added at 0° C. An LCMS after one hour indicated that the reaction was incomplete, thus more potassium hydride was added (approximately 43 mg, 1.06 mmol, as a 30% suspension in oil) at 0° C. The reaction was sealed well and was stirred for an additional 16 hours, during which time the bath temperature warmed to ambient temperature. The reaction was judged to be 46% complete by LCMS analysis. The reaction was chilled to 0° C. and saturated aqueous ammonium chloride (5 mL) was added to quench the potassium hydride. To the reaction was added 1M aqueous HCl (5 mL) and the reaction was diluted with ethyl acetate. The organic layer was washed once with brine and then dried over sodium sulfate, filtered, and concentrated in vacuo to give a residue that was purified by silica gel chromatography, eluting with a gradient of EtOAc:Hexanes—10:90 to 75:25, to give the title compound. MS: m/z=326 (M+1).

Step E. Potassium [(2S)-2-(3,5-difluorophenyl)-2,5,5-trimethyl-6-oxopiperidin-1-yl]acetate To a solution of methyl [(2S)-2-(3,5-difluorophenyl)-2,5,5-trimethyl-6-oxopiperidin-1-yl]acetate from Step D (298 mg, 0.916 mmol) in THF (9 mL) at ambient temperature was added potassium trimethylsilanolate (147 mg, 1.14 mmol). The reaction was stirred for 24 hours and found to be incomplete by LCMS analysis. Additional quantities of potassium trimethylsilanolate were added as needed. The reaction was concentrated in vacuo to give a residue that required no further purification. MS: m/z=312 (M+1 for parent acid).

Step F. 2-[(2S)-2-(3,5-Difluorophenyl)-2,5,5-trimethyl-6-oxo-1-piperidinyl]-N-[(4S)-3-methyl-2,5-dioxo-1',3'-dihydrospiro[imidazolidine-4,2'-inden]-5'-yl]acetamide Starting from potassium [(2S)-2-(3,5-difluorophenyl)-2,5,5-trimethyl-6-oxopiperidin-1-yl]acetate (182 mg, 0.522 mmol), Example 4 was prepared following the analogous procedure for the preparation of Example 1, Step B, to provide the title compound. MS: m/z=525 (M+1). HRMS: m/z=525.2326; calculated m/z=525.2308 for $C_{28}H_{30}F_2N_4O_4$.

Example 5

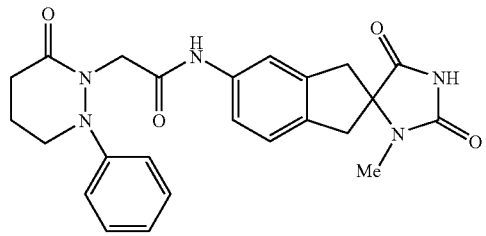

N-(3-Methyl-2,5-dioxo-1',3'-dihydrospiro[imidazolidine-4,2'-inden]-5'-yl)-2-(6-oxo-2-phenyltetrahydropyridazin-1(2H)-yl)acetamide Starting from 1-phenyltetrahydropyridazin-3(2H)-one (prepared according to Hwang, K.-J.; Park K.-H., Heterocycles, 1993, 36, 219-222), the compound in Example 5 was prepared following analogous procedures for the preparation of Example 1, to provide the title compound. MS: m/z=448 (M+1). HRMS: m/z=448.1965; calculated m/z=448.1980 for $C_{24}H_{26}N_5O_4$.

Example 6

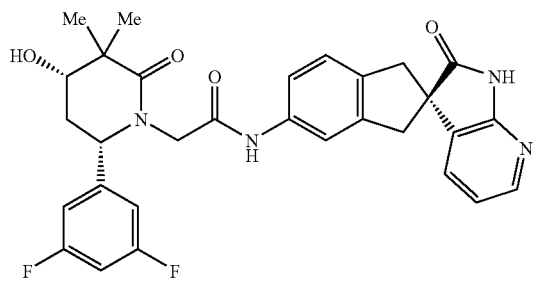

2-[(4S,6S)-6-(3,5-Difluorophenyl)-4-hydroxy-3,3-dimethyl-2-oxopiperidin-1-yl]-N-[(2R)-2'-oxo-1,1',2',3-tetrahydrospiro[indene-2,3'-pyrrolo[2,3-b]pyridin]-5-yl]acetamide A mixture of [(4S,6S)-6-(3,5-difluorophenyl)-4-hydroxy-3,3-dimethyl-2-oxopiperidin-1-yl]acetic acid (130 mg, 0.415 mmol, described in Intermediate 21), (R)-5-amino-1,3-dihydrospiro[indene-2,3'-pyrrolo[2,3-b]pyridin]-2'(1'H)-one (140 mg, 0.557 mmol, described in Intermediate 9), HOBT (82 mg, 0.535 mmol), and EDC (95 mg, 0.498 mmol) in DMF (2 mL) was stirred at ambient temperature for 6 h. The reaction mixture was partitioned between H₂O (50 mL), saturated aqueous NaHCO₃ (30 mL) and EtOAc (100 mL). The organic layer was dried over Na₂SO₄, filtered, and concentrated in vacuo. The crude product was purified by silica gel chromatography, eluting with a gradient of CH₂Cl₂:CH₃OH—100:0 to 90:10, to give the title compound. MS: m/z=547 (M+1). HRMS: m/z=547.2169; calculated m/z=547.2151 for $C_{30}H_{29}F_2N_4O_4$.

Example 7

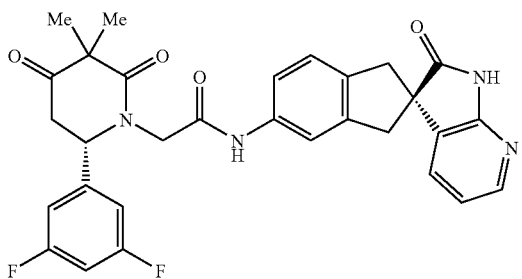

2-[(6S)-6-(3,5-Difluorophenyl)-3,3-dimethyl-2,4-dioxopiperidin-1-yl]-N-[(2R)-2'-oxo-1,1',2',3-tetrahydrospiro[indene-2,3'-pyrrolo[2,3-b]pyridin]-5-yl]acetamide A mixture of [(6S)-6-(3,5-difluorophenyl)-3,3-dimethyl-2,4-dioxopiperidin-1-yl]acetic acid (156 mg, 0.501 mmol, described in Intermediate 22), (R)-5-amino-1,3-dihydrospiro[indene-2,3'-pyrrolo[2,3-b]pyridin]-2'(1'H)-one (145 mg, 0.577 mmol, described in Intermediate 9), HOBT (95 mg, 0.620 mmol), and EDC (123 mg, 0.642 mmol) in DMF (2 mL) was stirred at ambient temperature for 16 h. The reaction mixture was partitioned between H₂O (60 mL) and EtOAc (100 mL). The organic layer was dried over Na₂SO₄, filtered, and concentrated in vacuo. The crude product was purified by silica gel chromatography, eluting with a gradient of CH₂Cl₂:CH₃OH—100:0 to 90:10, to give the title compound. MS: m/z=545 (M+1). HRMS: m/z=545.2025; calculated m/z=545.1995 for $C_{30}H_{27}F_2N_4O_4$.

Example 8

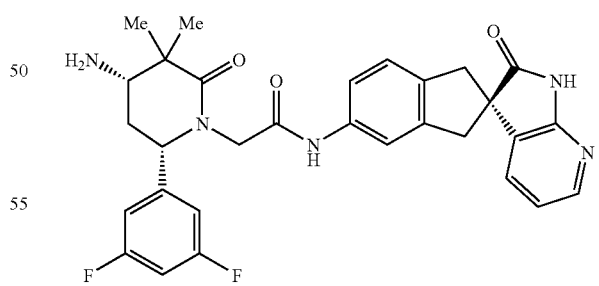

2-[(4S,6S)-4-Amino-6-(3,5-difluorophenyl)-3,3-dimethyl-2-oxopiperidin-1-yl]-N-[(2R)-2'-oxo-1,1',2',3-tetrahydrospiro[indene-2,3'-pyrrolo[2,3-b]pyridin]-5-yl]acetamide A mixture of 2-[(6S)-6-(3,5-difluorophenyl)-3,3-dimethyl-2,4-dioxopiperidin-1-yl]-N-[(2R)-2'-oxo-1,1',2',3-tetrahydrospiro[indene-2,3'-pyrrolo[2,3-b]pyridin]-5-yl]acetamide (380 mg, 0.698 mmol, described in Example 7) and NH$_4$OAc (571 mg, 7.41 mmol) in CH$_3$OH (2 mL) was stirred at ambient temperature for 20 min. NaCNBH$_3$ (498 mg, 7.92 mmol) was added and stirring was continued at ambient temperature for 12 h. The reaction mixture was diluted with H$_2$O (40 mL) and aqueous NaHCO$_3$ (70 mL) and extracted with EtOAc (2×100 mL). The combined organic layers were dried over Na$_2$SO$_4$, filtered, and concentrated in vacuo. The crude product was purified by silica gel chromatography, eluting with a gradient of CH$_2$Cl$_2$:CH$_3$OH—100:0 to 80:20, to give 2-[(4R,6S)-4-amino-6-(3,5-difluorophenyl)-3,3-dimethyl-2-oxopiperidin-1-yl]-N-[(2R)-2'-oxo-1,1',2',3-tetrahydrospiro[indene-2,3'-pyrrolo[2,3-b]pyridin]-5-yl]acetamide, which eluted first, and 2-[(4S,6S)-4-amino-6-(3,5-difluorophenyl)-3,3-dimethyl-2-oxopiperidin-1-yl]-N-[(2R)-2'-oxo-1,1',2',3-tetrahydrospiro[indene-2,3'-pyrrolo[2,3-b]pyridin]-5-yl]acetamide, which eluted second, the title compound. MS: m/z=546 (M+1). HRMS: m/z=546.2287; calculated m/z=546.2311 for C$_{30}$H$_{30}$F$_2$N$_5$O$_3$.

Example 9

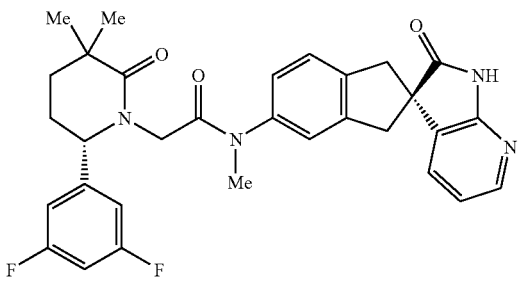

2-[(6S)-6-(3,5-Difluorophenyl)-3,3-dimethyl-2-oxopiperidin-1-yl]-N-methyl-N-[(2R)-2'-oxo-1,1',2',3-tetrahydrospiro[indene-2,3'-pyrrolo[2,3-b]pyridin]-5-yl]acetamide Step A. 2-[(6S)-6-(3,5-Difluorophenyl)-3,3-dimethyl-2-oxopiperidin-1-yl]-N-((2R)-2'-oxo-1'-{[2-(trimethylsilyl)ethoxy]methyl}-1,1',2',3-tetrahydrospiro[indene-2,3'-pyrrolo[2,3-b]pyridin]-5-yl] acetamide A mixture of [(6S)-6-(3,5-difluorophenyl)-3,3-dimethyl-2-oxopiperidin-1-yl]acetic acid (21 mg, 0.07 mmol, described in Intermediate 49), (R)-5-amino-1'-{[2-(trimethylsilyl)ethoxy]methyl}-1,3-dihydrospiro[indene-2,3'-pyrrolo[2,3-b]pyridin]-2'(1'H)-one (26 mg, 0.07 mmol, described in Intermediate 9, step B), HOBT (15 mg, 0.10 mmol), and EDC (19 mg, 0.10 mmol) in DMF (0.5 mL) was stirred at ambient temperature for 18 h. The reaction mixture was partitioned between saturated aqueous NaHCO$_3$ (10 mL) and EtOAc (20 mL). The organic layer was washed with brine, dried over Na$_2$SO$_4$, filtered, and concentrated in vacuo to give the title compound. MS: m/z=661 (M+1).

Step B. 2-[(6S)-6-(3,5-Difluorophenyl)-3,3-dimethyl-2-oxopiperidin-1-yl]-N-methyl-N-((2R)-2'-oxo-1'-{[2-(trimethylsilyl)ethoxy]methyl}-1,1',2',3-tetrahydrospiro[indene-2,3'-pyrrolo[2,3-b]pyridin]-5-yl]acetamide To a stirred solution of 2-[(6S)-6-(3,5-difluorophenyl)-3,3-dimethyl-2-oxopiperidin-1-yl]-N-((2R)-2'-oxo-1'-{[2-(trimethylsilyl)ethoxy]methyl}-1,1',2',3-tetrahydrospiro[indene-2,3'-pyrrolo[2,3-b]pyridin]-5-yl]acetamide from Step A (47 mg, 0.07 mmol) in DMF (1 mL) at 0° C. was added NaH (11 mg of a 60% dispersion in oil, 0.28 mmol). After 15 min, iodomethane (30 mg, 0.21 mmol) was added and the mixture was allowed to warm to ambient temperature and was stirred for 1 h. The reaction mixture was quenched with H$_2$O (5 mL) and the precipitate was isolated by filtration, washed with H$_2$O, and dried in vacuo to provide the title compound. MS: m/z=675 (M+1).

Step C. 2-[(6S)-6-(3,5-Difluorophenyl)-3,3-dimethyl-2-oxopiperidin-1-yl]-N-methyl-N-[(2R)-2'-oxo-1,1',2',3-tetrahydrospiro[indene-2,3'-pyrrolo[2,3-b]pyridin]-5-yl]acetamide To a solution of 2-[(6S)-6-(3,5-difluorophenyl)-3,3-dimethyl-2-oxopiperidin-1-yl]-N-methyl-N-((2R)-2'-oxo-1'-{[2-(trimethylsilyl)ethoxy]methyl}-1,1',2',3-tetrahydrospiro[indene-2,3'-pyrrolo[2,3-b]pyridin]-5-yl]acetamide from Step B (38 mg, 0.057 mmol) in CH$_2$Cl$_2$ (2 mL) was added TFA (1 mL) and the resulting mixture was stirred at ambient temperature for 1 h then concentrated to dryness in vacuo. The residue was dissolved in MeOH (1 mL) and the solution was adjusted to pH 10 by addition of 1 N aqueous NaOH and ethylenediamine (5.7 mg, 0.095 mmol). After 30 min, the mixture was partitioned between H$_2$O (30 mL) and EtOAc (40 mL). The organic layer was washed with brine, dried over Na$_2$SO$_4$, filtered, and concentrated in vacuo. The crude product was purified by silica gel chromatography, eluting with a gradient of CH$_2$Cl$_2$:CH$_3$OH—100:0 to 95:5, to give the title compound. MS: m/z=545 (M+1). HRMS: m/z=545.2388; calculated m/z=545.2359 for C$_{31}$H$_{31}$F$_2$N$_4$O$_3$.

Example 10

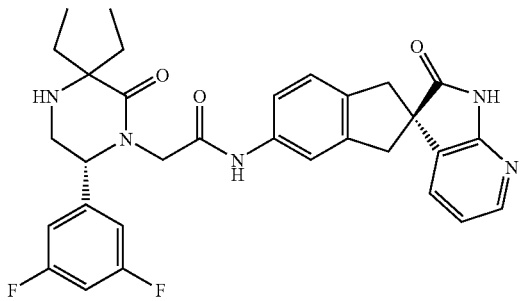

2-[(6R)-6-(3,5-Difluorophenyl)-3,3-diethyl-2-oxopiperazin-1-yl]-N-[(2R)-2'-oxo-1,1',2',3-tetrahydrospiro[indene-2,3'-pyrrolo[2,3-b]pyridin]-5-yl] acetamide A mixture of [(6R)-6-(3,5-difluorophenyl)-3,3-diethyl-2-oxopiperazin-1-yl]acetic acid hydrochloride (43 mg, 0.119 mmol, described in Intermediate 29), (R)-5-amino-1,3-dihydrospiro[indene-2,3'-pyrrolo[2,3-b]pyridin]-2'(1'H)-one (30 mg, 0.119 mmol, described in Intermediate 9), HOBT (27 mg, 0.179 mmol), and EDC (34 mg, 0.179 mmol) in DMF (0.5 mL) was stirred at ambient temperature for 18 h. The reaction mixture was purified directly by HPLC using a reversed phase C18 column and eluting with a gradient of $H_2O:CH_3CN:CF_3CO_2H$—90:10:0.1 to 5:95:0.1. The pure, product-containing fractions were combined, basified with saturated aqueous $NaHCO_3$, and extracted with EtOAc. The organic extracts were dried over $Na_2SO_4$, filtered, and concentrated in vacuo to give the title compound. MS: m/z=560 (M+1). HRMS: m/z=560.2469; calculated m/z=560.2468 for $C_{31}H_{32}F_2N_5O_3$.

Example 11

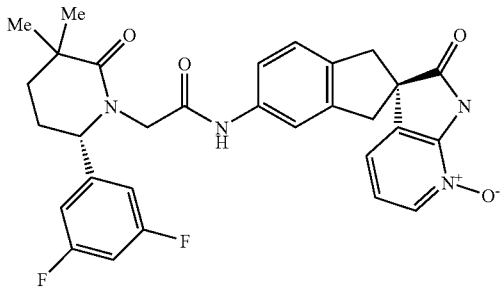

2-[(6S)-6-(3,5-Difluorophenyl)-3,3-dimethyl-2-oxopiperidin-1-yl]-N-[(2R)-7'-oxido-2'-oxo-1,1',2',3-tetrahydrospiro[indene-2,3'-pyrrolo[2,3-b]pyridin]-5-yl]acetamide A mixture of 2-[(6S)-6-(3,5-difluorophenyl)-3,3-dimethyl-2-oxopiperidin-1-yl]-N-[(2R)-2'-oxo-1,1',2',3-tetrahydrospiro[indene-2,3'-pyrrolo[2,3-b]pyridin]-5-yl]acetamide (20.0 mg, 0.038 mmol, described in Example 49) and Oxone® (70.0 mg, 0.113 mmol) in MeOH (0.5 mL) and water (0.5 mL) was stirred at ambient temperature for 3 h. The reaction mixture was purified directly by HPLC using a reversed phase C18 column and eluting with a gradient of $H_2O:CH_3CN:CF_3CO_2H$—90:10:0.1 to 5:95:0.1. Lyophilization provided the title compound. MS: m/z=547 (M+1). HRMS: m/z=547.2155; calculated m/z=547.2152 for $C_{30}H_{29}F_2N_4O_4$.

Example 12

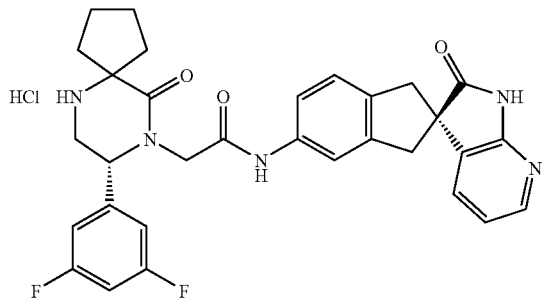

2-[(8R)-8-(3,5-Difluorophenyl)-10-oxo-6,9-diazaspiro[4.5]dec-9-yl]-N-[(2R)-2'-1,1',2',3-tetrahydrospiro[indene-2,3'-pyrrolo[2,3-b]pyridin]-5-yl] acetamide hydrochloride A mixture of lithium [(8R)-6-(tert-butoxycarbonyl)-8-(3,5-difluorophenyl)-10-oxo-6,9-diazaspiro[4.5]dec-9-yl]acetate (30 mg, 0.070 mmol, described in Intermediate 32), (R)-5-amino-1,3-dihydrospiro[indene-2,3'-pyrrolo[2,3-b]pyridin]-2'(1'H)-one (20 mg, 0.079 mmol, described in Intermediate 9), HOBT (14 mg, 0.092 mmol), and EDC (18 mg, 0.092 mmol) in DMF (0.5 mL) was stirred at ambient temperature for 18 h. The reaction mixture was diluted with EtOAc (5 mL) and washed successively with 10% citric acid (2 mL), $H_2O$ (2 mL), saturated aqueous $NaHCO_3$ (2 mL), and brine (2 mL). The organic layer was dried over $Na_2SO_4$, filtered, and concentrated in vacuo. The residue was purified by silica gel chromatography, eluting with $CH_2Cl_2$:EtOAc—100:0 to 0:100, to give the Boc-protected product. The Boc-protected product was dissolved in EtOAc (3 mL), the solution was cooled to 0° C., and HCl (g) was bubbled in for 1 min. The mixture was aged at 0° C. for 15 min and the title compound was isolated by filtration. MS: m/z=558 (M+1). HRMS: m/z=558.2300; calculated m/z=558.2311 for $C_{31}H_{30}F_2N_5O_3$.

Example 13

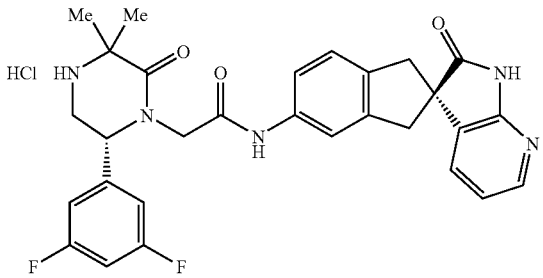

2-[(6R)-6-(3,5-Difluorophenyl)-3,3-dimethyl-2-oxopiperazin-1-yl]-N-[(2R)-2'-oxo-1,1',2',3-tetrahydrospiro[indene-2,3'-pyrrolo[2,3-b]pyridin]-5-yl] acetamide hydrochloride To a mixture of lithium [(6R)-4-(tert-butoxycarbonyl)-6-(3,5-difluorophenyl)-3,3-dimethyl-2-oxopiperazin-1-yl]acetate (1.12 g, 2.77 mmol, described in Intermediate 13), (R)-5-amino-1,3-dihydrospiro[indene-2,3'-pyrrolo[2,3-b]pyridin]-2'(1'H)-one (835 mg, 3.32 mmol, described in Intermediate 9), and HATU (1.26 g, 3.32 mmol) in DMF (12 mL) was added N-methylmorpholine (0.61 mL, 5.54 mmol) and the resulting mixture was stirred at ambient temperature for 90 min. The reaction mixture was diluted with EtOAc (500 mL) and washed successively with 10% citric acid (100 mL), $H_2O$ (100 mL), saturated aqueous $NaHCO_3$ (100 mL), and brine (100 mL). The organic layer was dried over $Na_2SO_4$, filtered, and concentrated in vacuo. The residue was purified by silica gel chromatography, eluting with $CH_2Cl_2$:MeOH—100:0 to 90:10, to give the Boc-protected product. The Boc-protected product was dissolved in EtOAc (75 mL), the solution was cooled to 0° C., and HCl (g) was bubbled in for 2 min. After 15 min, additional HCl (g) was bubbled in for 1 min. The mixture was aged at 0° C. for 30 min and concen-

Example 14

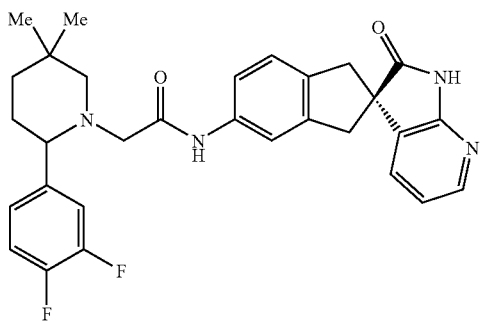

2-[2-(3,4-Difluorophenyl)-5,5-dimethylpiperidin-1-yl]-N-[(2R)-2'-oxo-1,1',2',3-tetrahydrospiro[indene-2,3'-pyrrolo[2,3-b]pyridin]-5-yl]acetamide Essentially following the procedures described for Example 6, but using [2-(3,4-difluorophenyl)-5,5-dimethylpiperidin-1-yl]acetic acid (described in Intermediate 23) in place of [(4S,6S)-6-(3,5-difluorophenyl)-4-hydroxy-3,3-dimethyl-2-oxopiperidin-1-yl]acetic acid, the title compound was obtained. MS: m/z=517 (M+1). HRMS: m/z=517.2432; calculated m/z=517.2410 for $C_{30}H_{31}F_2N_4O_2$.

Example 15

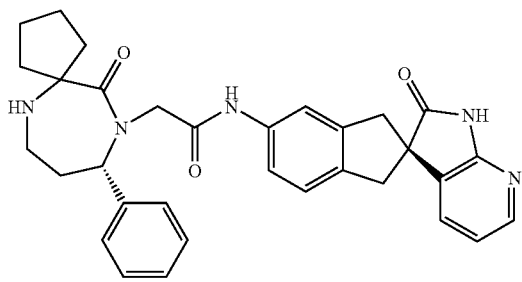

2-[(9S)-11-Oxo-9-phenyl-6,10-diazaspiro[4.6]undec-10-yl]-N-[(2R)-2'-oxo-1,1',2',3-tetrahydrospiro[indene-2,3'-pyrrolo[2,3-b]pyridin]-5-yl]acetamide

Step A. Methyl 1-({(3S)-3-[(2-oxo-2-{[(2R)-2'-oxo-1,1',2',3-tetrahydrospiro[indene-2,3'-b]pyridin]-5-yl]amino}ethyl)amino]-3-phenylpropyl}amino)cyclopentanecarboxylate To a cooled (0° C.) solution of (2R)-5-amino-1,3-dihydrospiro[indene-2,3'-pyrrolo[2,3-b]pyridin]-2'(1'H)-one (0.100 g, 0.398 mmol, Intermediate 9) and triethylamine (100. µL, 0.716 mmol) in THF (8 mL) was added bromoacetyl bromide (46.0 µL, 0.523 mmol). After allowing the reaction to warm to ambient temperature, triethylamine (0.230 mL, 1.67 mmol) and methyl 1-{[(3S)-3-amino-3-phenylpropyl]amino}cyclopentanecarboxylate bis-hydrochloride (0.139 g, 0.398 mmol, Intermediate 38) were added, prior to heating the reaction to 50° C. for 17 h. After cooling to ambient temperature, the reaction mixture was diluted with chloroform and saturated aqueous sodium bicarbonate. The aqueous layer was extracted twice with additional chloroform. The combined organics were dried over sodium sulfate, filtered and concentrated in vacuo to give an oil. This oil was purified by silica gel chromatography, eluting with a gradient of $CH_2Cl_2$:MeOH:$NH_4OH$—99:1:0.1 to 92:8:0.8, to give the title compound. MS: m/z=568 (M+1).

Step B. Potassium 1-({(3S)-3-[(2-oxo-2-{[(2R)-2'-oxo-1,1',2',3-tetrahydrospiro[indene-2,3'-pyrrolo[2,3-b]pyridin]-5-yl]amino}ethyl)amino]-3-phenylpropyl}amino)cyclopentanecarboxylate To a stirred solution of methyl 1-({(3S)-3-[(2-oxo-2-{[(2R)-2'-oxo-1,1',2',3-tetrahydrospiro[indene-2,3'-pyrrolo[2,3-b]pyridin]-5-yl]amino}ethyl)amino]-3-phenylpropyl}amino)cyclopentanecarboxylate from Step A (0.141 g, 0.249 mmol) in dry THF (5 mL) was added KOTMS (64.0 mg, 0.498 mmol) and the reaction mixture was heated to 40° C., at which point the desired product began to precipitate. Two additional quantities of KOTMS (~60 mg×2) were added over the next 2 h resulting in a complete consumption of starting material. The mixture was then allowed to cool to ambient temperature. The THF, which contained only traces of product, was then decanted away from the precipitated product. This solid was then washed with two additional quantities of anhydrous THF (5 mL×2), to provide the title compound. MS: m/z=554 (M+1).

Step C. 2-[(9S)-11-Oxo-9-phenyl-6,10-diazaspiro[4.6]undec-10-yl]-N-[(2R)-2'-oxo-1,1',2',3-tetrahydrospiro[indene-2,3'-pyrrolo[2,3-b]pyridin]-5-yl]acetamide To a stirred solution of potassium 1-({(3S)-3-[(2-oxo-2-{[(2R)-2'-oxo-1,1',2',3-tetrahydrospiro[indene-2,3'-pyrrolo[2,3-b]pyridin]-5-yl]amino}ethyl)amino]-3-phenylpropyl}amino)cyclopentanecarboxylate from Step B (0.147 g, 0.249 mmol) in DMF (8.3 mL) was added EDCI (0.0720 g, 0.374 mmol) and HOAt (0.0340 g, 0.249 mmol). The reaction mixture was then heated to 40° C. After 1 h, additional EDCI (0.0350 mg) was added and the reaction temperature was increased to 50° C., for 15 h. The reaction was allowed to cool to ambient temperature before being diluted with 5% aqueous sodium bicarbonate (100 mL) and chloroform (100 mL). The organics were washed successively with water (100 mL) and saturated brine (100 mL). The combined organics were dried over sodium sulfate, filtered and concentrated in vacuo to give an oil. This oil was purified by silica gel chromatography, eluting with a gradient of $CH_2Cl_2$:MeOH—99:1 to 91:9, to give the title compound. MS: m/z=536 (M+1). HRMS: m/z=536.2694; calculated m/z=536.2656 for $C_{32}H_{34}N_5O_3$.

Example 16

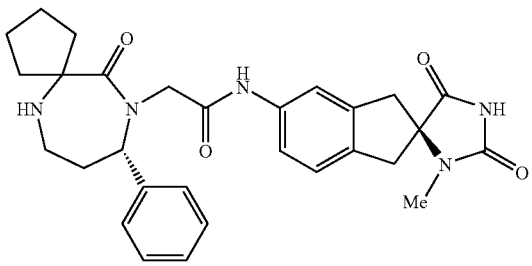

N-[(4S)-3-Methyl-2,5-dioxo-1',3'-dihydrospiro[imidazolidine-4,2'-inden]-5'-yl]-2-[(9S)-11-oxo-9-phenyl-6,10-diazaspiro[4.6]undec-10-yl]acetamide

Step A. (9S)-9-Phenyl-6,10-diazaspiro[4.6]undecan-11-one

Potassium trimethylsilanoate (1.21 g, 9.45 mmol) was added to a stirred suspension of methyl 1-{[(3S)-3-amino-3-phenylpropyl]amino}cyclopentanecarboxylate bis-hydrochloride (1.00 g, 2.86 mmol, Intermediate 38) in THF (5.0 mL) at ambient temperature. After 4 h, the reaction mixture was adjusted to pH=8 with aqueous 1 M HCl. To this mixture was added HOAt (0.195 g, 1.43 mmol), and EDCI (0.549 g, 2.87 mmol). After 1 h, the reaction was concentrated in vacuo. The residue was partitioned between $CH_2Cl_2$ and water. The aqueous phase was extracted several times with $CH_2Cl_2$. The combined organic extracts were washed with saturated brine, then dried over $MgSO_4$, filtered and concentrated in vacuo. The residue was purified by silica gel chromatography, eluting with $CH_2Cl_2$:MeOH:$NH_4OH$—89.9:10:0.1 to give the title compound. MS: m/z=245 (M+1).

Step B. Benzyl [(9S)-11-oxo-9-phenyl-6,10-diazaspiro[4.6]undec-10-yl]acetate To a suspension of sodium hydride (0.147 g, 6.14 mmol) in THF (10 mL) was added (9S)-9-phenyl-6,10-diazaspiro[4.6]undecan-11-one (0.300 g, 1.23 mmol) at ambient temperature. The reaction was warmed to 60° C. for 2 h, then cooled to ambient temperature. Benzyl bromoacetate (0.309 g, 1.35 mmol) was added dropwise to the reaction. After 1 h, the mixture was quenched with a saturated aqueous ammonium chloride solution. The mixture was concentrated in vacuo then partitioned between $H_2O$ and $CH_2Cl_2$. The aqueous phase was then extracted several times with $CH_2Cl_2$. The combined organic extracts were washed with saturated brine, then dried over $MgSO_4$, filtered and concentrated in vacuo The residue was purified by silica gel chromatography, eluting with a gradient of EtOAc:hexane—0:100 to 100:0, to yield the title compound. MS: m/z=393 (M+1).

Step C. [(9S)-11-Oxo-9-phenyl-6,10-diazaspiro[4.6]undec-10-yl]acetic acid

A solution of benzyl [(9S)-11-oxo-9-phenyl-6,10-diazaspiro[4.6]undec-10-yl]acetate from Step B (0.190 g, 0.484 mmol) in methanol (10 mL) was passed through an H-Cube™ continuous flow hydrogenation reactor at 50 Bar of $H_2$ using a Pd/C catalyst at ambient temperature. The solution was concentrated in vacuo to yield the title compound. MS: m/z=303 (M+1).

Step D. N-[(4S)-3-Methyl-2,5-dioxo-1',3'-dihydrospiro[imidazolidine-4,2'-inden]-5'-yl]-2-[(9S)-11-oxo-9-phenyl-6,10-diazaspiro[4.6]undec-10-yl]acetamide To a solution of [(9S)-11-oxo-9-phenyl-6,10-diazaspiro[4.6]undec-10-yl]acetic acid from Step C (0.0516 g, 0.171 mmol), (4S)-5'-amino-3-methyl-1',3'-dihydro-2H,5H-spiro[imidazolidine-4,2'-indene]-2,5-dione (0.0370 g, 0.162 mmol, prepared according to Bell, I. M., et al., PCT Int. Appl., WO 2004082605 A2), and HOAt (0.0120 g, 0.085 mmol) in THF (5 mL) was added 1-(3-dimethylaminopropyl)-3-ethylcarbodiimide hydrochloride (0.0460 g, 0.239 mmol), at ambient temperature. Upon completion of the reaction, as judged by LCMS, the reaction mixture was concentrated in vacuo. The residue was purified by silica gel chromatography, eluting with a gradient of EtOAc:hexane—5:95 to 100:0, followed by HPLC using a reversed phase C18 column and eluting with a gradient of $H_2O$:$CH_3CN$:$CF_3CO_2H$—95:5:0.1 to 65:35:0.1. The pure, product-containing fractions were concentrated in vacuo, neutralized with aqueous $NaHCO_3$, and extracted several times with $CH_2Cl_2$. The combined organic extracts were washed with saturated brine, dried over $MgSO_4$, filtered and concentrated in vacuo to yield the title compound. MS: m/z=516 (M+1). HRMS: m/z=516.2601; calculated m/z=516.2606 for $C_{29}H_{34}N_5O_4$.

Example 17

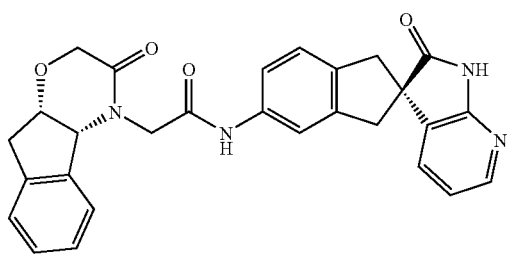

2-[(4aR,9aS)-3-Oxo-2,3,9,9a-tetrahydroindeno[2,1-b][1,4]oxazin-4(4aH)-yl]-N-[(2R)-2'-oxo-1,1',2',3-tetrahydrospiro[indene-2,3'-pyrrolo[2,3-b]pyridin]-5-yl]acetamide Essentially following the procedures described for Example 10, but using [(4aR,9aS)-3-oxo-2,3,9,9a-tetrahydroindeno[2,1-b][1,4]oxazin-4(4aH)-yl]acetic acid (described in Intermediate 39) in place of [(6R)-6-(3,5-difluorophenyl)-3,3-diethyl-2-oxopiperazin-1-yl]acetic acid hydrochloride, the title compound was obtained. MS: m/z=481 (M+1). HRMS: m/z=481.1865; calculated m/z=481.1871 for $C_{28}H_{25}N_4O_4$.

Example 18

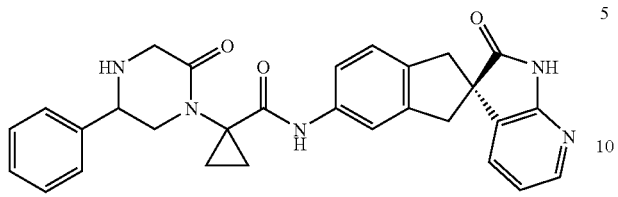

1-(2-Oxo-5-phenylpiperazin-1-yl)-N-[(2R)-2'-oxo-1, 1',2',3-tetrahydrospiro[indene-2,3'-pyrrolo[2,3-b]pyridin]-5-yl]cyclopropanecarboxamide Essentially following the procedures described for Example 10, but using 1-(2-oxo-5-phenylpiperazin-1-yl)cyclopropanecarboxylic acid (described in Intermediate 40) in place of [(6R)-6-(3,5-difluorophenyl)-3,3-diethyl-2-oxopiperazin-1-yl]acetic acid hydrochloride, the title compound was obtained. MS: m/z=494 (M+1). HRMS: m/z=494.2184; calculated m/z=494.2187 for $C_{29}H_{28}N_5O_3$.

Example 19

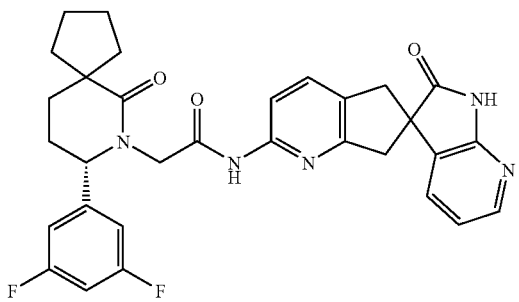

2-[(8S)-8-(3,5-Difluorophenyl)-6-oxo-7-azaspiro[4.5]dec-7-yl]-N-(2'-oxo-1',2',5,7-tetrahydrospiro[cyclopenta[b]pyridine-6,3'-pyrrolo[2,3-b]pyridin]-2-yl)acetamide A mixture of [(8S)-8-(3,5-difluorophenyl)-6-oxo-7-azaspiro[4.5]dec-7-yl]acetic acid (21 mg, 0.067 mmol, described in Intermediate 86), (±)-2-amino-5,7-dihydrospiro[cyclopenta[b]pyridine-6,3'-pyrrolo[2,3-b]pyridin]-2'(1'H)-one (17 mg, 0.067 mmol, described in Intermediate 43), PyClu (28 mg, 0.080 mmol), and N,N N-diisopropylethylamine (0.058 mL, 0.33 mmol) in THF (1 mL) was stirred at ambient temperature for 16 h. The reaction mixture was purified directly by HPLC using a reversed phase C18 column and eluting with a gradient of $H_2O:CH_3CN:CF_3CO_2H$—90:10:0.1 to 5:95:0.1. Lyophilization provided the title compound as the TFA salt. MS: m/z=558 (M+1). HRMS: m/z=558.2313; calculated m/z=558.2311 for $C_{31}H_{30}F_2N_5O_3$.

Example 20

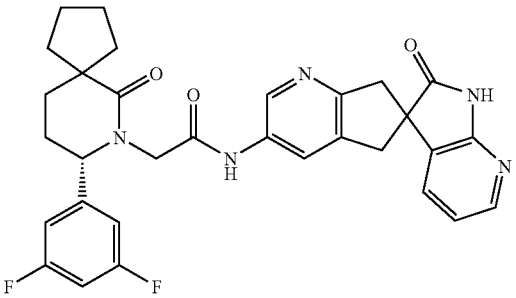

2-[(8S)-8-(3,5-Difluorophenyl)-6-oxo-7-azaspiro[4.5]dec-7-yl]-N-(2'-oxo-1',2',5,7-tetrahydrospiro[cyclopenta[b]pyridine-6,3'-pyrrolo[2,3-b]pyridin]-3-yl)acetamide, isomer A A mixture of [(8S)-8-(3,5-difluorophenyl)-6-oxo-7-azaspiro[4.5]dec-7-yl]acetic acid (50 mg, 0.16 mmol, described in Intermediate 86), 3-amino-5,7-dihydrospiro[cyclopenta[b]pyridine-6,3'-pyrrolo[2,3-b]pyridin]-2'(1'H)-one, isomer A (39 mg, 0.16 mmol, described in Intermediate 41), HATU (88 mg, 0.23 mmol), and N,N N-diisopropylethylamine (0.135 mL, 0.77 mmol) in DMF (1 mL) was stirred at ambient temperature for 16 h. NH$_4$OH (10 drops) was added and the reaction mixture was purified directly by HPLC using a reversed phase C18 column and eluting with a gradient of $H_2O:CH_3CN:CF_3CO_2H$—90:10:0.1 to 5:95:0.1. Lyophilization provided the title compound as the TFA salt. MS: m/z=558 (M+1). HRMS: m/z=558.2301; calculated m/z=558.2311 for $C_{31}H_{30}F_2N_5O_3$.

Example 21

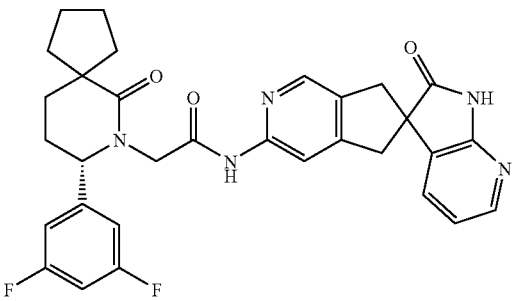

2-[(8S)-8-(3,5-Difluorophenyl)-6-oxo-7-azaspiro[4.5]dec-7-yl]-N-(2'-oxo-1',2',5,7-tetrahydrospiro[cyclopenta[c]pyridine-6,3'-pyrrolo[2,3-b]pyridin]-3-yl)acetamide, isomer A A mixture of [(8S)-8-(3,5-difluorophenyl)-6-oxo-7-azaspiro[4.5]dec-7-yl]acetic acid (128 mg, 0.395 mmol, described in Intermediate 86), 3-amino-5,7-dihydrospiro[cyclopenta[c]pyridine-6,3'-pyrrolo[2,3-b]pyridin]-2'(1'H)-one, isomer A (66.5 mg, 0.264 mmol, described in Intermediate 42), HATU (160 mg, 0.422 mmol), and N-methylmorpholine (0.087 mL, 0.791 mmol) in DMF (1 mL) was stirred at ambient temperature for 18 h. The reaction mixture was purified directly by HPLC using a reversed phase C18 column and eluting with a gradient of $H_2O:CH_3CN:CF_3CO_2H$—90:10:0.1 to 5:95:0.1. Lyophilization provided the title compound as the TFA salt. MS: m/z=558 (M+1). HRMS: m/z=558.2334; calculated m/z=558.2311 for $C_{31}H_{30}F_2N_5O_3$.

The examples appearing in the following tables were prepared by analogy to the above examples and intermediates, as described or prepared as a result of similar transformations with modifications known to those skilled in the art. The requisite starting materials and intermediates were described herein (vide supra), commercially available, known in the literature, or readily synthesized by one skilled in the art. In some cases, additional synthetic transformations that are well known to those skilled in the art were utilized after the key amide coupling to provide other products of interest. Straightforward protecting group strategies were applied in some routes. Some of the examples described in the tables were synthesized as mixtures of stereoisomers and subsequently purified to give individual isomers. In some cases, relevant experimental procedures are indicated in the tables.

TABLE 12

| Example | $R^6$ | $R^7$ | $R^{10}$ | $R^{11}$ | * | % | LCMS (M + 1) |
|---|---|---|---|---|---|---|---|
| 22 | H | H | H | phenyl | ± | S | 447 |
| 23 | Me | Me | H | 3,4-difluorophenyl | ± | S | 511 |
| 24 | Me | Me | H | 3,4-difluorophenyl | S | S | 511 |
| 25 | Me | Me | H | 3,4-difluorophenyl | R | S | 511 |
| 26 | Me | Me | H | 3,5-difluorophenyl | S | S | 511 |
| 27 | Me | Me | H | 3-methyl-2-thienyl | R | S | 495 |
| 28 | Me | Me | H | 3-methyl-2-thienyl | S | S | 495 |
| 29 | Me | Me | Me | 3,5-difluorophenyl | S | S | 525 |
| 30 | H | Ph | H | H | ± | S | 447 |
| 31 | H | Ph | H | H | ± | R | 447 |
| 32 | Et | Et | H | 3,5-difluorophenyl | S | S | 539 |

TABLE 13

| Example | $R^6$ | $R^7$ | $R^8$ | $R^9$ | $A^1$ | $R^{11}$ | * | LCMS (M + 1) |
|---|---|---|---|---|---|---|---|---|
| 33 | Me | Me | H | H | O | phenyl | | 477 |
| 34 | H | H | H | H | S | 3,5-difluorophenyl | | 501 |
| 35 | H | H | H | H | $SO_2$ | 3,5-difluorophenyl | | 533 |
| 36 | H | H | Me | Me | S | phenyl | | 493 |
| 37 | H | H | H | H | SO | 3,5-difluorophenyl | minor | 517 |
| 38 | H | H | H | H | SO | 3,5-difluorophenyl | major | 517 |
| 39 | Me | Me | H | H | SO | 3,5-difluorophenyl | minor | 545 |
| 40 | Et | Et | H | H | O | 3,5-difluorophenyl | | 541 |

TABLE 14

| Example | $R^6$ | $R^7$ | $R^{11}$ | * | % | LCMS (M + 1) |
|---|---|---|---|---|---|---|
| 41 | H | H | phenyl | ± | S | 447 |
| 42 | H | H | phenyl | ± | R | 447 |
| 43 | Cl | Cl | phenyl | ± | S | 515 |
| 44 | Cl | Cl | phenyl | ± | R | 515 |

TABLE 15

| Example | R⁶ | R⁷ | R | R¹¹ | * | % | LCMS (M + 1) | Relevant experimental procedures |
|---|---|---|---|---|---|---|---|---|
| 45 | Me | Me | OH | 3,4-difluorophenyl | S | S | 527 | Ex. 6 |

TABLE 16

| Example | R⁶ | R⁷ | R¹⁰ | R¹¹ | * | LCMS (M + 1) | Relevant experimental procedures |
|---|---|---|---|---|---|---|---|
| 46 | Me | Me | H | 3,4-difluorophenyl | ± | 531 | Ex. 10 |
| 47 | Me | Me | H | 3,4-difluorophenyl | R | 531 | Ex. 46 |
| 48 | Me | Me | H | 3,4-difluorophenyl | S | 531 | Ex. 46 |
| 49 | Me | Me | H | 3,5-difluorophenyl | S | 531 | Ex. 10 |
| 50 | Me | Me | H | 3-chloro-4-fluorophenyl | S | 547 | Ex. 10 |
| 51 | Me | Me | H | 3-fluoro-4-methylphenyl | S | 527 | Ex. 10 |
| 52 | Me | Me | H | 5-fluoro-2-methylphenyl | S | 527 | Ex. 10 |
| 53 | Me | Me | H | 4-fluoro-2-methylphenyl | S | 527 | Ex. 10 |
| 54 | Me | Me | H | 4-fluoro-3-methylphenyl | S | 527 | Ex. 10 |
| 55 | Me | Me | H | 5-fluoro-2-methoxyphenyl | S | 543 | Ex. 10 |
| 56 | Me | Me | H | 3-fluorophenyl | S | 513 | Ex. 10 |
| 57 | Me | Me | H | 4-chloro-3-fluorophenyl | S | 547 | Ex. 10 |
| 58 | Me | Me | H | 3-fluoro-2-methylphenyl | S | 527 | Ex. 10 |
| 59 | Me | Me | H | 2-methoxyphenyl | S | 525 | Ex. 10 |
| 60 | Me | Me | H | 4-methoxyphenyl | S | 525 | Ex. 10 |
| 61 | Me | Me | H | 3-methoxyphenyl | S | 525 | Ex. 10 |
| 62 | Me | Me | Me | 3,5-difluorophenyl | S | 545 | Ex. 10 |
| 63 | Me | Me | H | 3,5-dichlorophenyl | S | 563 | Ex. 10 |
| 64 | Me | Me | H | 3-thienyl | S | 501 | Ex. 10 |
| 65 | Me | Me | H | 2-thienyl | S | 501 | Ex. 10 |
| 66 | Me | Me | H | 5-chloro-2-thienyl | S | 535 | Ex. 10 |
| 67 | Me | Me | H | 1,3-benzodioxol-5-yl | S | 539 | Ex. 10 |
| 68 | Me | Me | H | 3-fluoro-4-methoxyphenyl | S | 543 | Ex. 10 |
| 69 | Me | Me | H | 3-chloro-5-fluorophenyl | S | 547 | Ex. 10 |
| 70 | Me | Me | H | phenyl | S | 495 | Ex. 10 |
| 71 | Me | Me | H | 2-trifluoromethylphenyl | S | 563 | Ex. 10 |
| 72 | Me | Me | H | 4-fluorophenyl | S | 513 | Ex. 10 |
| 73 | Me | Me | H | 2-(methylthio)phenyl | S | 541 | Ex. 10 |
| 74 | Me | Me | H | cyclohexyl | S | 501 | Ex. 10 |
| 75 | Me | Me | H | cyclopropyl | S | 459 | Ex. 10 |
| 76 | Me | Me | H | 3-chlorophenyl | S | 529 | Ex. 10 |
| 77 | Me | Me | H | 3,4-dichlorophenyl | S | 563 | Ex. 10 |
| 78 | Me | Me | H | 3-methylphenyl | S | 509 | Ex. 10 |
| 79 | Me | Me | H | 4-methylphenyl | S | 509 | Ex. 10 |
| 80 | Me | Me | H | 4-(methylthio)phenyl | S | 541 | Ex. 10 |
| 81 | Me | Me | H | 4-chloro-2-methylphenyl | S | 543 | Ex. 10 |
| 82 | Me | Me | H | benzyl | S | 509 | Ex. 10 |
| 83 | Me | Me | H | 4-chlorophenyl | S | 529 | Ex. 10 |
| 84 | Me | Me | H | isopropyl | | 461 | Ex. 10 |
| 85 | Me | Me | H | 4-trifluoromethylphenyl | | 563 | Ex. 10 |
| 86 | Me | Me | H | 2-(methylsulfonyl)phenyl | S | 573 | Ex. 73 |
| 87 | Me | Me | H | 4-(methylsulfonyl)phenyl | S | 573 | Ex. 80 |
| 88 | Me | Me | H | 3-trifluoromethylphenyl | ± | 563 | Ex. 10 |

TABLE 16-continued

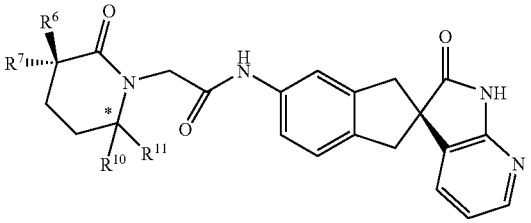

| Example | $R^6$ | $R^7$ | $R^{10}$ | $R^{11}$ | * | LCMS (M + 1) | Relevant experimental procedures |
|---|---|---|---|---|---|---|---|
| 89 | Me | Me | H | 6-bromo-2,3,4-trifluorophenyl | | 627 | Ex. 10 |
| 90 | Me | Me | H | 2-methylphenyl | S | 509 | Ex. 10 |
| 91 | Me | Me | H | 2,3,4-trifluorophenyl | | 549 | Ex. 10 |
| 92 | Me | Me | H | 3-chloro-2,4-difluorophenyl | | 565 | Ex. 10 |
| 93 | Me | H | H | 3,5-difluorophenyl | S | 517 | Ex. 10 |
| 94 | Et | Et | H | 3,5-difluorophenyl | S | 559 | Ex. 10 |

TABLE 17

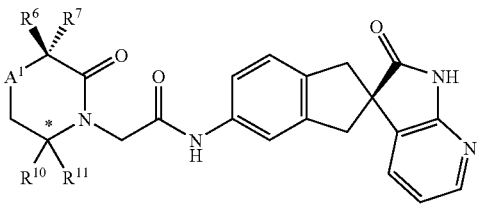

| Example | $R^6$ | $R^7$ | $A^1$ | $R^{10}$ | $R^{11}$ | * | LCMS (M + 1) | Relevant experimental procedures |
|---|---|---|---|---|---|---|---|---|
| 95 | Me | Me | O | H | phenyl | R | 497 | Ex. 6 |
| 96 | Me | H | O | H | phenyl | R | 483 | Ex. 6 |
| 97 | H | H | O | H | phenyl | R | 469 | Ex. 6 |
| 98 | Me | Me | O | H | 3,5-difluorophenyl | R | 533 | Ex. 6 |
| 99 | Et | Et | O | H | phenyl | R | 525 | Ex. 6 |
| 100 | H | Me | O | H | phenyl | R | 483 | Ex. 6 |
| 101 | Me | Me | O | H | 3,5-difluorophenyl | S | 533 | Ex. 6 |
| 102 | Me | Me | S | H | 3,5-difluorophenyl | R | 549 | Ex. 2 |
| 103 | H | Et | O | H | phenyl | R | 497 | Ex. 6 |
| 104 | Et | Et | O | H | 3,5-difluorophenyl | R | 561 | Ex. 6 |
| 105 | Me | Me | $CF_2$ | H | 3,5-difluorophenyl | S | 567 | Ex. 7 |
| 106 | Me | Me | 1,3-dioxolan-2-yl | H | 3,5-difluorophenyl | S | 589 | Ex. 7 |

TABLE 18

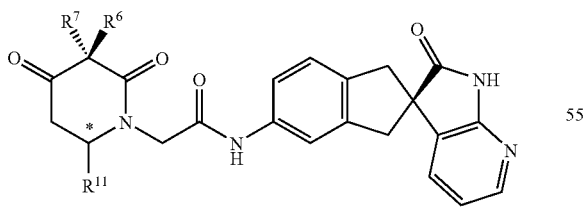

| Example | $R^6$ | $R^7$ | $R^{11}$ | * | LCMS (M + 1) | Relevant experimental procedures |
|---|---|---|---|---|---|---|
| 107 | Me | Me | 3,5-difluorophenyl | R | 545 | Ex. 7 |
| 108 | Et | Et | 3,5-difluorophenyl | S | 573 | Ex. 7 |
| 109 | Et | Et | 3,5-difluorophenyl | R | 573 | Ex. 7 |

TABLE 19

| Example | R[6] | R[7] | R | * | R[11] | % | LCMS (M + 1) | Relevant experimental procedures |
|---|---|---|---|---|---|---|---|---|
| 110 | Me | Me | H | R | 3,5-difluorophenyl | R | 547 | Ex. 6 |
| 111 | Me | Me | H | R | 3,5-difluorophenyl | S | 547 | Ex. 6 |
| 112 | Me | Me | H | S | 3,5-difluorophenyl | R | 547 | Ex. 6 |
| 113 | Me | Me | Me | S | 3,5-difluorophenyl | S | 561 | Ex. 6 |
| 114 | Et | Et | H | S | 3,5-difluorophenyl | S | 575 | Ex. 6 |
| 115 | Et | Et | H | R | 3,5-difluorophenyl | R | 575 | Ex. 6 |
| 116 | Et | Et | H | R | 3,5-difluorophenyl | S | 575 | Ex. 8 |
| 117 | Me | Me | Me | R | 3,5-difluorophenyl | R | 561 | Ex. 6 |

TABLE 20

| Example | R[6] | R[7] | R | * | R[11] | % | LCMS (M + 1) | Relevant experimental procedures |
|---|---|---|---|---|---|---|---|---|
| 118 | Me | Me | tert-butoxycarbonyl | ± | 3,5-difluorophenyl | S | 646 | Ex. 8 |
| 119 | Me | Me | H | ± | 3,5-difluorophenyl | S | 546 | Ex. 8 |
| 120 | Me | Me | Me | S | 3,5-difluorophenyl | S | 560 | Ex. 8 |
| 121 | Me | Me | H | S | 3,5-difluorophenyl | S | 546 | Ex. 8 |
| 122 | Me | Me | H | R | 3,5-difluorophenyl | S | 546 | Ex. 8 |
| 123 | Et | Et | H | S | 3,5-difluorophenyl | S | 574 | Ex. 8 |
| 124 | Et | Et | H | R | 3,5-difluorophenyl | S | 574 | Ex. 8 |

TABLE 21

| Example | R[6] | R[7] | R[1] | R[11] | * | LCMS (M + 1) | Relevant experimental procedures |
|---|---|---|---|---|---|---|---|
| 125 | Me | Me | tert-butoxycarbonyl | phenyl | ± | 596 | Ex. 12 |
| 126 | Me | Me | H | phenyl | ± | 496 | Ex. 12 |
| 127 | Me | Me | tert-butoxycarbonyl | phenyl | S | 596 | Ex. 12 |
| 128 | Me | Me | tert-butoxycarbonyl | phenyl | R | 596 | Ex. 12 |
| 129 | Me | Me | H | phenyl | R | 496 | Ex. 12 |
| 130 | Me | Me | tert-butoxycarbonyl | 3,5-difluorophenyl | S | 632 | Ex. 13 |
| 131 | Me | Me | tert-butoxycarbonyl | 3,5-difluorophenyl | R | 632 | Ex. 13 |
| 132 | Me | Me | Me | 3,5-difluorophenyl | R | 546 | Ex. 13 |
| 133 | Me | Me | acetyl | 3,5-difluorophenyl | R | 574 | Ex. 13 |

TABLE 21-continued

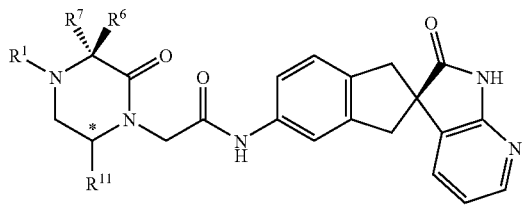

| Example | $R^6$ | $R^7$ | $R^1$ | $R^{11}$ | * | LCMS (M + 1) | Relevant experimental procedures |
|---|---|---|---|---|---|---|---|
| 134 | Me | Me | methylsulfonyl | 3,5-difluorophenyl | R | 610 | Ex. 13 |
| 135 | H | Me | Me | phenyl | ± | 496 | Ex. 10 |
| 136 | Me | H | Me | phenyl | ± | 496 | Ex. 10 |
| 137 | H | Bn | Me | phenyl | S | 572 | Ex. 10 |
| 138 | H | Bn | Me | phenyl | R | 572 | Ex. 10 |
| 139 | Et | Et | Me | phenyl | ± | 524 | Ex. 10 |
| 140 | Et | Et | H | phenyl | ± | 538 | Ex. 10 |
| 141 | Et | Et | H | 3,5-difluorophenyl | S | 560 | Ex. 10 |
| 142 | H | Ph | Me | phenyl | S | 558 | Ex. 10 |
| 143 | H | Ph | Me | phenyl | R | 558 | Ex. 10 |
| 144 | H | i-Pr | Me | phenyl | S | 524 | Ex. 10 |
| 145 | H | i-Pr | Me | phenyl | R | 524 | Ex. 10 |
| 146 | H | i-Bu | Me | phenyl | S | 538 | Ex. 10 |
| 147 | H | i-Bu | Me | phenyl | R | 538 | Ex. 10 |
| 148 | i-Bu | H | Me | phenyl | S | 538 | Ex. 10 |
| 149 | i-Bu | H | Me | phenyl | R | 538 | Ex. 10 |
| 150 | $CH_2CF_3$ | H | H | 3,5-difluorophenyl | R | 586 | Ex. 10 |
| 151 | $CH_2CF_3$ | H | H | 3,5-difluorophenyl | S | 586 | Ex. 10 |
| 152 | H | $CH_2CF_3$ | H | 3,5-difluorophenyl | R | 586 | Ex. 10 |
| 153 | Me | Me | $PhCH_2$ | 3,5-difluorophenyl | R | 622 | Ex. 13 |
| 154 | Me | Me | $CF_3CH_2$ | 3,5-difluorophenyl | R | 614 | Ex. 13 |
| 155 | Me | Me | H | 3,5-difluorophenyl | S | 532 | Ex. 13 |

TABLE 22

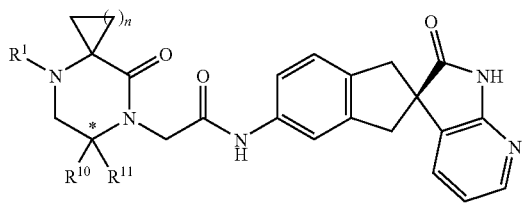

| Example | $R^1$ | n | $R^{10}$ | $R^{11}$ | * | LCMS (M + 1) | Relevant experimental procedures |
|---|---|---|---|---|---|---|---|
| 156 | H | 3 | H | phenyl | R | 522 | Ex. 10 |
| 157 | H | 3 | H | phenyl | S | 522 | Ex. 10 |
| 158 | Me | 1 | H | phenyl | ± | 508 | Ex. 10 |
| 159 | Me | 2 | H | phenyl | ± | 522 | Ex. 10 |
| 160 | tert-butoxycarbonyl | 3 | H | 3,5-difluorophenyl | R | 658 | Ex. 12 |
| 161 | H | 3 | H | 3,5-difluorophenyl | S | 558 | Ex. 12 |
| 162 | H | 4 | H | 3,5-difluorophenyl | R | 572 | Ex. 12 |
| 163 | H | 4 | H | 3,5-difluorophenyl | S | 572 | Ex. 12 |
| 164 | H | 3 | H | 2-bromo-3,5-difluorophenyl | R | 636 | Ex. 10 |
| 165 | H | 3 | H | 4-bromo-3,5-difluorophenyl | R | 636 | Ex. 10 |
| 166 | H | 4 | Me | 3,5-difluorophenyl | R | 586 | Ex. 13 |
| 167 | H | 4 | Me | 3,5-difluorophenyl | S | 586 | Ex. 13 |
| 168 | H | 5 | Me | 3,5-difluorophenyl | R | 600 | Ex. 13 |
| 169 | H | 5 | Me | 3,5-difluorophenyl | S | 600 | Ex. 13 |
| 170 | tert-butoxycarbonyl | 3 | Me | 3,5-difluorophenyl | R | 672 | Ex. 12 |
| 171 | tert-butoxycarbonyl | 3 | Me | 3,5-difluorophenyl | S | 672 | Ex. 12 |
| 172 | H | 3 | Me | 3,5-difluorophenyl | R | 572 | Ex. 12 |
| 173 | H | 3 | Me | 3,5-difluorophenyl | S | 572 | Ex. 12 |
| 174 | tert-butoxycarbonyl | 3 | H | 3,5-difluorophenyl | S | 658 | Ex. 12 |

TABLE 23

| Example | R⁶ | # | R¹¹ | * | LCMS (M + 1) | Relevant experimental procedures |
|---|---|---|---|---|---|---|
| 175 | H | S | phenyl | R | 508 | Ex. 10 |
| 176 | H | S | phenyl | S | 508 | Ex. 10 |
| 177 | H | R | phenyl | R | 508 | Ex. 10 |
| 178 | H | R | phenyl | S | 508 | Ex. 10 |
| 179 | Me | S | phenyl | R | 522 | Ex. 10 |
| 180 | Me | S | phenyl | S | 522 | Ex. 10 |
| 181 | Me | S | 3,5-difluorophenyl | R | 558 | Ex. 10 |
| 182 | Me | S | 3,5-difluorophenyl | S | 558 | Ex. 10 |

TABLE 24

| Example | R⁶ | R⁷ | R¹ | R² | # | R¹¹ | * | LCMS (M + 1) | Relevant experimental procedures |
|---|---|---|---|---|---|---|---|---|---|
| 183 | Me | Me | H | Me | R | phenyl | R | 510 | Ex. 10 |
| 184 | Me | Me | H | Me | S | phenyl | S | 510 | Ex. 10 |
| 185 | Me | Me | H | Me | R | 3,5-difluorophenyl | R | 546 | Ex. 10 |
| 186 | Me | Me | H | Me | S | 3,5-difluorophenyl | S | 546 | Ex. 10 |

TABLE 25

| Example | R¹ | X | R¹⁰ | R¹¹ | * | LCMS (M + 1) | Relevant experimental procedures |
|---|---|---|---|---|---|---|---|
| 187 | H | O | H | 3,5-difluorophenyl | R | 574 | Ex. 10 |
| 188 | H | O | H | 3,5-difluorophenyl | S | 574 | Ex. 10 |

TABLE 26

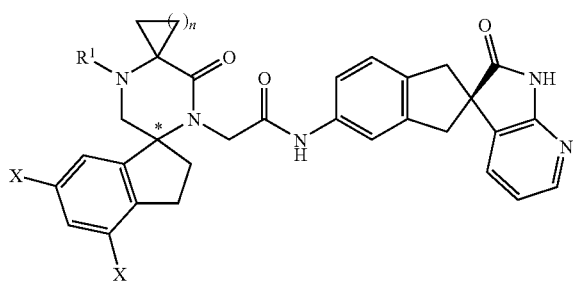

| Example | R¹ | n | X | * | LCMS (M + 1) | Relevant experimental procedures |
|---|---|---|---|---|---|---|
| 189 | tert-butoxycarbonyl | 3 | F | R | 684 | Ex. 13 |
| 190 | tert-butoxycarbonyl | 3 | F | S | 684 | Ex. 13 |
| 191 | H | 3 | F | R | 584 | Ex. 13 |
| 192 | H | 3 | F | S | 584 | Ex. 13 |
| 193 | tert-butoxycarbonyl | 3 | H | ± | 648 | Ex. 13 |
| 194 | H | 3 | H | ± | 548 | Ex. 13 |

TABLE 27

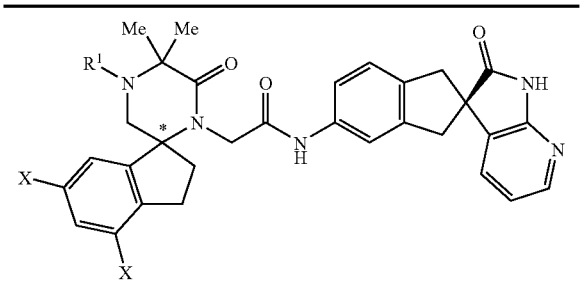

| Example | R¹ | n | X | * | LCMS (M + 1) | Relevant experimental procedures |
|---|---|---|---|---|---|---|
| 195 | tert-butoxycarbonyl | 3 | F | ± | 658 | Ex. 13 |

TABLE 27-continued

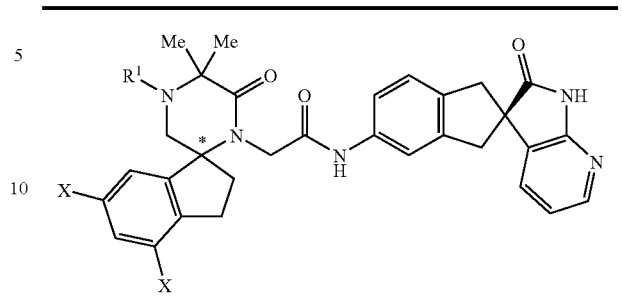

| Example | R¹ | n | X | * | LCMS (M + 1) | Relevant experimental procedures |
|---|---|---|---|---|---|---|
| 196 | H | 3 | F | ± | 558 | Ex. 13 |

TABLE 28

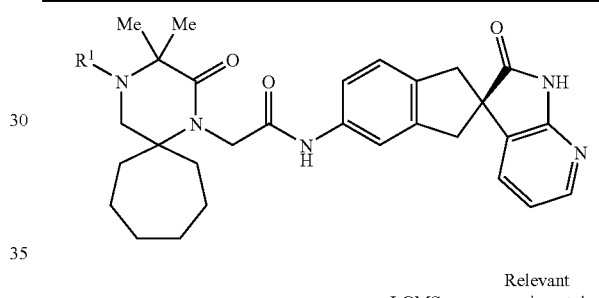

| Example | R¹ | LCMS (M + 1) | Relevant experimental procedures |
|---|---|---|---|
| 197 | tert-butoxycarbonyl | 602 | Ex. 13 |
| 198 | H | 502 | Ex. 13 |

TABLE 29

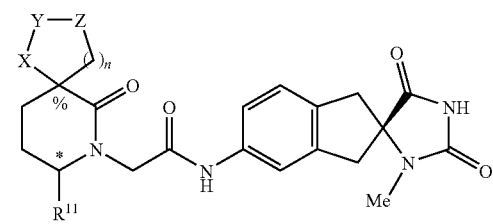

| Example | X | Y | Z | n | R¹¹ | * | % | LCMS (M + 1) | Relevant experimental procedures |
|---|---|---|---|---|---|---|---|---|---|
| 199 | CH₂ | CH₂ | CH₂ | 1 | 3,5-difluorophenyl | S |  | 537 | Ex. 10 |
| 200 | CH₂ | CH₂ | O | 2 | 3,5-difluorophenyl | S |  | 553 | Ex. 10 |
| 201 | CH₂ | CH₂ | CH₂ | 2 | 3,5-difluorophenyl | S |  | 551 | Ex. 10 |
| 202 | NEt | CH₂ | CH₂ | 1 | 3,5-difluorophenyl | S | R | 566 | Ex. 10 |
| 203 | NH | CH₂ | CH₂ | 1 | 3,5-difluorophenyl | S | R | 538 | Ex. 10 |

TABLE 30

| Example | X | Y | Z | n | R¹¹ | * | % | LCMS (M + 1) | Relevant experimental procedures |
|---|---|---|---|---|---|---|---|---|---|
| 204 | CH₂ | CH₂ | CH₂ | 1 | 3,5-difluorophenyl | S | | 557 | Ex. 10 |
| 205 | CH₂ | CH₂ | NH | 2 | 3,5-difluorophenyl | S | | 572 | Ex. 10 |
| 206 | CH₂ | CH₂ | NMe | 2 | 3,5-difluorophenyl | S | | 586 | Ex. 10 |
| 207 | CH₂ | bond | bond | 1 | phenyl | ± | | 493 | Ex. 10 |
| 208 | CH₂ | CH₂ | O | 2 | 3,5-difluorophenyl | S | | 573 | Ex. 10 |
| 209 | NH | CH₂ | CH₂ | 1 | 3,5-difluorophenyl | S | R | 558 | Ex. 10 |
| 210 | NCO₂CH₂Ph | CH₂ | CH₂ | 1 | 3,5-difluorophenyl | S | R | 692 | Ex. 10 |
| 211 | NMe | CH₂ | CH₂ | 1 | 3,5-difluorophenyl | S | R | 572 | Ex. 10 |
| 212 | NCH₂CF₃ | CH₂ | CH₂ | 1 | 3,5-difluorophenyl | S | R | 640 | Ex. 10 |
| 213 | CH₂ | CH₂ | NCO₂CH₂Ph | 2 | 3,5-difluorophenyl | S | | 706 | Ex. 10 |

TABLE 31

| Example | X | Y | Z | A¹ | n | R¹⁰ | R¹¹ | * | % | LCMS (M + 1) | Relevant experimental procedures |
|---|---|---|---|---|---|---|---|---|---|---|---|
| 214 | CH₂ | CH₂ | CH₂ | CH₂ | 1 | H | 3,5-difluorophenyl | S | ± | 558 | Ex. 20 |
| 215 | CH₂ | CH₂ | CH₂ | CH₂ | 1 | H | 3,5-difluorophenyl | S | Isomer B | 558 | Ex. 20 |
| 216 | CH₂ | CH₂ | CH₂ | NH | 1 | H | 3,5-difluorophenyl | R | Isomer A | 559 | Ex. 20 |
| 217 | CH₂ | CH₂ | O | CH₂ | 2 | H | 3,5-difluorophenyl | S | Isomer A | 574 | Ex. 20 |
| 218 | CH₂ | CH₂ | CH₂ | NH | 1 | Me | 3,5-difluorophenyl | R | Isomer A | 573 | Ex. 20 |

TABLE 32

| Example | X | Y | Z | A¹ | n | R¹⁰ | R¹¹ | * | % | LCMS (M + 1) | Relevant experimental procedures |
|---|---|---|---|---|---|---|---|---|---|---|---|
| 219 | CH₂ | CH₂ | CH₂ | CH₂ | 1 | H | 3,5-difluorophenyl | S | Isomer B | 558 | Ex. 21 |
| 220 | CH₂ | CH₂ | CH₂ | NH | 1 | H | 3,5-difluorophenyl | R | Isomer A | 559 | Ex. 21 |
| 221 | CH₂ | CH₂ | CH₂ | NH | 1 | H | 3,5-difluorophenyl | R | Isomer B | 559 | Ex. 21 |
| 222 | CH₂ | CH₂ | CH₂ | NH | 1 | H | 3,5-difluorophenyl | R | ± | 559 | Ex. 21 |
| 223 | CH₂ | CH₂ | O | CH₂ | 2 | H | 3,5-difluorophenyl | S | Isomer A | 574 | Ex. 21 |
| 224 | CH₂ | CH₂ | CH₂ | NH | 1 | Me | 3,5-difluorophenyl | R | Isomer A | 573 | Ex. 21 |

TABLE 33

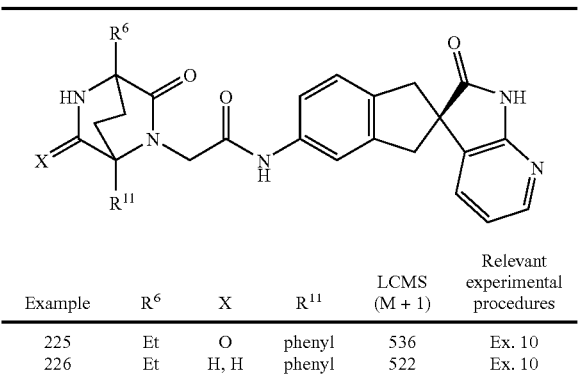

| Example | R[6] | X | R[11] | LCMS (M + 1) | Relevant experimental procedures |
|---------|------|------|--------|--------------|----------------------------------|
| 225 | Et | O | phenyl | 536 | Ex. 10 |
| 226 | Et | H, H | phenyl | 522 | Ex. 10 |

Although specific enantiomers and diastereomers appear in the above Examples and Intermediates, it is well understood by those skilled in the art that modifications to reaction conditions and reagents (for example, but not limited to: using the opposite chirality for starting materials; different catalysts; using the opposite chirality for reagents; choosing to use a different enantiomer or diastereomer subsequent to a chiral resolution) will provide alternative enantiomers and diastereomers, all of which are included in the spirit and scope of the invention. It is intended that all of the possible optical isomers and diastereomers in mixtures and as pure or partially purified compounds are included within the ambit of this invention. The present invention is meant to comprehend all such isomeric forms of these compounds.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

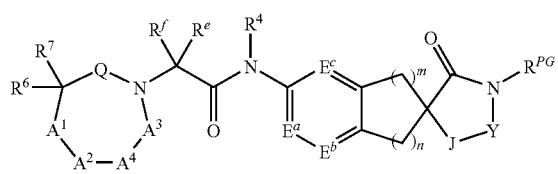

wherein:

$A^1$ is selected from:
(1) —O—,
(2) —S(O)$_v$—,
(3) —Si(OR$^a$)—C$_{1-4}$alkyl-, where alkyl is unsubstituted or substituted with 1-5 halo,
(4) —Si(C$_{1-4}$alkyl)$_2$, where each alkyl is independently unsubstituted or substituted with 1-5 halo,
(5) —CR$^6$R$^7$—,
(6) —N(R$^8$)—,
(7) —(C=O)—,
(8) —C(R$^8$)(R$^a$)—,
(9) —C(N(R$^b$)—SO$_2$R$^d$)(R$^a$)—,
(10) —C(N(R$^b$)(C=O)R$^a$)(R$^a$)—,
(11) —C(N(R$^b$)(C=O)OR$^a$)(R$^a$)—,
(12) —CR$^{10}$R$^{11}$—, and
(13) —N(R$^{11}$)—;

$A^2$ is selected from:
(1) —CR$^6$R$^7$—,
(2) —CR$^{10}$R$^{11}$—, and
(3) —(C=O)—;

$A^3$ selected from:
(1) —CR$^6$R$^7$—,
(2) —N(R$^8$)—,
(3) —CR$^{10}$R$^{11}$—, and
(4) —N(R$^{11}$)—;

$A^4$ is selected from:
(1) —CR$^6$R$^7$—,
(2) —(C=O)—,
(3) —N(R$^8$)—,
(4) —CR$^{10}$R$^{11}$—,
(5) —N(R$^{11}$)—, and
(6) a bond between $A^2$ and $A^3$;

$E^a$ is
—C(R$^{5a}$)=;

$E^b$ is
—C(R$^{5b}$)=;

$E^c$ is
—C(R$^{5c}$)=;

Q is
—(C=O)—;

$R^4$ is selected from:
(1) hydrogen,
(2) —C$_{1-6}$alkyl, which is unsubstituted or substituted with 1-5 substituents each independently selected from:
   (a) halo,
   (b) —C$_{3-6}$cycloalkyl,
   (c) —CF$_3$, and
   (d) —O—R$^a$,
(3) —C$_{3-6}$cycloalkyl,
(4) benzyl, and
(5) phenyl;

$R^{5a}$, $R^{5b}$ and $R^{5c}$ are each independently selected from:
(1) hydrogen,
(2) —C$_{1-6}$alkyl, which is unsubstituted or substituted with 1-6 halo,
(3) halo,
(4) —OR$^a$, and
(5) —CN;

$R^6$ and $R^7$ are each independently selected from:
(1) hydrogen,
(2) —C$_{1-6}$alkyl, which is unsubstituted or substituted with 1-5 substituents each independently selected from:
   (a) halo,
   (b) —OR$^a$,
   (c) —C$_{3-6}$cycloalkyl, (d) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl, indolyl, indazolyl, benzimidazolyl and oxazolyl, which phenyl or heterocycle is unsubstituted or substituted with 1-5 substituents each independently selected from:
- (i) halo,
- (ii) —$C_{1-6}$alkyl, which is unsubstituted or substituted with 1-5 halo,
- (iii) —$OR^a$,
- (iv) —$NR^bR^c$,
- (v) —CN, and
- (vi) oxo;

(e) —$CO_2R^a$,
(f) —$C(=O)NR^bR^c$,
(g) —$S(O)_vR^d$,
(h) —CN,
(i) —$NR^bR^c$,
(j) —$N(R^b)C(=O)R^a$,
(k) —$N(R^b)SO_2R^d$,
(l) —$CF_3$,
(m) —$O$—$CO_2R^d$,
(n) —O—(C=O)—$NR^bR^c$,
(o) —$NR^b$—(C=O)—$NR^bR^c$, and
(p) —$C(=O)R^a$, (3) —$C_{3-8}$cycloalkyl, which is unsubstituted or substituted with 1-5 substituents each independently selected from:
- (a) halo,
- (b) —CN,
- (c) —$C_{1-4}$alkyl, which is unsubstituted or substituted with 1-3 halo, and
- (d) —$OR^a$, (4) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
- (a) halo,
- (b) —$OR^a$,
- (c) —$C_{3-6}$cycloalkyl,
- (d) phenyl, which is unsubstituted or substituted with 1-5 substituents each independently selected from:
  - (i) halo,
  - (ii) —$C_{1-6}$alkyl, which is unsubstituted or substituted with 1-6 halo, and
  - (iii) —$OR^a$,
- (e) —$CO_2R^a$,
- (f) —$C(=O)NR^bR^c$,
- (g) —$S(O)_vR^d$,
- (h) —CN,
- (i) —$NR^bR^c$,
- (j) —$N(R^b)C(=O)R^a$,
- (k) —$N(R^b)SO_2R^d$,
- (l) —$O$—$CO_2R^d$,
- (m) —O—(C=O)—$NR^bR^c$,
- (n) —$NR^b$—(C=O)—$NR^bR^c$,
- (o) —$C(=O)R^a$,
- (p) —$C_{1-6}$alkyl, which is unsubstituted or substituted with 1-6 halo, and
- (q) oxo;

(5) halo,
(6) —$OR^a$,
(7) —CN,
(8) —$CO_2R^a$,
(9) —$N(R^b)C(=O)R^a$,
(10) —$NR^bR^c$,
(11) —$C(=O)NR^bR^c$, and
(12) —$O(C=O)R^a$;

or $R^6$ and $R^7$ and the carbon atom or atoms to which they are attached join to form a ring selected from cyclopropyl, cyclobutyl, cyclopentyl, cyclohexyl, cycloheptyl, cyclooctyl, cyclononyl, cyclobutenyl, cyclopentenyl, cyclohexenyl, cycloheptenyl, cyclooctenyl, dioxolanyl, dioxanyl, aziridinyl, azetidinyl, pyrrolidinyl, piperidinyl, piperazinyl, morpholinyl, tetrahydrofuranyl, tetrahydropyranyl, tetrahydrothiopyranyl, oxetanyl, thietanyl and tetrahydrothienyl, wherein the sulfur is optionally oxidized to the sulfone or sulfoxide, which ring is unsubstituted or substituted with 1-5 substituents each independently selected from:

(a) —$C_{1-6}$alkyl, which is unsubstituted or substituted with 1-3 substituents each independently selected from:
- (i) halo,
- (ii) —$OR^a$,
- (iii) —$C_{3-6}$cycloalkyl,
- (iv) —$CO_2R^a$,
- (v) —$NR^bR^c$,
- (vi) —$S(O)_vR^d$,
- (vii) —$C(=O)NR^bR^c$, and
- (viii) phenyl, (b) —$C_{3-6}$cycloalkyl, wherein the $C_{3-6}$cycloalkyl group is optionally fused to the ring, and which $C_{3-6}$cycloalkyl group is unsubstituted or substituted with 1-3 substituents each independently selected from:
- (i) halo,
- (ii) —$OR^a$,
- (iii) —$C_{3-6}$cycloalkyl,
- (iv) —$CO_2R^a$,
- (v) —$NR^bR^c$,
- (vi) —$S(O)_vR^d$,
- (vii) —$C(=O)NR^bR^c$, and
- (viii) phenyl, (c) phenyl or heterocycle, wherein heterocycle is selected from: pyridyl, pyrimidinyl, pyrazinyl, pyridazinyl, piperidinyl, piperazinyl, pyrrolidinyl, thienyl, morpholinyl, imidazolyl, furanyl, tetrahydrofuranyl, thiazolyl and oxazolyl, wherein the phenyl or heterocycle is optionally fused to the ring, and which phenyl or heterocycle is unsubstituted or substituted with 1-5 substituents each independently selected from:
- (i) halo,
- (ii) —$C_{1-6}$alkyl, which is unsubstituted or substituted with 1-5 halo,
- (iii) —$OR^a$,
- (iv) —$CO_2R^a$,
- (v) —$O(C=O)R^a$,
- (vi) —CN,
- (vii) —$NR^bR^c$,
- (viii) oxo,
- (ix) —$C(=O)NR^bR^c$,
- (x) —$N(R^b)C(=O)R^a$,
- (xi) —$N(R^b)CO_2R^a$,
- (xii) —$O(C=O)NR^bR^c$, and
- (xiii) —$S(O)_vR^d$, (d) —$OR^a$,
(e) —$CO_2R^a$, (f) —C(=O)NR$^b$R$^c$,
(g) —S(O)$_v$R$^d$,
(h) —CN,
(i) halo,
(j) —NR$^b$R$^c$,
(k) —N(R$^b$)C(=O)R$^a$,
(l) —N(R$^b$)SO$_2$R$^d$,
(m) —O—CO$_2$R$^d$,
(n) —O—(C=O)—NR$^b$R$^c$,
(o) —NR$^b$—(C=O)—NR$^b$R$^c$,
(p) —C(=O)R$^a$, and
(q) oxo;

R$^8$ is independently selected from:
(1) hydrogen,
(2) —C(=O)R$^a$,
(3) —CO$_2$R$^a$,
(4) —S(=O)R$^d$,
(5) —SO$_2$R$^d$,
(6) —C(=O)NR$^b$R$^c$,
(7) —C$_{1-6}$alkyl, which is unsubstituted or substituted with 1-5 substituents each independently selected from:
 (a) halo,
 (b) —OR$^a$,
 (c) —C$_{3-6}$cycloalkyl,
 (d) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
  (i) halo,
  (ii) —C$_{1-6}$alkyl, which is unsubstituted or substituted with 1-5 halo, and
  (iii) —OR$^a$,
  (iv) —NR$^b$R$^c$,
  (v) —C(=O)R$^a$,
  (vi) —CO$_2$R$^a$, and
  (vii) oxo,
 (e) —CO$_2$R$^a$,
 (f) —C(=O)NR$^b$R$^c$,
 (g) —S(O)$_v$R$^d$,
 (h) —CN,
 (i) —NR$^b$R$^c$,
 (j) —N(R$^b$)C(=O)R$^a$,
 (k) —N(R$^b$)SO$_2$R$^d$,
 (l) —CF$_3$,
 (m) —O—CO$_2$R$^d$,
 (n) —O—(C=O)—NR$^b$R$^c$,
 (o) —NR$^b$—(C=O)—NR$^b$R$^c$, and
 (p) —C(=O)R$^a$,
(8) —C$_{3-6}$cycloalkyl, which is unsubstituted or substituted with 1-6 substituents each independently selected from:
 (a) halo,
 (b) —CN,
 (c) —OR$^a$, and
 (d) C$_{1-6}$alkyl, which is unsubstituted or substituted with 1-6 halo;
or R$^7$ and R$^8$ and the atoms to which they are attached join to form a 4-, 5-, 6- or 7-membered alkyl- or heteroalkyl-ring optionally containing an additional heteroatom selected from N, O, and S, wherein the sulfur is optionally oxidized to the sulfone or sulfoxide, which ring is unsubstituted or substituted with 1-4 substituents each independently selected from:
 (a) halo,
 (b) phenyl, which is unsubstituted or substituted with 1-3 substituents each independently selected from: halo, OR$^a$, CN, and —C(=O)OR$^a$,
 (c) —OR$^a$, and
 (d) —C$_{1-6}$alkyl, which is unsubstituted or substituted with 1-6 halo;

R$^{10}$ is independently selected from:
(1) hydrogen,
(2) —C$_{1-6}$alkyl, which is unsubstituted or substituted with 1-5 substituents each independently selected from:
 (a) halo,
 (b) —OR$^a$,
 (c) —CN,
 (d) phenyl, and
 (e) —C$_{3-6}$cycloalkyl, which is unsubstituted or substituted with 1-6 halo,
(3) —C$_{3-6}$cycloalkyl, which is unsubstituted or substituted with 1-6 halo;

R$^{11}$ independently selected from the group consisting of:
phenyl, naphthyl, tetrahydronaphthyl, indanyl, biphenyl, phenanthryl, anthryl, azepinyl, azepanyl, azetidinyl, benzimidazolyl, benzisoxazolyl, benzofuranyl, benzofurazanyl, benzopyranyl, benzothiopyranyl, benzofuryl, 1,3-benzodioxolyl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiamorpholinyl sulfone, thiazolyl, thiazolinyl, thienofuryl, thienothienyl, thienyl, triazolyl, isoxazolyl, tetrahydrothienyl, tetrahydropyranyl, oxetanyl, tetrahydrothiopyranyl, and thietanyl, where R$^{11}$ is unsubstituted or substituted with 1-5 substituents each independently selected from R$^{12}$, R$^{13}$, R$^{14}$, R$^{15a}$ and R$^{15b}$;

R$^{12}$, R$^{13}$, R$^{14}$, R$^{15a}$ and R$^{15b}$ are each independently selected from:
(1) —C$_{1-6}$alkyl, which is unsubstituted or substituted with 1-5 substituents each independently selected from:
 (a) halo,
 (b) —OR$^a$,
 (c) —C$_{3-6}$cycloalkyl,
 (d) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
  (i) halo, (ii) —$C_{1-6}$alkyl, which is unsubstituted or substituted with 1-5 halo, and
(iii) —$OR^a$,
(e) —$CO_2R^a$,
(f) —$C(=O)NR^bR^c$,
(g) —$S(O)_vR^d$,
(h) —CN,
(i) —$NR^bR^c$,
(j) —$N(R^b)C(=O)R^a$,
(k) —$N(R^b)SO_2R^d$,
(l) —$CF_3$,
(m) —O—$CO_2R^d$,
(n) —O—(C=O)—$NR^bR^c$,
(o) —$NR^b$—(C=O)—$NR^bR^c$, and
(p) —$C(=O)R^a$,
(2) —$C_{1-6}$cycloalkyl, which is unsubstituted or substituted with 1-5 substituents each independently selected from:
(a) halo,
(b) —CN,
(c) —$C_{1-6}$alkyl, which is unsubstituted or substituted with 1-5 halo,
(d) —$OR^a$, and
(e) phenyl, which is unsubstituted or substituted with 1-5 substituents where the substituents are each independently selected from:
(i) —$OR^a$,
(ii) halo,
(iii) —CN, and
(iv) —$C_{1-6}$alkyl, which is unsubstituted or substituted with 1-5 halo,
(3) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
(a) halo,
(b) —$OR^a$,
(c) —$C_{3-6}$cycloalkyl,
(d) phenyl, which is unsubstituted or substituted with 1-5 substituents each independently selected from:
(i) halo,
(ii) —$C_{1-6}$alkyl, which is unsubstituted or substituted with 1-6 halo, and
(iii) —$OR^a$,
(e) —$CO_2R^a$,
(f) —$C(=O)NR^bR^c$,
(g) —$S(O)_vR^d$,
(h) —CN,
(i) —$NR^bR^c$,
(j) —$N(R^b)C(=O)R^a$,
(k) —$N(R^b)SO_2R^d$,
(l) —O—$CO_2R^d$,
(m) —O—(C=O)—$NR^bR^c$,
(n) —$NR^b$—(C=O)—$NR^bR^c$,
(o) —$C(=O)R^a$, and
(p) —$C_{1-6}$alkyl, which is unsubstituted or substituted with 1-6 halo,
(4) halo,
(5) oxo,
(6) —$OR^a$,
(7) —CN,
(8) —$CO_2R^a$,
(9) —$C(=O)R^a$,
(10) —$NR^bR^c$,
(11) —$S(O)_vR^d$,
(12) —$C(=O)NR^bR^c$,
(13) —O—$CO_2R^d$,
(14) —$N(R^b)CO_2R^d$,
(15) —O—(C=O)—$NR^bR^c$,
(16) —$NR^b$—(C=O)—$NR^bR^c$,
(17) —$SO_2NR^bR^c$,
(18) —$N(R^b)SO_2R^d$,
or $R^{15a}$ and $R^{15b}$ and the atom(s) to which they are attached join to form a ring selected from cyclopropyl, cyclobutyl, cyclopentyl, cyclohexyl, cycloheptyl, aziridinyl, azetidinyl, pyrrolidinyl, piperidinyl, piperazinyl, morpholinyl, thietanyl and tetrahydrothienyl, wherein the sulfur is optionally oxidized to the sulfone or sulfoxide, which ring is unsubstituted or substituted with 1-5 substituents each independently selected from:
(a) —$C_{1-6}$alkyl, which is unsubstituted or substituted with 1-3 substituents each independently selected from:
(i) halo,
(ii) —$OR^a$,
(iii) —$C_{3-6}$cycloalkyl,
(iv) —$CO_2R^a$,
(v) —$NR^bR^c$,
(vi) —$S(O)_vR^d$,
(vii) —$C(=O)NR^bR^c$, and
(viii) phenyl,
(b) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
(i) halo,
(ii) —$C_{1-6}$alkyl, which is unsubstituted or substituted with 1-5 halo, and
(iii) —$OR^a$,
(c) —$OR^a$,
(d) halo,
(e) —$CO_2R^a$,
(f) —$C(=O)NR^bR^c$,
(g) —$S(O)_vR^d$,
(h) —CN,
(i) —$NR^bR^c$,
(j) —$N(R^b)C(=O)R^a$,
(k) —$N(R^b)SO_2R^d$,
(l) —O—$CO_2R^d$,
(m) —O—(C=O)—$NR^bR^c$,
(n) —$NR^b$—(C=O)—$NR^bR^c$, and
(o) —$C(=O)R^a$;
$R^{PG}$ is independently selected from:
(1) hydrogen,
(2) —$C_{1-6}$alkyl which is unsubstituted or substituted with 1-5 halo,
(3) —$CH_2OR^a$,
(4) —$CH_2$—O—$CH_2CH_2Si(CH_3)_3$,
(5) —$CH_2OP(=O)(OR^c)_2$,
(6) —$(CH_2)_k$-phenyl, which is unsubstituted or substituted with 1-3 substituents each independently selected from:
(a) halo,
(b) —$OR^a$,
(c) —CN, and
(d) —$C_{1-6}$alkyl, which is unsubstituted or substituted with 1-6 halo;

J is independently selected from:
- (1) =C(R$^{16a}$)—,
- (2) —CR$^{17}$R$^{18}$—,
- (3) —C(=O)—, and
- (4) —N(R$^b$)—;

Y is independently selected from:
- (1) =C(R$^{16b}$)—,
- (2) —CR$^{17}$R$^{18}$—,
- (3) —C(=O)—,
- (4) =N—, and
- (5) —N(R$^{16b}$)—;

R$^{17}$ and R$^{18}$ are each independently selected from:
- (1) hydrogen,
- (2) halo,
- (3) —OR$^a$,
- (4) —C$_{1-6}$alkyl, which is unsubstituted or substituted with 1-4 substituents each independently selected from:
  - (a) halo,
  - (b) —OR$^a$,
  - (c) —CN,
  - (d) phenyl or heterocycle, wherein said heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from:
    - (i) —OR$^a$,
    - (ii) halo,
    - (iii) —CN,
    - (iv) —C$_{1-6}$alkyl which is unsubstituted or substituted with 1-6 halo,
- (5) phenyl or heterocycle wherein heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from:
  - (a) halo,
  - (b) —CN,
  - (c) —OR$^a$,
  - (d) nitro,
  - (e) —C$_{1-6}$alkyl which is unsubstituted or substituted with 1-6 halo;
- or R$^{17}$ and R$^{18}$ and the atom to which they are attached join to form a 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
  - (a) halo,
  - (b) —OR$^a$,
  - (c) —C$_{1-6}$alkyl, which is unsubstituted or substituted with 1-6 halo, and
  - (d) phenyl;

R$^{16a}$ and R$^{16b}$ are each independently selected from:
- (1) hydrogen,
- (2) —C$_{1-4}$alkyl, which is unsubstituted or substituted with 1-5 substituents each independently selected from:
  - (a) halo,
  - (b) —OR$^a$,
  - (c) —C$_{3-6}$cycloalkyl,
  - (d) phenyl or heterocycle, wherein said heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl, isoxazolyl and morpholinyl, which phenyl or heterocycle is unsubstituted or substituted with 1-3 substituents each independently selected from:
    - (i) halo,
    - (ii) —OR$^a$,
    - (iii) —CN, and
    - (iv) C$_{1-6}$alkyl, which is unsubstituted or substituted with 1-6 halo,
- (3) phenyl or heterocycle, wherein heterocycle is selected from: imidazolyl, oxazolyl, pyridyl, pyrimidinyl, pyrazinyl, pyridazinyl, tetrahydrofuryl, piperidinyl, piperazinyl, pyrrolidinyl, azetidinyl, thiazolyl, thienyl, triazolyl, isoxazolyl and morpholinyl, which phenyl or heterocycle is unsubstituted or substituted with 1-3 substituents each independently selected from:
  - (a) halo,
  - (b) —OR$^a$,
  - (c) —C$_{3-6}$cycloalkyl,
  - (d) —C$_{1-4}$alkyl which is unsubstituted or substituted with 1-6 halo, and
  - (e) phenyl, which is unsubstituted or substituted with 1-5 substituents each independently selected from:
    - (i) halo,
    - (ii) —C$_{1-6}$alkyl, which is unsubstituted or substituted with 1-6 halo, and
    - (iii) —OR$^a$,
- (4) halo,
- (5) —OR$^a$,
- (6) —CN,
- (7) —CO$_2$R$^a$,
- (8) —NR$^b$R$^c$, and
- (9) —C(=O)NR$^b$R$^c$;
- or R$^{16a}$ and R$^{16b}$ and the atom(s) to which they are attached join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
  - (a) —C$_{1-6}$alkyl, which is unsubstituted or substituted with 1-3 substituents each independently selected from:
    - (i) halo,
    - (ii) —OR$^a$,
    - (iii) —C$_{3-6}$cycloalkyl,
    - (iv) phenyl or heterocycle, wherein heterocycle is selected from pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from:
      - (I) —OR$^a$,
      - (II) halo,
      - (III) —CN, and
      - (IV) —C$_{1-6}$alkyl which is unsubstituted or substituted with 1-6 halo,
    - (v) —CO$_2$R$^a$,
    - (vi) —NR$^b$R$^c$,
    - (vii) —S(O)$_v$R$^d$, (viii) —C(=O)NR$^b$R$^c$,
(ix) —N(R$^b$)CO$_2$R$^a$, and
(x) —N(R$^b$)SO$_2$R$^d$,
(b) phenyl or heterocycle, wherein said heterocycle is selected from pyridyl, pyrimidinyl, pyrazinyl, pyridazinyl, piperidinyl, azetidinyl, piperazinyl, pyrrolidinyl, thienyl and morpholinyl, which phenyl or heterocycle is unsubstituted or substituted with 1-5 substituents each independently selected from:
  (i) halo,
  (ii) —OR$^a$,
  (iii) —CN, and
  (iv) —C$_{1-6}$alkyl which is unsubstituted or substituted with 1-6 halo,
(c) halo,
(d) —S(O)$_v$R$^d$,
(e) —OR$^a$,
(f) —CN,
(g) —C(=O)R$^a$,
(h) —NR$^b$R$^c$,
(i) —C(=O)NR$^b$R$^c$,
(j) —CO$_2$R$^a$,
(k) —(NR$^b$)CO$_2$R$^a$,
(l) —O—(C=O)—NR$^b$R$^c$,
(m) —(NR$^b$)—(C=O)—NR$^b$R$^c$,
(n) oxido,
(o) oxo, and
(p) —(NR$^b$)SO$_2$R$^d$;
R$^a$ is independently selected from:
  (1) hydrogen,
  (2) C$_{1-6}$alkyl, which is unsubstituted or substituted with 1-7 substituents each independently selected from:
    (a) halo,
    (b) —O—C$_{1-6}$alkyl, which is unsubstituted or substituted with 1-6 halo,
    (c) hydroxyl,
    (d) —CN, and
    (e) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
      (i) halo,
      (ii) —O—C$_{1-6}$alkyl, which is unsubstituted or substituted with 1-6 halo,
      (iii) —CN,
      (iv) nitro,
      (v) hydroxyl, and
      (vi) —C$_{1-6}$alkyl, which is unsubstituted or substituted with 1-6 halo,
  (3) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (a) halo,
    (b) —CN,
    (c) —O—C$_{1-6}$alkyl, which is unsubstituted or substituted with 1-6 halo,
    (d) nitro,
    (e) hydroxyl, and
    (f) —C$_{1-6}$alkyl, which is unsubstituted or substituted with 1-6 halo, and
  (4) —C$_{3-6}$cycloalkyl, which is unsubstituted or substituted with 1-6 halo;
R$^b$ and R$^c$ are independently selected from:
  (1) hydrogen,
  (2) C$_{1-6}$alkyl, which is unsubstituted or substituted with 1-7 substituents each independently selected from:
    (a) halo,
    (b) —OR$^a$,
    (c) —CN,
    (d) —CO$_2$R$^a$,
    (e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
      (i) halo,
      (ii) —OR$^a$,
      (iii) —C$_{1-6}$alkyl, which is unsubstituted or substituted with 1-6 halo, and
      (iv) nitro,
  (3) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (a) halo,
    (b) —OR$^a$,
    (c) —C$_{1-6}$alkyl, which is unsubstituted or substituted with 1-6 halo,
    (d) —C$_{3-6}$cycloalkyl, which is unsubstituted or substituted with 1-6 halo,
    (e) —CN, and
    (f) —CO$_2$R$^a$,
  (4) —C$_{3-6}$cycloalkyl, which is unsubstituted or substituted with 1-6 halo; or R$^b$ and R$^c$ and the nitrogen to which they are attached join to form a 4-, 5-, or 6-membered ring optionally containing an additional heteroatom selected from N, O, and S, wherein the sulfur is optionally oxidized to the sulfone or sulfoxide, which ring is unsubstituted or substituted with 1-4 substituents each independently selected from:
    (a) halo,
    (b) —OR$^a$, and
    (c) —C$_{1-6}$alkyl, which is unsubstituted or substituted with 1-6 halo, and
    (d) phenyl;
R$^d$ is independently selected from:
  (1) C$_{1-6}$alkyl, which is unsubstituted or substituted with 1-4 substituents each independently selected from:
    (a) halo,
    (b) —OR$^a$,
    (c) —CO$_2$R$^a$,
    (d) —CN, and
    (e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
  (i) halo,
  (ii) —OR$^a$,
  (iii) —C$_{1-6}$alkyl, which is unsubstituted or substituted with 1-6 halo, and
  (iv) nitro,
(2) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
  (a) halo,
  (b) —OR$^a$,
  (c) —C$_{1-6}$alkyl, which is unsubstituted or substituted with 1-6 halo,
  (d) —C$_{3-6}$cycloalkyl, which is unsubstituted or substituted with 1-6 halo
  (e) —CN, and
  (f) —CO$_2$R$^a$, and
(3) —C$_{3-6}$cycloalkyl, which is unsubstituted or substituted with 1-6 halo;
R$^e$ and R$^f$ are independently selected from:
  (1) hydrogen,
  (2) —C$_{1-4}$alkyl, which is unsubstituted or substituted with 1-6 halo,
  (3) phenyl, and
  (4) benzyl;
  or where R$^e$ and R$^f$ and the atom to which they are attached join to form a 3-, 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
  (a) halo,
  (b) —OR$^a$,
  (c) —C$_{1-6}$alkyl, which is unsubstituted or substituted with 1-6 halo, and
  (d) phenyl;
m is 1;
n is 1;
v is 0, 1, or 2;
k is 0, 1, or 2;
or a pharmaceutically acceptable salt, individual enantiomer or diastereomer thereof.

2. The compound of claim 1 having the formula Ia:

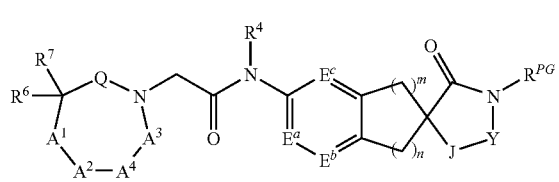

or a pharmaceutically acceptable salt, individual enantiomer or diastereomer thereof.

3. The compound of claim 1 having the formula Ib:

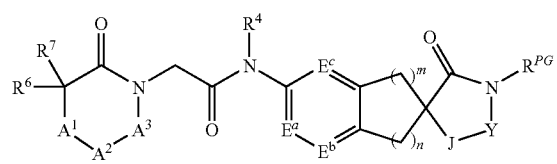

or a pharmaceutically acceptable salt, individual enantiomer or diastereomer thereof.

4. The compound of claim 1 having the formula Ic:

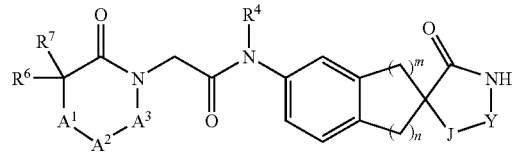

or a pharmaceutically acceptable salt, individual enantiomer or diastereomer thereof.

5. The compound of claim 1 having the formula Id:

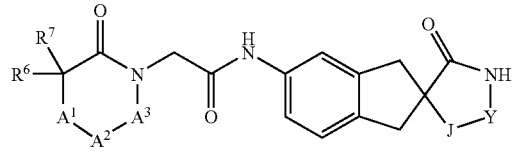

or a pharmaceutically acceptable salt, individual enantiomer or diastereomer thereof.

6. The compound of claim 1 having the formula Ie:

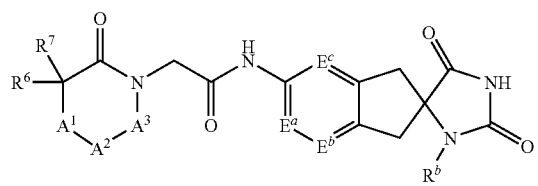

or a pharmaceutically acceptable salt, individual enantiomer or diastereomer thereof.

7. The compound of claim 1 having the formula If:

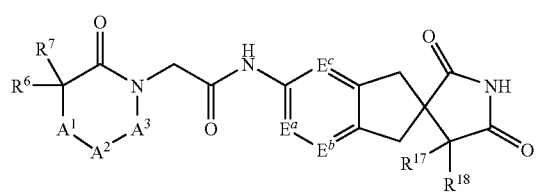

or a pharmaceutically acceptable salt, individual enantiomer or diastereomer thereof.

8. The compound of claim 1 having the formula Ig:

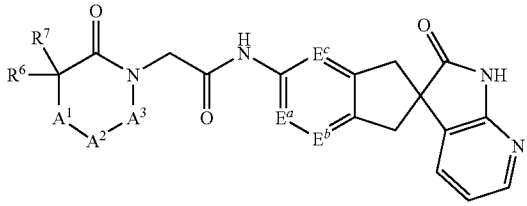

or a pharmaceutically acceptable salt, individual enantiomer or diastereomer thereof.

9. The compound of claim 1 having the formula Ih:

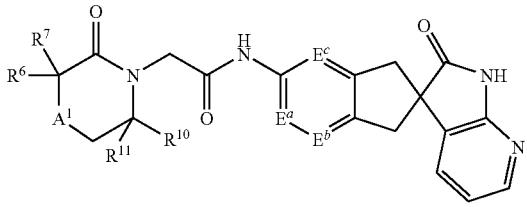

or a pharmaceutically acceptable salt, individual enantiomer or diastereomer thereof.

10. The compound of claim 1, wherein $A^1$ is independently selected from:
(1) —O—,
(2) —S(O)$_v$—,
(3) —Si(OR$^a$)(C$_{1-4}$alkyl), which alkyl is unsubstituted or substituted with 1-5 halo,
(4) —Si(C$_{1-4}$alkyl)$_2$, —Si(C$_{1-4}$alkyl)$_2$, where each alkyl is independently unsubstituted or substituted with 1-5 halo-,
(5) —CR$^6$R$^7$—,
(6) —N(R$^8$)—,
(7) —(C=O)—,
(8) —C(R$^8$)(R$^a$)—,
(9) —C(N(R$^b$)—SO$_2$R$^d$)(R$^a$)—,
(10) —C(N(R$^b$)(C=O)R$^a$)(R$^a$)—,
(11) —C(N(R$^b$)(C=O)OR$^a$)(R$^a$)—,
(12) —CR$^{10}$R$^{11}$—, and
(13) —N(R$^{11}$)—.

11. The compound of claim 1, wherein $A^2$ is independently selected from:
(1) —CR$^6$R$^7$—,
(2) —CR$^{10}$R$^{11}$—, and
(3) —(C=O)—.

12. The compound of claim 1, wherein $A^3$ is independently selected from:
(1) —CR$^6$R$^7$—,
(2) —CR$^{10}$R$^{11}$—, and
(3) —N(R$^{11}$)—.

13. The compound of claim 1, wherein $A^4$ is independently selected from:
(1) —CR$^6$R$^7$—,
(2) —CR$^{10}$R$^{11}$—,
(3) —N(R$^{11}$)—,
(4) —N(R$^8$)—, and
(5) a bond between $A^2$ and $A^3$.

14. The compound of claim 1, wherein $R^4$ is selected from: hydrogen and —C$_{1-6}$alkyl, which is unsubstituted or substituted with 1-5 fluoro.

15. The compound of claim 1, wherein $R^{5a}$, $R^{5b}$ and $R^{5c}$ are independently selected from hydrogen, halo, and —C$_{1-6}$alkyl, which is unsubstituted or substituted with 1-5 fluoro.

16. The compound of claim 1, wherein $R^6$ and $R^7$ are independently selected from:
(1) hydrogen,
(2) —C$_{1-6}$alkyl, which is unsubstituted or substituted with 1-5 substituents where the substituents are each independently selected from: halo, phenyl, and —OR$^a$,
(3) —C$_{3-6}$cycloalkyl, which is unsubstituted or substituted with 1-5 fluoro,
(4) phenyl or heterocycle, which is unsubstituted or substituted with 1-5 halo,
(5) halo,
(6) —OR$^a$,
(7) —NR$^b$R$^c$, and
(8) —O(C=O)R$^a$.

17. The compound of claim 1, wherein $R^6$ and $R^7$ and the carbon atom or atoms to which they are attached join to form a ring selected from cyclopropyl, cyclobutyl, cyclopentyl, cyclohexyl, cycloheptyl, cyclooctyl, cyclopentenyl, cyclohexenyl, cycloheptenyl, dioxolanyl, dioxanyl, tetrahydrofuranyl, tetrahydropyranyl, pyrrolidinyl, and piperidinyl, which ring is unsubstituted or substituted with 1-6 substituents each independently selected from:
(1) —C$_{1-6}$alkyl, which is unsubstituted or substituted with 1-3 substituents where the substitutents are each independently selected from: halo, —OR$^a$, and phenyl,
(2) —C$_{3-6}$cycloalkyl, wherein the C$_{3-6}$cycloalkyl group is optionally fused to the ring, and which C$_{3-6}$cycloalkyl group is unsubstituted or substituted with 1-3 substituents each independently selected from: halo, —OR$^a$, and phenyl,
(3) phenyl or heterocycle, wherein heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, wherein the phenyl or heterocycle is optionally fused to the ring, and which phenyl or heterocycle is unsubstituted or substituted with 1-3 substituents each independently selected from: halo, —OR$^a$, and —C$_{1-4}$alkyl, which is unsubstituted or substituted with 1-5 fluoro,
(4) halo,
(5) oxo,
(6) —CO$_2$R$^a$, and
(7) —C(=O)R$^a$.

18. The compound of claim 1, wherein $R^8$ is selected from: hydrogen, —C(=O)R$^a$, —CO$_2$R$^a$, —SO$_2$R$^d$, and —C$_{1-6}$alkyl, which is unsubstituted or substituted with 1-5 fluoro.

19. The compound of claim 1, wherein $R^8$ and $R^7$ and the atoms to which they are attached join to form a 4-, 5-, 6- or 7-membered alkyl- or heteroalkyl-ring optionally containing an additional heteroatom selected from N, O, and S, wherein the sulfur is optionally oxidized to the sulfone or sulfoxide, which ring is unsubstituted or substituted with 1-4 substituents each independently selected from:
(1) halo,
(2) phenyl, which is unsubstituted or substituted with 1-3 substituents each independently selected from: halo, OR$^a$, CN, and —C(=O)OR$^a$,
(3) —OR$^a$, and
(4) —C$_{1-6}$alkyl, which is unsubstituted or substituted with 1-6 halo.

20. The compound of claim 1, wherein $R^{10}$ is selected from: hydrogen, and —$C_{1-6}$alkyl, which is unsubstituted or substituted with fluoro.

21. The compound of claim 1, wherein $R^{11}$ is independently selected from the group consisting of:

phenyl, naphthyl, tetrahydronaphthyl, indanyl, biphenyl, phenanthryl, anthryl, azepinyl, azepanyl, azetidinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiamorpholinyl sulfone, thiazolyl, thiazolinyl, thienofuryl, thienothienyl, thienyl, triazolyl, isoxazolyl, tetrahydrothienyl, tetrahydropyranyl, oxetanyl, tetrahydrothiopyranyl, and thietanyl, where $R^{11}$ is unsubstituted or substituted with 1-5 substituents each independently selected from $R^{12}$, $R^{13}$, $R^{14}$, $R^{15a}$ and $R^{15b}$.

22. The compound of claim 1, wherein $R^{PG}$ is selected from:
(1) hydrogen,
(2) —$C_{1-6}$alkyl, which is unsubstituted or substituted with 1-3 halo,
(3) —$CH_2OR^a$,
(4) —$CH_2$—O—$CH_2CH_2Si(CH_3)_3$, and
(5) $CH_2OP(=O)(OR^c)_2$
wherein $R^a$ is defined herein.

23. The compound of claim 1, wherein J is =$C(R^{16a})$—, —$CR^{17}R^{18}$— or —$N(R^b)$—.

24. The compound of claim 1, wherein Y is =$C(R^{16b})$—, —$CR^{17}R^{18}$— or —$C(=O)$—.

25. The compound of claim 1, wherein $R^{16a}$ and $R^{16b}$ are independently selected from:
(1) hydrogen,
(2) —$C_{1-4}$alkyl, which is unsubstituted or substituted with 1-3 substituents each independently selected from: halo, —$OR^a$, —$C_{3-6}$cycloalkyl, and phenyl,
(3) phenyl or heterocycle, wherein heterocycle is selected from: pyridyl, pyrimidinyl, pyrazinyl, thiazolyl, thienyl, triazolyl, isoxazolyl and morpholinyl, which phenyl or heterocycle is unsubstituted or substituted with 1-3 substituents each independently selected from: —$C_{1-4}$alkyl which is unsubstituted or substituted with 1-3 halo, —$OR^a$, and halo,
(4) halo,
(5) $OR^a$, and
(6) —$NR^bR^c$.

26. The compound of claim 1, wherein $R^{16a}$ and $R^{16b}$ and the atom(s) to which they are attached join to form a ring selected from cyclohexenyl, phenyl, pyridyl, pyrimidinyl, pyrazinyl, pyridazinyl, furanyl, oxazolyl, isoxazolyl, imidazolyl, and thienyl, which ring is unsubstituted or substituted with 1-3 substituents each independently selected from:

(1) —$C_{1-6}$alkyl, which is unsubstituted or substituted with 1-3 substituents each independently selected from: halo, $OR^a$, —$CO_2R^a$, —$NR^bR^c$, and $CONR^bR^c$,
(2) phenyl or heterocycle, wherein heterocycle is selected from pyridyl, pyrimidinyl, pyrazinyl, pyridazinyl, piperidinyl, azetidinyl, piperazinyl, pyrrolidinyl, thienyl and morpholinyl, which phenyl or heterocycle is unsubstituted or substituted with 1-3 substituents each independently selected from: halo, $OR^a$ and —$C_{1-4}$alkyl, which is unsubstituted or substituted with 1-3 fluoro,
(3) halo,
(4) $OR^a$,
(5) —CN,
(6) —$NR^bR^c$,
(7) $CONR^bR^c$, and
(8) oxo.

27. A compound selected from:

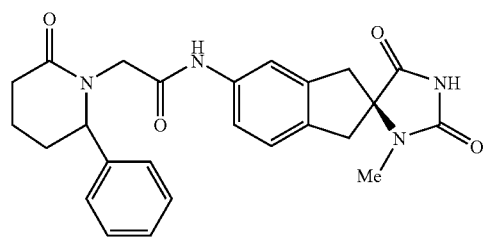

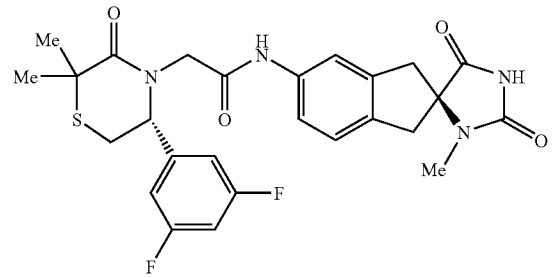

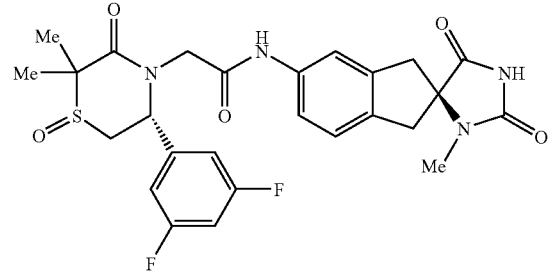

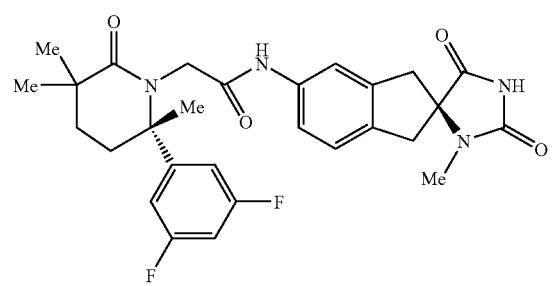

-continued
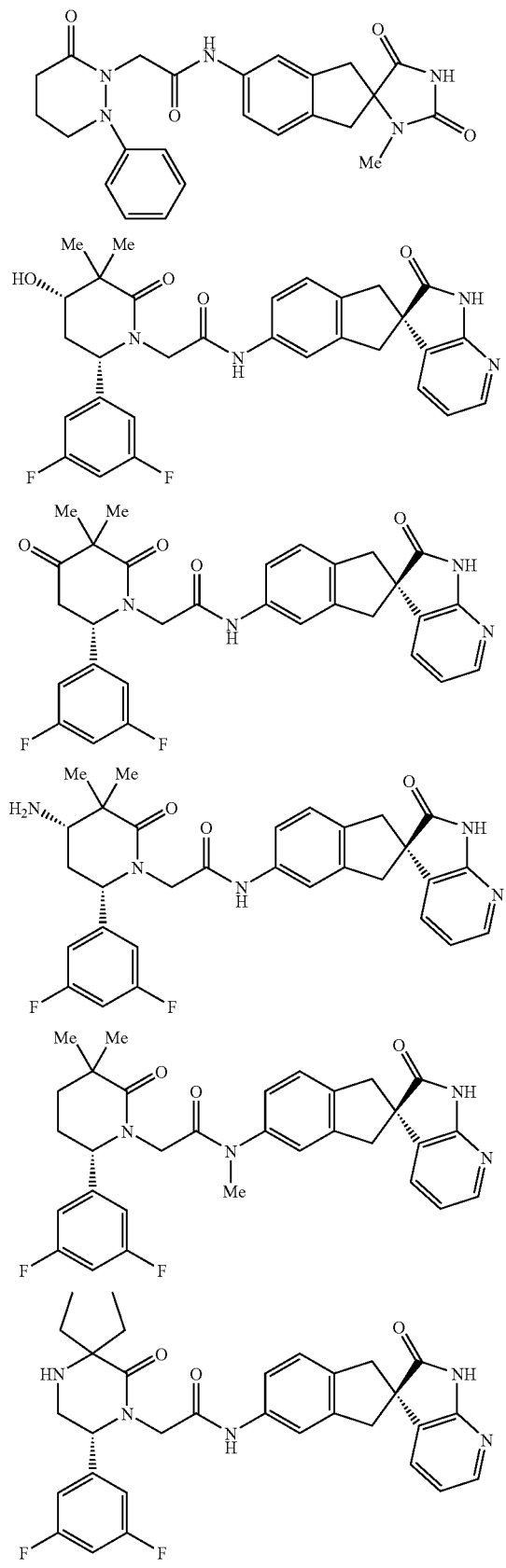
-continued
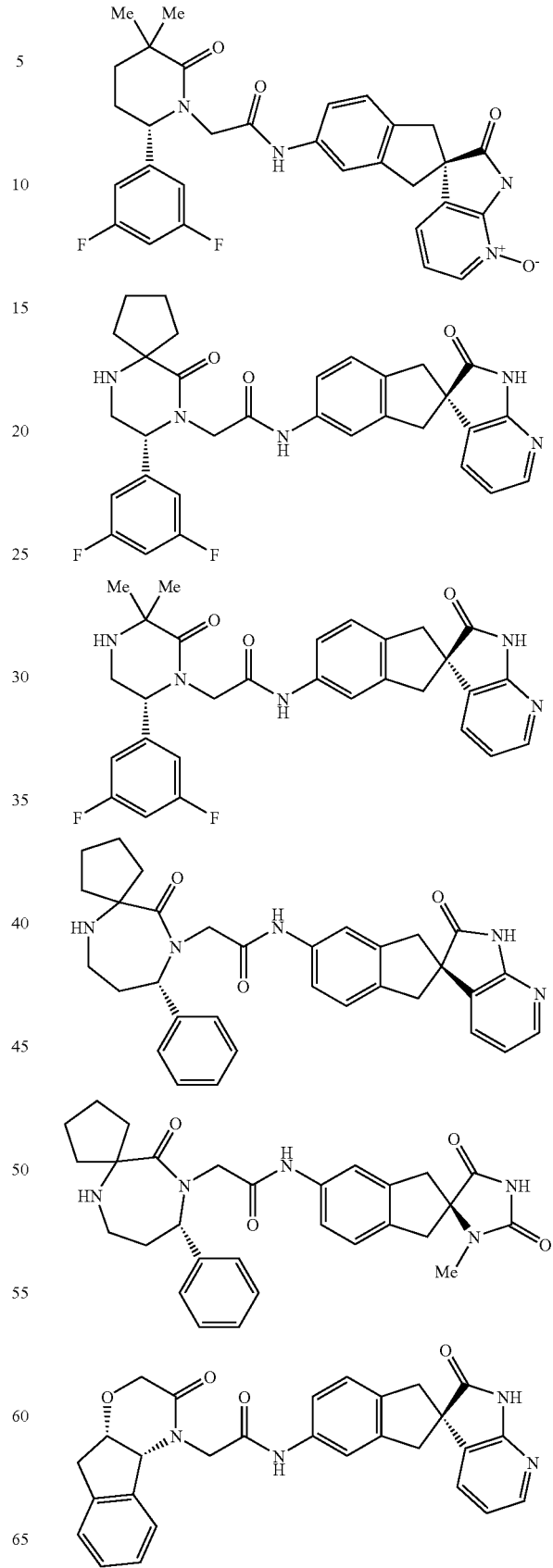

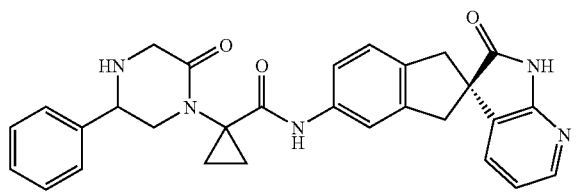
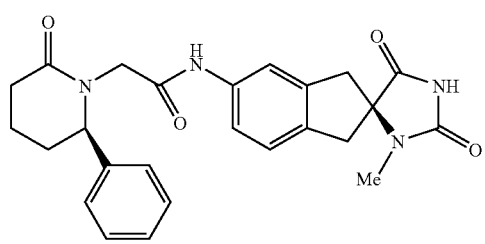
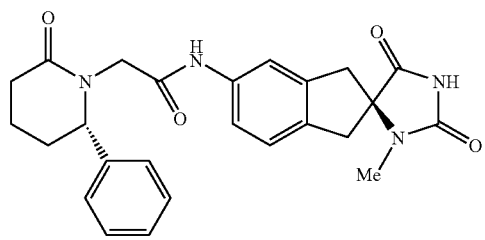
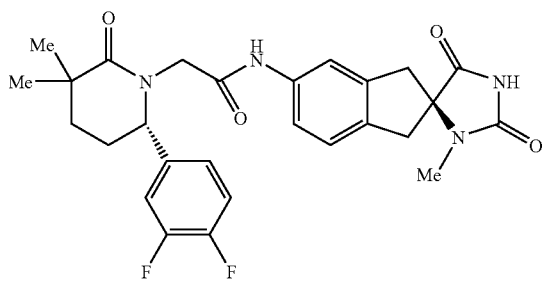
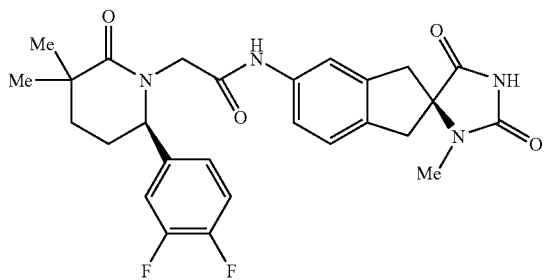
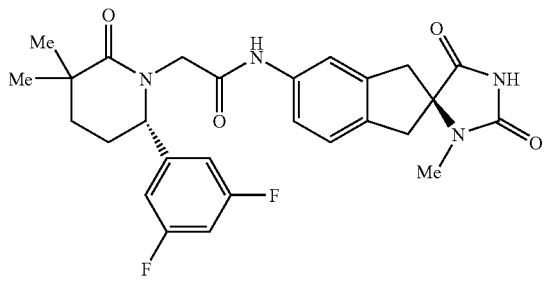
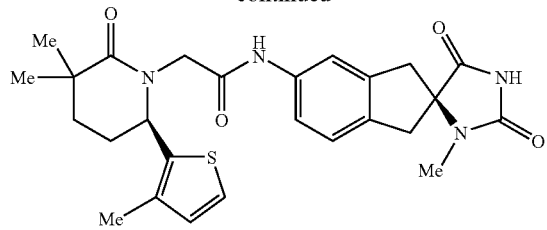
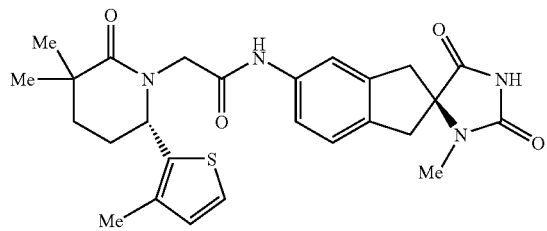
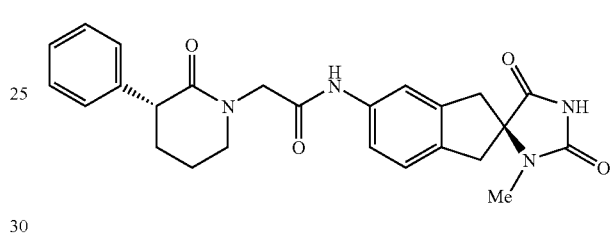
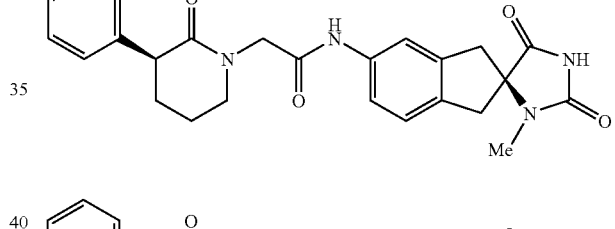
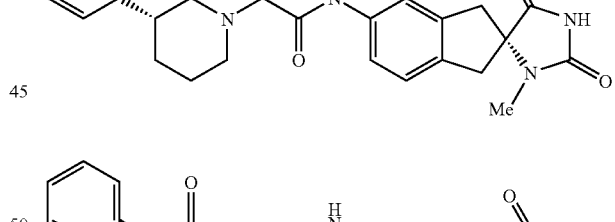
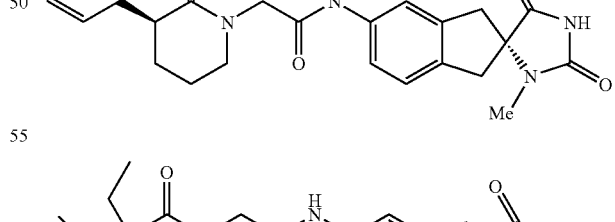
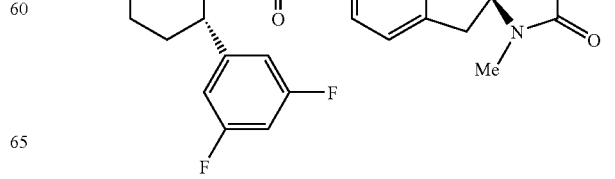

185
-continued
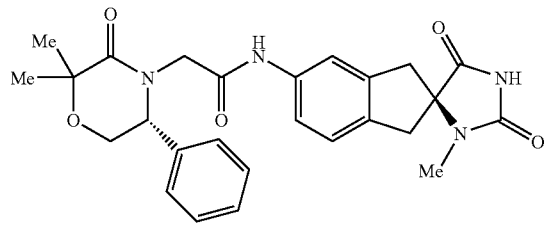
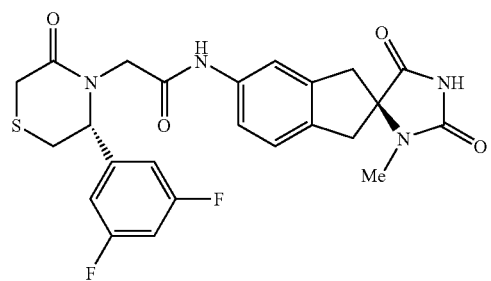
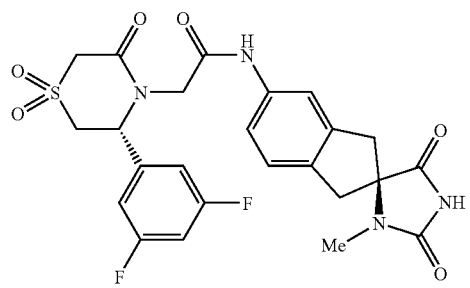
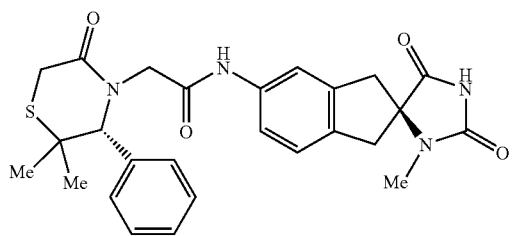
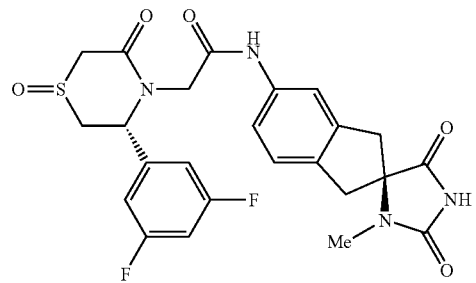
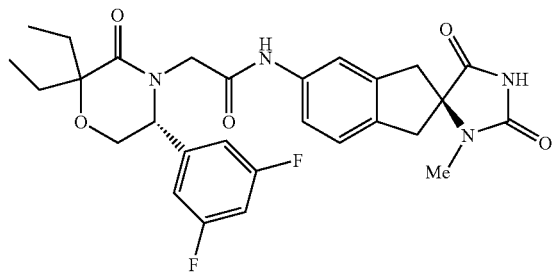
186
-continued
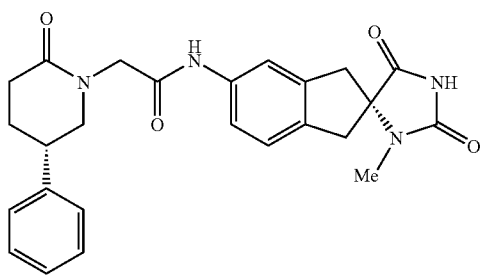
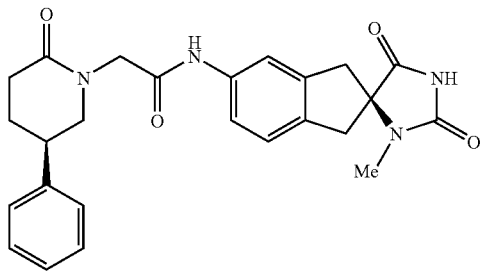
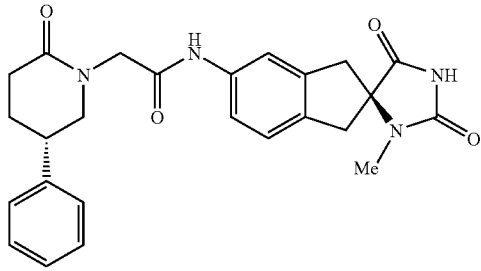
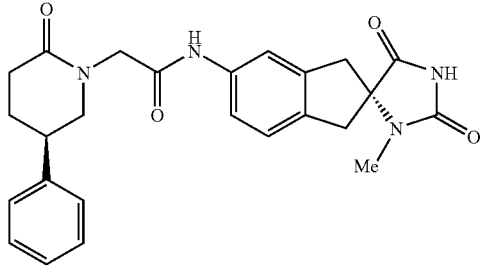
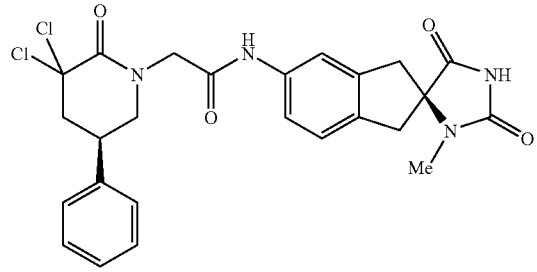
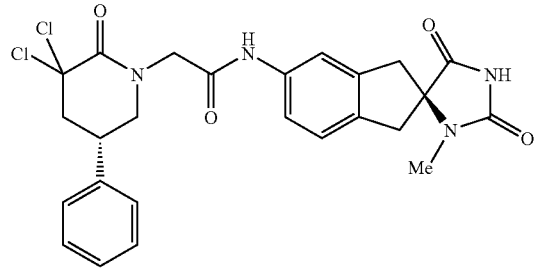

187
-continued
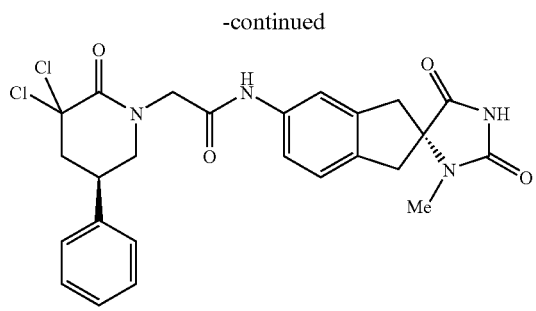
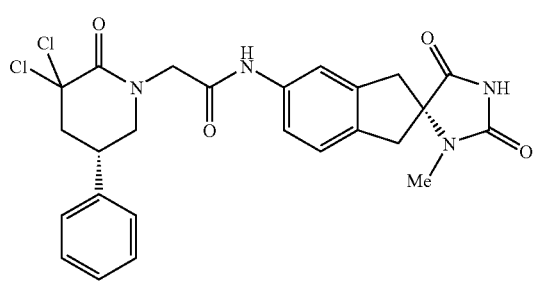
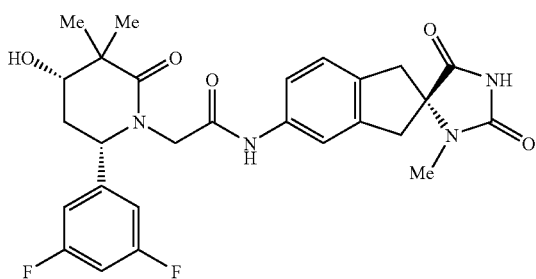
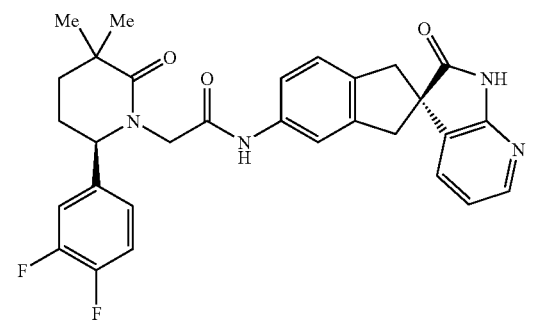
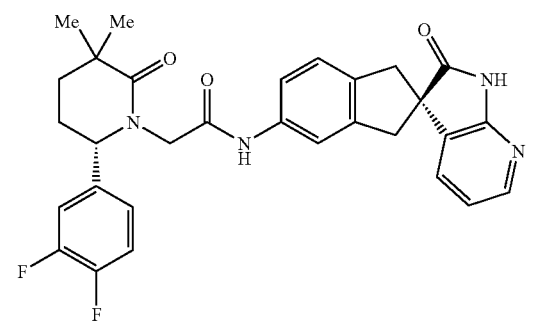
188
-continued
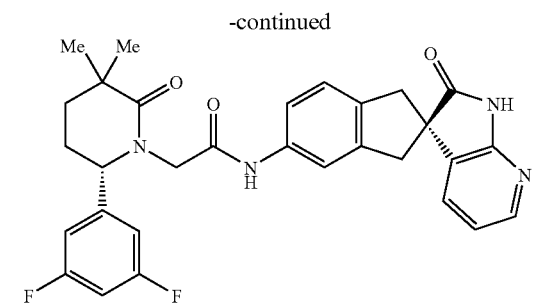
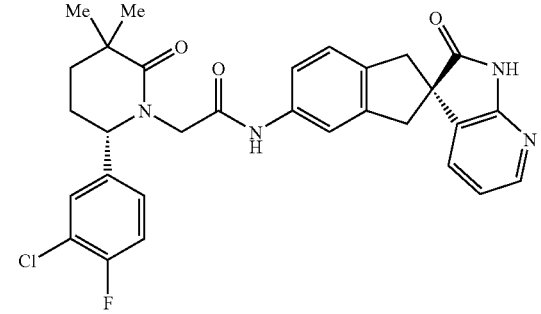
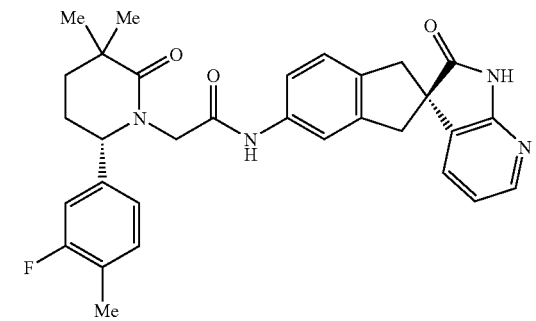
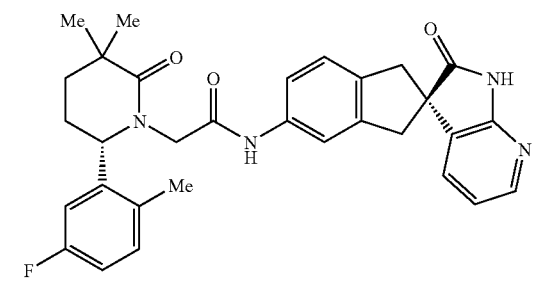
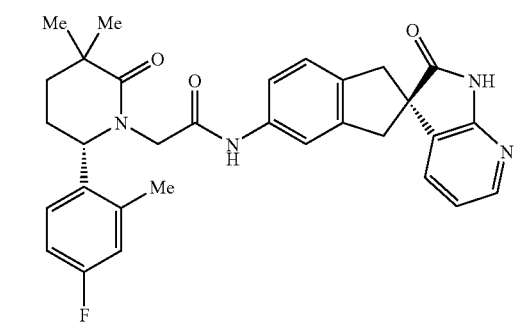

189
-continued
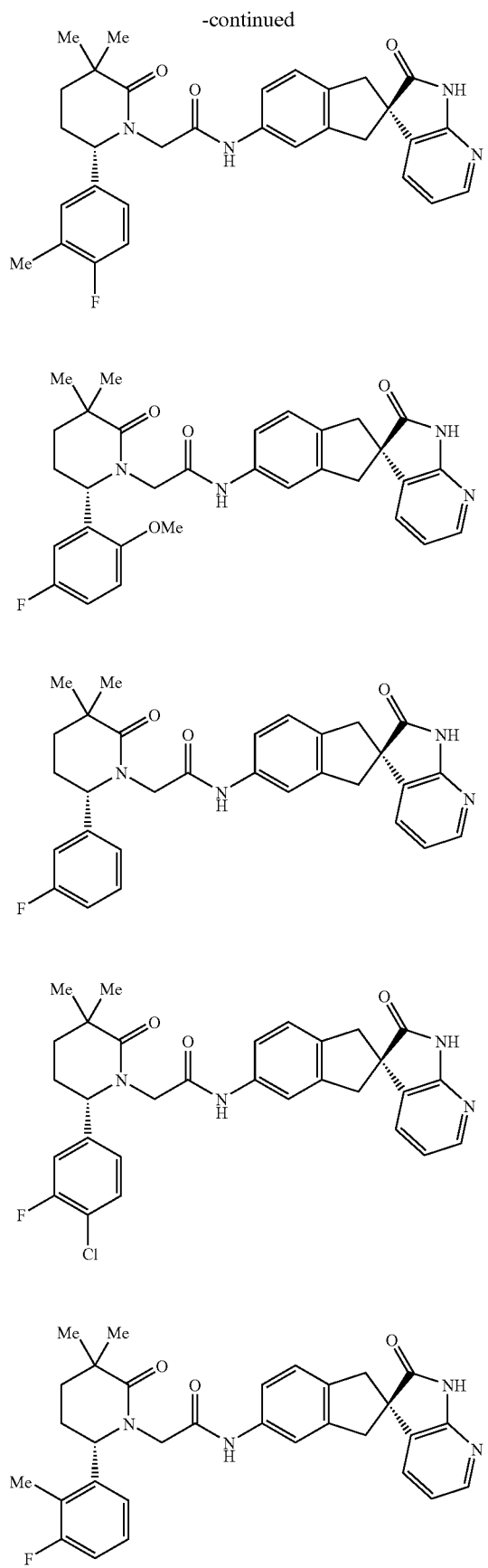
190
-continued
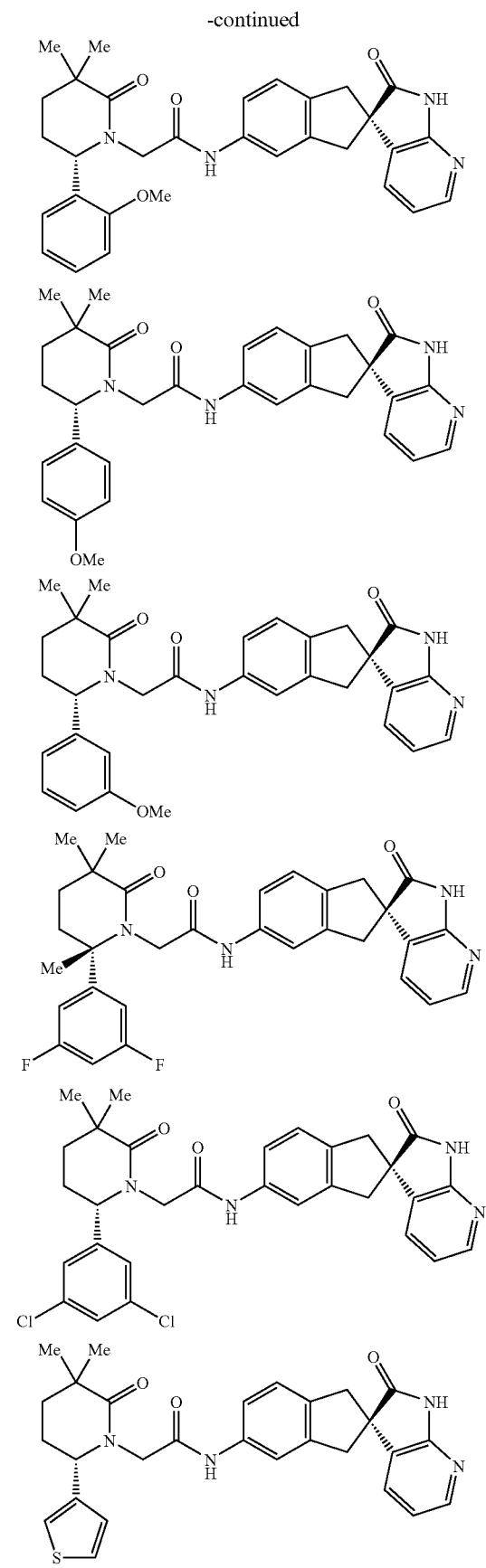

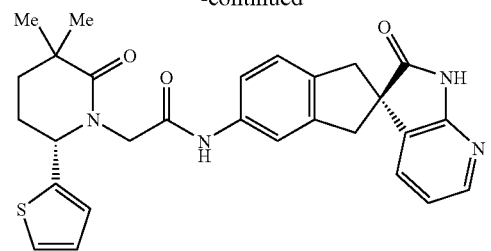
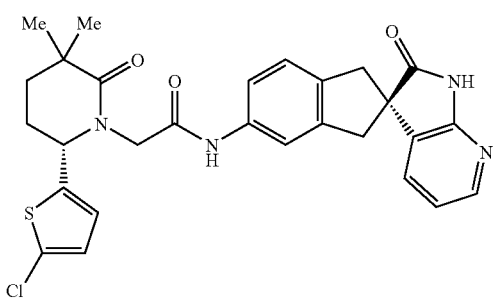
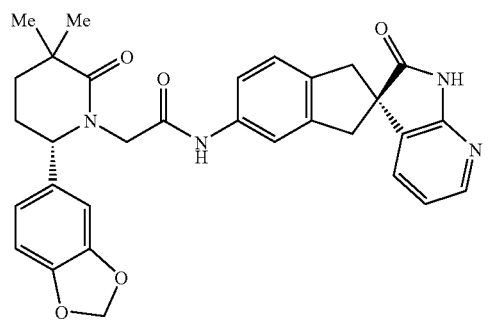
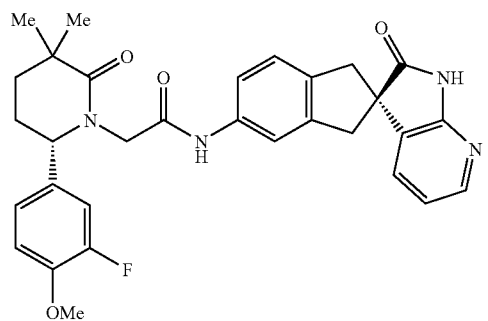
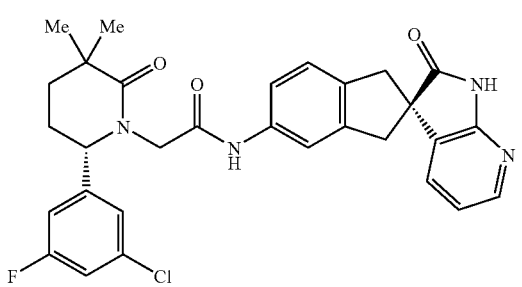
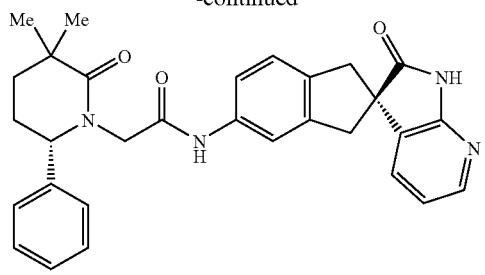
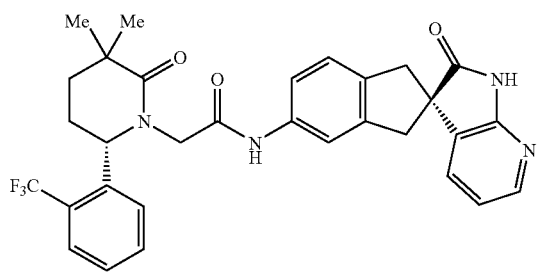
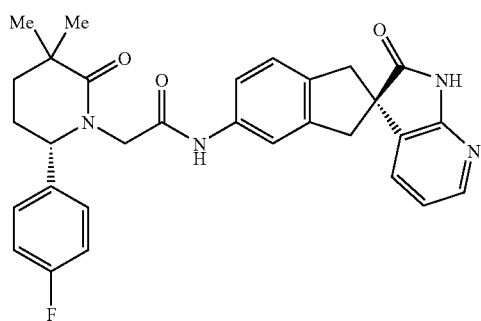
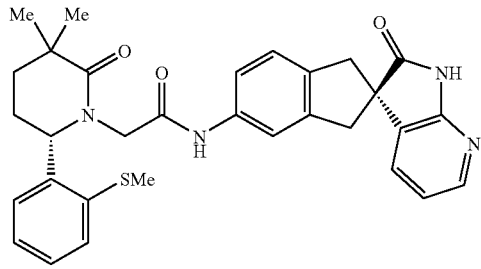
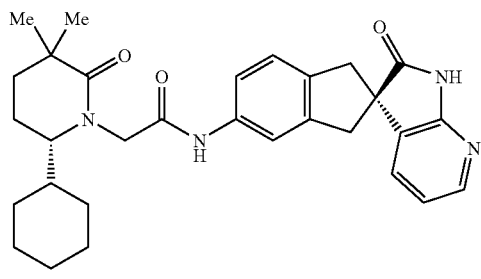
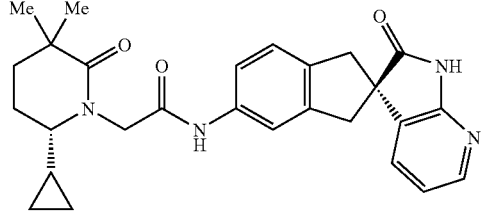

-continued
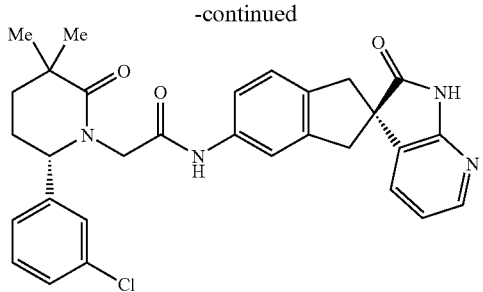
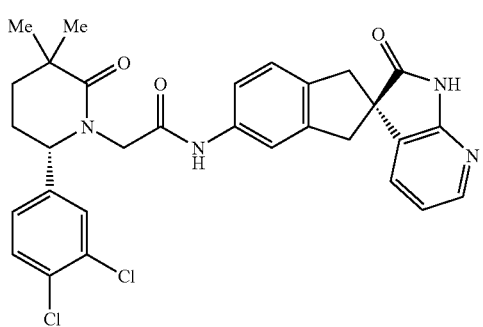
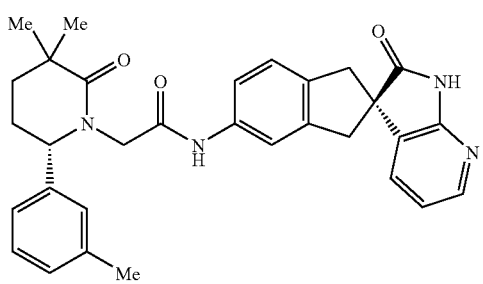
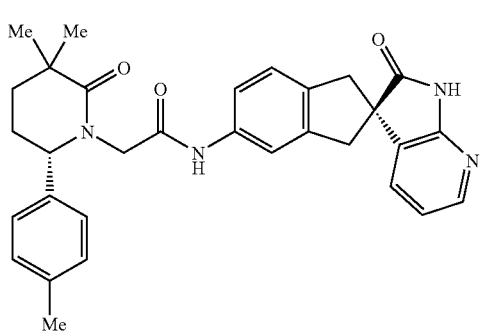
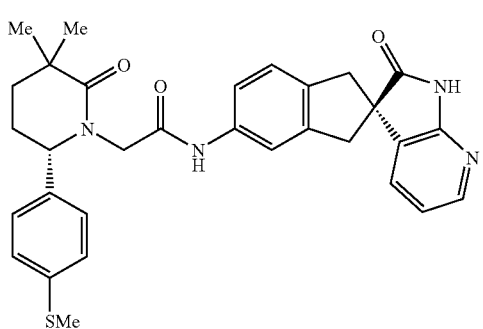
-continued
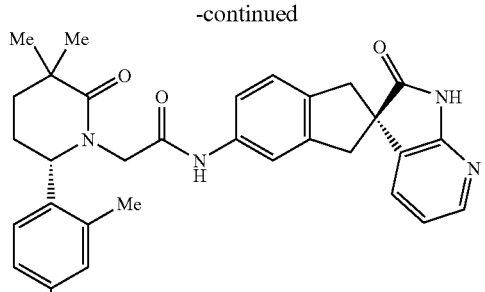
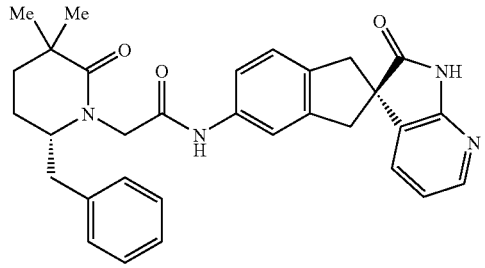
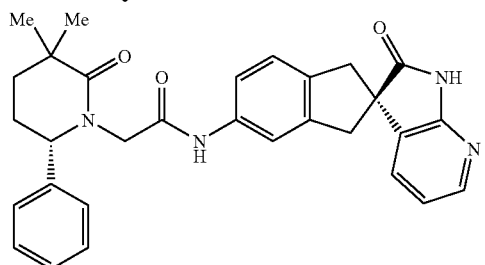
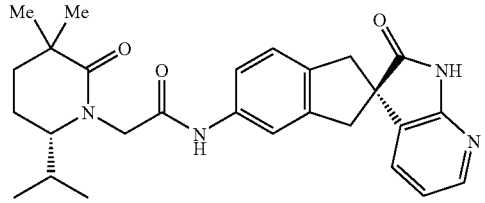
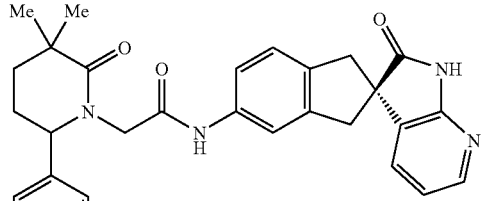
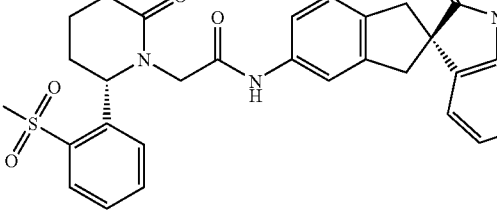

195
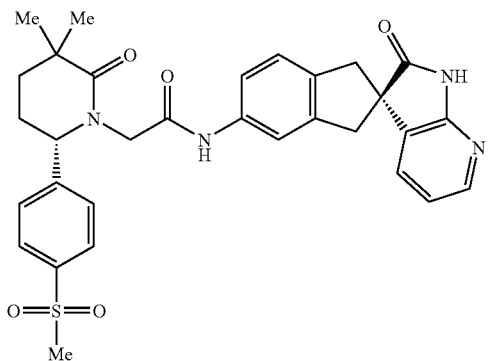
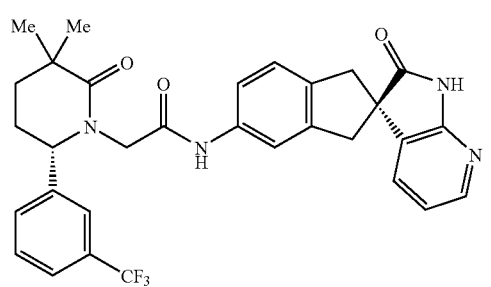
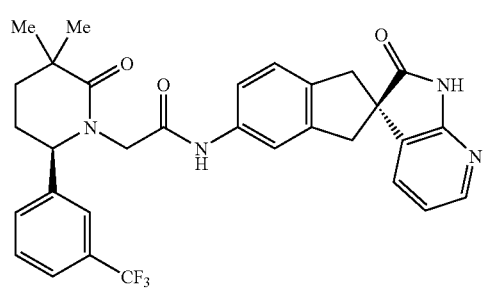
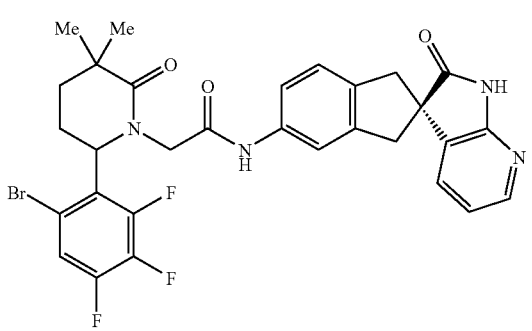
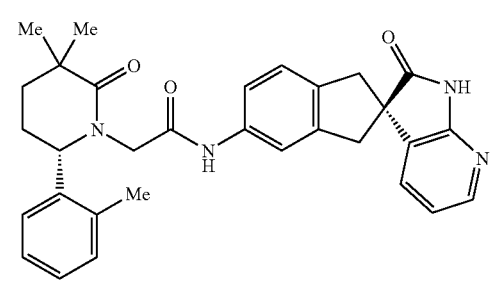
196
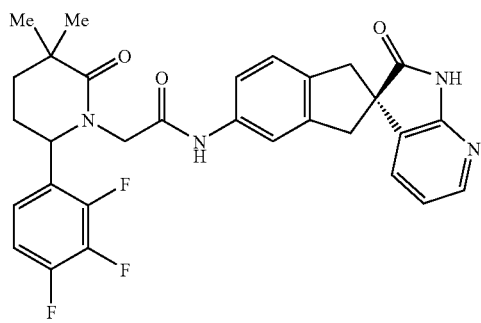
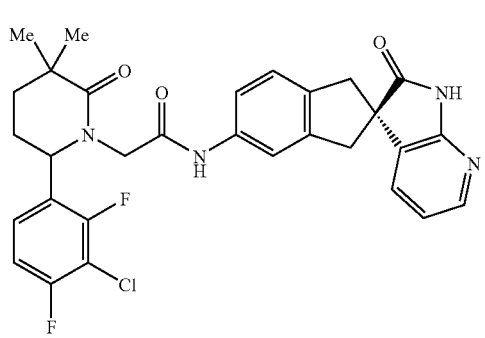
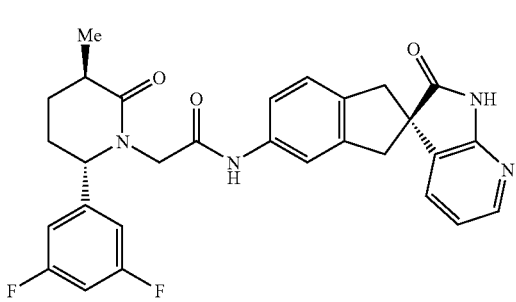
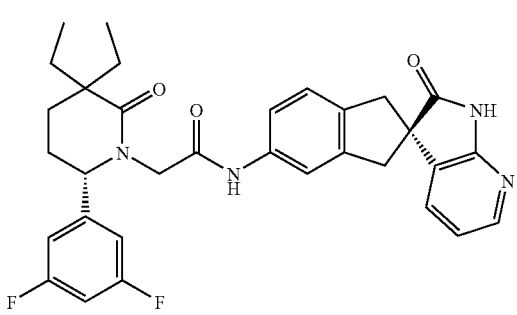
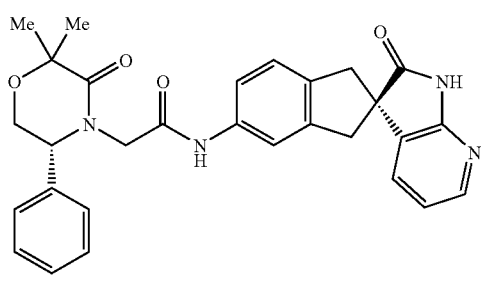

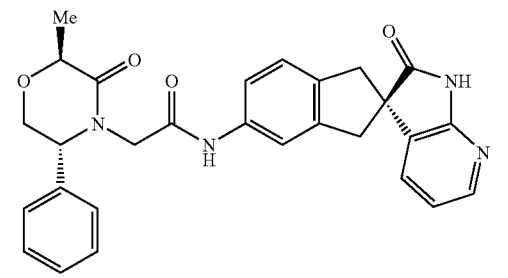
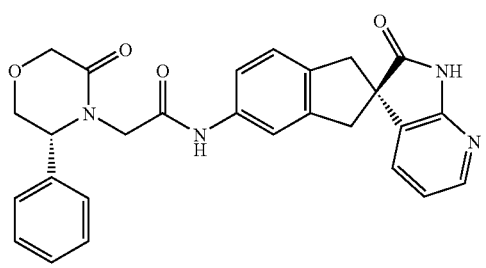
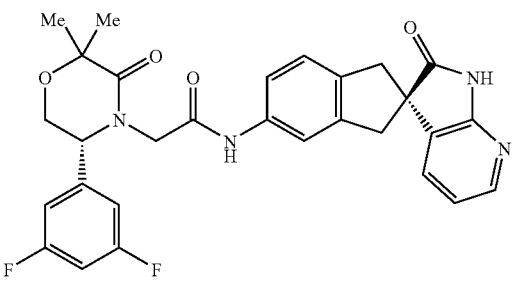
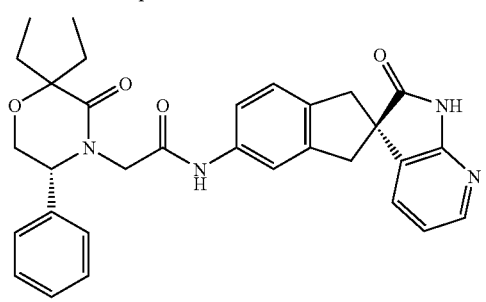
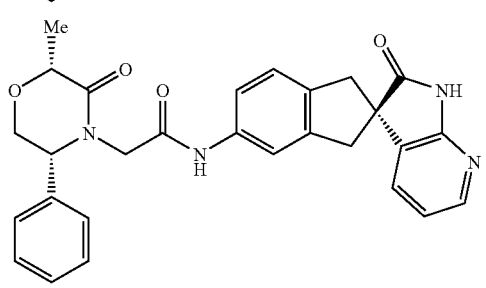
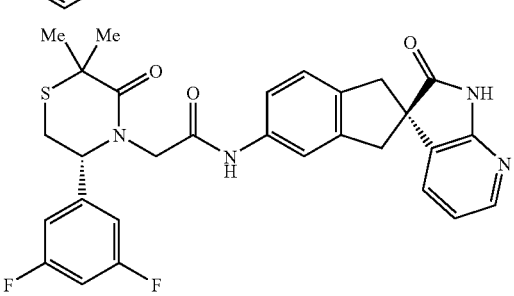
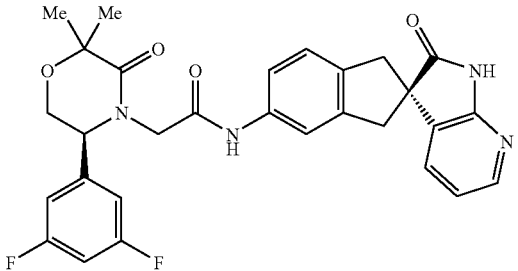
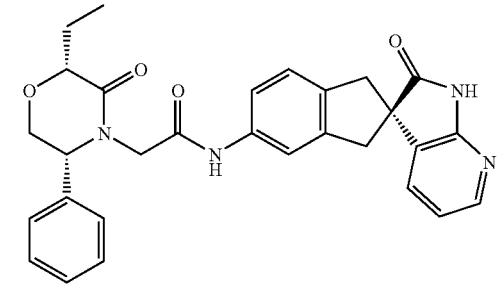
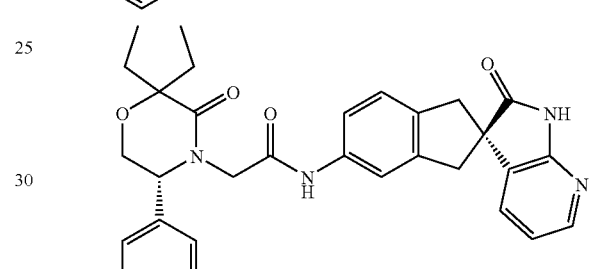
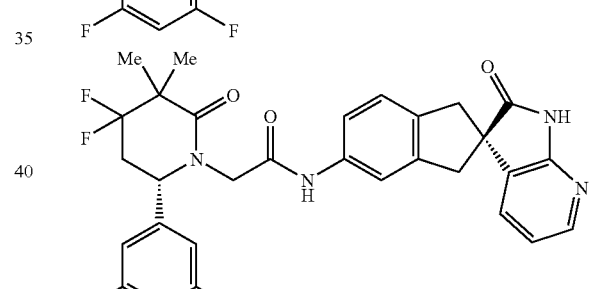
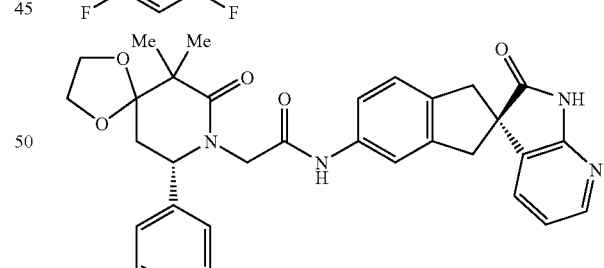
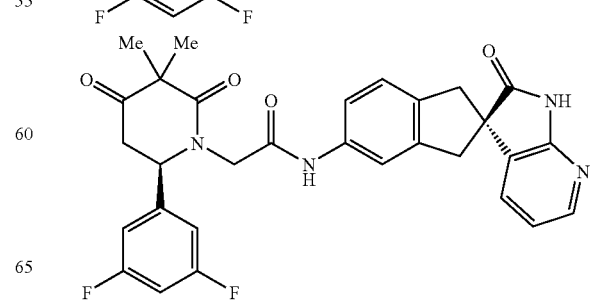

-continued
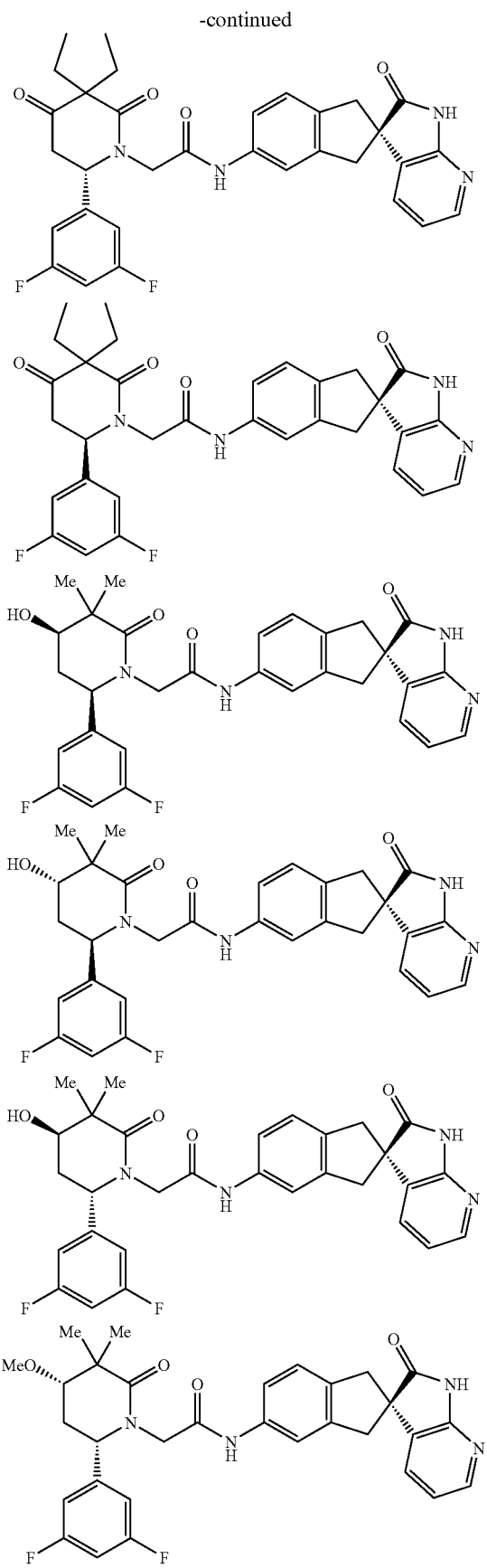
-continued
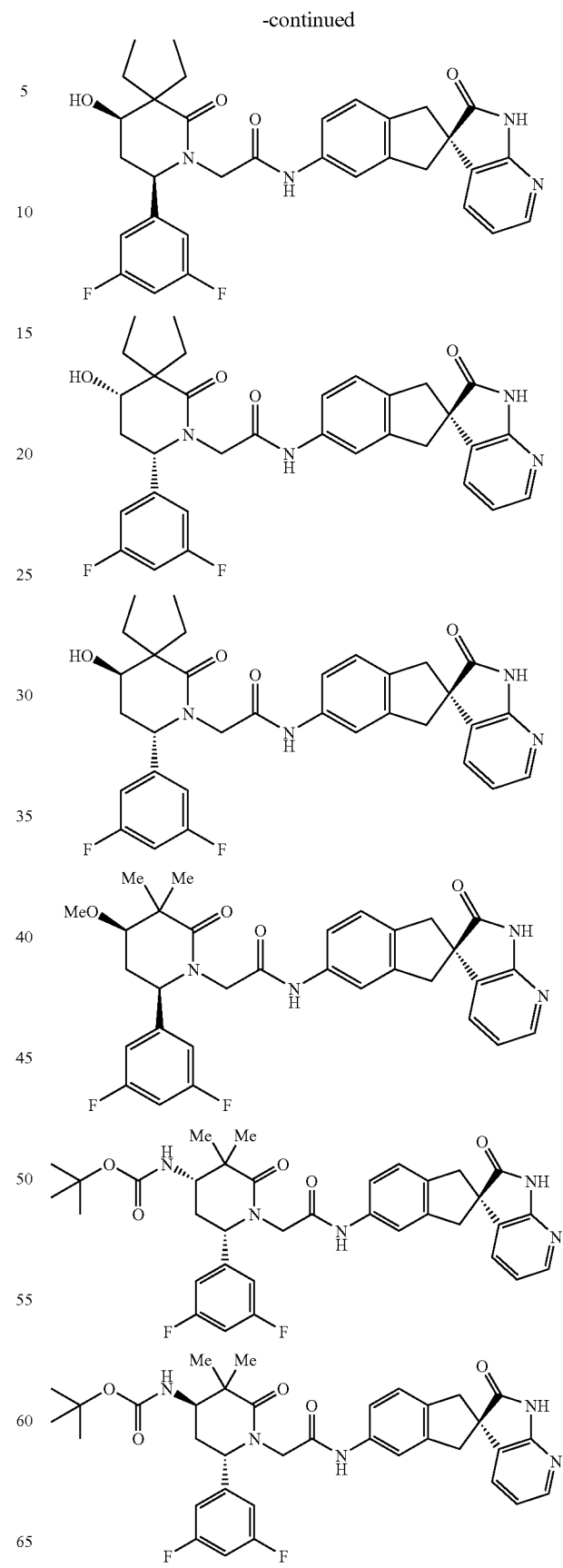

-continued
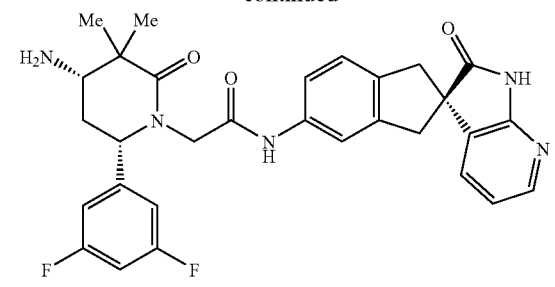
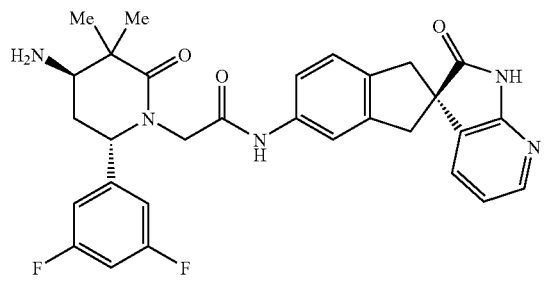
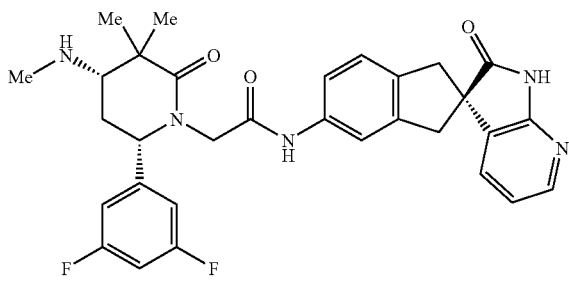
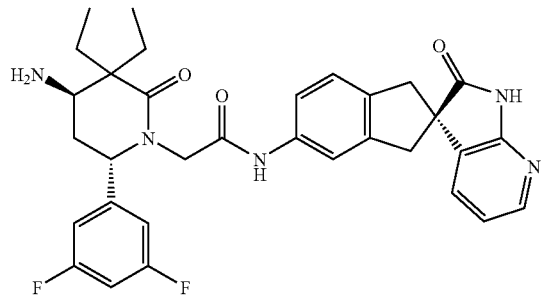
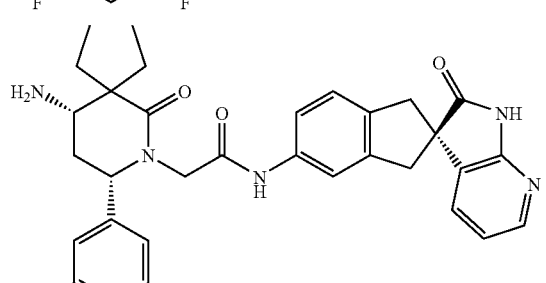
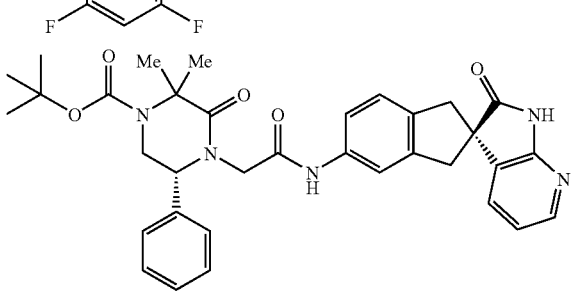
-continued
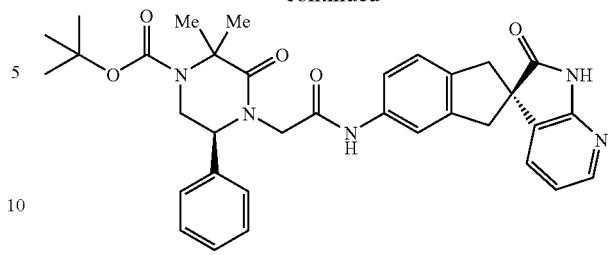
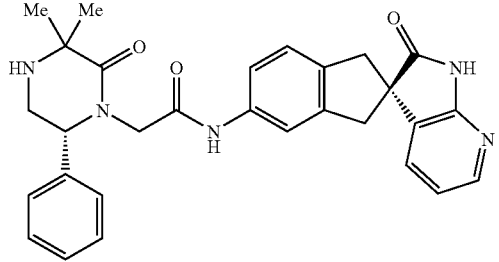
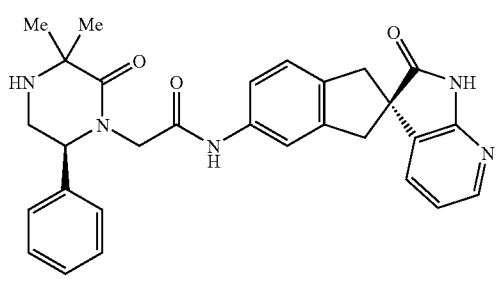
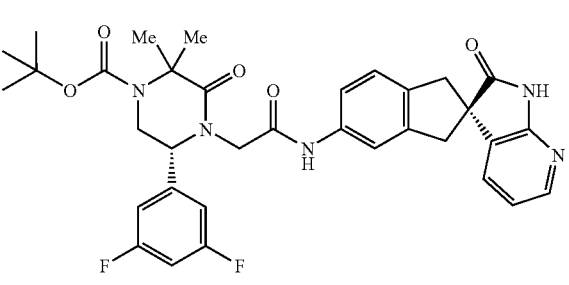
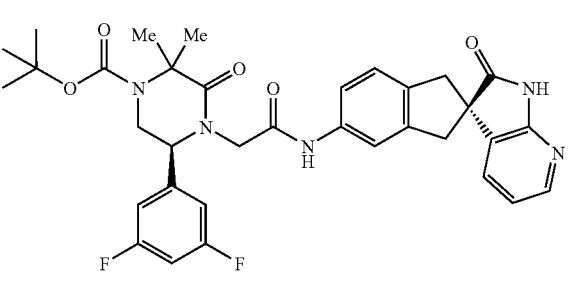
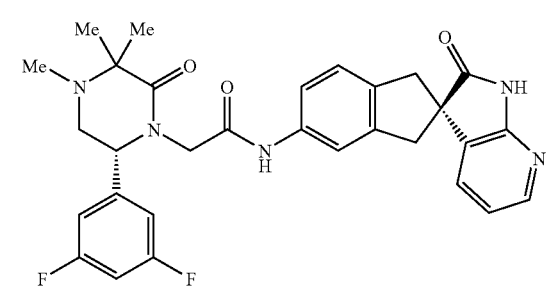

203
-continued
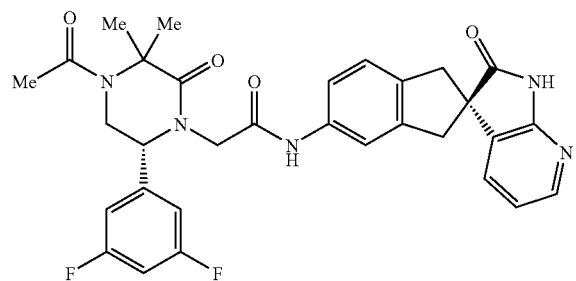
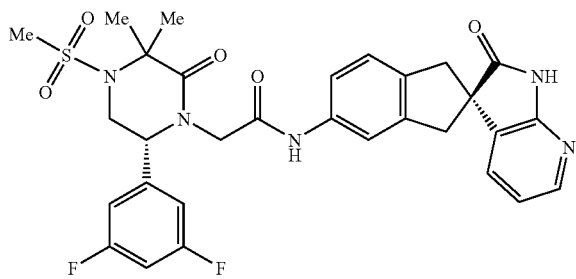
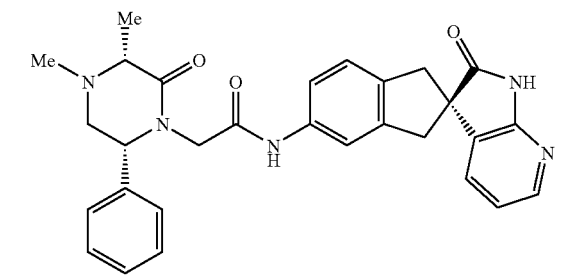
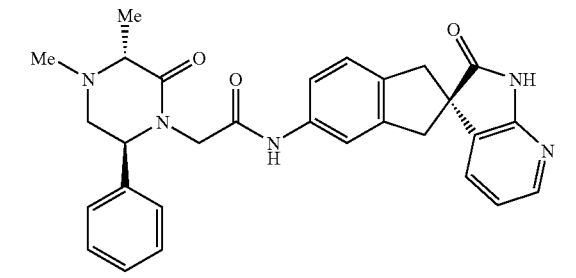
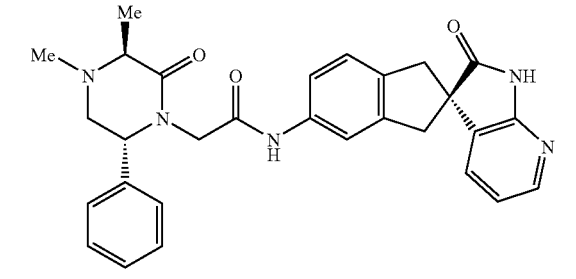
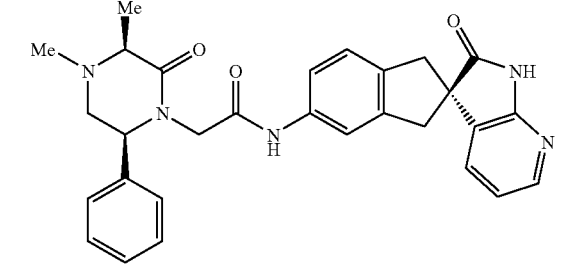
204
-continued
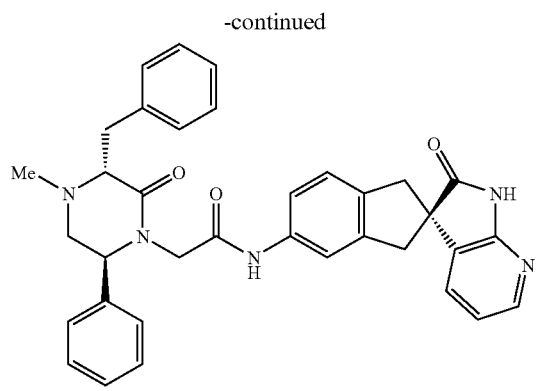
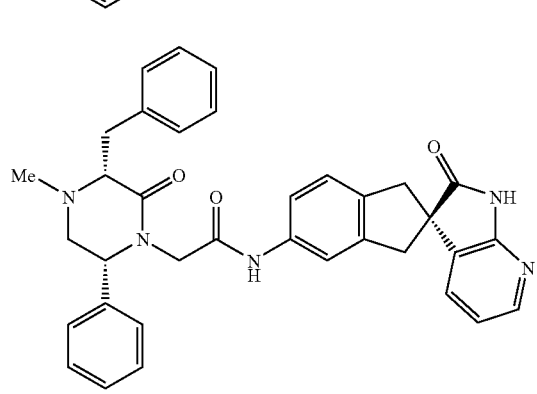
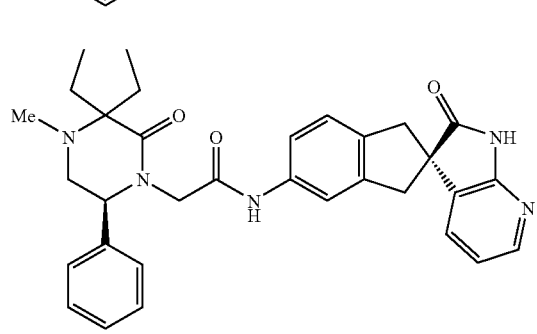
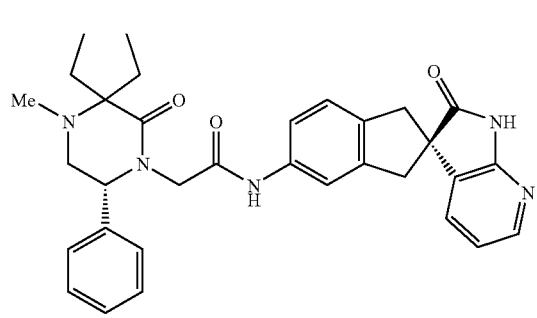
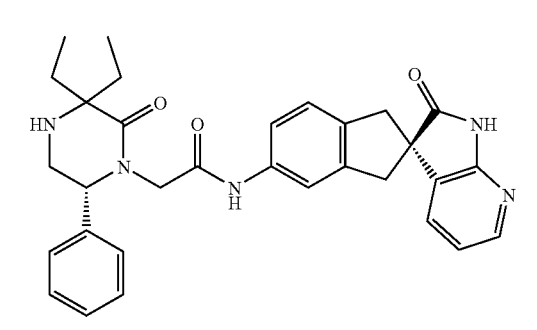

205
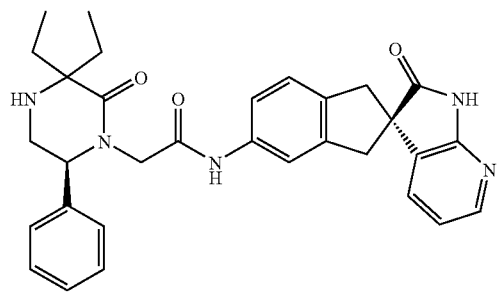
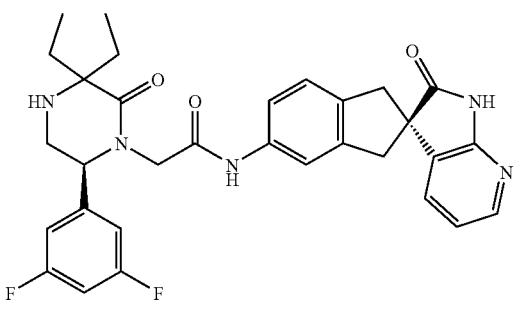
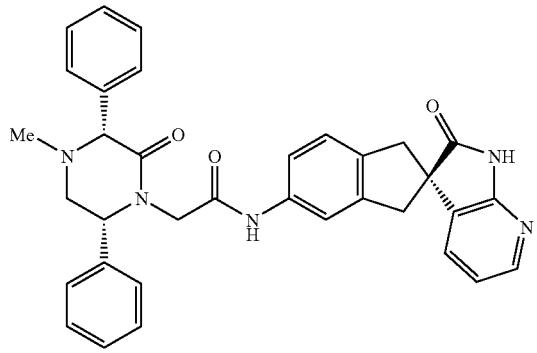
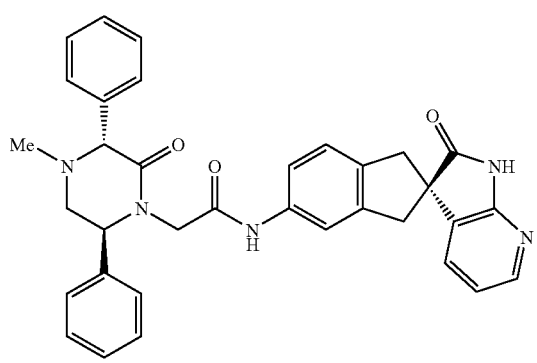
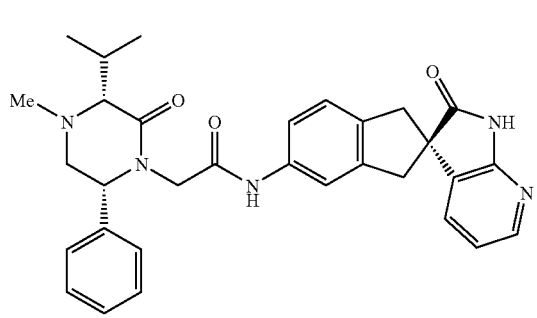
206
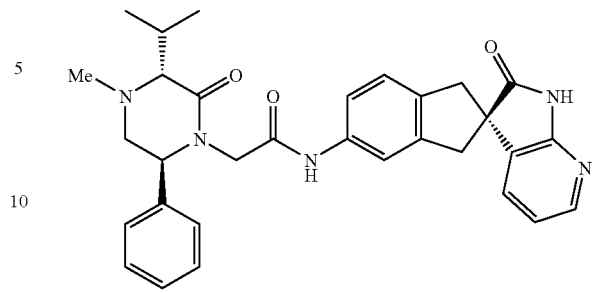
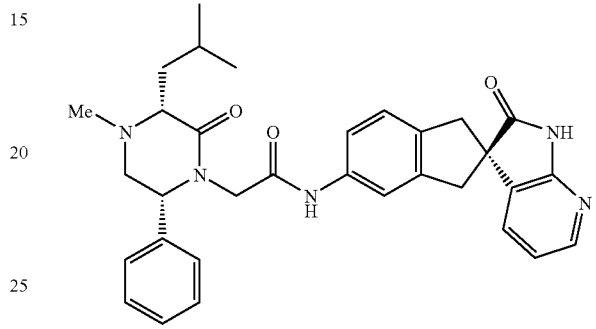
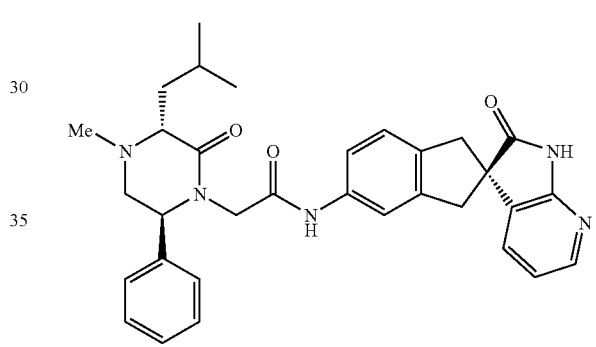
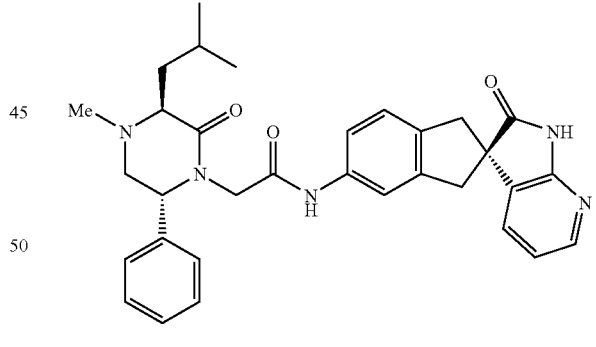
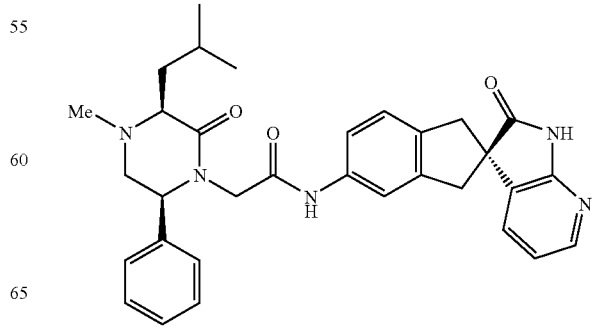

207
-continued
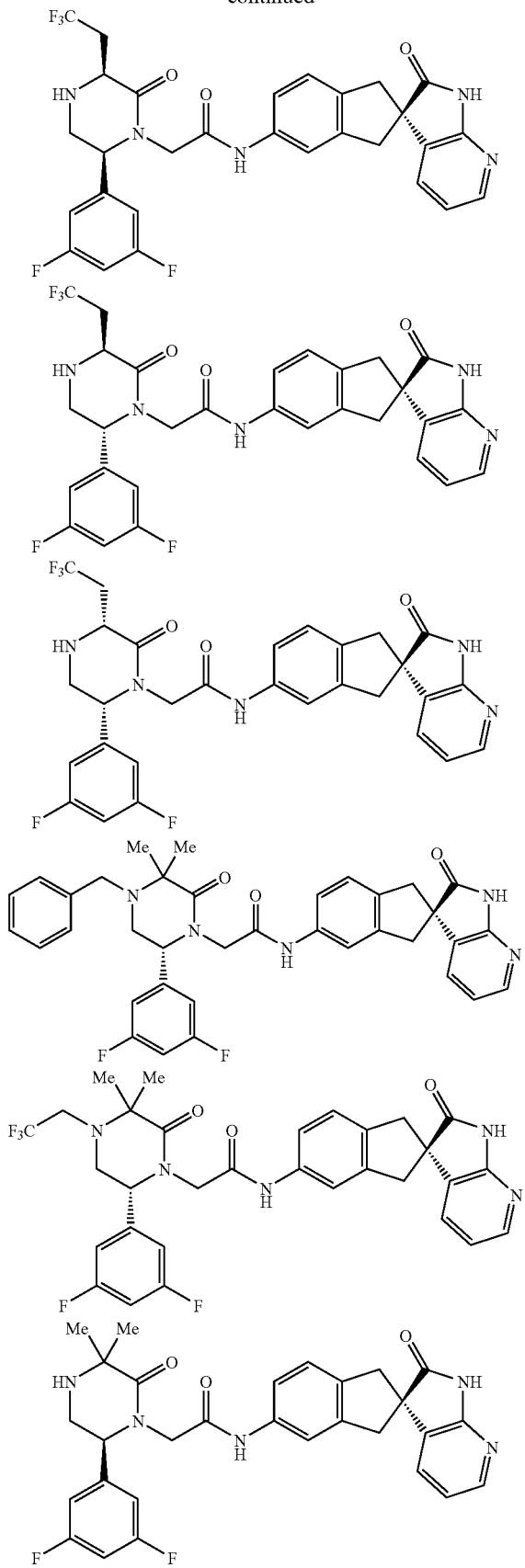
208
-continued
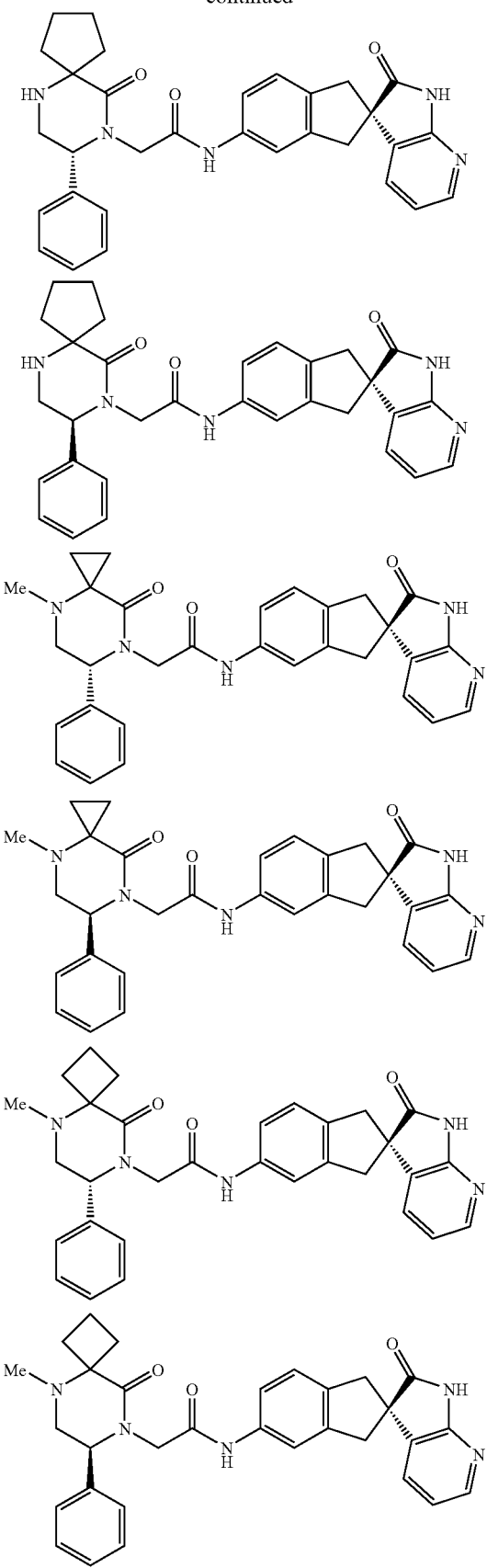

-continued
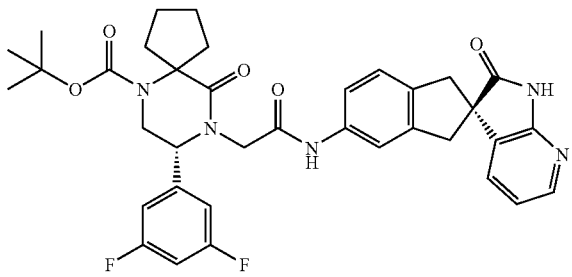
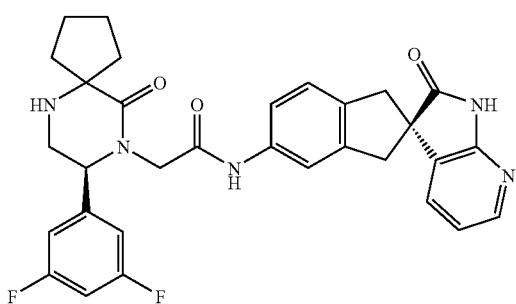
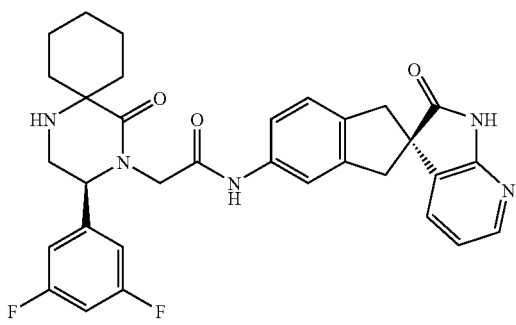
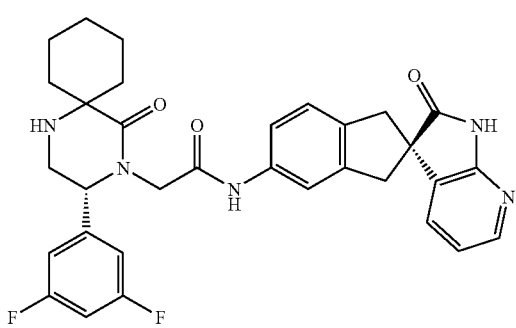
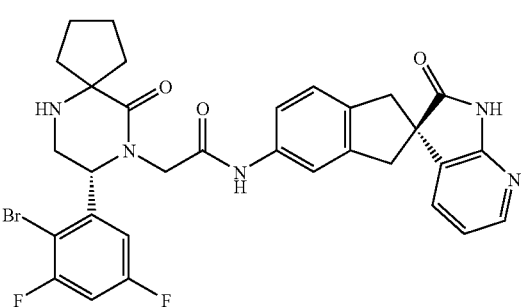
-continued
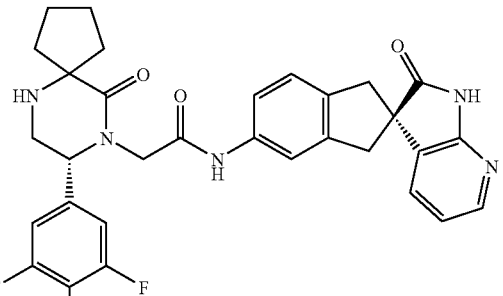
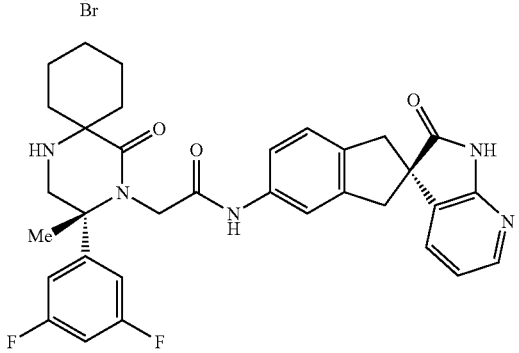
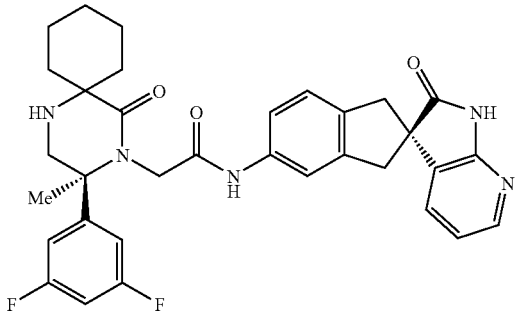
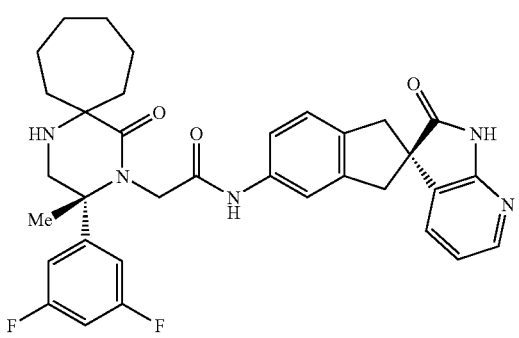
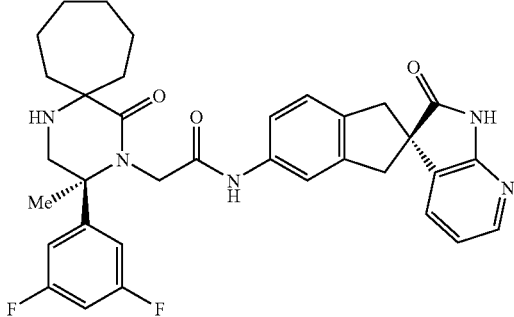

211
-continued
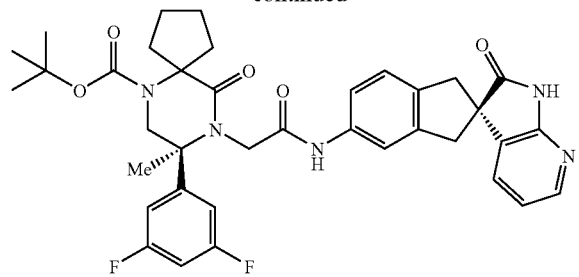
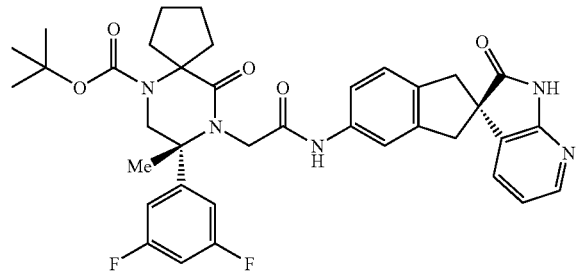
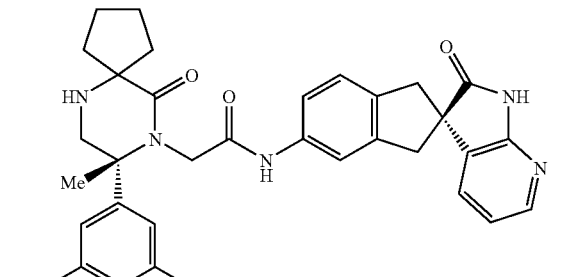
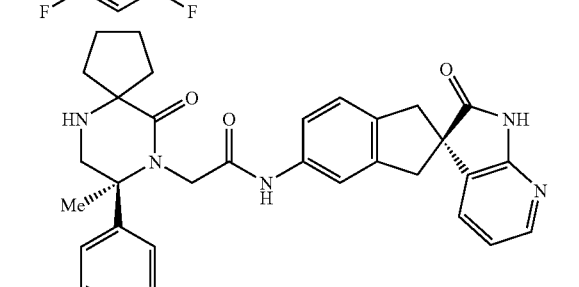
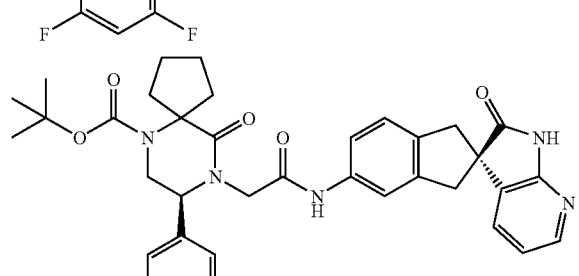
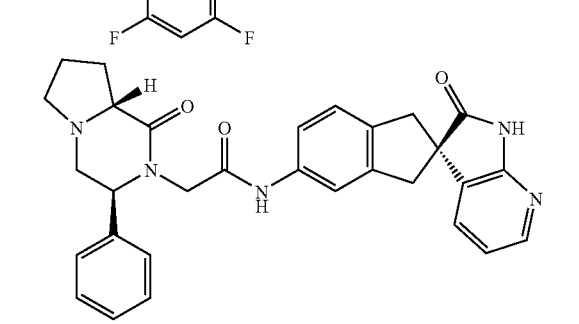
212
-continued -continued
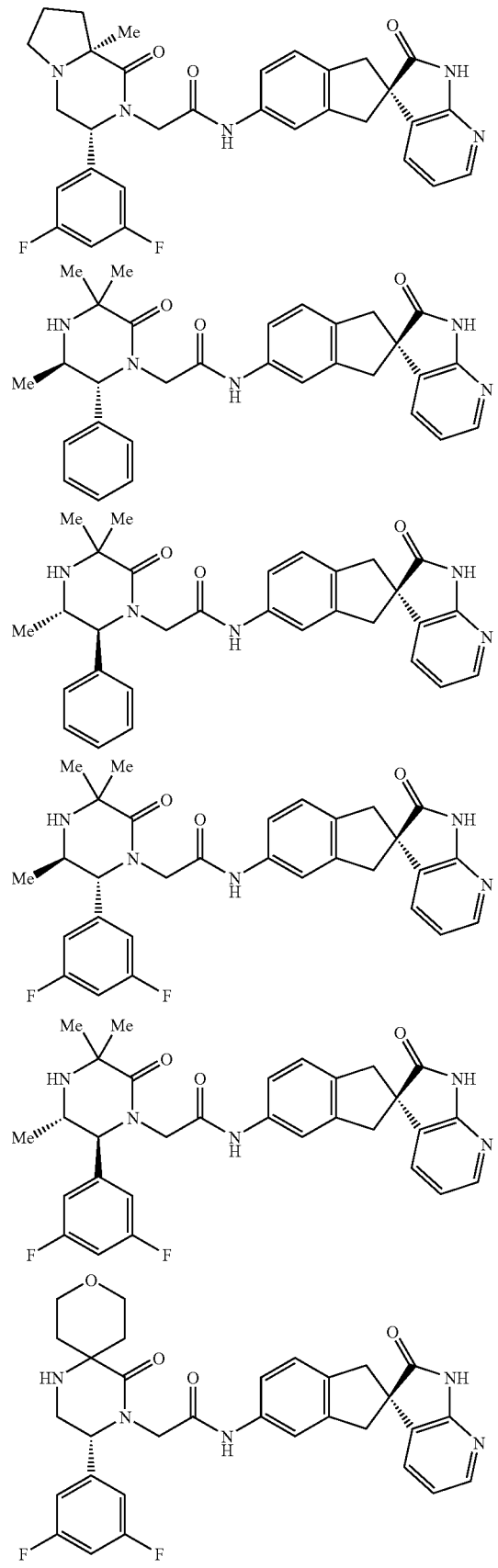
-continued
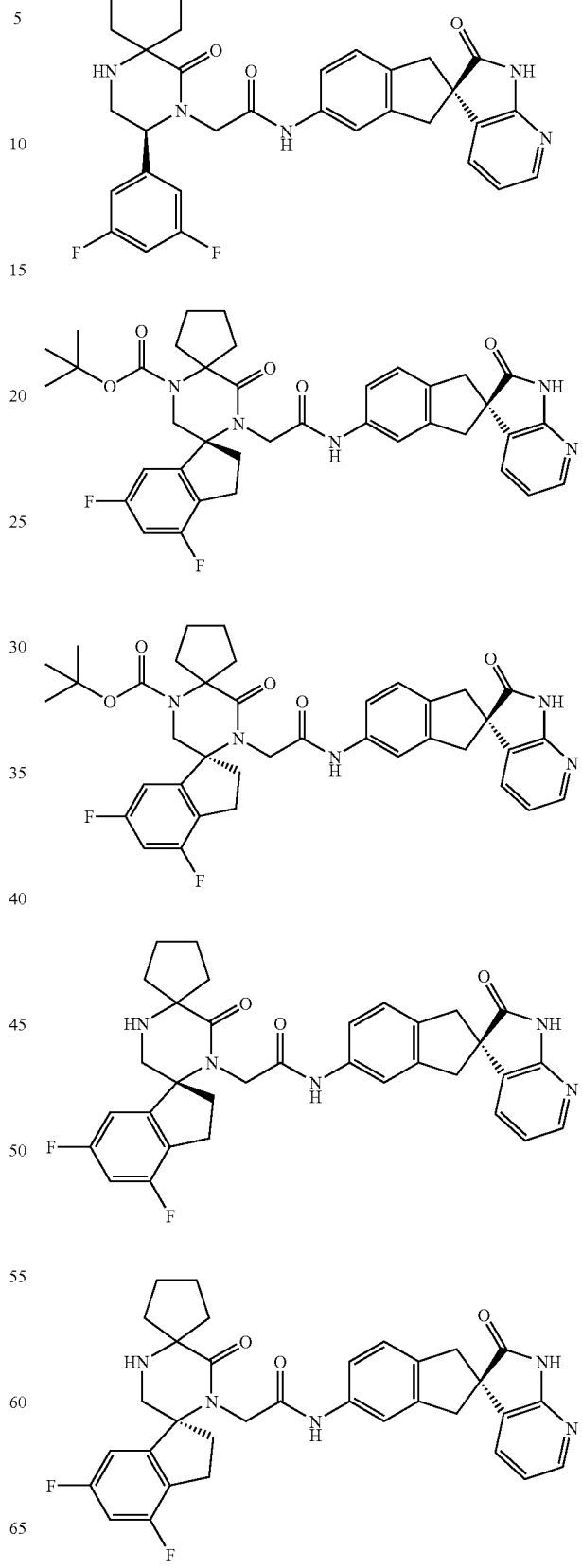

-continued
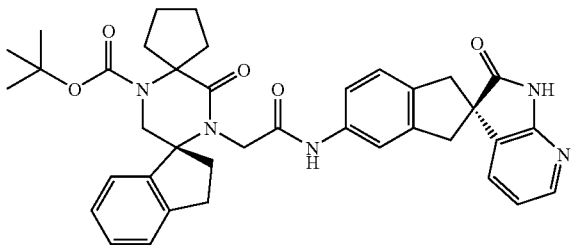
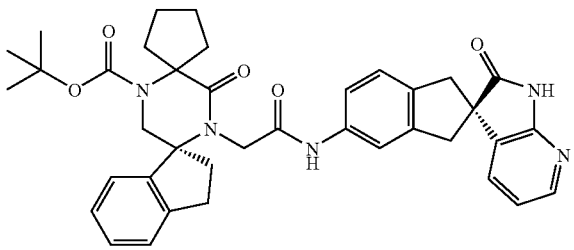
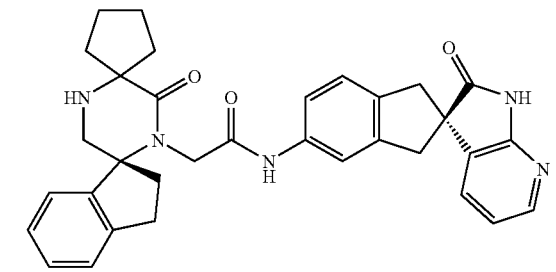
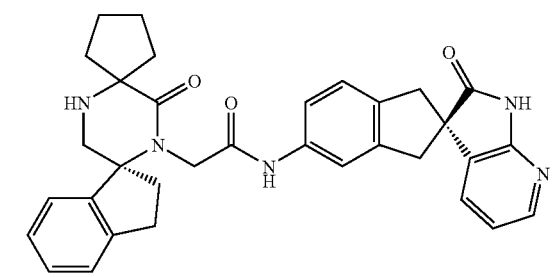
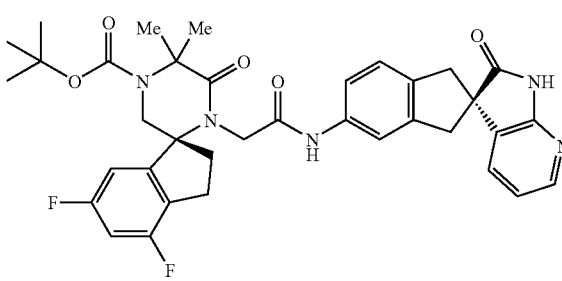
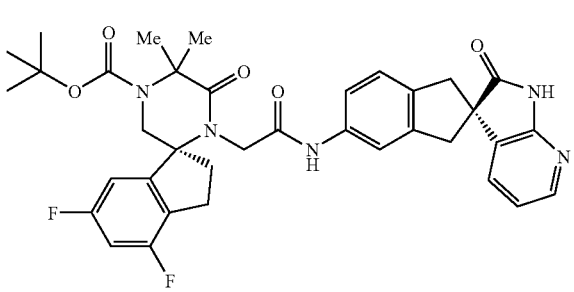
-continued
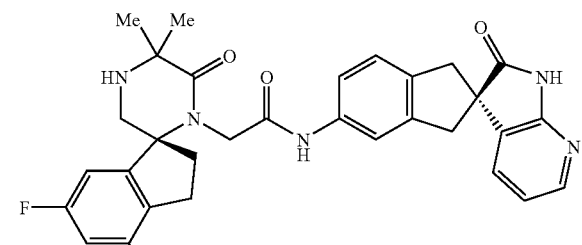
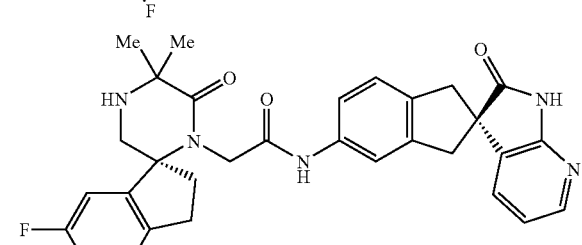
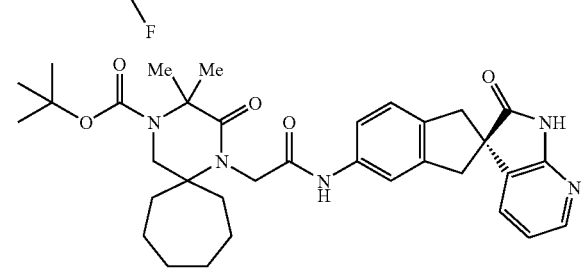
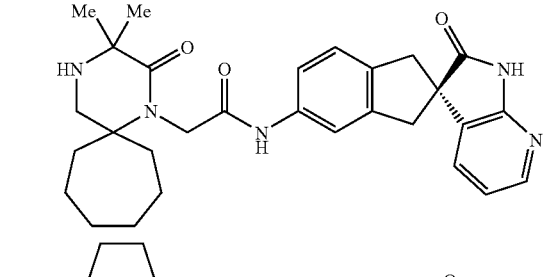
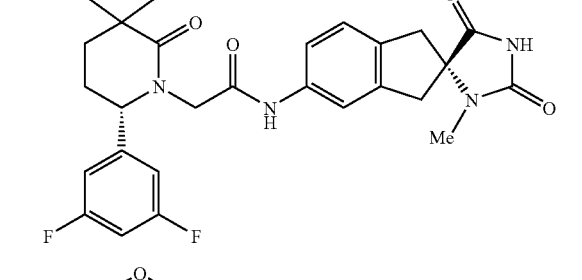
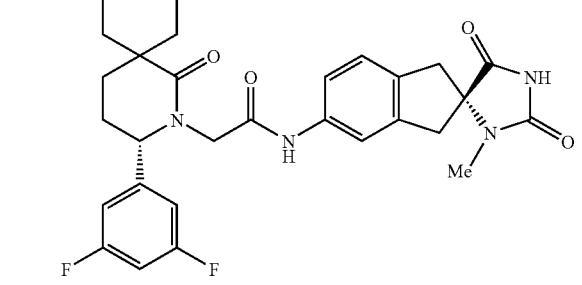

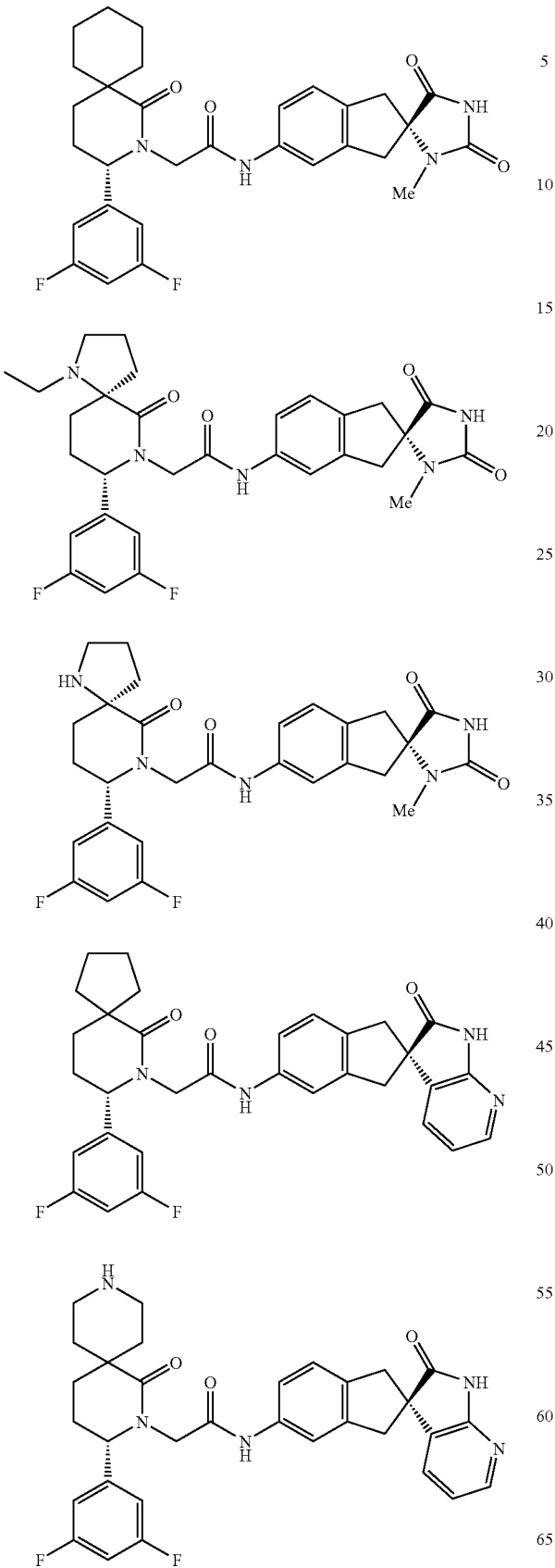
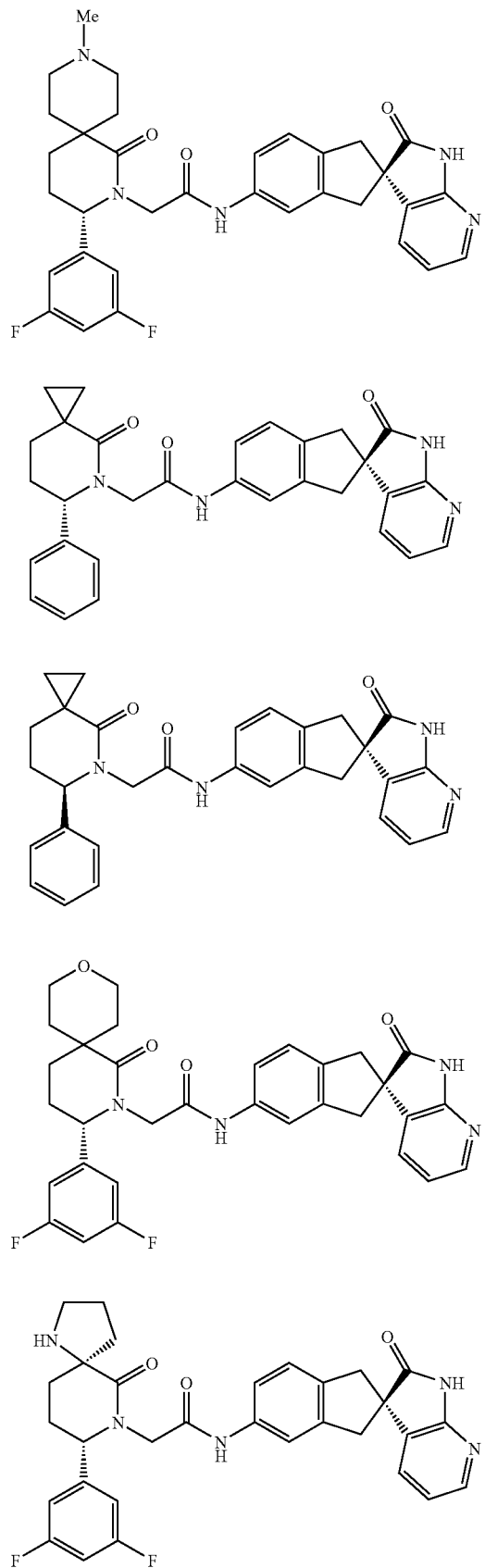

219
-continued
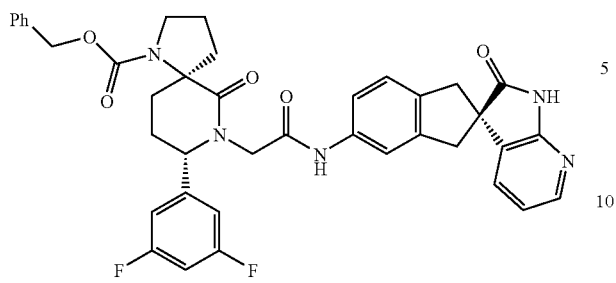
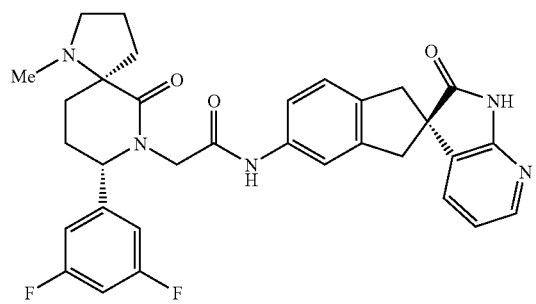
220
-continued
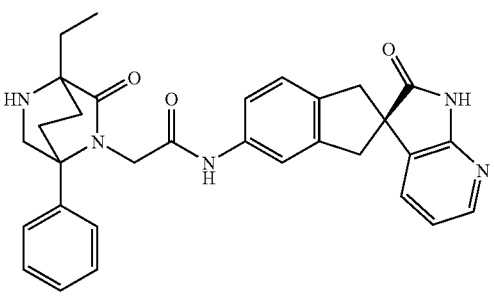
or a pharmaceutically acceptable salt, individual enantiomer or diastereomer thereof.
28. A compound selected from:
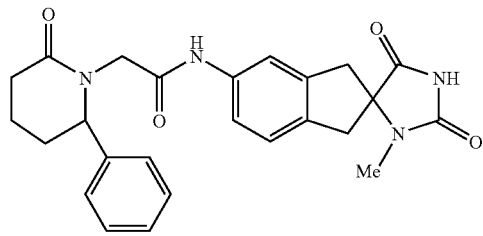

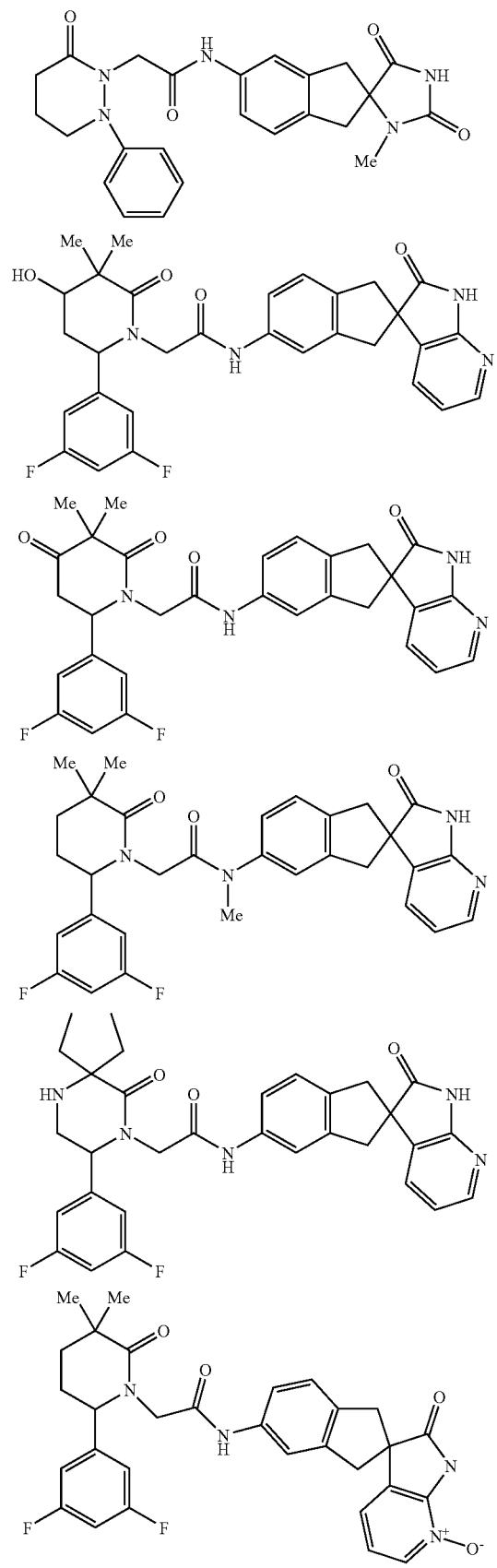

-continued
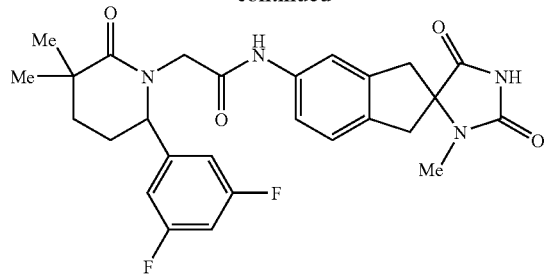
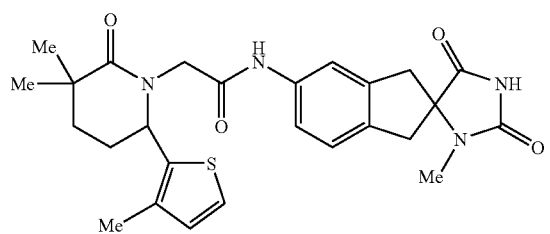
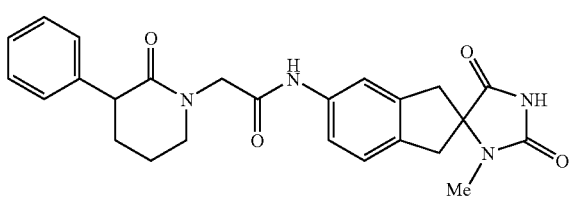
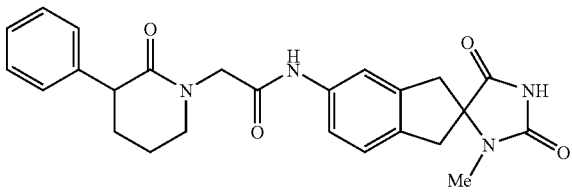
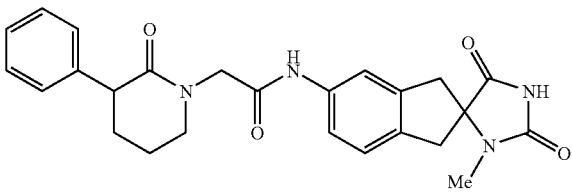
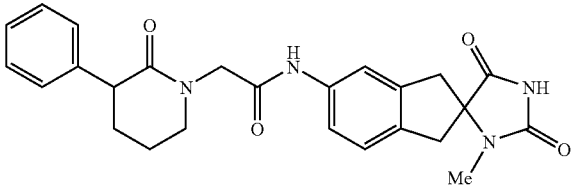
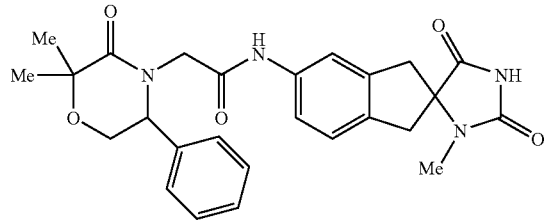
-continued
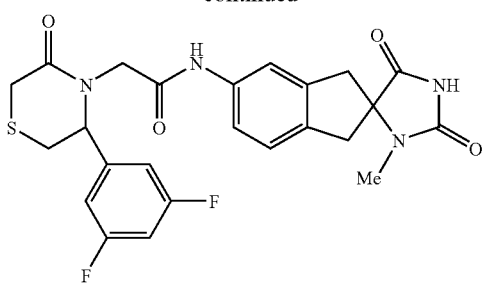
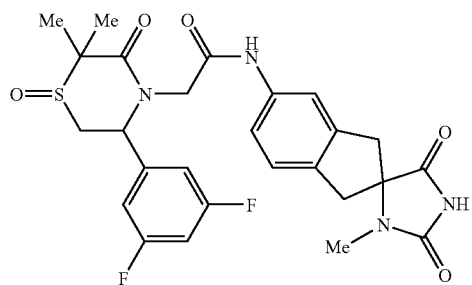
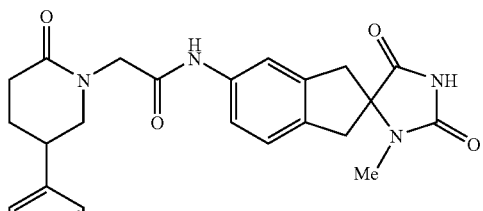
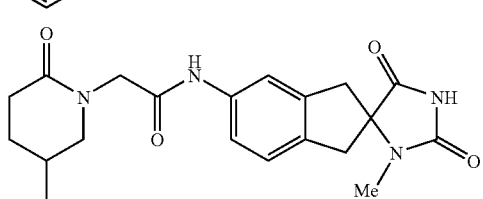
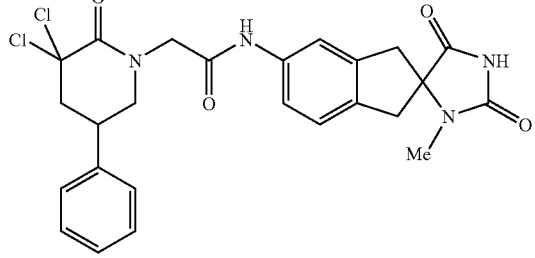
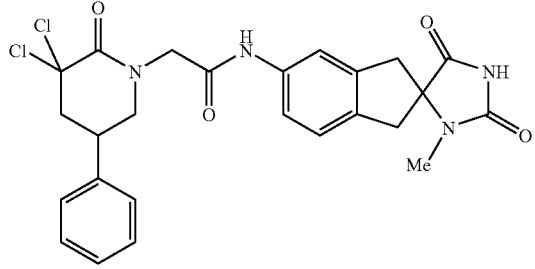

-continued
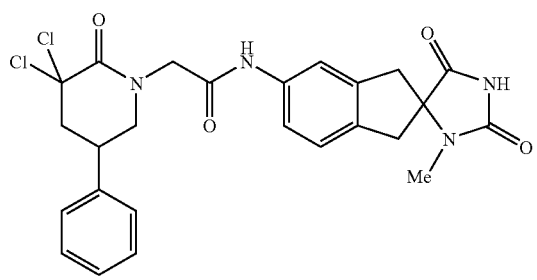
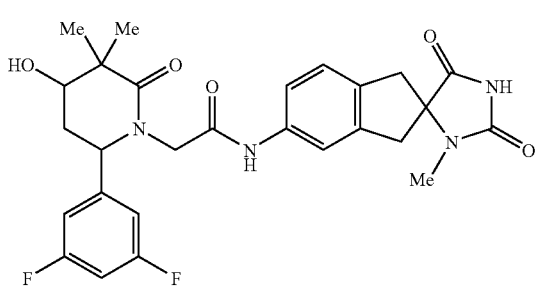
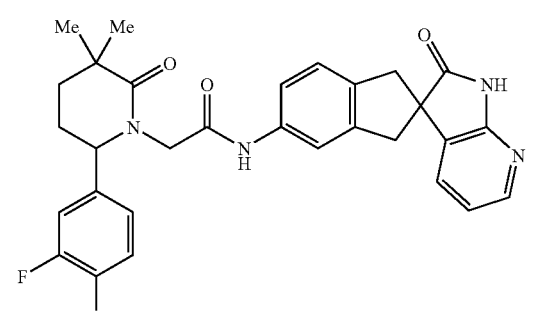
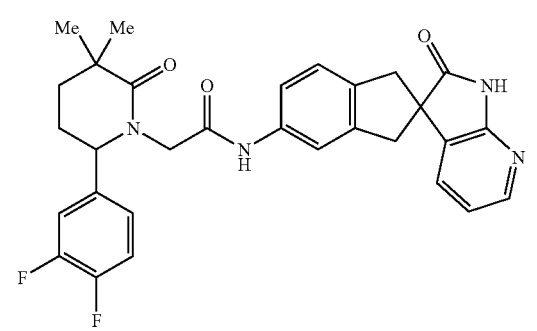
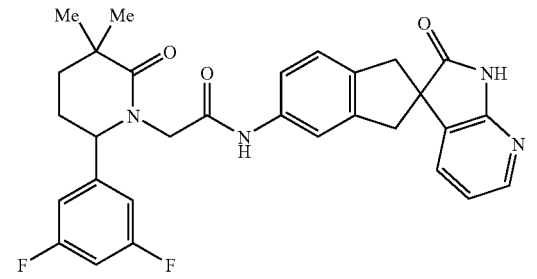
-continued
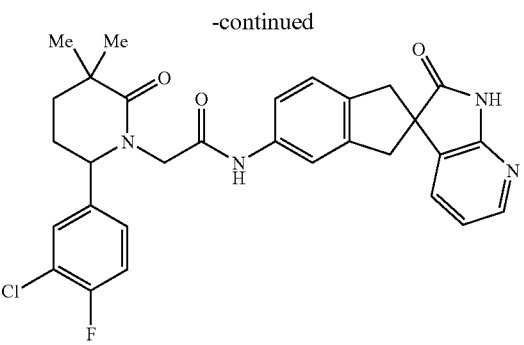
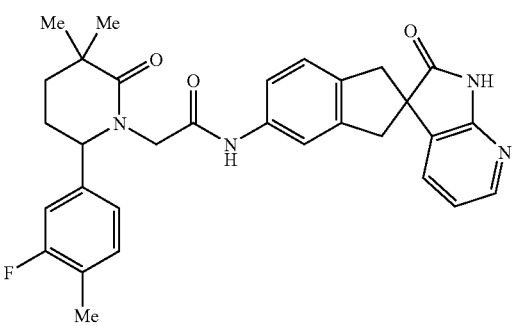
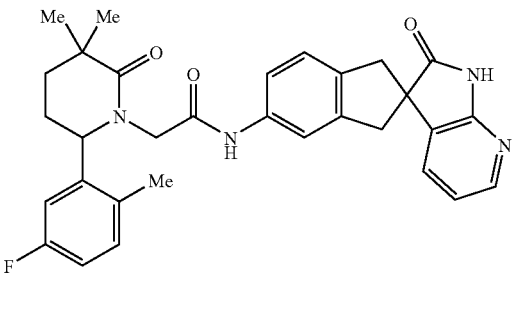
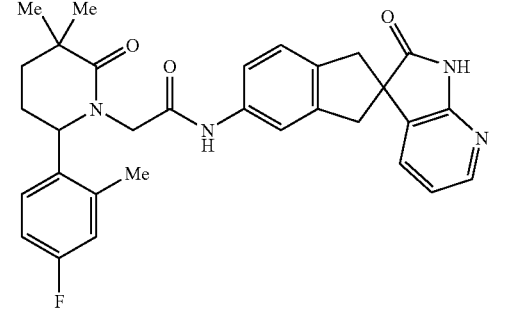
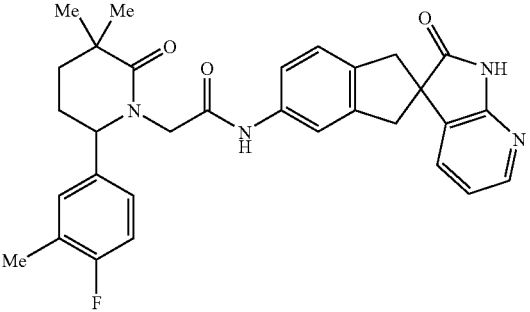

-continued
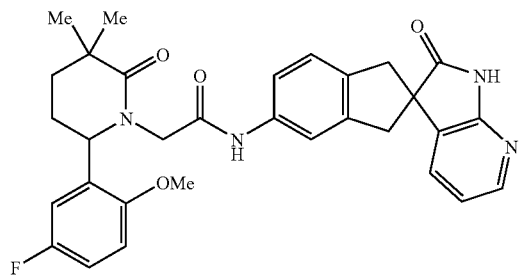
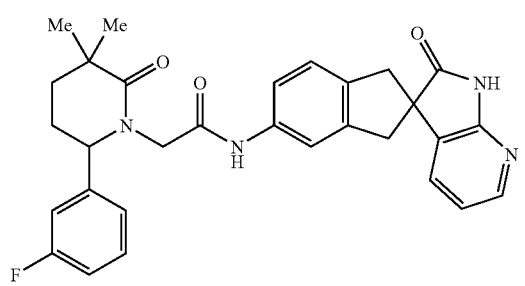
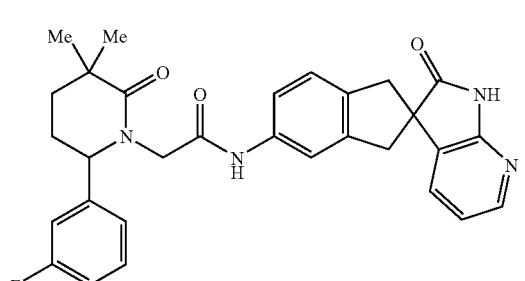
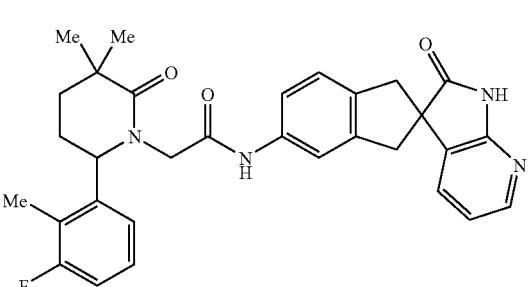
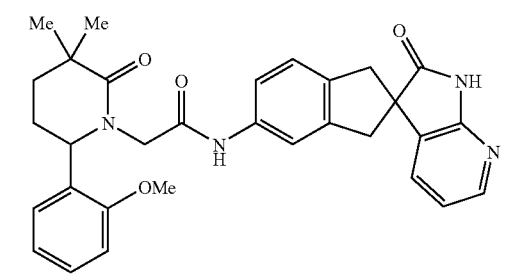
-continued
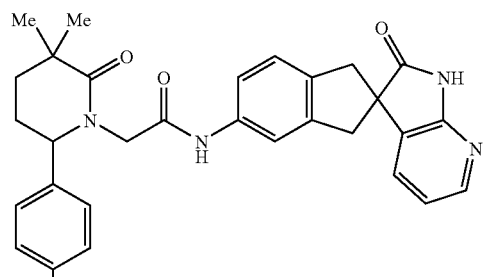
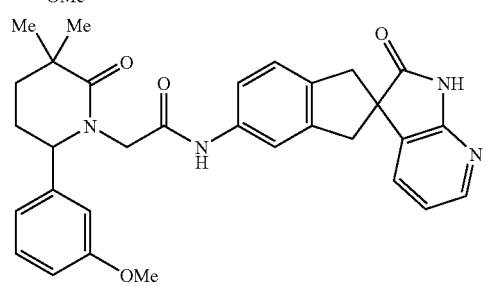
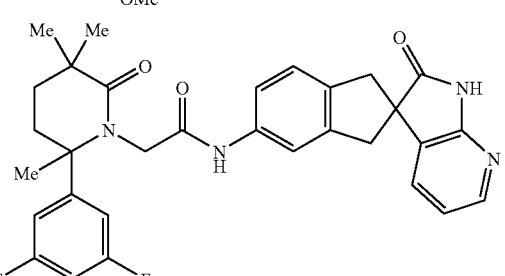
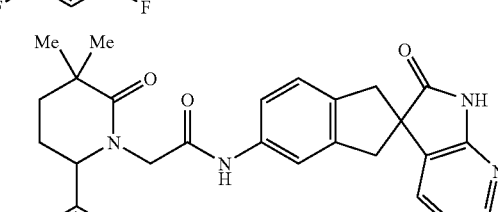
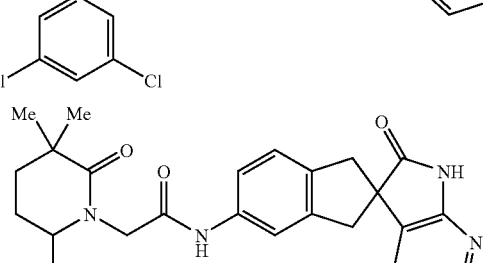
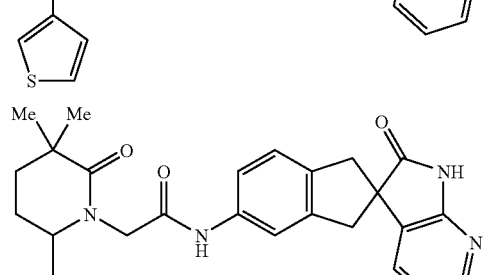

-continued
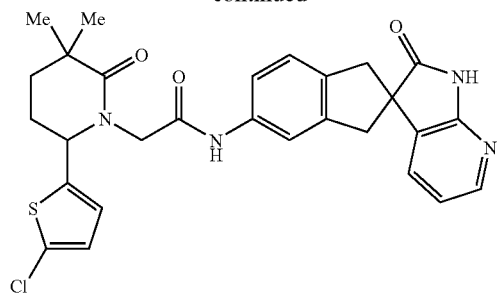
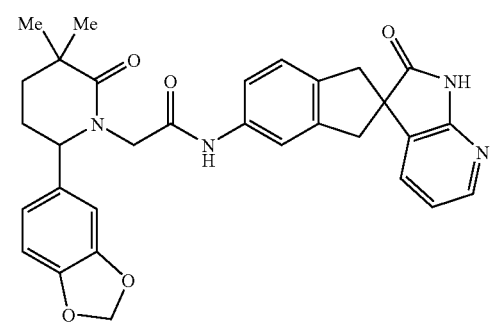
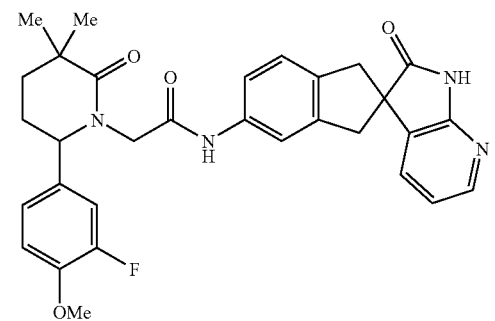
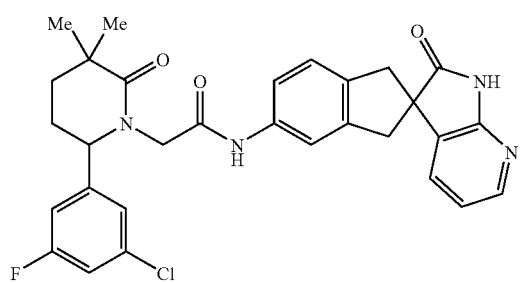
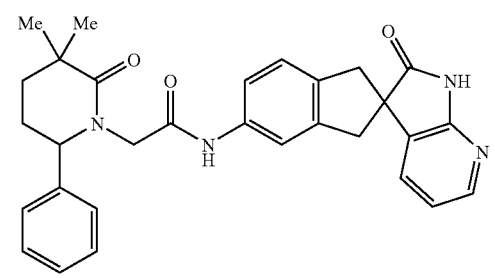
-continued
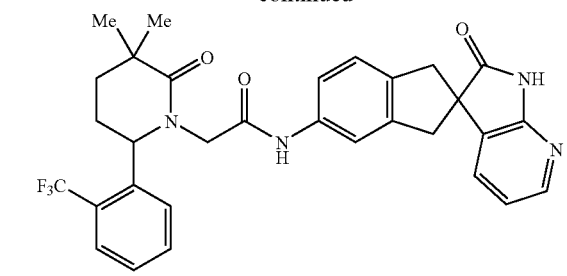
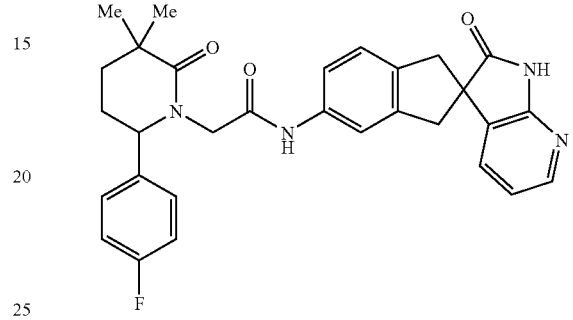
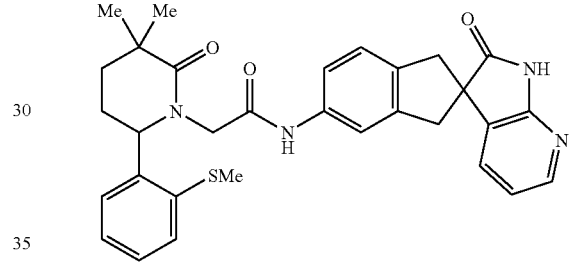
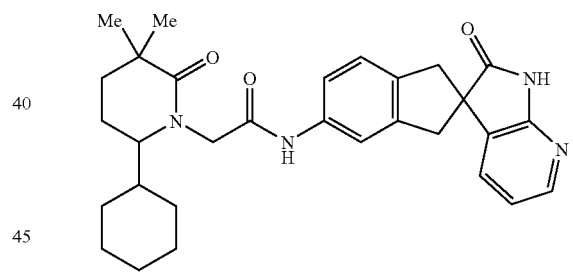
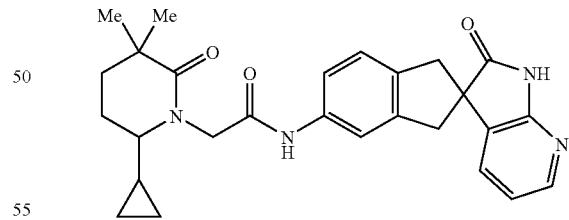
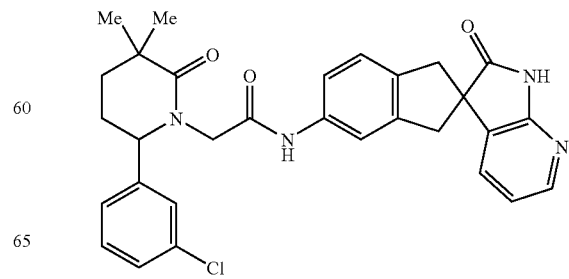

231
-continued
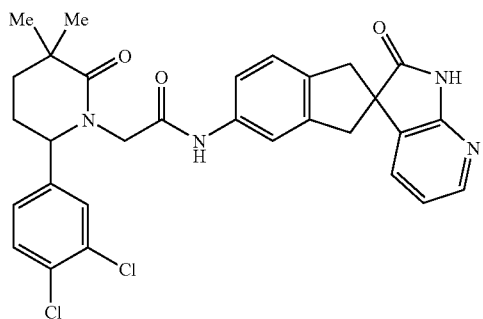
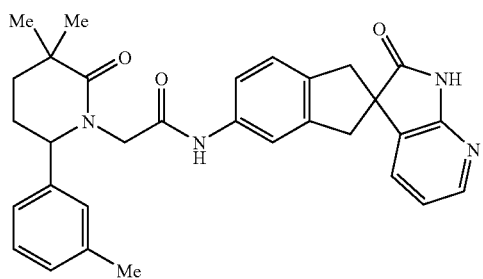
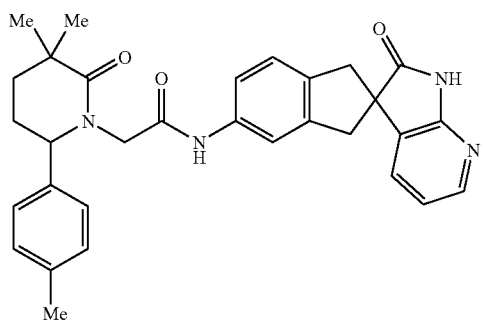
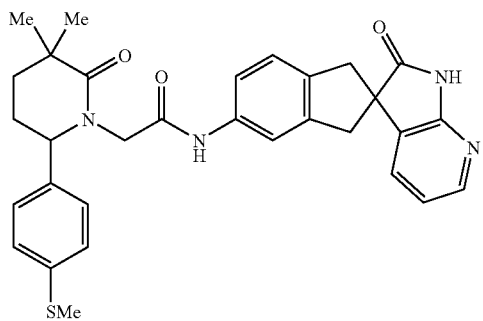
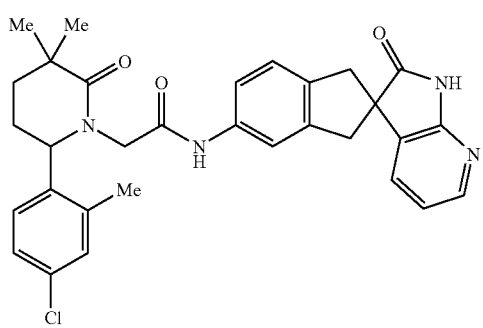
232
-continued
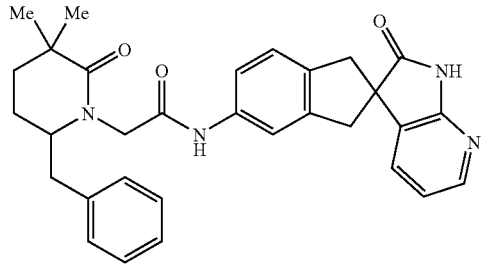
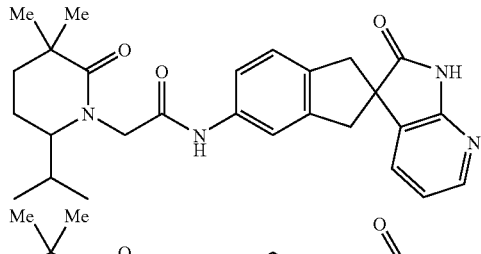
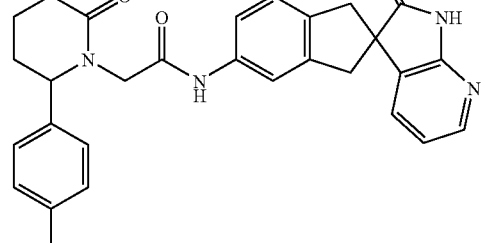
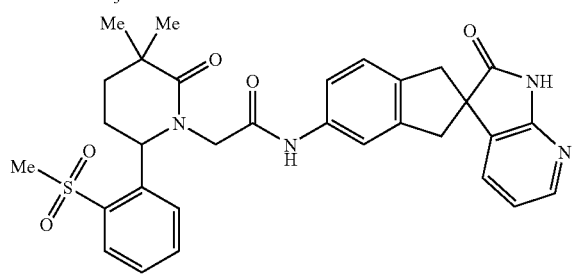
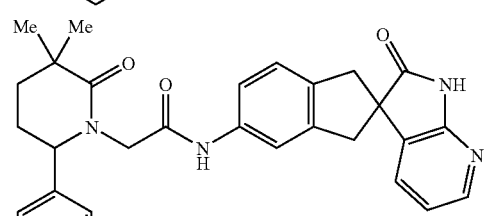
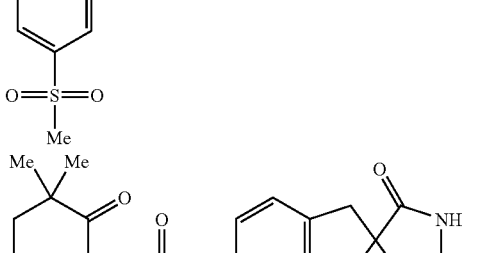
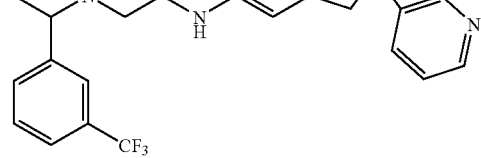

-continued
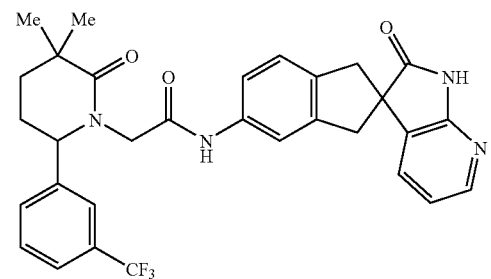
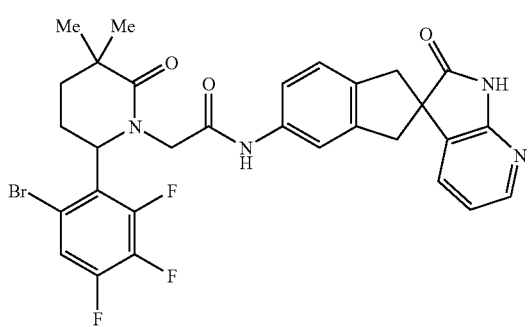
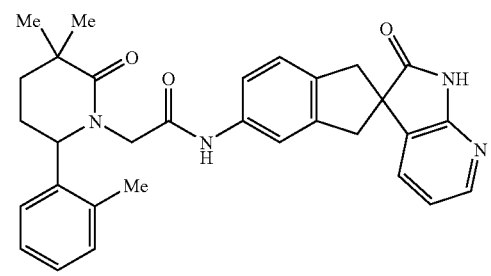
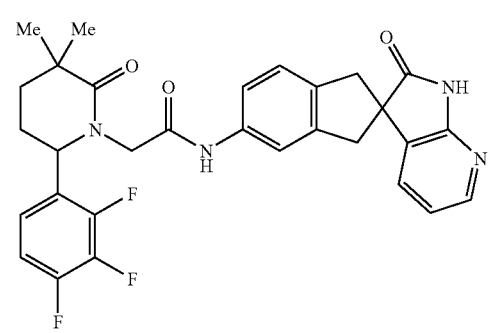
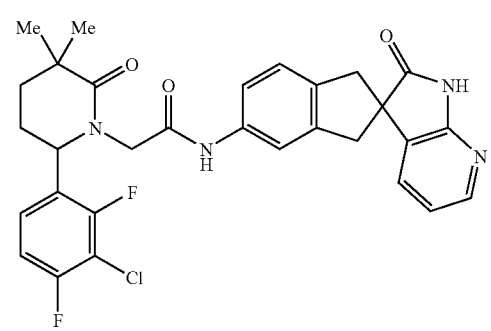
-continued
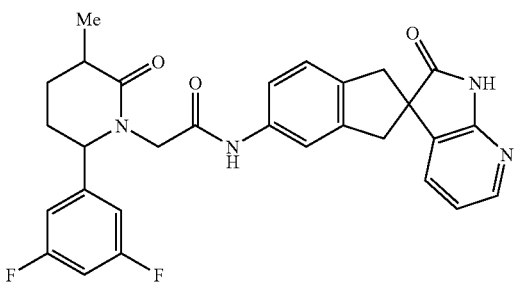
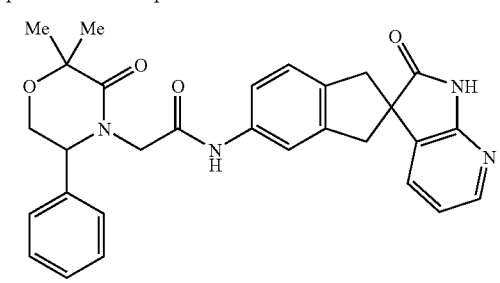
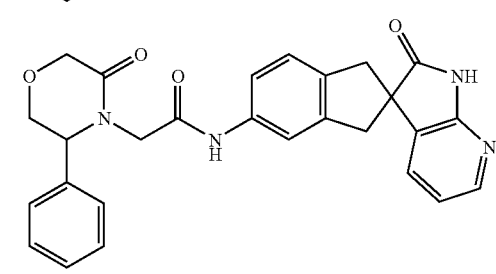
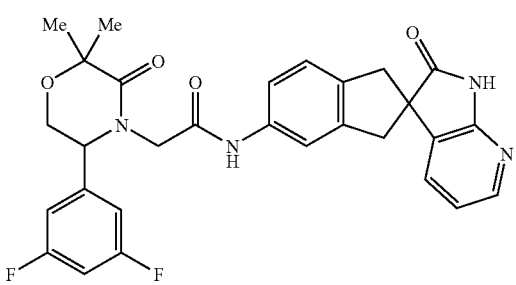
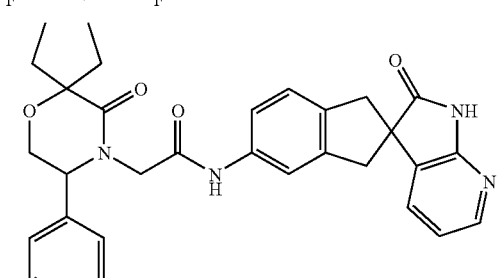
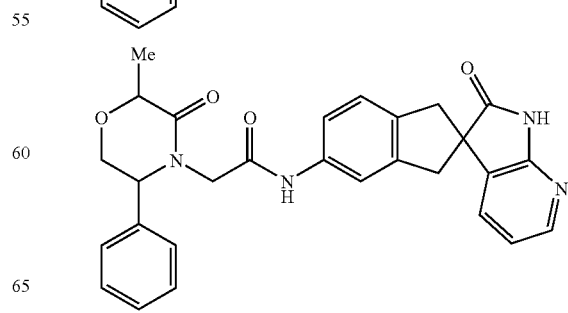

-continued
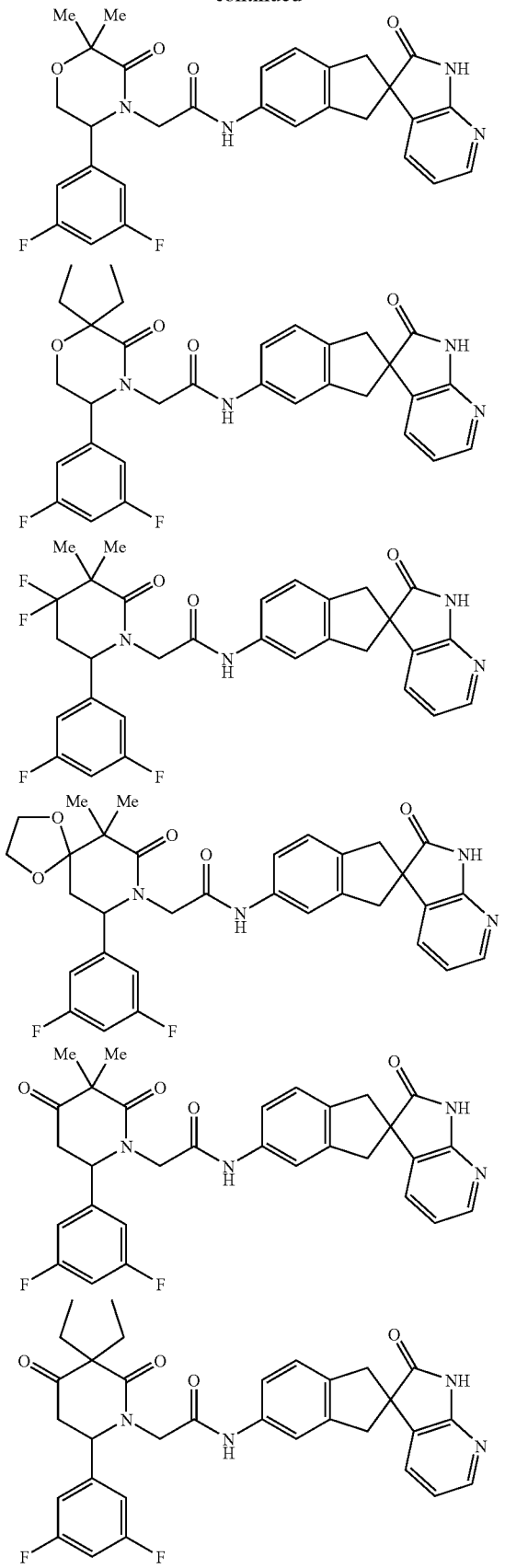
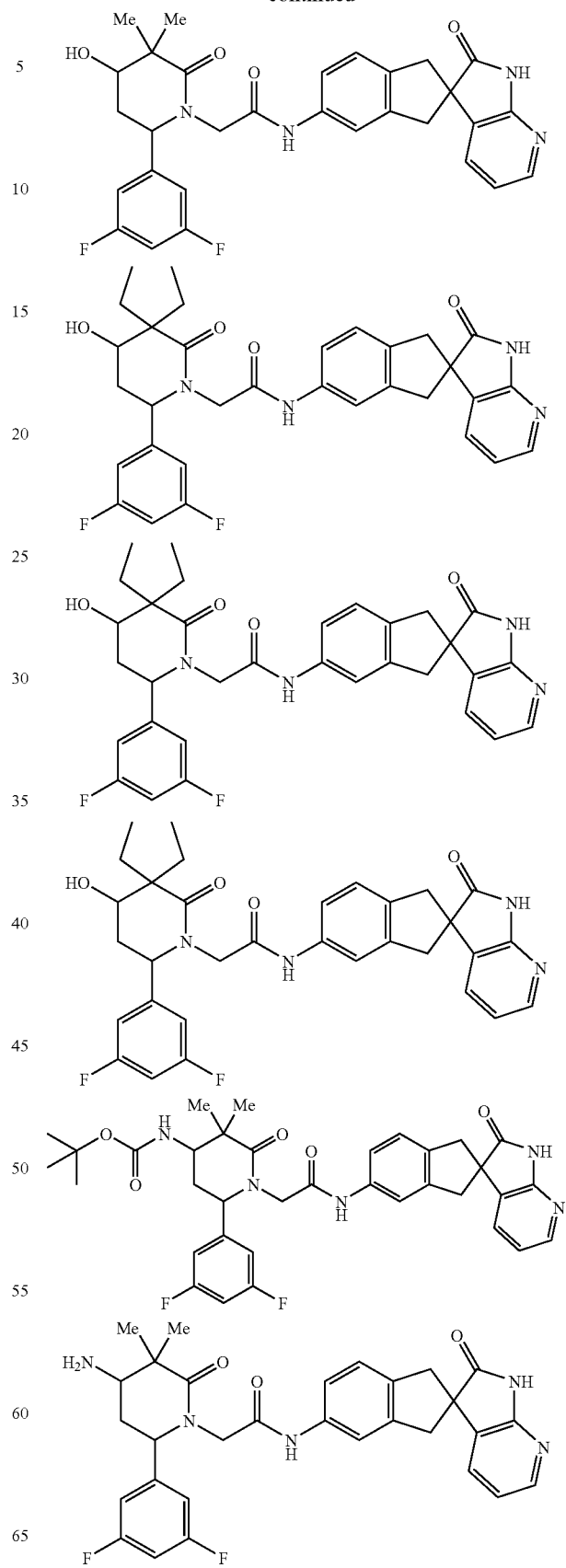

-continued
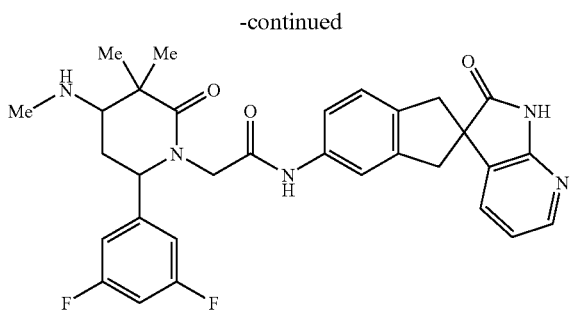
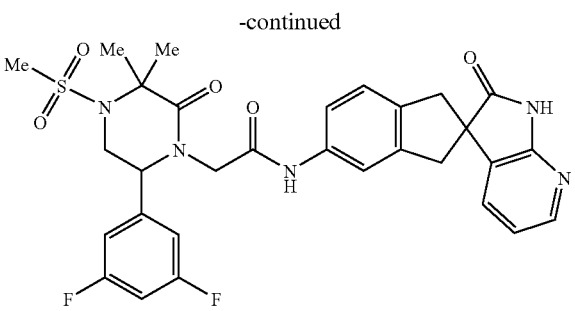

-continued
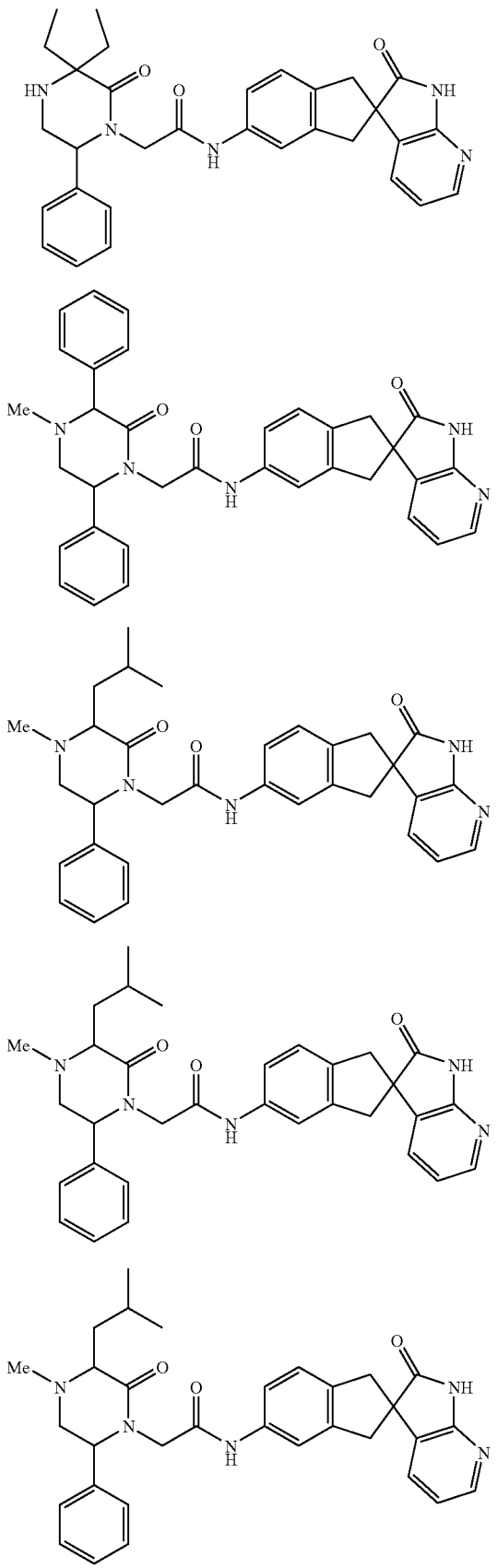
-continued
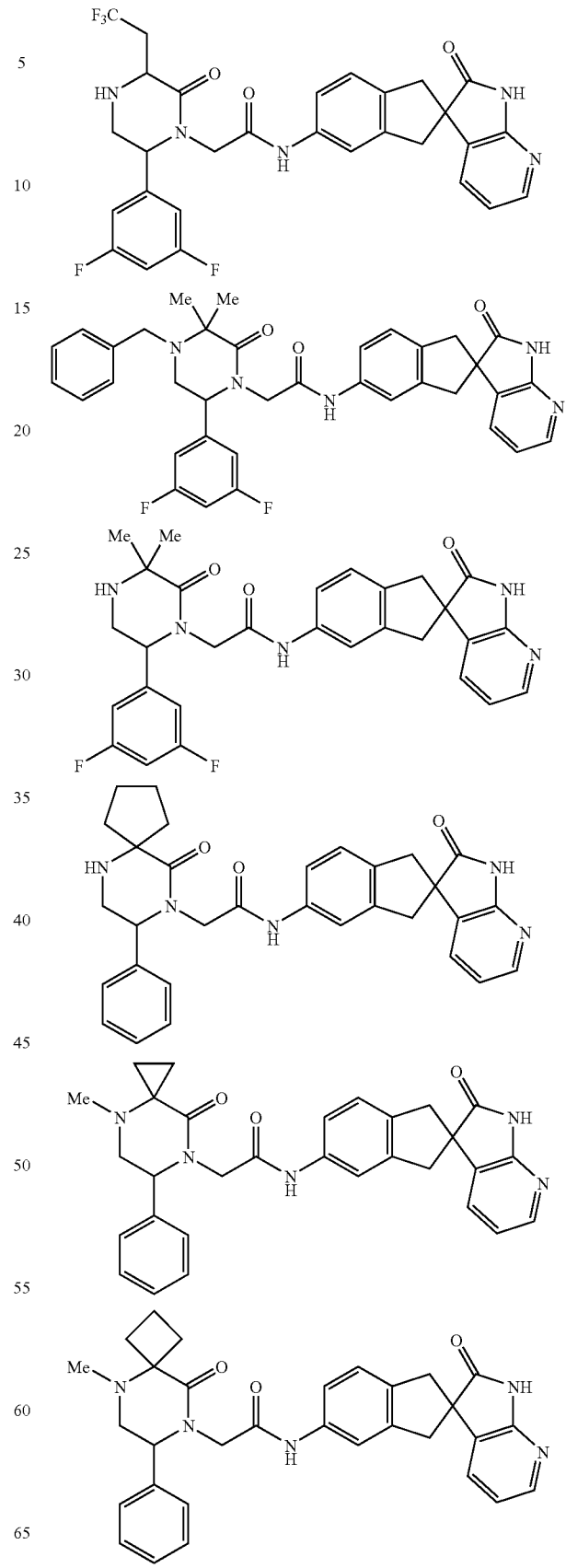

241
-continued
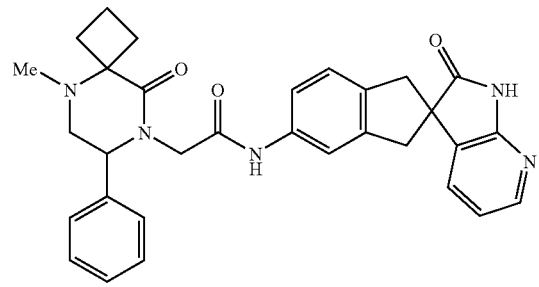
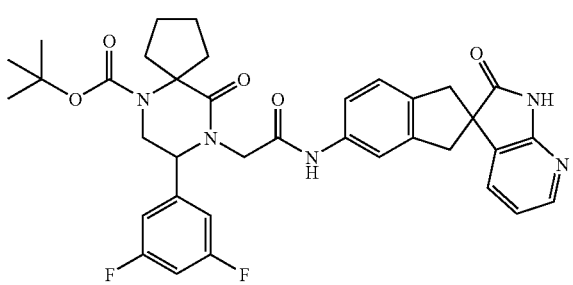
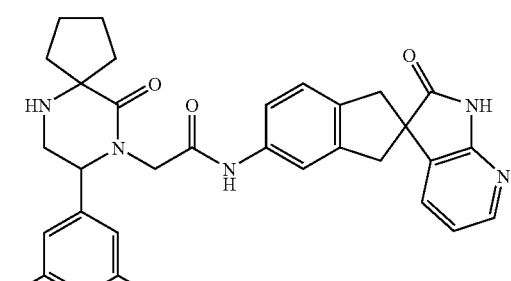
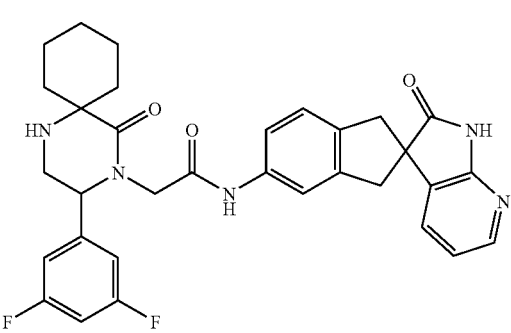
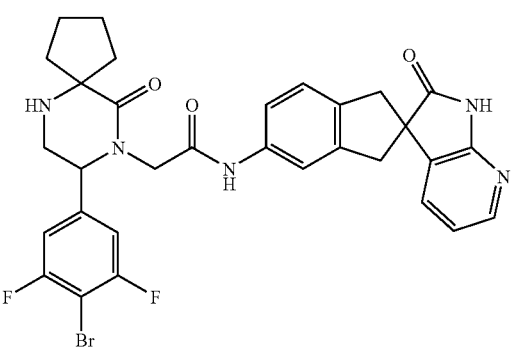
242
-continued
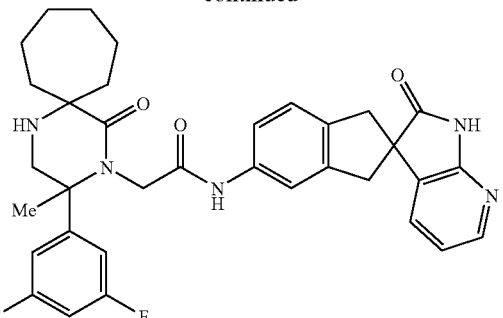
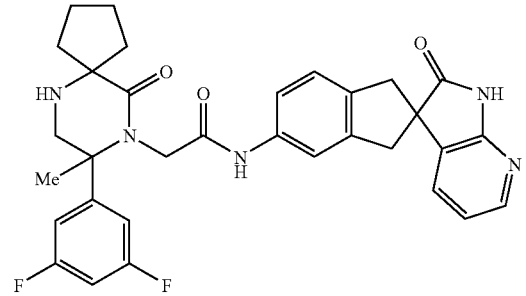
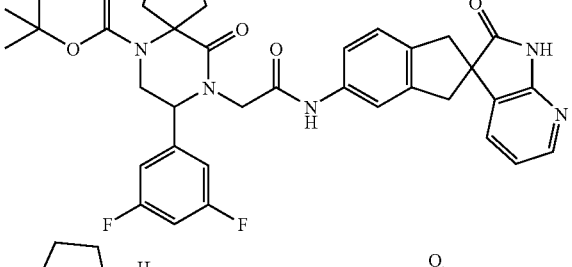
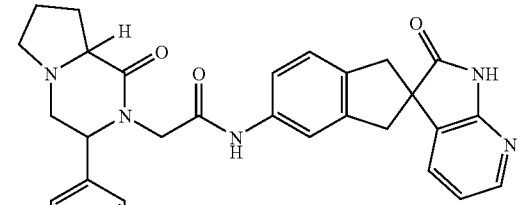
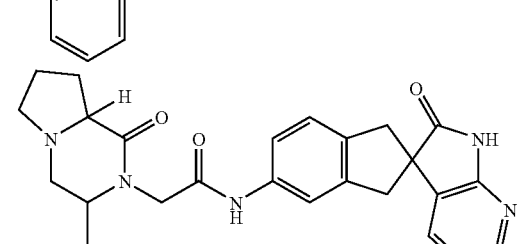
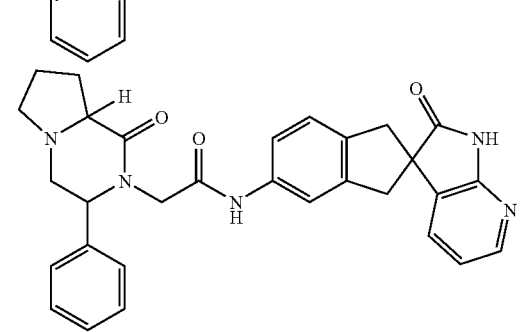

243
-continued
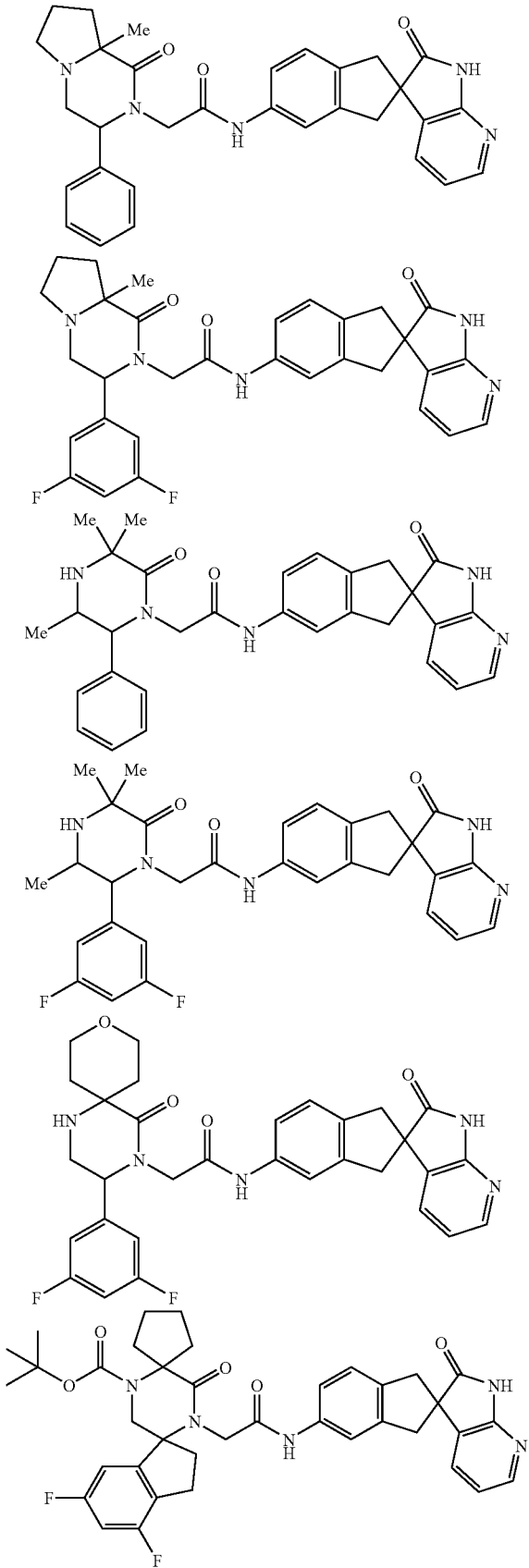
244
-continued
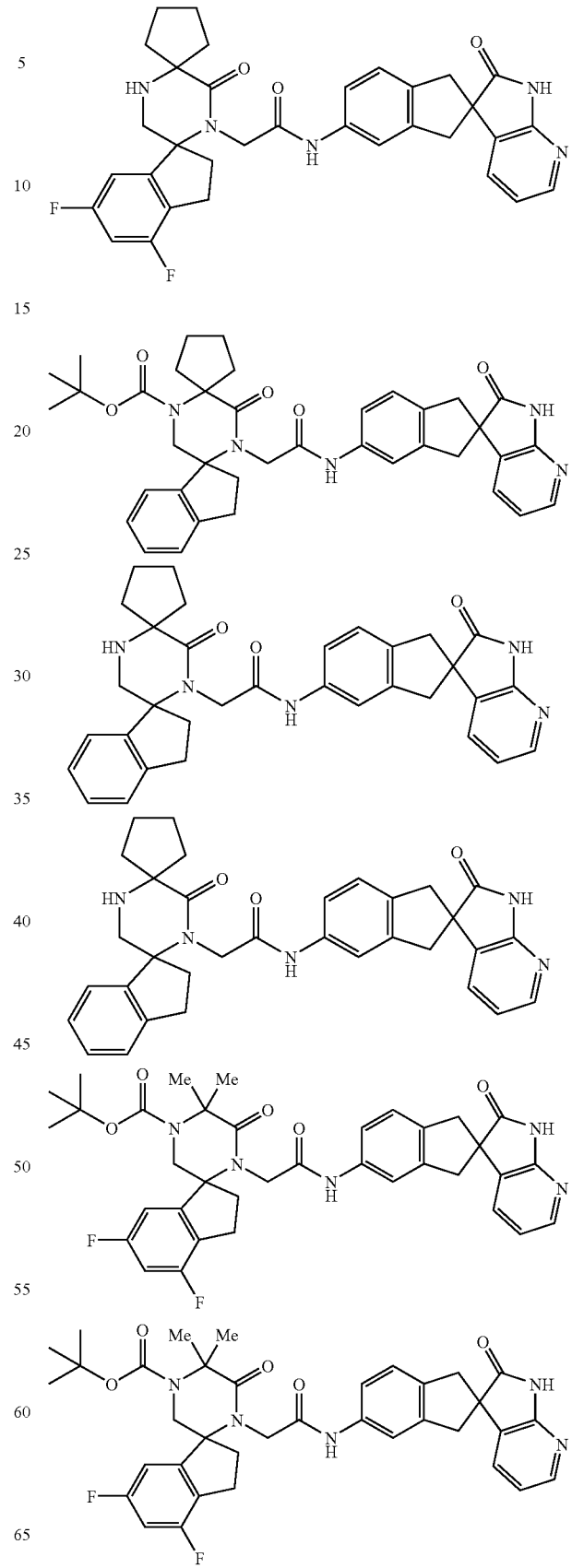

-continued
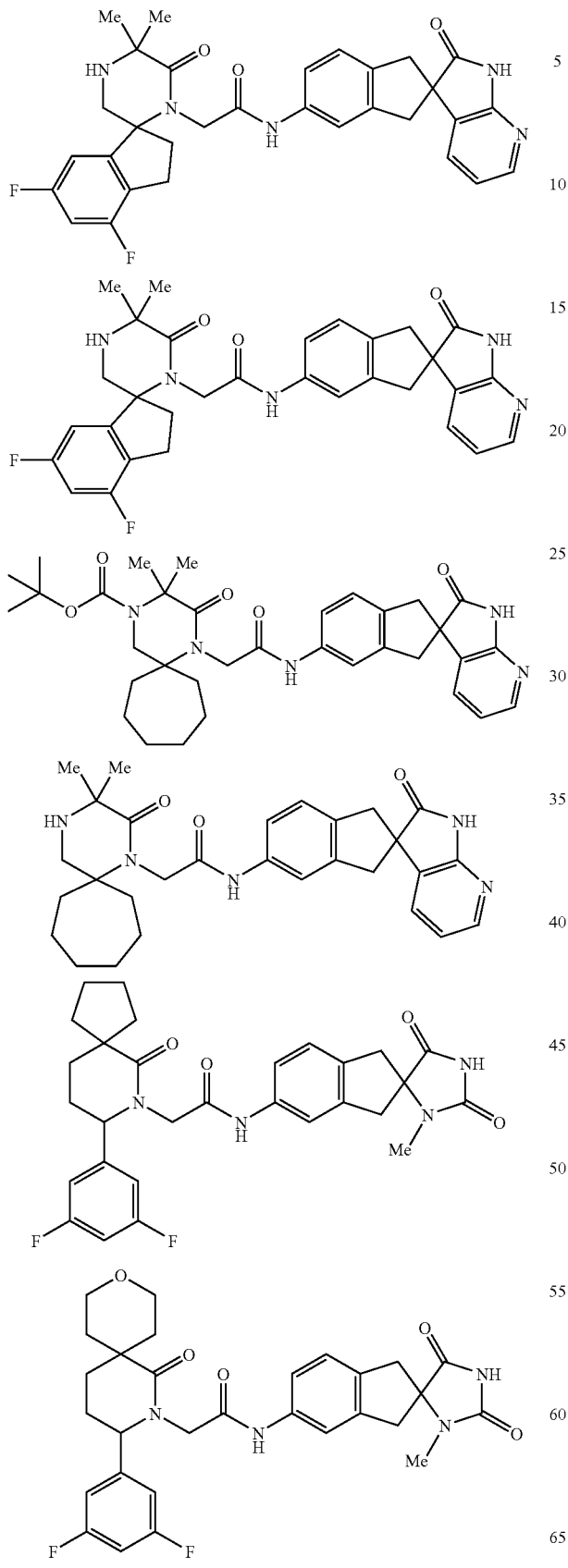
-continued
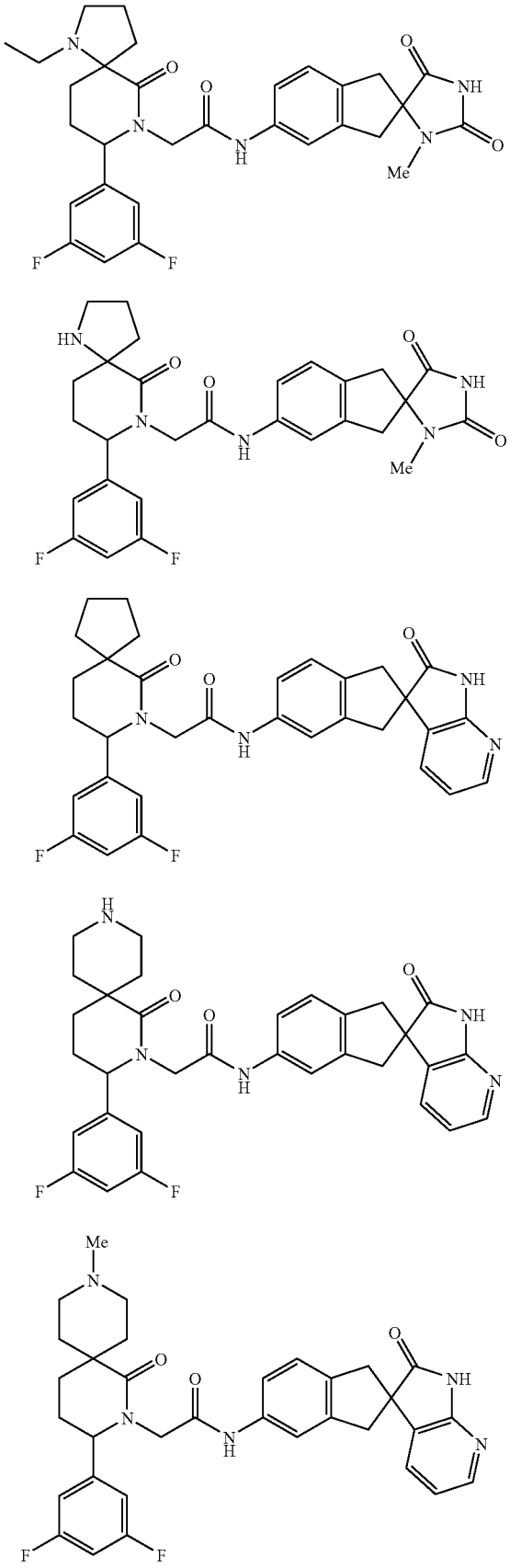

-continued

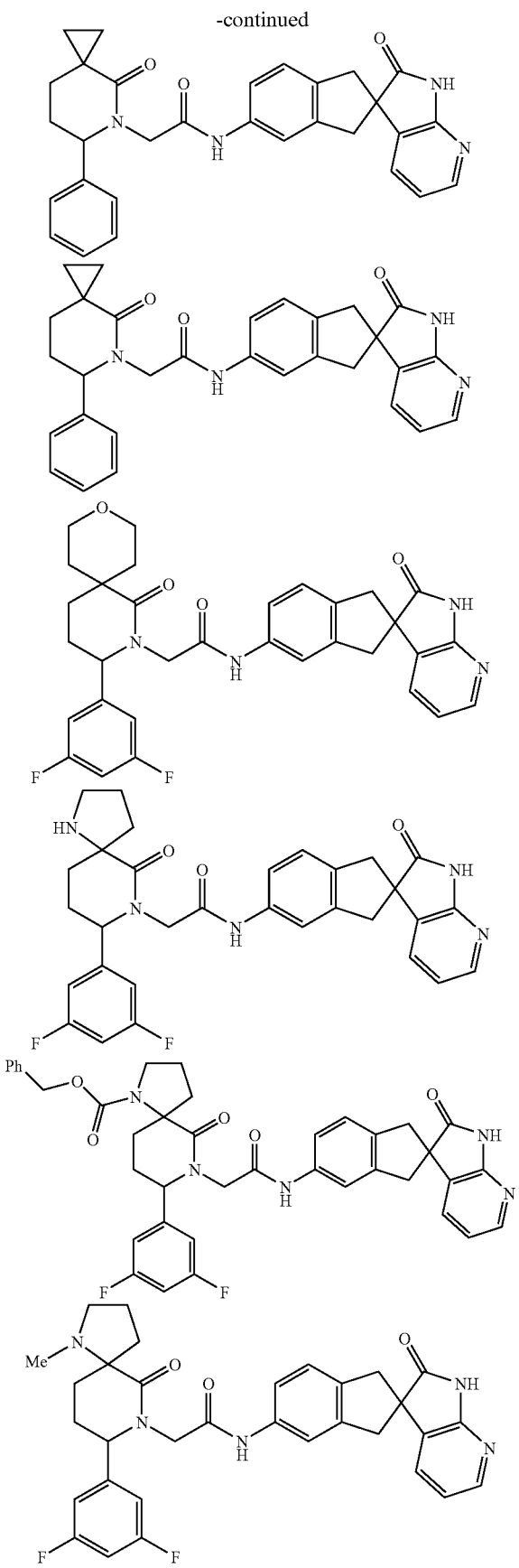

-continued

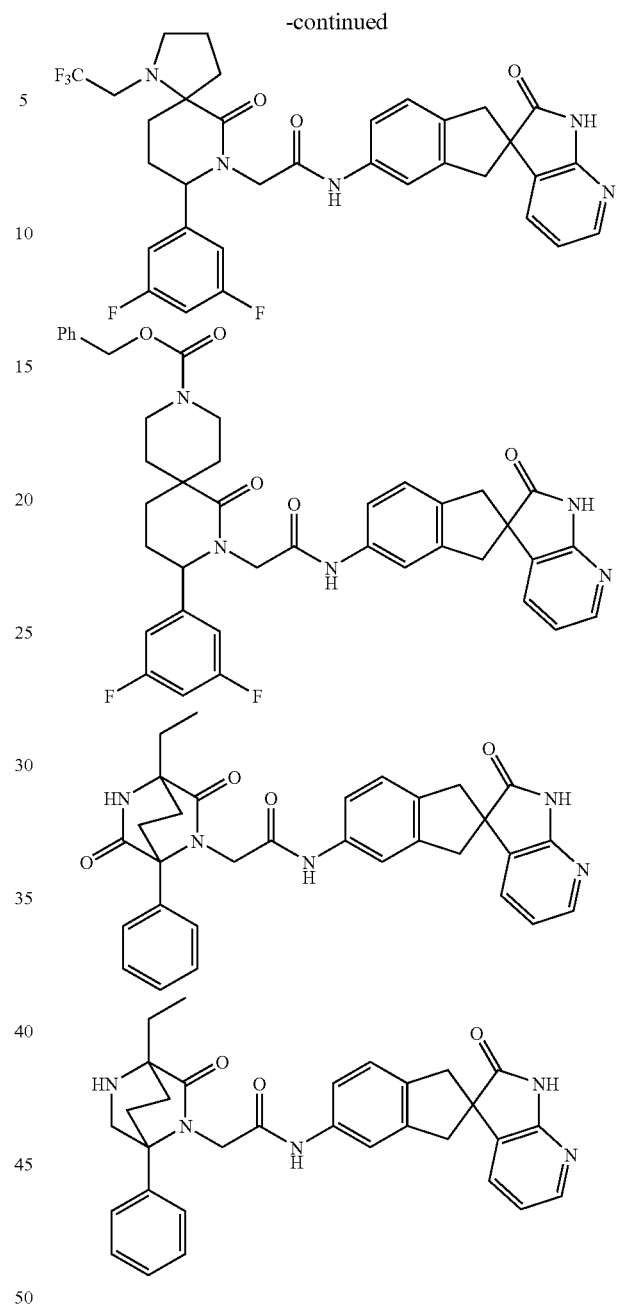

or a pharmaceutically acceptable salt, individual enantiomer or diastereomer thereof.

29. A pharmaceutical composition which comprises an inert carrier and the compound of claim 1 or a pharmaceutically acceptable salt thereof.

30. A method for treating headache, migraine or cluster headache in a mammalian patient in need of such which comprises administering to the patient a therapeutically effective amount of the compound of claim 1 or a pharmaceutically acceptable salt thereof.

31. A method of treating migraine headaches, cluster headaches, and headaches, said method comprising the co-administration, to a person in need of such treatment, of:

a therapeutically effective amount of the compound of claim 1 or a pharmaceutically acceptable salt thereof; and a therapeutically effective amount of a second agent selected from serotonin agonists, analgesics, anti-inflamatory agents, anti-hypertensives and anticonvulsants.

32. A compound which is

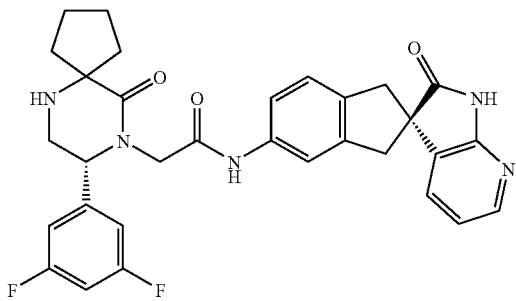

or a pharmaceutically acceptable salt thereof.

33. A pharmaceutical composition which comprises an inert carrier and the compound of claim 32 or a pharmaceutically acceptable salt thereof.

34. A method for the acute treatment of migraine in a human patient in need thereof which comprises administering to the patient a therapeutically effective amount of the compound of claim 32 or a pharmaceutically acceptable salt thereof.

35. A method for treating headache, migraine or cluster headache in a mammalian patient in need of such which comprises administering to the patient a therapeutically effective amount of the compound of claim 32 or a pharmaceutically acceptable salt thereof.

36. A method of treating migraine headaches, cluster headaches, and headaches, said method comprising the co-administration, to a person in need of such treatment, of:
   a therapeutically effective amount of the compound of claim 32 or a pharmaceutically acceptable salt thereof; and
   a therapeutically effective amount of a second agent selected from serotonin agonists, analgesics, anti-inflamatory agents, anti-hypertensives and anticonvulsants.

37. A compound which is

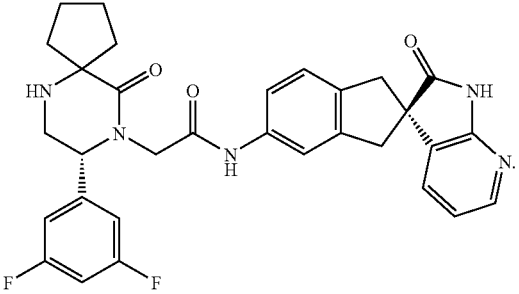

38. A pharmaceutical composition which comprises an inert carrier and the compound of claim 37.

39. A method for the acute treatment of migraine in a human patient in need thereof which comprises administering to the patient a therapeutically effective amount of the compound of claim 37.

40. A method for treating headache, migraine or cluster headache in a mammalian patient in need of such which comprises administering to the patient a therapeutically effective amount of the compound of claim 37.

41. A method of treating migraine headaches, cluster headaches, and headaches, said method comprising the co-administration, to a person in need of such treatment, of:
   a therapeutically effective amount of the compound of claim 37 or a pharmaceutically acceptable salt thereof; and
   a therapeutically effective amount of a second agent selected from serotonin agonists, analgesics, anti-inflamatory agents, anti-hypertensives and anticonvulsants.

* * * * *